(12) United States Patent
Matsumoto et al.

(10) Patent No.: US 7,851,473 B2
(45) Date of Patent: Dec. 14, 2010

(54) AMIDE COMPOUND

(75) Inventors: Takahiro Matsumoto, Osaka (JP); Masakuni Kori, Osaka (JP); Junichi Miyazaki, Osaka (JP); Yoshihiro Kiyota, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 182 days.

(21) Appl. No.: 11/667,821

(22) PCT Filed: Nov. 17, 2005

(86) PCT No.: PCT/JP2005/021136

§ 371 (c)(1), (2), (4) Date: Apr. 22, 2008

(87) PCT Pub. No.: WO2006/054652

PCT Pub. Date: May 26, 2006

(65) Prior Publication Data

US 2008/0312226 A1    Dec. 18, 2008

(30) Foreign Application Priority Data

Nov. 18, 2004   (JP) .............................. 2004-334748
Aug. 4, 2005    (JP) .............................. 2005-226950

(51) Int. Cl.
*A61K 31/501* (2006.01)
*A61K 31/497* (2006.01)
*C07D 401/12* (2006.01)
*C07D 403/12* (2006.01)
*C07D 413/12* (2006.01)

(52) U.S. Cl. .................... 514/252.02; 514/253.01; 514/253.1; 514/254.04; 544/238; 544/360; 544/364; 544/367

(58) Field of Classification Search ............ 514/252.02, 514/253.01, 253.1, 254.04; 544/238, 360, 544/364, 367
See application file for complete search history.

(56) References Cited

U.S. PATENT DOCUMENTS

| 6,525,059 B1 | 2/2003 | Anantanarayan et al. |
| 2003/0092734 A1 | 5/2003 | Boger |
| 2004/0006091 A1 | 1/2004 | Kyle et al. |
| 2006/0089344 A1 | 4/2006 | Abouabdellah et al. |
| 2006/0173184 A1 | 8/2006 | Apodaca et al. |
| 2007/0004741 A1 | 1/2007 | Apodaca et al. |

FOREIGN PATENT DOCUMENTS

| FR | 2854633 | | 11/2004 |
| HU | 9903870 | * | 5/2000 |
| WO | WO 99/16751 | | 4/1999 |
| WO | WO 99/19303 | | 4/1999 |
| WO | WO 99/32121 | | 7/1999 |
| WO | WO 01/44201 | | 6/2001 |
| WO | WO 02/062963 | | 8/2002 |
| WO | WO 02/087569 | | 11/2002 |
| WO | WO 03/039440 | | 5/2003 |
| WO | WO 03/051797 | | 6/2003 |
| WO | WO 03/065989 | | 8/2003 |
| WO | WO 03/103669 | | 12/2003 |
| WO | WO 2004018439 | * | 3/2004 |
| WO | WO 2005/070910 | | 8/2005 |
| WO | WO 2005/090347 | | 9/2005 |
| WO | WO 2006/088075 | | 8/2006 |

OTHER PUBLICATIONS

Kenneth et al., Synthesis and evaluation of Pyridazinylpiperazines as vanilloid receptor 1 antagonists; Bioorganic & Medicinal Chemistry Letters (2004), 14(22), 5513-5519.*

International Search Report for International Publication No. PCT/JP2005/021136 dated Feb. 14, 2006.

Kathuria et al., "Modulation of anxiety through blockade of anandamide hydrolysis" Nature of Medicine. vol. 9. No. 1 pp. 81 Jan. 2003.

Registry (STN Files) [online], Registry No. 681136-29-8 Registry, Entered STN: May 11, 2001. Chemical Library (Supplier: Maybridge plc) [retrieval date Feb. 1, 2006], internet, <URL: https://stnweb-japan.cas.org/>.

(Continued)

*Primary Examiner*—James O Wilson
*Assistant Examiner*—Ebenezer Sackey
(74) *Attorney, Agent, or Firm*—Hamre, Schumann, Mueller & Larson, P.C.

(57) ABSTRACT

There is provided a FAAH inhibitor and a prophylactic or therapeutic agent for cerebrovascular disorders or sleep disorders comprising it. The prophylactic or therapeutic agent comprises a compound of the formula ($I_0$):

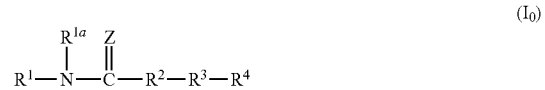

($I_0$)

wherein Z is oxygen or sulfur; $R^1$ is aryl which may be substituted, or a heterocyclic group which may be substituted; $R^{1a}$ is a hydrogen atom, a hydrocarbon group which may be substituted, hydroxyl, etc.; $R^2$ is piperidin-1,4-diyl which may be substituted, or piperazin-1,4-diyl which may be substituted; $R^3$ is a group formed by eliminating two hydrogen atoms from a 5-membered aromatic heterocyclic group having 1 to 3 heteroatoms selected from nitrogen, oxygen and sulfur, which may be further substituted, —CO—, etc.; and $R^4$ is a hydrocarbon group which may be substituted, or a heterocyclic group which may be substituted; or a salt thereof.

15 Claims, 1 Drawing Sheet

OTHER PUBLICATIONS

Registry (STN Files) [online], Registry No. 681136-27-6 Registry, Entered STN: May 11, 2001. Chemical Library (Supplier: Maybridge plc) [retrieval date Feb. 1, 2006], internet, <URL: https://stnweb-japan.cas.org/>.

Registry (STN Files) [online], Registry No. 606088-64-6 Registry, Entered STN: May 11, 2001. Chemical Library (Supplier: Maybridge plc) [retrieval date Feb. 1, 2006], internet, <URL: https://stnweb-japan.cas.org/>.

Registry (STN Files) [online], Registry No. 606088-85-01 Registry, Entered STN: May 11, 2001. Chemical Library (Supplier: Maybridge plc) [retrieval date Feb. 1, 2006], internet, <URL: https://stnweb-japan.cas.org/>.

Database Registry [Online], Chemical Abstracts Service, Columbus, Ohio, US; May 11, 2004, XP002538499, retrieved from STN, Database accession No. 681136-26-5.

* cited by examiner

AMIDE COMPOUND

TECHNICAL FIELD

The present invention relates to a novel cerebro-neuroprotective agent, and in particular to a cerebro-neuroprotective agent which is effective in prevention and treatment of cerebrovascular disorders such as cerebral infarction, cerebral hemorrhage and subarachnoid hemorrhage, or head injury.

BACKGROUND ART

Cerebrovascular disorders are diseases causing an enormous loss in healthcare economy, as they are the $2^{nd}$ and $3^{rd}$ most frequent causes of death in Japan, U.S.A. and Europe as well as the $1^{st}$ most frequent cause of severe sequelae. At present, although active causal treatment is implemented for some patients of cerebral embolism and cerebral thrombosis (e.g., tPA, etc.), the portion of the subject under the benefit is limited to a few percents of the total patients' group, owing to the restriction in therapeutic time window. In most cases, patients are provided only with maintenance therapy for the purpose of preventing cerebral edema and suppressing recurrence and augmentation of the disorder (e.g., antithrombolytic drug), and an effective medicine targeting radical treatment and cerebroprotection is still not available.

It is well recognized that cells of the central nervous system are vulnerable to ischemic stress, and according to basic experiments using a cerebral ischemic model, it is reported that an ischemic state maintained for only a few minutes can cause irreversible impairment and finally death of neuronal cells. It is undeniable that such results have brought about great despair in the clinical field of cerebral stroke. However, in recent years, active research in the realm of neural science has revealed various potential aspects in solving problems such as response to various stresses at the level of individual cells upon ischemic loading, crosstalk between neuronal cells and glial cells, and programmed cell death, and these aspects are highly expected to be linked to the keys to proactive therapeutic strategy. However, although a number of products under development which have various action mechanisms, for example, glutamate antagonist, calcium antagonist, antioxidant and the like have been on trial heretofore, they all failed in the clinical tests. In Japan, Radicut (registered trademark, Mitsubishi Welpharma Kabushiki Kaisha), which is an antioxidant agent, has been approved, but this agent is not yet approved in abroad countries, and a cerebroprotective agent that has been approved worldwide is not available yet.

In association with an improvement in the intensive care system for patients having stroke, brain hypothermia treatment is available as a cerebroprotective therapy, effectiveness of which has been clinically reexamined. The brain hypothermia treatment is based on lowering of the brain temperature (cerebral temperature) to 32 to 35° C. and maintaining at that temperature, and is increasingly getting attention for its remarkable cerebroprotective effect. However, this treatment requires intensive treatment facilities and 24-hour intensive care by a plurality of medical staffs, such that propagation of the treatment as a general therapeutic method is still difficult.

Meanwhile, cannabinoid receptors have been identified since 1990's as receptors for Δ9-tetrahydrocannabinol (Δ9-THC), which is an active substance obtained from the hemp plant. At present, the CB1 receptor (see Nature, Vol. 346, p. 561 (1990)), its splice variant CB1a (see J. Biol. Chem., Vol. 270, p. 3726 (1995)), and the CB2 receptor (see Eur. J. Biochem., Vol. 232, p. 54 (1995)) are known. Almost around the same time, N-arachidonoylethanolamine (anandamide), an endogenous ligand for the CB1 receptor, was discovered from the brain of a pig (see Science, Vol. 258, p. 1946 (1992)). Anandamide belongs to the family of N-acylated ethanolamine, as does N-palmitoylethanolamine or N-oleoylethanolamine. Fatty acid amides including these N-acylated ethanolamines are found to have effect on physiological functions such as pain (see Nature, Vol. 394, p. 277 (1998); and Pain, Vol. 76, p. 189 (1998)), dietary regulation (see Nature, Vol. 414, p. 209 (2001)) and promotion of sleep (see Science, Vol. 268, p. 1506 (1995)). The route for biosynthesis or decomposition of fatty acid amides has been investigated since 1980's. First, a calcium-dependent transacylase produces anandamide, which is N-acylphosphatidylethanolamine, (see J. Neurochem., Vol. 41, p. 1303 (1983)), and then a fatty acid amide is released therefrom by the action of phospholipase D (see J. Neurochem., Vol. 42, p. 1613 (1984)). The existence of an enzymatic activity which hydrolyzes a fatty acid amide into the corresponding fatty acid, thereby eliminating its physiological activity, was suggested earlier but was confirmed only in the later half of 1990's. An active substance hydrolyzing oleamide was isolated from a rat, and its cDNA was cloned (see Nature, Vol. 384, p. 83 (1996)). The enzyme produced by genetic recombination of the cDNA was able to hydrolyze various fatty acid amides including oleamide and anandamide, and was named as fatty acid amide hydrolase (hereinafter, sometimes abbreviated to "FAAH" in the present specification). Still, it is not sufficiently clear about the enzyme responsible for biosynthesis of fatty acid amides. However, the fact that fatty acid amides are produced from neuronal cells in a calcium-dependent, that is, neuronal activity-dependent manner (see Nature, Vol. 372, p. 686 (1994)), is highly meaningful for development of a therapeutic agent. Furthermore, an FAAH knockout mouse has been produced, and an FAAH inhibitory agent has been discovered, so that the physiological significance of FAAH inhibition is being revealed. In the FAAH knockout mouse, the content of fatty acid amides, including anandamide, in the brain increased by 10 to 15 times, but the mobility, body weight and body temperature of the mouse were normal. However, a decrease in the responsiveness to pain was observed, and this was interrelated to the content of fatty acid amides in the brain (see Proc. Natl. Acad. Sci. USA, Vol. 98, p. 9371 (2001)). For the FAAH inhibitor, trifluoromethyl ketone derivatives (see J. Am. Chem. Soc., 118, 5938 (1996)), alpha-keto heterocyclic ring derivatives (see Proc. Natl. Acad. Sci. USA, Vol. 97, p. 5044 (2000)), sulfonylfluoride derivatives (see Biochem. Biophys. Res. Commun., Vol. 231, p. 217 (1997)), fluorophosphonate derivatives (see Biochem. Pharmacol., Vol. 53, p. 255 (1997)), and arylcarbamate derivatives (see Nat. Med., Vol. 9, p. 76 (2003)) are known.

In addition to this, FAAH or anandamide is reported to be involved with various diseases, and it has been reported that large quantities of FAAH are found in the brain of Alzheimer's patients (see The Journal of Neuroscience, Vol. 23, p. 1136 (2003)). It has been also discovered by a test using rats that an increase in the amount of anandamide results in an antiparkinsonian activity (see Neuropsychopharmacology, Vol. 29, p. 1134 (2004)). It has been also reported that women having miscarriage show decreased levels of FAAH (see J. Clin. Endocrinol. Metab., 89, 5168 (2004)). Anandamide is reported to inhibit propagation of rectal cancer (see Gastroenterology, Vol. 125, p. 677 (2003)). It is reported that an FAAH knockout mouse is not susceptible to colonitis or colitis (see J. Clin. Invest., Vol. 113, p. 1202 (2004)). An FAAH inhibiting drug is reported to exhibit an antidepressant and anxiolytic activity (see Nature Medicine, Vol. 9, p. 76 (2003)). FAAH is reported to be an enzyme hydrolyzing oleylethanolamide, which is a satiety factor present in the small intestine (see Nature, Vol. 414, p. 209 (2001)). FAAH is a hydrolytic enzyme for stearoylethanolamide, and it is reported that administration of stearoylethanolamide to a mouse suppresses eating (see FASEB Journal, Vol. 18, p. 1580 (2004)). Since anandamide is an agonist of the vanilloid receptor, which is a nociceptor, the FAAH inhibitory agent is expected to have the same activity as that of the vanilloid receptor agonist (for example, prophylactic and/or therapeutic activity for frequent urination, urinary incontinence, interstitial cystitis) (see JP 2002-202204 A).

As such, FAAH is reported to be involved with various diseases, but there has been no report to the present, demonstrating the cerebro-neuroprotective effect of FAAH.

Since FAAH is an enzyme which hydrolyzes an endogenous sleep substance, oleamide, a FAAH inhibitory agent suppresses the decomposition of oleamide to induce sleep (US 2003/0092734 A).

DISCLOSURE OF THE INVENTION

Problem to be Solved by the Invention

Currently, the treatment of cerebrovascular disorders in most cases need to be carried out only after obtaining a confirmatory diagnosis such as a diagnosis using X-ray, CT or MRI imaging, and thus the therapeutic time window is limited thereby. Accordingly, establishment of a novel prophylactic and/or therapeutic means for cerebrovascular disorders, which is not selective on the disease type and does not require confirmatory diagnosis, is highly demanded.

A main object of the present invention is to provide a highly safe prophylactic or therapeutic agent for cerebrovascular disorders.

Means for Solving the Problem

The present inventors have found, in the course of investigating a variety of drugs for their cerebroprotective effect using a rat cerebral ischemic model so as to achieve the above-described object, that an FAAH inhibitory agent markedly reduced infarct volumes of cerebral ischemic rats, and thus found that a fatty acid amide hydrolase inhibitory agent is effective for prevention and treatment of neural disorders, in particular, of cerebrovascular disorders such as cerebral infarction, cerebral hemorrhage and subarachnoid hemorrhage, or head injury. Furthermore, the present inventors have found that a compound represented by the following formula ($I_0$'), and a compound represented by the formula (I') which is included in the scope thereof, or a salt thereof (hereinafter, sometimes, referred to as Compound ($I_0$') and Compound (I'), respectively) has an FAAH inhibitory activity and is useful as a cerebro-neuroprotective agent, and further that Compound ($I_0$') is useful as a prophylactic or therapeutic agent for sleep disorders, thus completing the invention. In addition, among the family of Compounds ($I_0$') and (I'), compounds represented by the formula ($I_0$) and (I) or salts thereof (hereinafter, sometimes, referred to as Compounds ($I_0$) and (I)) are novel compounds. In the present specification, sometimes, Compound ($I_0$), Compound ($I_0$'), Compound (I) and Compound (I') are collectively referred to as the compound of the present invention.

Thus, the present invention provides:

(1) A compound represented by the formula ($I_0$):

wherein Z is oxygen or sulfur; $R^1$ is aryl which may be substituted, or a heterocyclic group which may be substituted; $R^{1a}$ is a hydrogen atom, a hydrocarbon group which may be substituted, hydroxyl, alkoxy which may be substituted, aryloxy which may be substituted, amino which may be substituted, or 5- to 7-membered saturated cycloamino which may be substituted; $R^2$ is piperidin-1,4-diyl which may be substituted, or piperazin-1,4-diyl which may be substituted; $R^3$ is a group formed by eliminating two hydrogen atoms from a 5-membered aromatic heterocyclic group having 1 to 3 heteroatoms selected from nitrogen, oxygen and sulfur, which may be further substituted, —CO—, —CO—O— or —CO—NH—; and $R^4$ is a hydrocarbon group which may be substituted, or a heterocyclic group which may be substituted, provided that when $R^3$ is —CO—, —CO—O— or —CO—NH—, $R^1$ is benzisoxazolyl; (provided that N-(4-fluorophenyl)-4-[5-(4-fluorophenyl)-4-pyridin-4-yl-1H-pyrazol-3-yl]piperidine-1-carboxamide, N-phenyl-4-{4-[3-(trifluoromethyl)phenyl]-1H-imidazol-2-yl}piperazine-1-carboxamide and 4-[4-(4-methylphenyl)-5-(2-{[2-(trifluoromethyl)pyrimidin-4-yl]methyl}pyrimidin-5-yl)-1H-imidazol-1-yl]-N-[3-(trifluoromethyl)phenyl] piperidine-1-carboxamide are excluded), or a salt thereof;

(2) A compound represented by the formula (I):

wherein $R^1$ is aryl which may be substituted, or a heterocyclic group which may be substituted; $R^{1a}$ is a hydrogen atom, a hydrocarbon group which may be substituted, hydroxyl, alkoxy which may be substituted, aryloxy which may be substituted, amino which may be substituted, or 5- to 7-membered saturated cycloamino which may be substituted; $R^2$ is piperidin-1,4-diyl which may be substituted, or piperazin-1,4-diyl which may be substituted; $R^3$ is a group formed by eliminating two hydrogen atoms from a 5-membered aromatic heterocyclic group having 1 to 3 heteroatoms selected from nitrogen, oxygen and sulfur, which may be further substituted, —CO—, —CO—O— or —CO—NH—; and $R^4$ is a hydrocarbon group which may be substituted, or a heterocyclic group which may be substituted, provided that when $R^3$ is —CO—, —CO—O— or —CO—NH—, $R^1$ is benzisoxazolyl; (provided that N-(4-fluorophenyl)-4-[5-(4-fluorophenyl)-4-pyridin-4-yl-1H-pyrazol-3-yl]piperidine-1-carboxamide, N-phenyl-4-{4-[3-(trifluoromethyl)phenyl]-1H-imidazol-2-yl}piperazine-1-carboxamide and 4-[4-(4-methylphenyl)-5-(2-{[2-(trifluoromethyl)pyrimidin-4-yl]methyl}pyrimidin-5-yl)-1H-imidazol-1-yl]-N-[3-(trifluoromethyl)phenyl]piperidine-1-carboxamide are excluded), or a salt thereof;

(3) The compound according to the above (1), wherein the moiety represented by the formula:

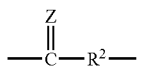

is that represented by the formula:

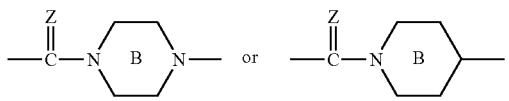

wherein the ring B is piperidine or piperazine which may be substituted with one or more substituents;

(4) The compound according to the above (1), wherein $R^2$ is piperazin-1,4-diyl;

(5) The compound according to the above (1), wherein $R^3$ is a group formed by eliminating two hydrogen atoms from a 5-membered aromatic heterocyclic group having 1 to 3 heteroatoms selected from nitrogen, oxygen and sulfur, which may be further substituted;

(6) The compound according to the above (1), wherein $R^4$ is optionally substituted phenyl, or an optionally substituted 5- or 6-membered heterocyclic group having 1 to 4 heteroatoms selected from nitrogen, oxygen and sulfur in addition to carbon atoms;

(7) The compound according to the above (1), wherein $R^3$ is a group formed by eliminating 2 hydrogen atoms from thiazole or thiadiazole, and $R^4$ is optionally substituted phenyl, or an optionally substituted 5- or 6-membered heterocyclic group having 1 to 4 heteroatoms selected from nitrogen, oxygen and sulfur in addition to carbon atoms;

(8) The compound according to the above (1), which is:
N-1,2-Benzisoxazol-3-yl-4-(3-phenyl-1,2,4-thiadiazol-5-yl) piperazine-1-carboxamide,
4-(3-Phenyl-1,2,4-thiadiazol-5-yl)-N-pyridin-3-ylpiperazine-1-carboxamide hydrochloride,
4-(4-Phenyl-1,3-thiazol-2-yl)-N-pyridin-3-ylpiperazine-1-carboxamide,
4-(3-Phenyl-1,2,4-thiadiazol-5-yl)-N-pyridazin-3-ylpiperazine-1-carboxamide,
4-(4-Phenyl-1,3-thiazol-2-yl)-N-pyrazin-2-ylpiperazine-1-carboxamide,
N-(3,4-Dimethylisoxazol-5-yl)-4-[4-(4-fluorophenyl)-1,3-thiazol-2-yl]piperidine-1-carboxamide,
N-(3,4-Dimethylisoxazol-5-yl)-4-(4-phenyl-1,3-thiazol-2-yl)piperidine-1-carboxamide,
4-[4-(3-Fluorophenyl)-1,3-thiazol-2-yl]-N-pyridazin-3-ylpiperazine-1-carboxamide,
4-[4-(3-Fluorophenyl)-1,3-thiazol-2-yl]-N-pyrazin-2-ylpiperazine-1-carboxamide,
4-[4-(2,4-Difluorophenyl)-1,3-thiazol-2-yl]-N-(3,4-dimethylisoxazol-5-yl)piperazine-1-carboxamide,
4-[4-(2,3-Difluorophenyl)-1,3-thiazol-2-yl]-N-pyridin-3-ylpiperazine-1-carboxamide,
4-[4-(2-Fluorophenyl)-1,3-thiazol-2-yl]-N-(1-methyl-1H-pyrazol-5-yl)piperazine-1-carboxamide,
4-[4-(2,3-Difluorophenyl)-1,3-thiazol-2-yl]-N-pyridazin-3-ylpiperazine-1-carboxamide,
4-[4-(3-Methylphenyl)-1,3-thiazol-2-yl]-N-pyridin-3-ylpiperazine-1-carboxamide,
4-[4-(3-Chlorophenyl)-1,3-thiazol-2-yl]-N-(3,4-dimethylisoxazol-5-yl)piperazine-1-carboxamide,
N-(3,4-Dimethylisoxazol-5-yl) 4-[4-(3-methoxyphenyl)-1,3-thiazol-2-yl]piperazine-1-carboxamide,
N-(3,4-Dimethylisoxazol-5-yl)-4-{4-[3-(trifluoromethyl)phenyl]-1,3-thiazol-2-yl}piperazine-1-carboxamide,
N-(3,4-Dimethylisoxazol-5-yl)-4-[4-(3-methylphenyl)-1,3-thiazol-2-yl]piperazine-1-carboxamide,
4-[4-(2,3-Dichlorophenyl)-1,3-thiazol-2-yl]-N-pyridin-3-ylpiperazine-1-carboxamide, or
4-[4-(2,3-Dichlorophenyl)-1,3-thiazol-2-yl]-N-(3,4-dimethylisoxazol-5-yl)piperazine-1-carboxamide;

(9) A prodrug of the compound according to the above (1);

(10) A medicine comprising the compound according to the above (1) or the prodrug according to the above (9);

(11) A fatty acid amide hydrolase inhibitor comprising the compound according to the above (1) or the prodrug according to the above (9);

(12) Use of the compound according to the above (1) or the prodrug according to the above (9) for the manufacture of a fatty acid amide hydrolase inhibitor;

(13) A method of inhibition of fatty acid amide hydrolase in a mammal, which comprises administering an effective amount of the compound according to the above (1) or the prodrug according to the above (9) to the mammal in need thereof;

(14) A cerebro-neuroprotective agent comprising the compound according to the above (1) or the prodrug according to the above (9);

(15) Use of the compound according to the above (1) or the prodrug according to the above (9) for the manufacture of a cerebro-neuroprotective agent;

(16) A method of protection of brain cells and/or neuronal cells in a mammal, which comprises administering an effective amount of the compound according to the above (1) or the prodrug according to the above (9) to the mammal in need thereof;

(17) A prophylactic or therapeutic agent for cerebrovascular disorders, head injury or spinal cord damage comprising the compound according to the above (1) or the prodrug according to the above (9);

(18) Use of the compound according to the above (1) or the prodrug according to the above (9) for the manufacture of a prophylactic or therapeutic agent for cerebrovascular disorders, head injury or spinal cord damage;

(19) A method of prevention or treatment of cerebrovascular disorders, head injury or spinal cord damage in a mammal, which comprises administering an effective amount of the compound according to the above (1) or the prodrug according to the above (9) to the mammal in need thereof;

(20) A prophylactic or therapeutic agent for nausea, sicchasia or vomiting caused by anticancer agent; cancer- or infection-associated apocleisis or cachectic anorexia; convulsion, pain, tremor, nystagmus or enuresis due to multiple sclerosis; neuropathic pain; chronic pain; Huntington's chorea; Tourette's syndrome; dyskinesia; locomotor disorder; asthma; glaucoma; allergy; inflammation; epilepsy; autoimmune diseases; diarrhea; obesity; sleep disorder; depression; anxiety; mental diseases; Crohn's disease; Alzheimer's disease; interstitial cystitis; AIDS; colonitis; colitis; colon cancer; rectal cancer; hypertriglyceridemia; hyperlipidemia; diabetes mellitus; arteriosclerosis; or Parkinson's disease; or a contraceptive, which comprises the compound according to the above (1) or the prodrug according to the above (9);

(21) Use of the compound according to the above (1) or the prodrug according to the above (9) for the manufacture of a prophylactic or therapeutic agent for nausea, sicchasia or vomiting caused by anticancer agent; cancer- or infection-associated apocleisis or cachectic anorexia; convulsion, pain, tremor, nystagmus or enuresis due to multiple sclerosis; neuropathic pain; chronic pain; Huntington's chorea; Tourette's syndrome; dyskinesia; locomotor disorder; asthma; glaucoma; allergy; inflammation; epilepsy; autoimmune diseases; diarrhea; obesity; sleep disorder; depression; anxiety; mental diseases; Crohn's disease; Alzheimer's disease; interstitial cystitis; AIDS; colonitis; colitis; colon cancer; rectal cancer; hypertriglyceridemia; hyperlipidemia; diabetes mellitus; arteriosclerosis; or Parkinson's disease; or a contraceptive;

(22) A method of prevention or treatment for nausea, sicchasia or vomiting caused by anticancer agent; cancer- or infection-associated apocleisis or cachectic anorexia; convulsion, pain, tremor, nystagmus or enuresis due to multiple sclerosis; neuropathic pain; chronic pain; Huntington's chorea; Tourette's syndrome; dyskinesia; locomotor disorder; asthma; glaucoma; allergy; inflammation; epilepsy; autoimmune diseases; diarrhea; obesity; sleep disorder; depression; anxiety; mental diseases; Crohn's disease; Alzheimer's disease; interstitial cystitis; AIDS; colonitis; colitis; colon cancer; rectal cancer; hypertriglyceridemia; hyperlipidemia; diabetes mellitus; arteriosclerosis; or Parkinson's disease; or of contraception in a mammal, which comprises administering an effective amount of the compound according to the above (1) or the prodrug according to the above (9) to the mammal in need thereof;

(23) A cerebro-neuroprotective agent comprising a compound having a fatty acid amide hydrolase inhibitory activity;

(24) Use of a compound having a fatty acid amide hydrolase inhibitory activity for the manufacture of a cerebro-neuroprotective agent;

(25) A method of protection of brain cells and/or neuronal cells in a mammal, which comprises administering an effective amount of a compound having a fatty acid amide hydrolase inhibitory activity to the mammal in need thereof;

(26) A cerebro-neuroprotective agent comprising a piperazine compound having a fatty acid amide hydrolase inhibitory activity;

(27) A prophylactic or therapeutic agent for cerebrovascular disorders, head injury or spinal cord damage comprising a compound having a fatty acid amide hydrolase inhibitory activity;

(28) The cerebro-neuroprotective agent according to the above (14), wherein the compound having a fatty acid amide hydrolase inhibitory activity is a compound represented by formula (I'):

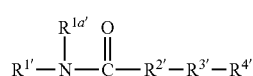

(I')

wherein $R^{1'}$ is aryl which may be substituted, or a heterocyclic group which may be substituted; $R^{1a'}$ is a hydrogen atom, a hydrocarbon group which may be substituted, hydroxyl, alkoxy which may be substituted, aryloxy which may be substituted, amino which may be substituted, or 5- to 7-membered saturated cycloamino which may be substituted; $R^{2'}$ is piperidin-1,4-diyl which may be substituted, or piperazin-1,4-diyl which may be substituted; $R^{3'}$ is a group formed by eliminating two hydrogen atoms from a 5-membered aromatic heterocyclic group having 1 to 3 heteroatoms selected from nitrogen, oxygen and sulfur, which may be further substituted, —CO—, —CO—O— or —CO—NH—; and $R^{4'}$ is a hydrocarbon group which may be substituted, or a heterocyclic group which may be substituted; or a salt thereof or a prodrug thereof;

(29) A method for measuring a fatty acid amide hydrolase activity or a fatty acid amide hydrolase inhibitory activity, which comprises adsorbing a fatty acid amide onto a resin having a polar group;

(30) A kit for measuring a fatty acid amide hydrolase activity or a fatty acid amide hydrolase inhibitory activity, which comprises a resin having a polar group;

(31) A prophylactic or therapeutic agent for sleep disorders, which comprises a compound represented by formula $(I_0')$:

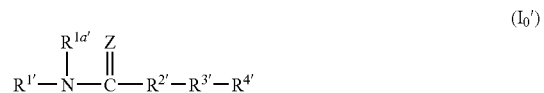

$(I_0')$ wherein Z is oxygen or sulfur; $R^{1'}$ is aryl which may be substituted, or a heterocyclic group which may be substituted; $R^{1a'}$ is a hydrogen atom, a hydrocarbon group which may be substituted, hydroxyl, alkoxy which may be substituted, aryloxy which may be substituted, amino which may be substituted, or 5- to 7-membered saturated cycloamino which may be substituted; $R^{2'}$ is piperidin-1,4-diyl which may be substituted, or piperazin-1,4-diyl which may be substituted; $R^{3'}$ is a group formed by eliminating two hydrogen atoms from a 5-membered aromatic heterocyclic group having 1 to 3 heteroatoms selected from nitrogen, oxygen and sulfur, which may be further substituted, —CO—, —CO—O— or —CO—NH—; and $R^{4'}$ is a hydrocarbon group which may be substituted, or a heterocyclic group which may be substituted; or a salt thereof or a prodrug thereof;

(32) Use of the compound represented by the formula $(I_0')$ in the above (31), or a salt or a prodrug thereof in the manufacture of a prophylactic or therapeutic agent for sleep disorders;

(33) A method of prevention or treatment of sleep disorders in a mammal, which comprises administering an effective amount of the compound represented by the formula $(I_0')$ in the above (31), or a salt or a prodrug thereof to the mammal in need thereof;

(34) A process for producing a compound represented by the formula:

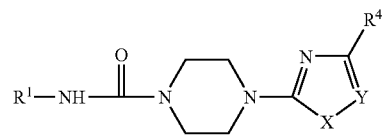

wherein $R^1$ is aryl which may be substituted, or a heterocyclic group which may be substituted; $R^4$ is a hydrocarbon group which may be substituted, or a heterocyclic group which may be substituted; X is an oxygen atom or a sulfur atom; and Y is a nitrogen atom or a carbon atom, or a salt thereof, which comprises subjecting a compound represented by the formula:

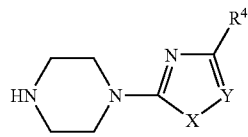

wherein each symbol is as defined above, or a salt thereof to a ureidation reaction; and the like.

Effect of the Invention

The compound of the present invention has a protective effect for brain cells and neuronal cells, and in particular, a protective effect for brain cells and neuronal cells on the occasion of cerebrovascular disorders or head injury. Accordingly, the compound of the present invention is useful in prevention and/or treatment of diseases for which protection of brain cells and neuronal cells from cell damage is effective in prevention and/or treatment thereof, preferably prevention and/or treatment of cerebrovascular disorders or head injury. In addition, the compound of the present invention has an excellent FAAH inhibitory activity and is useful in prevention and/or treatment of sleep disorders.

BEST MODE FOR CARRYING OUT THE INVENTION

Figure 1:
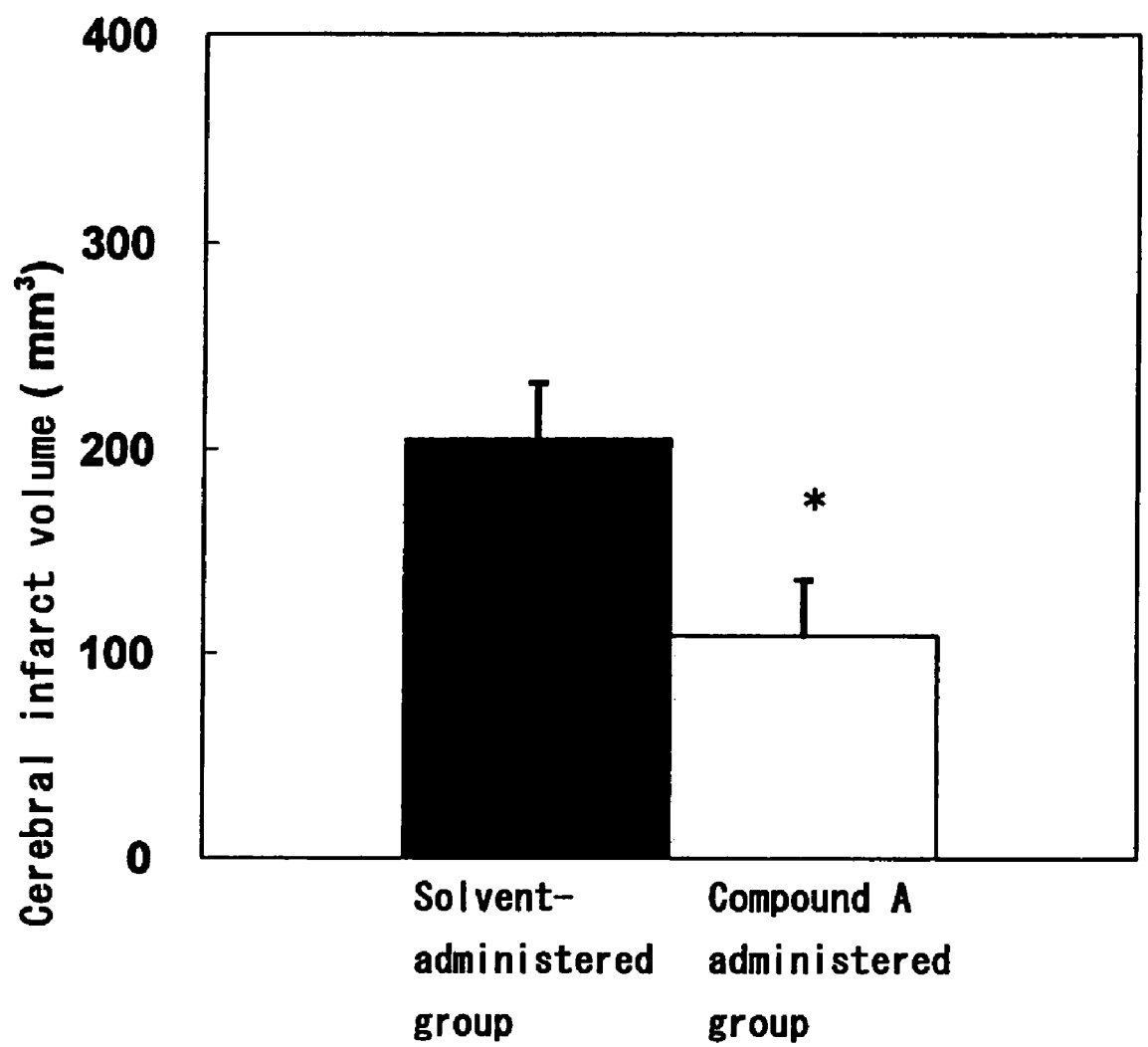
FIG. 1 is a graph illustrating the effect of administration of Compound A on the cerebral infarct volume in a rat cerebral ischemic model. The graph shows cerebral infarct volumes after 2 days in rats administered with Compound A immediately after ischemic reperfusion and after 2, 4 and 6 hours, respectively. In the graph, * indicates that p<0.05 by Student's t-test with respect to the solvent-administered group.

The present invention relates to a cerebro-neuroprotective agent comprising a compound having fatty acid amide hydrolase inhibitory activity. Herein, the "compound having fatty acid amide hydrolase inhibitory activity" is defined as a substance capable of directly or indirectly lowering fatty acid amide hydrolase activity. Also, the phrase "protection of brain cells and neuronal cells" means the action of inhibiting (or at least delaying) brain cells and/or neuronal cells that are subject to or may possibly be subject to cell damage, from undergoing cell death, the causes for cell damage not being particularly limited. The fatty acid amide hydrolase refers to herein an enzyme hydrolyzing a fatty acid amide (for example, N-acylated ethanolamine such as anandamide) into the corresponding fatty acid.

In the above-described formulas $(I_0)$, $(I_0')$, $(I)$ and $(I')$, $R^1$ and $R^{1'}$ each represent aryl which may be substituted, or heterocyclic which may be substituted; $R^{1a}$ and $R^{1a'}$ each represent a hydrogen atom, a hydrocarbon group which may be substituted, hydroxyl, alkoxy which may be substituted, aryloxy which may be substituted, amino which may be substituted, or 5- to 7-membered saturated cycloamino which may be substituted; $R^2$ and $R^{2'}$ each represent piperidin-1,4-diyl which may be substituted, or piperazin-1,4-diyl which may be substituted; $R^3$ and $R^{3'}$ each represent a group formed by eliminating two hydrogen atoms from a 5-membered aromatic heterocyclic group having 1 to 3 heteroatoms selected from nitrogen, oxygen and sulfur, which may be further substituted, —CO—, —CO—O— or —CO—NH—; and $R^4$ and $R^{4'}$ each represent a hydrocarbon group which may be substituted, or a heterocyclic group which may be substituted.

The "aryl" represented by $R^1$ or $R^{1'}$ may be exemplified by $C_{6-10}$ aryl such as phenyl, 1-naphthyl or 2-naphthyl, or the like.

The "aryl" may have 1 to 5, and preferably 1 to 3, substituents on possible positions. Herein, when the number of substituents is 2 or more, the substituents may be the same or different from each other. Examples of such substituent include a halogen atom (e.g., fluorine, chlorine, bromine, iodine, etc.), a nitro group, a cyano group, a hydroxyl group, a lower alkyl group which may be halogenated, hydroxylated or oxolated (e.g., a $C_{1-6}$ alkyl group which may be halogenated such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, or 6,6,6-trifluorohexyl, etc., a $C_{1-6}$ alkyl group which may be hydroxylated such as hydroxymethyl, hydroxyethyl, etc., a $C_{1-6}$ alkyl group which may be oxolated such as 2-oxopropyl, 2-oxobutyl, etc.), a lower alkoxy group (e.g., a $C_{1-6}$ alkoxy group such as methoxy, ethoxy, propoxy, isopropoxy, butoxy, isobutoxy, pentyloxy, hexyloxy, etc.) which may be halogenated, an amino group, a mono-lower alkylamino group (e.g., a mono-$C_{1-6}$ alkylamino group such as methylamino, ethylamino, etc.), a di-lower alkylamino group (e.g., a di-$C_{1-6}$ alkylamino group such as dimethylamino, diethylamino, etc.), a lower alkyl-lower alkyl carbonylamino group (e.g., N-methylacetyl, etc.), a carboxyl group, a lower alkylcarbonyl group (e.g., a $C_{1-6}$ alkylcarbonyl group such as acetyl, propionyl, etc.), a lower alkoxycarbonyl group (e.g., a $C_{1-6}$ alkoxycarbonyl group such as methoxycarbonyl, ethoxycarbonyl, propoxycarbonyl, butoxycarbonyl, etc.), a carbamoyl group, a thiocarbamoyl group, a mono-lower alkylcarbamoyl group (e.g., a mono-$C_{1-6}$ alkylcarbamoyl group such as methylcarbamoyl, ethylcarbamoyl, etc.), a di-lower alkylcarbamoyl group (e.g., a di-$C_{1-6}$ alkylcarbamoyl group such as dimethylcarbamoyl, diethylcarbamoyl, etc.), an arylcarbamoyl group (e.g., a $C_{6-10}$ arylcarbamoyl group such as phenylcarbamoyl, naphthylcarbamoyl, etc.), an aryl group (e.g., a $C_{6-10}$ aryl group such as phenyl, naphthyl, etc.), an aryloxy group (e.g., a $C_{6-10}$ aryloxy group such as phenyloxy, naphthyloxy, etc.), a lower alkylcarbonylamino group which may be halogenated (e.g., a $C_{1-6}$ alkylcarbonylamino group which may be halogenated, such as acetylamino, trifluoroacetylamino, etc.), a 5- or 6-membered heterocyclic group (e.g., imidazolyl, etc.), and the like.

Examples of the "heterocyclic" represented by $R^1$ or $R^{1'}$ include a 5- to 14-membered (preferably, 5- to 10-membered) (monocyclic to tricyclic, preferably monocyclic or bicyclic) heterocyclic group containing 1 to 4 (preferably, 1 to 3) heteroatoms of one or two species selected from nitrogen, oxygen and sulfur atoms in addition to carbon atoms. Examples thereof include a 5-membered cyclic group containing 1 to 4 heteroatoms selected from oxygen, sulfur and nitrogen atoms in addition to carbon atoms such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,3,4-thiadiazol-2-yl, 1,2,4-thiadiazol-5-yl, 1,2,3-triazolyl, 1,2,4-triazolyl or 1H- or 2H-tetrazolyl; a 6-membered cyclic group containing 1 to 4 heteroatoms selected from oxygen, sulfur and nitrogen atoms in addition to carbon atoms such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxadinyl, 1,4-thiadinyl, 1,3-thiadinyl, piperazinyl, triazinyl, 3- or 4-pyridazinyl, pyrazinyl or N-oxido-3- or 4-pyridazinyl; a bicyclic or tricyclic fused-ring group containing 1 to 4 heteroatoms selected from oxygen, sulfur and nitrogen atoms in addition to carbon atoms (preferably, a group formed by condensing the above-mentioned 5- to 6-membered ring with one or two 5- to 6-membered cyclic groups which may contain 1 to 4 heteroatoms selected from oxygen, sulfur and nitrogen atoms in addition to carbon atoms) such as indolyl, benzofuryl, benzothiazolyl, benzisoxazolyl, benzoxazolyl, benzimidazolyl, indazolyl, isoxazolopyridyl, benzothienyl, 1,1-benzothienyl, benzoxazinyl, benzotriazolyl, benzodioxolyl, quinolyl, isoquinolyl, phthalazinyl, quinazolinyl, quinoxalinyl, indolizinyl, quinolizinyl, 1,8-naphthylidinyl, dibenzofuranyl, carbazolyl, acridinyl, phenanthridinyl, chromanyl, phenothiazinyl, phenoxazinyl, dihydroindolyl, 2-oxo-2,3-dihydroindolyl, dihydrobenzofuryl, imidazopyridinyl, imidazopyridazinyl, etc.; and the like. Among these, a bicyclic heterocyclic group in which a 5- to 7-membered (preferably, 5- or 6-membered) heterocyclic ring containing 1 to 3 heteroatoms selected from oxygen, sulfur and nitrogen atoms in addition to carbon atoms is condensed with a benzene ring is preferred.

The "heterocyclic group" may have 1 to 5, preferably 1 to 3 substituents on substitutable positions. Herein, when the number of substituents is two or more, the substituents may be the same or different from each other. Examples of such substituent include a halogen atom (e.g., fluorine, chlorine, bromine, iodine, etc.), a lower alkyl group which may be halogenated, hydroxylated or oxolated (e.g., a $C_{1-6}$ alkyl group such as methyl, ethyl, propyl, isopropyl, butyl, isobutyl, sec-butyl, tert-butyl, pentyl, hexyl, etc., a $C_{1-6}$ alkyl group which may be hydroxylated such as hydroxymethyl, hydroxyethyl, etc., a $C_{1-6}$ alkyl group which may be oxolated such as 2-oxopropyl, 2-oxobutyl, etc.), a cycloalkyl group (e.g., a $C_{3-6}$ cycloalkyl group such as cyclopropyl, cyclobutyl, cyclopentyl, cyclohexyl, etc.), a lower alkynyl group (e.g., a $C_{2-6}$ alkynyl group such as ethynyl, 1-propynyl, propargyl, etc.), a lower alkenyl group (e.g., a $C_{2-6}$ alkenyl group such as vinyl, allyl, isopropenyl, butenyl, isobutenyl, etc.), an aralkyl group (e.g., a $C_{7-11}$ aralkyl group such as benzyl, α-methylbenzyl, phenethyl, etc.), an aryl group (e.g., a $C_{6-10}$ aryl group such as phenyl or naphthyl, etc., and preferably a phenyl group, etc.), a lower alkoxy group (e.g., a $C_{1-6}$ alkoxy group such as methoxy, ethoxy, propoxy, isopropoxy, butoxy, isobutoxy, sec-butoxy, tert-butoxy, etc.), an aryloxy group (e.g., a $C_{6-10}$ aryloxy group such as phenoxy, etc.), a lower alkanoyl group (e.g., formyl; a $C_{1-6}$ alkyl-carbonyl group such as acetyl, propionyl, butyryl, isobutyryl, etc.), an arylcarbonyl group (e.g., a $C_{6-10}$ aryl-carbonyl group such as benzoyl or naphthoyl, etc.), a lower alkanoyloxy group (e.g., formyloxy; a $C_{1-6}$ alkyl-carbonyloxy group such as acetyloxy, propionyloxy, butyryloxy, isobutyryloxy, etc.), an arylcarbonyloxy group (e.g., a $C_{6-10}$ aryl-carbonyloxy group such as benzoyloxy, naphthoyloxy, etc.), a carboxyl group, a lower alkoxy-carbonyl group (e.g., a $C_{1-6}$ alkoxy-carbonyl group such as methoxycarbonyl, ethoxycarbonyl, propoxycarbonyl, isopropoxycarbonyl, butoxycarbonyl, isobutoxycarbonyl, tert-butoxycarbonyl, etc.), an aralkyloxycarbonyl group (e.g., a $C_{7-11}$ aralkyloxycarbonyl group such as benzyloxycarbonyl, etc.), a carbamoyl group, a mono-, di- or tri-halogeno-lower alkyl group (e.g., a mono-, di- or tri-halogeno-$C_{1-4}$ alkyl group such as chloromethyl, dichloromethyl, trifluoromethyl, 2,2,2-trifluoroethyl, etc.), an oxo group, an amidino group, an imino group, an amino group, a mono-lower alkylamino group (e.g., a mono-$C_{1-4}$ alkylamino group such as methylamino, ethylamino, propylamino, isopropylamino, butylamino, etc.), a di-lower alkylamino group (e.g., a di-$C_{1-4}$ alkylamino group such as dimethylamino, diethylamino, dipropylamino, diisopropylamino, dibutylamino, methylethylamino, etc.), a lower alkyl-lower alkylcarbonylamino group (e.g., N-methylacetyl, etc.) a lower alkylcarbonylamino group which may be halogenated (e.g., acetylamino, trifluoroacetylamino, etc.) a 3- to 6-membered cycloamino group which may contain 1 to 3 heteroatoms selected from oxygen, sulfur and nitrogen atoms in addition to carbon atoms and one nitrogen atom (e.g., a 3- to 6-membered cycloamino group such as aziridinyl, azetidinyl, pyrrolidinyl, pyrrolinyl, pyrrolyl, imidazolyl, pyrazolyl, imidazolidinyl, piperidyl, morpholinyl, dihydropyridyl, pyridyl, N-methylpiperazinyl or N-ethylpiperazinyl, etc.), an alkylenedioxy group (e.g., a $C_{1-3}$ alkylenedioxy group such as methylenedioxy or ethylenedioxy, etc.), a hydroxyl group, a nitro group, a cyano group, a mercapto group, a sulfo group, a sulfino group, a phosphono group, a sulfamoyl group, a monoalkylsulfamoyl group (e.g., mono-$C_{1-6}$ alkylsulfamoyl group such as N-methylsulfamoyl, N-ethylsulfamoyl, N-propylsulfamoyl, N-isopropylsulfamoyl, N-butylsulfamoyl, etc.), a dialkylsulfamoyl group (e.g., a di-$C_{1-6}$ alkylsulfamoyl group such as N,N-dimethylsulfamoyl, N,N-diethylsulfamoyl, N,N-dipropylsulfamoyl, N,N-dibutylsulfamoyl, etc.), an alkylthio group (e.g., a $C_{1-6}$ alkylthio group such as methylthio, ethylthio, propylthio, isopropylthio, butylthio, sec-butylthio, tert-butylthio, etc.), an arylthio group (e.g., a $C_{6-10}$ arylthio group such as phenylthio, naphthylthio, etc.), a lower alkylsulfinyl group (e.g., a $C_{1-6}$ alkylsulfinyl group such as methylsulfinyl, ethylsulfinyl, propylsulfinyl, butylsulfinyl, etc.), an arylsulfinyl group (e.g., a $C_{6-10}$ arylsulfinyl group such as phenylsulfinyl, naphthylsulfinyl, etc.), a lower alkylsulfonyl group (e.g., a $C_{1-6}$ alkylsulfonyl group such as methylsulfonyl, ethylsulfonyl, propylsulfonyl, butylsulfonyl, etc.), an arylsulfonyl group (e.g., a $C_{6-10}$ arylsulfonyl group such as phenylsulfonyl, naphthylsulfonyl, etc.) and the like.

Examples of the "hydrocarbon group" represented by $R^{1a}$ and $R^{1a'}$ include an aliphatic hydrocarbon group, a monocyclic saturated hydrocarbon group and an aromatic hydrocarbon group, which have preferably 1 to 16 carbon atoms. Specific examples thereof include an alkyl group, an alkenyl group, an alkynyl group, a cycloalkyl group and an aryl group.

The "alkyl group" is preferably, for example, a lower alkyl group, and examples thereof include a $C_{1-6}$ alkyl group such as methyl, ethyl, propyl, isopropyl, butyl, isobutyl, sec-butyl and tert-butyl, pentyl, hexyl, and the like.

The "alkenyl group" is preferably, for example, a lower alkenyl group, and examples thereof include a $C_{2-6}$ alkenyl group such as vinyl, 1-propenyl, allyl, isopropenyl, butenyl, isobutenyl, and the like.

The "alkynyl group" is preferably, for example, a lower alkynyl group, and examples thereof include a $C_{2-6}$ alkynyl group such as ethynyl, propargyl, 1-propynyl, and the like.

The "cycloalkyl group" is preferably, for example, a lower cycloalkyl group, and examples thereof include a $C_{3-6}$ cycloalkyl group such as cyclopropyl, cyclobutyl, cyclopentyl, cyclohexyl, and the like.

The "aryl group" is preferably, for example, a $C_{6-14}$ aryl group such as phenyl, 1-naphthyl, 2-naphthyl, biphenylyl, 2-anthryl, or the like, and for example, a phenyl group is used.

The "hydrocarbon group" may have 1 to 5, preferably 1 to 3 substituents on possible positions. Herein, when the number of substituents is 2 or more, the substituents may be the same or different from each other. Examples of such substituent include a halogen atom (e.g., fluorine, chlorine, bromine, iodine, etc.), a nitro group, a cyano group, a hydroxyl group, a lower alkyl group which may be halogenated (e.g., a $C_{1-6}$ alkyl group which may be halogenated such as methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, or 6,6,6-trifluorohexyl, etc.), a lower alkoxy group (e.g., a $C_{1-6}$ alkoxy group such as methoxy, ethoxy, propoxy, isopropoxy, butoxy, isobutoxy, pentyloxy, hexyloxy, etc.), an amino group, a mono-lower alkylamino group (e.g., a mono-$C_{1-6}$ alkylamino group such as methylamino, ethylamino, etc.), a di-lower alkylamino group (e.g., a di-$C_{1-6}$ alkylamino group such as dimethylamino, diethylamino, etc.), a carboxyl group, a lower alkylcarbonyl group (e.g., a $C_{1-6}$ alkyl-carbonyl group such as acetyl, propionyl, etc.), a lower alkoxycarbonyl group (e.g., a $C_{1-6}$ alkoxy-carbonyl group such as methoxycarbonyl, ethoxycarbonyl, propoxycarbonyl, butoxycarbonyl, etc.), a carbamoyl group, a thiocarbamoyl group, a mono-lower alkylcarbamoyl group (e.g., a mono-$C_{1-6}$ alkyl-carbamoyl group such as methylcarbamoyl, ethylcarbamoyl, etc.), a di-lower alkylcarbamoyl group (e.g., a di-$C_{1-6}$ alkyl-carbamoyl group such as dimethylcarbamoyl, diethylcarbamoyl, etc.), an arylcarbamoyl group (e.g., a $C_{6-10}$ aryl-carbamoyl group such as phenylcarbamoyl, naphthylcarbamoyl, etc.), an aryl group (e.g., a $C_{6-10}$ aryl group such as phenyl, naphthyl, etc.), an aryloxy group (e.g., a $C_{6-10}$ aryloxy group such as phenyloxy, naphthyloxy, etc.), a lower alkylcarbonylamino group which may be halogenated (e.g., a $C_{1-6}$ alkyl-carbonylamino group which may be halogenated, such as acetylamino, trifluoroacetylamino, etc.), an oxo group and the like.

Examples of the "alkoxy" of the "alkoxy which may be substituted" represented by $R^{1a}$ and $R^{1a'}$ include $C_{1-6}$ alkoxy such as methoxy, ethoxy, propoxy, isopropoxy, butoxy, isobutoxy, sec-butoxy or tert-butoxy, and examples of the substituent which may be carried by the "alkoxy" include the same substituents as those which may be carried by the "hydrocarbon group" of the above-described "hydrocarbon group which may be substituted".

Examples of the "aryloxy" for "$C_{6-14}$ aryloxy which may be substituted" represented by $R^{1a}$ and $R^{1a'}$ include $C_{6-14}$ aryloxy such as phenyloxy or naphthyloxy, and examples of the substituent which may be carried by the "aryloxy" include the same substituents as those which may be carried by the "aryl" of the above-described "aryl which may be substituted" represented by $R^1$.

Examples of the "amino which may be substituted" represented by $R^{1a}$ and $R^{1a'}$ include amino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, etc.), di-$C_{6-14}$ arylamino (e.g., diphenylamino, etc.) or acylamino.

Examples of the acylamino include $C_{1-6}$ alkyl-carbonylamino such as acetylamino, propionylamino, butyrylamino or isobutyrylamino.

Examples of the "5- to 7-membered saturated cycloamino" of the "5- to 7-membered saturated cycloamino which may be substituted" represented by $R^{1a}$ and $R^{1a'}$ include a 5- to 7-membered cycloamino group which may contain 1 to 3 heteroatoms selected from oxygen, sulfur and nitrogen atoms in addition to carbon atoms and one nitrogen atom. Specific examples thereof include a 5- to 7-membered cycloamino group such as pyrrolidinyl, pyrazolidinyl, imidazolidinyl, thiazolidinyl, oxazolidinyl, piperidyl, morpholinyl, thiomorpholinyl, piperazinyl or azepinyl.

Examples of the substituent which may be carried by the "5- to 7-membered saturated cycloamino" include the same substituents as those which may be carried by the "hydrocarbon group" of the above-described "hydrocarbon group which may be substituted."

Examples of the substituent which may be carried by the "piperidin-1,4-diyl which may be substituted" or "piperazin-1,4-diyl which may be substituted" as represented by $R^2$ or $R^{2'}$ include the same substituents as those which may be carried by the "aryl" of the above-described "aryl which may be substituted" as represented by $R^1$. In addition, when $R^2$ or $R^{2'}$ is "piperidin-1,4-diyl which may be substituted", its direction may be in any direction, as indicated in the following formula:

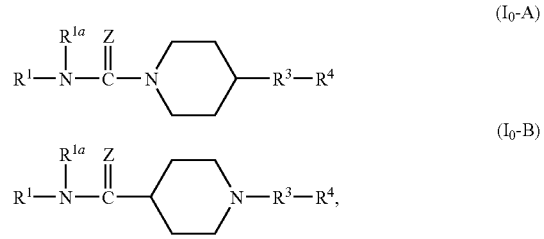

and in particular, the direction as indicated in the formula ($I_0$-A) is more preferred.

That is, the moiety represented by the formula:
—C(=Z)—$R^2$— is preferably a moiety represented by the formula:

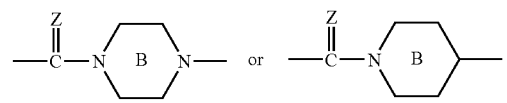

wherein the ring B is piperidine or piperazine which may be substituted with one or more substituents selected from the group consisting of optionally halogenated or oxolated $C_{1-6}$ alkyl, optionally halogenated or oxolated $C_{1-6}$ alkoxy, optionally halogenated or oxolated $C_{1-6}$ acylamino, N—($C_{1-6}$ alkyl) $C_{1-6}$ acylamino, optionally halogenated or oxolated $C_{1-6}$ acyl, $C_{1-6}$ alkylamino, di$C_{1-6}$ alkylamino, optionally halogenated or oxolated $C_{1-6}$ alkenyl, optionally halogenated or oxolated $C_{1-6}$ alkynyl, $C_{1-6}$ alkyloxycarbonyl, carbamoyl, carboxy, optionally halogenated or oxolated $C_{1-6}$ alkylsulfonylamido, optionally halogenated or oxolated $C_{1-6}$ alkylthio, optionally halogenated or oxolated $C_{1-6}$ alkylsulfinyl, amino, hydroxy, halogen, nitrile, 2-oxopyrrolydin-1-yl and 2-oxopropyl.

Examples of the "group formed by eliminating two hydrogen atoms from a 5-membered aromatic heterocyclic group having 1 to 3 heteroatoms selected from nitrogen, oxygen and sulfur" of the above-described "group formed by eliminating two hydrogen atoms from a 5-membered aromatic heterocyclic group having 1 to 3 heteroatoms selected by nitrogen, oxygen and sulfur, which may be further substituted" as represented by $R^3$ or $R^{3'}$ include a group formed by eliminating two hydrogen atoms from a 5-membered aromatic heterocyclic such as thiophene, furan, pyrrole, oxazole, isoxazole, thiazole, isothiazole, imidazole, pyrazole, 1,2,3-oxadiazole, 1,2,4-oxadiazole, 1,2,5-oxadiazole, 1,3,4-oxadiazole, 1,2,3- thiadiazole, 1,2,4-thiadiazole, 1,2,5-thiadiazole, 1,3,4-thiadiazole, 1,2,3-triazole or 1,2,4-triazole. Specifically, thiophen-2,5-diyl, thiophen-2,4-diyl, thiophen-2,3-diyl, furan-2,5-diyl, furan-2,4-diyl, furan-2,3-diyl, pyrrol-2,5-diyl, pyrrol-2,4-diyl, pyrrol-2,3-diyl, pyrrol-3,4-diyl, oxazol-2,5-diyl, oxazol-2,4-diyl, oxazol-4,5-diyl, isoxazol-3,5-diyl, isoxazol-4,5-diyl, isoxazol-3,4-diyl, thiazol-2,5-diyl, thiazol-2,4-diyl, thiazol-4,5-diyl, isothiazol-3,5-diyl, isothiazol-4,5-diyl, isothiazol-3,4-diyl, imidazol-2,5-diyl, imidazol-2,4-diyl, imidazol-4,5-diyl, pyrazol-3,5-diyl, pyrazol-4,5-diyl, pyrazol-3,4-diyl, 1,2,3-oxadiazol-4,5-diyl, 1,2,4-oxadiazol-3,5-diyl, 1,2,5-oxadiazol-3,4-diyl, 1,3,4-oxadiazol-2,5-diyl, 1,2,3-thiadiazol-4,5-diyl, 1,2,4-thiadiazol-3,5-diyl, 1,2,5-thiadiazol-3,4-diyl, 1,3,4-thiadiazol-2,5-diyl, 1,2,3-triazol-4,5-diyl, 1,2,4-triazol-3,5-diyl and the like can be mentioned, and among these, 1,2,4-thiadiazole, 1,3-thiazole, 1,3-oxazole, 1,2,4-oxadiazole and the like are preferably used.

Further, such "group formed by eliminating two hydrogen atoms from a 5-membered aromatic heterocyclic having 1 to 3 heteroatoms selected from nitrogen, oxygen and sulfur" may have substituents on possible positions, and examples of such substituent include a hydrocarbon group, an aryl group, a heterocyclic group, chlorine, fluorine, bromine, iodine, amino, hydroxyl, cyano, alkylthio, alkyloxy, dialkylamino, monoalkylamino, arylamino, acylamino, nitro, mercapto, alkylthio or the like.

As the divalent group represented by $R^3$ or $R^{3'}$, a divalent group represented by the formula:

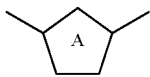

wherein the ring A represents a 5-membered aromatic heterocyclic ring having one to three heteroatoms selected from nitrogen, oxygen and sulfur, which may be substituted is preferred.

Examples of the "hydrocarbon group" of the "hydrocarbon group which may be substituted" as represented by $R^4$ or $R^{4'}$ include the same "hydrocarbon group" of the above-described "hydrocarbon group which may be substituted" as represented by $R^{1a}$ or $R^{1a'}$. Among them, phenyl is preferable. Furthermore, examples of the substituent which may be carried by the "hydrocarbon group" of the "hydrocarbon group which may be substituted" as represented by $R^4$ or $R^{4'}$ include the same substituents as those listed as the substituents which may be carried by the "hydrocarbon group" of the above-described "hydrocarbon group which may be substituted" as represented by $R^{1a}$ or $R^{1a'}$. Such group may have 1 to 5, preferably 1 to 3, of such substituents on possible positions. When the number of substituents is 2 or more, the substituents may be the same or different from each other.

Examples of the "heterocyclic group" of the "heterocyclic group which may be substituted" as represented by $R^4$ or $R^{4'}$ include the same heterocyclic group as the "heterocyclic group" of the above-described "heterocyclic group which may be substituted" as represented by $R^1$. Further, examples of the substituent which may be carried by the "heterocyclic group" of the "heterocyclic group which may be substituted" as represented by $R^4$ or $R^{4'}$ include the same substituents as those listed as the substituents which may be carried by the "heterocyclic group" of the above-described "heterocyclic group which may be substituted" as represented by $R^1$. Among them, an optionally substituted 5- or 6-membered heterocyclic group having 1 to 4 heteroatoms selected from an oxygen atom, a sulfur atom or and a nitrogen atom in addition to carbon atoms is preferable. The "heterocyclic group" of the "heterocyclic group which may be substituted" may have 1 to 5, preferably 1 to 3, of such substituents on possible positions. When the number of substituents is 2 or more, the substituents may be the same or different from each other.

Particularly preferable examples of the compounds represented by the formulas $(I_0)$, $(I_0')$, (I) and (I') include:
N-1,2-Benzisoxazol-3-yl-4-(3-phenyl-1,2,4-thiadiazol-5-yl)piperazine-1-carboxamide,
4-(3-Phenyl-1,2,4-thiadiazol-5-yl)-N-pyridin-3-ylpiperazine-1-carboxamide hydrochloride,
4-(4-Phenyl-1,3-thiazol-2-yl)-N-pyridin-3-ylpiperazine-1-carboxamide,
4-(3-Phenyl-1,2,4-thiadiazol-5-yl)-N-pyridazine-1-carboxamide,
4-(4-Phenyl-1,3-thiazol-2-yl)-N-pyrazin-2-ylpiperazine-1-carboxamide,
N-(3,4-Dimethylisoxazol-5-yl)-4-[4-(4-fluorophenyl)-1,3-thiazol-2-yl]piperidine-1-carboxamide,
N-(3,4-Dimethylisoxazol-5-yl)-4-(4-phenyl-1,3-thiazol-2-yl)piperidine-1-carboxamide,
4-[4-(3-Fluorophenyl)-1,3-thiazol-2-yl]-N-pyridazin-3-ylpiperazine-1-carboxamide,
4-[4-(3-Fluorophenyl)-1,3-thiazol-2-yl]-N-pyrazin-2-ylpiperazine-1-carboxamide,
4-[4-(2,4-Difluorophenyl)-1,3-thiazol-2-yl]-N-(3,4-dimethylisoxazol-5-yl)piperazine-1-carboxamide,
4-[4-(2,3-Difluorophenyl)-1,3-thiazol-2-yl]-N-pyridin-3-ylpiperazine-1-carboxamide,
4-[4-(2-Fluorophenyl)-1,3-thiazol-2-yl]-N-(1-methyl-1H-pyrazol-5-yl)piperazine-1-carboxamide,
4-[4-(2,3-Difluorophenyl)-1,3-thiazol-2-yl]-N-pyridazin-3-ylpiperazine-1-carboxamide,
4-[4-(3-Methylphenyl)-1,3-thiazol-2-yl]-N-pyridin-3-ylpiperazine-1-carboxamide,
4-[4-(3-Chlorophenyl)-1,3-thiazol-2-yl]-N-(3,4-dimethylisoxazol-5-yl)piperazine-1-carboxamide,
N-(3,4-Dimethylisoxazol-5-yl)-4-[4-(3-methoxyphenyl)-1,3-thiazol-2-yl]piperazine-1-carboxamide,
N-(3,4-Dimethylisoxazol-5-yl)-4-{4-[3-(trifluoromethyl)phenyl]-1,3-thiazol-2-yl}piperazine-1-carboxamide,
N-(3,4-Dimethylisoxazol-5-yl)-4-[4-(3-methylphenyl)-1,3-thiazol-2-yl]piperazine-1-carboxamide,
4-[4-(2,3-Dichlorophenyl)-1,3-thiazol-2-yl]-N-pyridin-3-ylpiperazine-1-carboxamide, and
4-[4-(2,3-Dichlorophenyl)-1,3-thiazol-2-yl]-N-(3,4-dimethylisoxazol-5-yl)piperazine-1-carboxamide.

Examples of the salt of the compound represented by the formula $(I_0)$, $(I_0')$, (I) or (I') include metal salts, ammonium salts, salts with organic bases, salts with inorganic acids, salts with organic acids, salts with basic or acidic amino acids, and the like. Suitable examples of the metal salt include alkali metal salts such as sodium salts and potassium salts; alkaline earth metal salts such as calcium salts, magnesium salts and barium salts; aluminum salts; and the like. Suitable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Suitable examples of the salt with inorganic acid include salts with hydrochloric acid, hydrobromic acid, nitric acid, sulfuric acid, phosphoric acid and the like. Suitable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Suitable examples of the salt with basic amino acid include salts with arginine, lysine, ornithine and the like, and suitable examples of the salt with acidic amino acid include salts with aspartic acid, glutamic acid and the like.

Among these, pharmaceutically acceptable salts are preferred. For example, in case the compound has an acidic functional group, inorganic salts such as alkali metal salts (e.g., sodium salts, potassium salts, etc.) and alkaline earth metal salts (e.g., calcium salts, magnesium salts, barium salts, etc.), ammonium salts, and the like may be used, while in case the compound has a basic functional group, salts with inorganic acids such as hydrochloric acid, hydrobromic acid, nitric acid, sulfuric acid and phosphoric acid, and salts with organic acids such as acetic acid, phthalic acid, fumaric acid, oxalic acid, tartaric acid, maleic acid, citric acid, succinic acid, methanesulfonic acid, p-toluenesulfonic acid and the like, may be used.

A prodrug of Compound $(I_0)$, $(I_0')$, (I) or (I') refers to a compound that is converted to Compound $(I_0)$, $(I_0')$, (I) or (I') by a reaction induced by enzyme, gastric acid or the like under the physiological conditions in vivo, that is, a compound that is converted to Compound $(I_0)$, $(I_0')$, (I) or (I') by enzymatic oxidation, reduction, hydrolysis or the like, or a compound that is converted to Compound $(I_0)$, $(I_0')$, (I) or (I') of the present invention by gastric acid-induced hydrolysis.

Examples of the prodrug of Compound $(I_0)$, $(I_0')$, (I) or (I') include a compound in which an amino group of Compound $(I_0)$, $(I_0')$, (I) or (I') is acylated, alkylated or phosphorylated (e.g., a compound in which an amino group of Compound $(I_0)$, $(I_0')$, (I) or (I') of the invention is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated or the like); a compound in which a hydroxyl group of Compound $(I_0)$, $(I_0')$, (I) or (I') is acylated, alkylated, phosphorylated or borated (e.g., a compound in which a hydroxyl group of Compound $(I_0)$, $(I_0')$, (I) or (I') is acetylated, palmitoylated, propanoylated, pivaloylated, succinylated, fumarylated, alanylated, dimethylaminomethylcarbonylated or the like); a compound in which a carboxyl group of Compound $(I_0)$, $(I_0')$, (I) or (I') is esterified or amidated (e.g., a compound in which a carboxyl group of Compound $(I_0)$, $(I_0')$, (I) or (I') is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonyl ethyl esterified, methylamidated or the like); and the like. Such compound can be prepared from Compound $(I_0)$, $(I_0')$, (I) or (I') of the present invention by a method known per se in the art.

In addition, the prodrug of Compound $(I_0)$, $(I_0')$, (I) or (I') may be a compound which is converted to Compound $(I_0)$, $(I_0')$, (I) or (I') of the present invention under the physiological conditions as described in "Pharmaceutical Research and Development", Vol. 7 Drug Design, Hirokawa publishing co., pages 163-198 (1990).

When Compound $(I_0)$, $(I_0')$, (I) or (I') has isomers such as optical isomers, stereoisomers, regioisomers or rotational isomers, Compound $(I_0)$, $(I_0')$, (I) or (I') encompasses such one isomer and a mixtures of isomers. For example, when optical isomers of Compound $(I_0)$, $(I_0')$, (I) or (I') are present, optical isomers obtained by resolution of racemates are also included in Compound $(I_0)$, $(I_0')$, (I) or (I'). Such isomers each can be obtained as a single product by synthetic means or separation means known per se in the art (concentration, solvent extraction, column chromatography, recrystallization, etc.).

Compound $(I_0)$, $(I_0')$, (I) or (I') may be in the form of crystals, and Compound $(I_0)$, $(I_0')$, (I) or (I') encompasses both single crystalline forms and mixed crystalline forms. Crystals can be prepared by crystallization according to crystallization methods known per se in the art.

Compound $(I_0)$, $(I_0')$, (I) or (I') may be either a solvate (e.g., hydrate, etc.) or a non-solvate, and both of them are encompassed in Compound $(I_0)$, $(I_0')$, (I) or (I').

Compound $(I_0)$, $(I_0')$, (I) or (I') also encompasses compounds labeled with isotopes (e.g., $^3H$, $^{14}C$, $^{35}S$, $^{125}I$, etc.).

Hereinafter, a process for preparation of Compound $(I_0)$, $(I_0')$, (I) or (I') will be illustrated. Although Compound $(I_0)$ or (I) wherein $R^2$ is piperazin-1,4-diyl or piperidin-1,4-diyl will be specifically explained herein, other compounds can be also easily prepared according to this process.

[Preparation Process 1]

Compound (I) of the present invention can be prepared, for example, according to Preparation Process 1 represented by the following scheme or a process equivalent thereto:

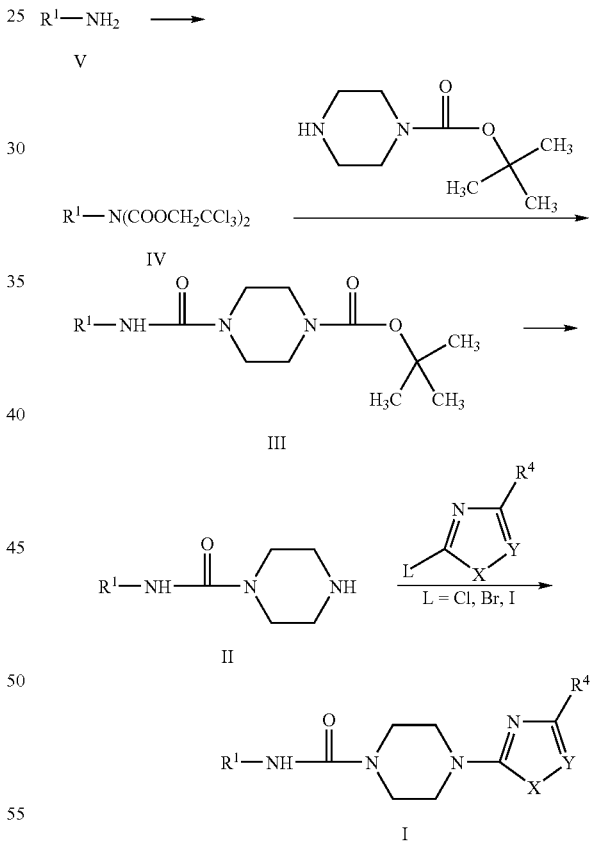

wherein X is an oxygen atom or a sulfur atom; Y is a nitrogen atom or a carbon atom; and the other symbols are as defined above.

According to the scheme, first, Compound (IV) is prepared by subjecting Compound (V) to a reaction of converting to 2,2,2-trichloroethoxycarbamate.

The reaction of converting to 2,2,2-trichloroethoxycarbamate is carried out according to a conventional method in the presence of a base and 2,2,2-trichloroethylchloroformate in a solvent that does not have influence on the reaction. Examples of the base include pyridine, triethylamine, diisopropylethylamine, potassium carbonate, sodium carbonate, sodium hydride, potassium hydride and the like.

The amounts of the base and halide to be used are preferably about 1 to about 5 molar equivalents, respectively, relative to Compound (V).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of such solvent to be used is, for example, 1 to 100 fold-volumes relative to Compound (V).

The reaction temperature is typically from about −50° C. to about 250° C., and preferably from 0° C. to 120° C.

The reaction time is typically from about 0.5 to about 24 hours. Thus obtained Compound (IV) can be isolated and purified by known separation and purification means such as concentration, reduced pressure concentration, solvent extraction, crystallization, recrystallization, phase transfer or chromatography. Compound (IV) may be also used in the subsequent reaction without being isolated.

Next, Compound (III) is prepared by subjecting Compound (IV) to a ureidation reaction.

This reaction is carried out according to a conventional method, in the presence of a base and tert-butyl piperazine-1-carboxylate in a solvent that does not have influence on the reaction. Examples of the base include pyridine, triethylamine, diisopropylethylamine, potassium carbonate, sodium carbonate, sodium hydride, potassium hydride and the like.

Examples of the solvent that does not have influence on the reaction include ethers such as tetrahydrofuran; halogenated hydrocarbons such as chloroform; aromatic hydrocarbons such as toluene; amides such as N,N-dimethylformamide, sulfoxides such as dimethylsulfoxide; and the like. Such solvent may be used as a mixture of two or more kinds at an appropriate ratio. The amount of such solvent to be used is, for example, 1 to 100 fold-volumes relative to Compound (IV).

The reaction temperature is typically from about −50° C. to 200° C.

The reaction time is typically from about 0.5 to about 24 hours.

Thus obtained Compound (III) can be isolated and purified by known separation and purification means such as concentration, reduced pressure concentration, solvent extraction, crystallization, recrystallization, phase transfer or chromatography. Compound (III) may be also used in the subsequent reaction without being isolated.

Next, Compound (II) is prepared by eliminating a tert-butoxycarbonyl group from Compound (III).

This reaction is carried out by reacting an acid in a solvent that does not have adverse influence on the reaction according to a conventional method.

Examples of the acid include hydrochloric acid, hydrobromic acid, sulfuric acid, trifluoroacetic acid, trifluoromethanesulfonic acid and the like. The amount of the acid to be used is preferably from about 1 to about 100 molar equivalents relative to Compound (III).

Examples of the solvent that does not have influence on the reaction include alcohols such as methanol; ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of such solvent to be used is, for example, 1 to 100 fold-volumes relative to Compound (III).

The reaction temperature is typically from about −50° C. to about 250° C., and preferably from 0° C. to 120° C.

The reaction time is typically from about 0.5 to about 24 hours.

Thus obtained Compound (II) can be isolated and purified by known separation and purification means such as concentration, reduced pressure concentration, solvent extraction, crystallization, recrystallization, phase transfer or chromatography.

Next, Compound (I) is prepared by subjecting Compound (II) to a substitution reaction.

The substitution reaction is carried out according to a conventional method in the presence of a base and a halide in a solvent that does not have influence on the reaction. Examples of the base include potassium carbonate, sodium carbonate, sodium hydride, potassium hydride and the like.

The amounts of the base and halide to be used are preferably about 1 to about 5 molar equivalents, respectively, relative to Compound (II).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of such solvent to be used is, for example, 1 to 100 fold-volumes relative to Compound (II).

The reaction temperature is typically from about −50° C. to about 250° C., and preferably from 0° C. to 120° C.

The reaction time is typically from about 0.5 to about 24 hours. Thus obtained Compound (I) can be isolated and purified by known separation and purification means such as concentration, reduced pressure concentration, solvent extraction, crystallization, recrystallization, phase transfer or chromatography.

[Preparation Process 2]

Compound (I) can be prepared, for example, according to Preparation Process 2 represented by the following scheme or a process equivalent thereto:

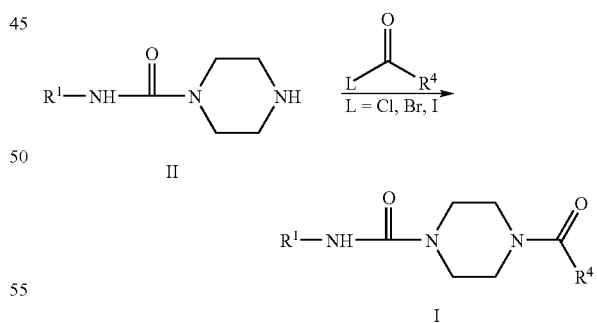

wherein each symbol is as defined above.

Compound (I) is prepared by subjecting Compound (II) to an acylation reaction.

The acylation reaction is carried out according to a conventional method in the presence of a base and an acyl halide in a solvent that does not have influence on the reaction. Examples of the base include triethylamine, tributylamine, diisopropylethylamine, potassium carbonate, sodium carbonate, sodium hydride, potassium hydride and the like.

Examples of the acyl halide include acyl chloride, acyl bromide, acyl iodide and the like.

The amounts of the base and acyl halide to be used are preferably about 1 to about 5 molar equivalents, respectively, relative to Compound (II).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of use of such solvent is, for example, 1 to 100 fold-volumes relative to Compound (II).

The reaction temperature is typically from about −50° C. to about 250° C., and preferably from 0° C. to 120° C.

The reaction time is typically from about 0.5 to about 24 hours. Thus obtained Compound (I) can be isolated and purified by known separation and purification means such as concentration, reduced pressure concentration, solvent extraction, crystallization, recrystallization, phase transfer or chromatography.

[Preparation Process 3]

Compound (I) can be prepared, for example, according to Preparation Process 3 represented by the following scheme or a process equivalent thereto:

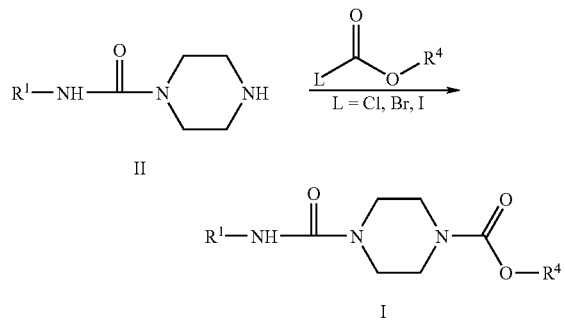

wherein each symbol is as defined above.

Compound (I) is prepared by subjecting Compound (II) to an acylation reaction.

The acylation reaction is carried out according to a conventional method in the presence of a base and an acyl halide, in a solvent that does not have influence on the reaction. Examples of the base include triethylamine, tributylamine, diisopropylethylamine, potassium carbonate, sodium carbonate, sodium hydride, potassium hydride and the like.

Examples of the acyl halide include acyl chloride, acyl bromide, acyl iodide and the like.

The amounts of the base and halide to be used are preferably about 1 to about 5 molar equivalents, respectively, relative to Compound (II).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of use of such solvent is, for example, 1 to 100 fold-volumes relative to Compound (II).

The reaction temperature is typically from about −50° C. to about 250° C., and preferably from 0° C. to 120° C.

The reaction time is typically from about 0.5 to about 24 hours. Thus obtained Compound (I) can be isolated and purified by known separation and purification means such as concentration, reduced pressure concentration, solvent extraction, crystallization, recrystallization, phase transfer or chromatography.

[Preparation Process 4]

Compound (I) can be prepared, for example, according to Preparation Process 4 represented by the following scheme or a process equivalent thereto:

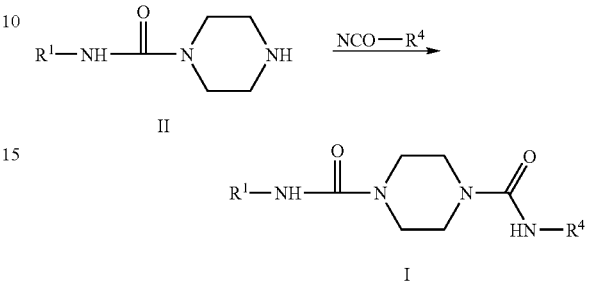

wherein each symbol is as defined above.

Compound (I) is prepared by subjecting Compound (II) to a ureidation reaction.

The ureidation reaction is carried out according to a conventional method in the presence of a base and isocyanate in a solvent that does not have influence on the reaction. Examples of the base include triethylamine, tributylamine, diisopropylethylamine, potassium carbonate, sodium carbonate, sodium hydride, potassium hydride and the like.

Examples of the isocyanate include aryl isocyanate, heteroaryl isocyanate, alkyl isocyanate and the like.

The amounts of the base and isocyanate to be used are preferably about 1 to about 5 molar equivalents, respectively, relative to Compound (II).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of such solvent to be used is, for example, 1 to 100 fold-volumes relative to Compound (II).

The reaction temperature is typically from about −50° C. to about 250° C., and preferably from 0° C. to 120° C.

The reaction time is typically from about 0.5 to about 24 hours. Thus obtained Compound (I) can be isolated and purified by known separation and purification means such as concentration, reduced pressure concentration, solvent extraction, crystallization, recrystallization, phase transfer or chromatography.

[Preparation Process 5]

Compound (I) can be prepared, for example, according to Preparation Process 5 represented by the following scheme or a process equivalent thereto:

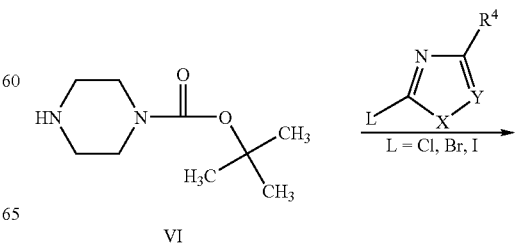

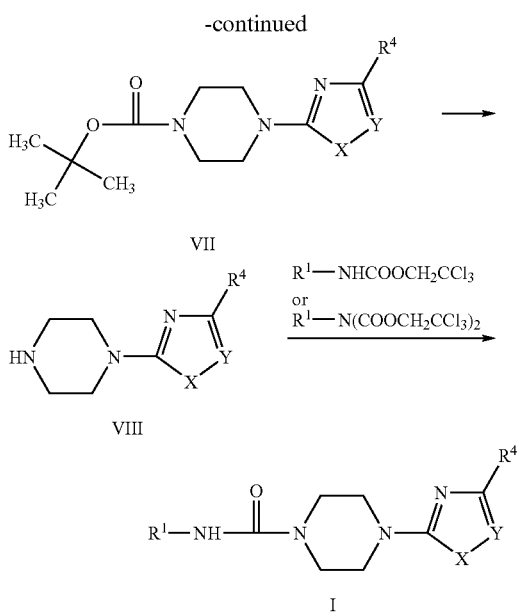

wherein each symbol is as defined above.

According to Preparation Process 5, first, Compound (VII) is prepared by subjecting Compound (VI) to a substitution reaction.

The substitution reaction is carried out according to a conventional method in the presence of a base and a halide in a solvent that does not have influence on the reaction. Examples of the base include potassium carbonate, sodium carbonate, sodium hydride, potassium hydride and the like.

The amounts of the base and halide to be used are preferably about 1 to about 5 molar equivalents, respectively, relative to Compound (VI).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of use of such solvent to be used is, for example, 1 to 100 fold-volumes relative to Compound (VI).

The reaction temperature is typically from about −50° C. to about 250° C., and preferably from 0° C. to 120° C.

The reaction time is typically from about 0.5 to about 36 hours. Thus obtained Compound (VII) can be isolated and purified by known separation and purification means such as concentration, reduced pressure concentration, solvent extraction, crystallization, recrystallization, phase transfer or chromatography. Compound (VII) may be also used in the subsequent reaction without being isolated.

Next, Compound (VIII) is prepared by eliminating a tert-butoxycarbonyl group from Compound (VII).

This reaction is carried out by reacting an acid in a solvent that does not have adverse influence on the reaction according to a conventional method.

Examples of the acid include hydrochloric acid, hydrobromic acid, sulfuric acid, trifluoroacetic acid, trifluoromethanesulfonic acid and the like. The amount of the acid to be used is preferably about 1 to about 100 molar equivalents relative to Compound (VII).

Examples of the solvent that does not have influence on the reaction include alcohols such as methanol; ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of such solvent to be used is, for example, 1 to 100 fold-volumes relative to Compound (VII).

The reaction temperature is typically from about −50° C. to about 250° C., and preferably from 0° C. to 120° C.

The reaction time is typically from about 0.5 to about 24 hours.

Thus obtained Compound (VIII) can be isolated and purified by known separation and purification means such as concentration, reduced pressure concentration, solvent extraction, crystallization, recrystallization, phase transfer or chromatography. Compound (VIII) may be also used in the subsequent reaction without being isolated.

Next, Compound (I) is prepared by subjecting Compound (VIII) to a ureidation reaction.

This reaction is carried out according to a conventional method in the presence of a base and 2,2,2-trichloroethoxycarbamate in a solvent that does not have adverse influence on the reaction. Examples of the base include pyridine, triethylamine, diisopropylethylamine, potassium carbonate, sodium carbonate, sodium hydride, potassium hydride and the like.

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of such solvent to be used is, for example, 1 to 100 fold-volumes relative to Compound (VIII).

The reaction temperature is typically from about −50° C. to about 200° C.

The reaction time is typically from about 0.5 to about 36 hours.

Thus obtained Compound (I) can be isolated and purified by known separation and purification means such as concentration, reduced pressure concentration, solvent extraction, crystallization, recrystallization, phase transfer or chromatography.

[Preparation Process 6]

Compound (I) can be prepared, for example, according to Preparation Process 6 represented by the following scheme or a process equivalent thereto:

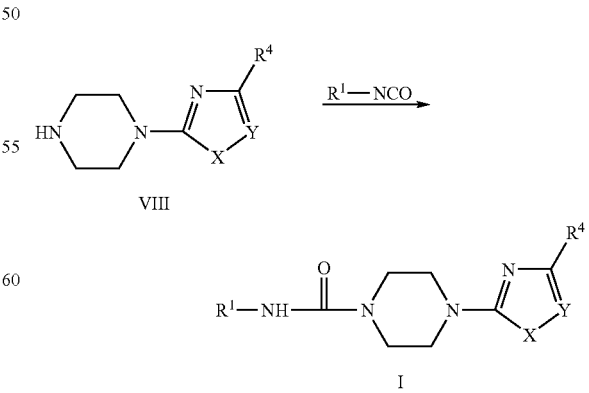

wherein each symbol is as defined above.

Compound (I) is prepared by subjecting Compound (VIII) to a ureidation reaction.

The ureidation reaction is carried out according to a conventional method, in the presence of a base and isocyanate in a solvent that does not have influence on the reaction. Examples of the base include triethylamine, tributylamine, diisopropylethylamine, potassium carbonate, sodium carbonate, sodium hydride, potassium hydride and the like.

The amounts of the base and isocyanate to be used are preferably about 1 to about 5 molar equivalents, respectively, relative to Compound (VIII).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent can be used as a mixture of two or more kinds at an appropriate ratio. The amount of such solvent to be used is, for example, 1 to 100 fold-volumes relative to compound (VIII).

The reaction temperature is typically from about −50° C. to about 250° C., and preferably from 0° C. to 120° C.

The reaction time is typically from about 0.5 to about 24 hours. Thus obtained Compound (I) can be isolated and purified by known separation and purification means such as concentration, reduced pressure concentration, solvent extraction, crystallization, recrystallization, phase transfer or chromatography.

[Preparation Process 7]

Compound (I) can be prepared, for example, according to Preparation Process 7 represented by the following scheme or a process equivalent thereto:

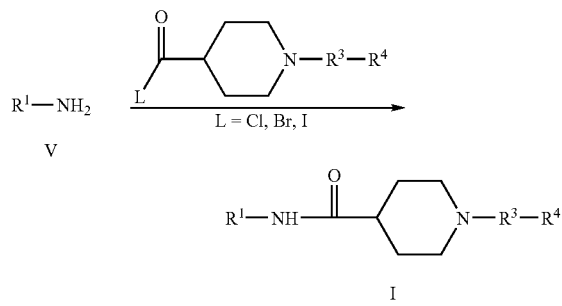

wherein each symbol is as defined above.

Compound (I) is prepared by subjecting Compound (V) to an acylation reaction.

The acylation reaction is carried out according to a conventional method in the presence of a base and an acyl halide in a solvent that does not have influence on the reaction. Examples of the base include triethylamine, tributylamine, diisopropylethylamine, potassium carbonate, sodium carbonate, sodium hydride, potassium hydride and the like.

Examples of the acyl halide include acyl chloride, acyl bromide, acyl iodide and the like.

The amounts of the base and acyl halide to be used are preferably about 1 to about 5 molar equivalents, respectively, relative to Compound (V).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent can be used as a mixture of two or more kinds at an appropriate ratio. The amount of such solvent to be used is, for example, 1 to 100 fold-volumes relative to Compound (II).

The reaction temperature is typically from about −50° C. to about 250° C., and preferably from 0° C. to 120° C.

The reaction time is typically from about 0.5 to about 24 hours. Thus obtained Compound (I) can be isolated and purified by known separation and purification means such as concentration, reduced pressure concentration, solvent extraction, crystallization, recrystallization, phase transfer or chromatography.

[Preparation Process 8]

Compound (I) can be prepared, for example, according to Preparation Process 8 represented by the following scheme or a process equivalent thereto:

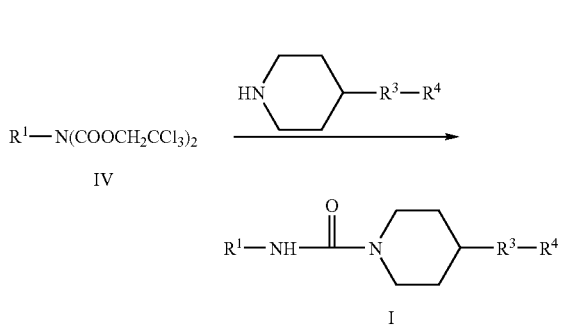

wherein each symbol is as defined above.

Compound (I) is prepared by subjecting Compound (IV) to ureidation.

This reaction is carried out according to a conventional method in the presence of a base and a piperidine derivative in a solvent that does not have influence on the reaction. Examples of the base include pyridine, triethylamine, diisopropylethylamine, potassium carbonate, sodium carbonate, sodium hydride, potassium hydride and the like.

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent can be used as a mixture of two or more kinds at an appropriate ratio. The amount of such solvent to be used is, for example, 1 to 100 fold-volumes relative to Compound (IV).

The reaction temperature is typically from about −50° C. to about 200° C.

The reaction time is typically from about 0.5 to about 24 hours.

Thus obtained Compound (I) can be isolated and purified by known separation and purification means such as concentration, reduced pressure concentration, solvent extraction, crystallization, recrystallization, phase transfer or chromatography.

[Preparation Process 9]

Compound ($I_0$) can be prepared, for example, according to Preparation Process 9 represented by the following scheme or a process equivalent thereto:

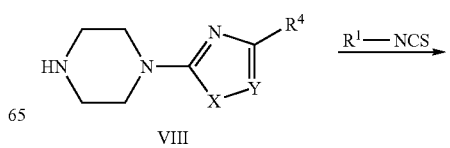

-continued

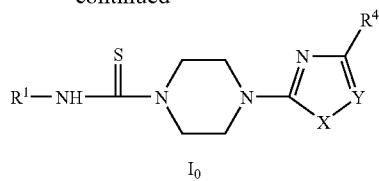

wherein each symbol is as defined above.

Compound ($I_0$) is prepared by subjecting Compound (VIII) to thioureidation.

This thioureidation reaction is carried out according to a conventional method in the presence of a base and isothiocyanate in a solvent that does not have influence on the reaction. Examples of the base include triethylamine, tributylamine, diisopropylethylamine, potassium carbonate., sodium carbonate, sodium hydride, potassium hydride and the like.

The amounts of the base and isothiocyanate are preferably about 1 to about 5 molar equivalents, respectively, relative to Compound (VIII).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent can be used as a mixture of two or more kinds at an appropriate ratio. The amount of such solvent to be used is, for example, 1 to 100 fold-volumes relative to Compound (VIII).

The reaction temperature is typically from about −50° C. to about 50° C., preferably 0° C. to 120° C.

The reaction time is typically from about 0.5 to about 24 hours. Thus obtained Compound ($I_0$) can be isolated and purified by known separation and purification means such as concentration, reduced pressure concentration, solvent extraction, crystallization, recrystallization, phase transfer or chromatography.

[Preparation Process 10]

Compound ($I_0$) can be prepared, for example, according to Preparation Process 10 represented by the following scheme or a process equivalent thereto:

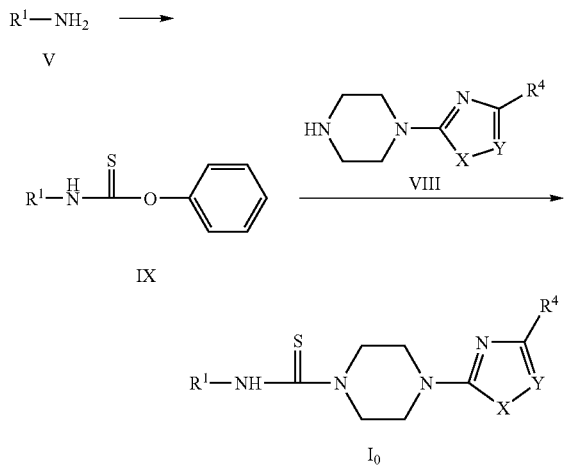

wherein each symbol is as defined above.

According to this scheme, first, Compound (IX) is prepared by subjecting Compound (V) to formation of thiocarbamate.

The thiocarbamate formation is carried out according to a conventional method in the presence of a base and phenyl chlorothiocarbonate in a solvent that does not have influence on the reaction. Examples of the base include pyridine, triethylamine, diisopropylethylamine, potassium carbonate, sodium carbonate, sodium hydride, potassium hydride and the like.

The amounts of the base and phenyl chlorothiocarbonate are preferably about 1 to about 5 molar equivalents, respectively, relative to Compound (V).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent can be used as a mixture of two or more kinds at an appropriate ratio. The amount of such solvent to be used is, for example, 1 to 100 fold-volumes relative to Compound (V).

The reaction temperature is typically from about −50° C. to about 250° C., preferably 0° C. to 120° C.

The reaction time is typically from about 0.5 to about 24 hours.

Thus obtained Compound (IV) can be isolated and purified by known separation and purification means such as concentration, reduced pressure concentration, solvent extraction, crystallization, recrystallization, phase transfer or chromatography. Compound (IX) may be also used in the subsequent reaction without being isolated.

Next, Compound ($I_0$) is prepared by subjecting Compound (IX) to a thioureidation reaction.

This reaction is carried out according to a conventional method in the presence of a base and Compound (VIII) in a solvent that does not have adverse influence on the reaction. Examples of the base include pyridine, triethylamine, diisopropylethylamine, 1,8-diazabicyclo[5.4.0]undecene, potassium carbonate, sodium carbonate, sodium hydride, potassium hydride and the like.

The amounts of the base and Compound (VIII) are preferably about 1 to about 5 molar equivalents, respectively, relative to Compound (IX).

Examples of the solvent that does not have influence on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. Such solvent may be used as a mixture of two or more kinds at an appropriate ratio. The amount of such solvent to be used is, for example, 1 to 100 fold-volumes relative to Compound (IX).

The reaction temperature is typically from about −50° C. to about 200° C.

The reaction time is typically from about 0.5 to about 24 hours.

Thus obtained Compound ($I_0$) can be isolated and purified by known separation and purification means such as concentration, reduced pressure concentration, solvent extraction, crystallization, recrystallization, phase transfer or chromatography.

As described in Examples hereinafter, administration of a compound having FAAH inhibitory activity markedly reduces infarct volume in a cerebral ischemic model, and this implies that a compound having FAAH inhibitory activity has a cerebro-neuroprotective effect, in particular, a cerebro-neuroprotective effect against cerebrovascular disorders, head injury or spinal cord damage. Therefore, the compound having FAAH inhibitory activity is useful in prevention and treatment of diseases for which protection of brain cells and neuronal cells from cell damage is effective, preferably cerebrovascular disorders (e.g., cerebral infarction, cerebral hemorrhage, subarachnoid hemorrhage, etc.), head injury and spinal cord damage. Further, examples of the diseases that are believed to be benefited by the compound of the present invention in prevention and treatment thereof include, but not limited to, diseases similarly caused by disorders of brain cells and neuronal cells, such as brain disorders upon resuscitation after cardiac arrest, decrease in brain function before and after brain surgery, hypoxia, hypoglycemia, brain or spinal cord trauma, drug intoxication, gas poisoning, diabetes mellitus, administration of antitumor agent, nervous system disorders due to alcohol or the like, senile dementia such as Alzheimer's disease, Parkinson's disease, Huntington's chorea, prion disease, amyotrophic lateral sclerosis, spinocerebellar degeneration, anxiety, depression, sleep disorders, eating disorders, obesity, frequent urination, urinary incontinence, interstitial cystitis, Crohn's disease, colonitis, colitis, colon cancer, large intestine cancer, contraception and AIDS. Such compound having FAAH inhibitory activity is particularly preferably a piperazine compound and Compound (I') or a salt or prodrug thereof (hereinafter, referred to as the compound of the present invention in some cases).

Meanwhile, since Compound (I') of the present invention has FAAH inhibitory activity, it is useful, based on the above-described knowledge in the art, as a prophylactic and/or therapeutic agent for nausea, sicchasia or vomiting caused by anticancer agent; cancer- or infection (e.g., AIDS, etc.)-associated apocleisis or cachectic anorexia; convulsion, pain, tremor, nystagmus or enuresis due to multiple sclerosis; neuropathic pain; chronic pain; Huntington's chorea; Tourette's syndrome; dyskinesia; locomotor disorder; asthma; glaucoma; allergy; inflammation; epilepsy; autoimmune diseases; diarrhea; obesity; sleep disorder; depression; anxiety; mental diseases; Crohn's disease; Alzheimer's disease; interstitial cystitis; AIDS; colonitis; colitis; colon cancer; rectal cancer; hypertriglyceridemia; hyperlipidemia; diabetes mellitus; arteriosclerosis; or Parkinson's disease, or as a contraceptive.

Furthermore, since FAAH is an enzyme which hydrolyzes an endogenous sleep substance, oleamide, a FAAH inhibitory agent induces sleep by suppressing the decomposition of oleamide. Therefore, the Compound ($I_0$)' and the like of the present invention is a useful prophylactic and/or therapeutic agent of sleep abnormality such as sleep disorders, for example, intrinsic sleep disorders (e.g., psychophysiological insomnia), extrinsic sleep disorders, circadian rhythm disorders (e.g., time zone change (jet lag) syndrome, shift work sleep disorder, irregular sleep-wake pattern, delayed sleep phase syndrome, advanced sleep phase syndrome, non-24 hour sleep-wake), and the like; parasomunias; and sleep disorders associated with medical or neurological disorders (e.g., chronic obstructive pulmonary disease, Alzheimer's disease, Parkinson's disease, cerebrovascular dementia, schizophrenia, depression, anxiety neurosis).

The FAAH inhibitory activity of a compound can be conveniently and simply measured by a method for measuring fatty acid amide hydrolase activity or fatty acid amide hydrolase inhibitory activity, which has been newly developed by the present inventors. The present inventors have surprisingly found that a resin having a polar group which is generally used in adsorption of proteins or nucleic acids, can also adsorb fatty acid amides of medium- to long-chained fatty acids having 8 or more carbon atoms, thus completing the method of the present invention. This method is characterized by adsorption of a fatty acid amide onto a resin having a polar group.

One of such measurements comprises the following steps:

Step 1: A compound to be tested, FAAH and a fatty acid amide as a substrate are provided.

Step 2: The compound to be tested, FAAH and the substrate are mixed and subjected to an enzymatic reaction.

Step 3: A liquid reaction mixture obtained from Step 2 is brought into contact with a resin having a polar group so that the fatty acid amide is adsorbed onto the resin.

Step 4: The fatty acid amide adsorbed on the resin is quantified.

The FAAH can be obtained by, for example, extraction and purification from natural animal tissues or cells by a known method. It can also be obtained by extraction and purification from cells in which the FAAH gene is introduced and FAAH is expressed according to a known method. This FAAH may be selected according to a particular purpose. For example, the FAAH may be that of mammal origin such as human origin.

As the "fatty acid amide as a substrate", fatty acid amides which can serve as the substrate for FAAH may be appropriately selected, and among those, N-acylated ethanolamine formed from a fatty acid such as medium-chained fatty acid (fatty acid having 8 or more carbon atoms) and long-chained fatty acid (fatty acid having 12 or more carbon atoms), and ethanolamine is preferred, anandamide being particularly preferred. The upper limit of the number of carbon atoms in such a fatty acid is not particularly limited, but the number is preferably not more than 24. Also, such fatty acid may be either saturated or unsaturated, but in particular, fatty acids of polyvalent unsaturated fatty acids are preferred. When N-acylated ethanolamine is hydrolyzed with FAAH, a fatty acid and ethanolamine are produced. For example, in the case of anandamide, arachidonic acid and ethanolamine are produced. It is desirable that such enzymatic reaction is carried out under appropriate conditions, for example, in a reaction buffer at pH 8 to 10 at a temperature of 20° C. to 45° C. for 10 minutes to 1 hour.

In case that the reaction has proceeded, thus obtained liquid reaction mixture contains an unreacted fatty acid amide, a fatty acid and ethanolamine.

Examples of the "resin having a polar group" which is contacted with such liquid reaction mixture include nitrocellulose and polyvinylidene fluoride (PVDF) (e.g., Immobilon). Such resin may be not necessarily a single compound, and mixtures of nitrocellulose and cellulose (e.g., HA-filter, Millipore Corp.) and the like are used suitably.

The form of the "resin having a polar group" is not particularly limited, but a membrane having micropores is particularly preferred.

When the above-described liquid reaction mixture is brought into contact with the "resin having a polar group", the unreacted fatty acid amide and the fatty acid produced by the reaction are adsorbed onto the resin, whereas ethanolamine produced by the reaction is not adsorbed onto the resin. Thus, the two substance groups can be highly separated. Specifically, in the case of a microporous membrane made of a basic resin, the two substance groups can be easily separated by eliminating a liquid containing ethanolamine by pressurization or suction. In this case, a commercially available plate equipped with a plurality of such membranes (e.g., 96-well MultiScreen-HA filter plate, Millipore Corp.) can be used conveniently.

After separating ethanolamine produced by the reaction from the unreacted fatty acid amide and the fatty acid produced by the reaction in this manner, the FAAH inhibitory activity of the substance to be tested can be measured by quantifying the unreacted fatty acid amide and/or ethanolamine.

This quantification can be carried out easily by using, for example, a fatty acid amide labeled with a radioisotope (e.g., ethanolamine 1-$^3$H) or the like as the substrate. That is, for example, in the case that ethanolamine 1-$^3$H is used, because unreacted ethanolamine 1-$^3$H and arachidonic acid are present on the resin, while [$^3$H]-ethanolamine is present in the liquid, the two substance groups may be separated as described above, and then the amount of radiation of at least one of the groups may be measured with a scintillation counter.

Herein, measurement of the FAAH activity according to the above-described method will be easily understood by a person skill in the art.

Further, sleep action can be evaluated by orally administrating a test compound to a rat, measuring the electroencephalogram (EEG) and electromyogram (EMG) from immediately after administration, and analyzing the resulting EEG and EMG for change in sleep-wake time during the measuring period with an EEG analyzing program, Sleep-Sign Ver. 2 (Kissei Comtech).

The compound of the present invention is low in toxicity, and it can be administered as it is or as a pharmaceutical composition in a suitable dosage form obtained by mixing with a pharmacologically acceptable carrier, orally or parenterally (e.g., topical, intravenous drip infusion, rectal, intraarticular administration) to human or other mammals (e.g., rat, rabbit, sheep, pig, cow, cat, dog, monkey, etc.).

Herein, as the pharmacologically acceptable carrier, a variety of organic or inorganic carrier materials that are conventionally used as materials used for preparation can be used, and they are incorporated as excipient, lubricant, binder or disintegrant in solid preparations; and as solvent, solubilizing agent, suspending agent, isotonic agent, buffer, soothing agent or the like in liquid preparations. In addition, preparation additives such as antiseptic, antioxidant, colorant or sweetener can be also used, if necessary.

Examples of the dosage form of the above-described pharmaceutical composition include oral preparations such as tablet, capsule (including soft capsule and microcapsule), granule, powder, syrup, emulsion and suspension; and parenteral preparations such as injectable preparation (e.g., subcutaneous injection, intradermal injection, intravenous injection, intramuscular injection, intraperitoneal injection, intraarticular injection, etc.), external preparation (e.g., transnasal preparation, transdermal preparation, ointment, etc.), suppository (e.g., rectal suppository, vaginal suppository, etc.), pellet, drip infusion, and sustained release preparation (e.g., sustained release microcapsule, etc.). These can be safely administered orally or parenterally.

The pharmaceutical composition can be prepared by a method conventionally used in the art of formulation technology, for example, a method described in the Japanese Pharmacopeia. Hereinafter, specific methods for formulation will be described in detail. The content of Compound ($I_0$') or (I') of the present invention in the pharmaceutical composition may vary depending on the dosage form, amount of the compound administered and the like, but it is, for example, from about 0.1 to 100% by weight.

Specifically, an injectable preparation is prepared by dissolving, suspending or emulsifying the active ingredient in an aqueous solvent (e.g., distilled water, physiologic saline, Ringer's solution, etc.) or an oily solvent (e.g., vegetable oil such as olive oil, sesame oil, cotton seed oil or corn oil, propylene glycol, etc.) together with dispersant (e.g., Polysorbate 80, polyoxyethylene hydrogenated castor oil 60, polyethylene glycol, carboxymethylcellulose, sodium alginate, etc.), preservative (e.g., methylparaben, propylparaben, benzyl alcohol, chlorobutanol, phenol, etc.), isotonic agent (e.g., sodium chloride, glycerin, D-mannitol, D-sorbitol, glucose, etc.), solubilizing agent (e.g., cyclodextrin [e.g., α-, β- or γ-cyclodextrin, 2-hydroxypropyl-β-cyclodextrin or methyl-β-cyclodextrin, etc.]) and the like. At this time, additives such as solubilizing agent (e.g., sodium salicylate, sodium acetate, etc.), stabilizing agent (e.g., human serum albumin, etc.), soothing agent (e.g., benzyl alcohol, etc.) or the like may be used if necessary. The injectable liquid is usually filled in appropriate ampoules.

Furthermore, the above-described composition may contain other active ingredients as long as they do not cause undesirable interaction upon mixing with the compound of the present invention.

Examples of such other active ingredient include thrombolytic agent (e.g., tissue plasminogen activator, urokinase, etc.), anticoagulant (e.g., Argatroban, warfarin, etc.), Factor 10 inhibitor, thromboxane synthetase inhibitor (e.g., ozagrel, etc.), antioxidant (e.g., edaravone, etc.), antiedema agent (e.g., glycerol, mannitol, etc.), neurogenesis and/or neuroregeneration promoting agent (e.g., Akt/PKB activating agent, GSK-3β inhibitor, etc.), acetylcholinesterase inhibitor (e.g., donepezil, rivastigmine, galantamine, zanapezil, etc.), β-amyloid protein production, secretion, accumulation, aggregation and/or deposition inhibitor [β-secretase inhibitor (e.g., compound described in WO 98/38156, compounds described in WO 02/2505, WO 02/2506 and WO 02/2512, OM99-2 (WO 01/00663)), γ-secretase inhibitor, β-amyloid protein aggregation inhibitor (e.g., PTI-00703, ALZHEMED (NC-531), PPI-368 (JP 11-514333 A), PPI-558 (JP 2001-500852 A), SKF-74652 (Biochem. J., 340(1), 283-289 (1999))), β-amyloid vaccine, β-amyloid cleaving enzyme, etc.], brain-activating drug (e.g., aniracetam, nicergolin, etc.), other therapeutic agent for Parkinson's disease [(e.g., dopamine receptor agonist (L-DOPA, bromocriptine, pergolide, talipexol, pramipexol, cabergoline, adamantadine, etc.), monoamine oxidase (MAO) inhibitor (e.g., deprenyl, selgiline (selegiline), remacemide, riluzole, etc.), anticholinergic agent (e.g., trihexyphenidyl, biperiden, etc.)) COMT inhibitor (e.g., entacapone, etc.)], therapeutic agent for amyotrophic lateral sclerosis (e.g., riluzole, etc., neurotrophic factor, etc.), therapeutic agent for hyperlipidemia such as cholesterol-lowering drug [statins (e.g., pravastatin sodium, atorvastatin, simvastatin, lovastatin, etc.), fibrates (e.g., clofibrate, etc.), squalene synthetase inhibitor], therapeutic agent for abnormal behavior, wandering or the like associated with progress of dementia (e.g., sedative, anxiolytic, etc.), apoptosis inhibitor (e.g., CPI-1189, IDN-6556, CEP-1347, etc.), neuronal differentiation and/or regeneration promoting agent (e.g., leteprinim, xaliproden (SR-57746-A), SB-216763, etc.), hypotensor [angiotensin II receptor antagonist (e.g., candesartan cilexetil, losartan, valsartan, etc.), calcium receptor antagonist (e.g., manidipine, nicardipine, amlodipine, etc.)], antidiabetic drug [insulin secretion promoter (e.g., glibenpyramide, glimepiride, nateglinide, etc.), α-glucosidase inhibitor (e.g., voglybose, acarbose, etc.), biguanide drug (e.g., metformin hydrochloride, etc.), thiazolidine derivative (e.g., pioglitazone, rosiglitazone, etc.)], antidepressant [SSRI (e.g., fluoxetine, fluvoxamine, paroxetine, etc.), SNRI (e.g., venlafazine, milnacipran, etc.), tricyclic antidepressant (e.g., imipramine, decipramine, etc.)], anxiolytic [benzodiazepine drug (e.g., etizolam, diazepam, chlordiazepoxide, etc.), non-benzodiazepine drug (e.g., tandospirone, etc.)], non-steroidal anti-inflammatory drug (e.g., meloxicam, tenoxicam, indomethacin, ibuprofen, celecoxib, rofecoxib, aspirin, indomethacin, etc.), disease-modifying antirheumatic drug (DMARDs), anticytokine drug (e.g., TNF inhibitor, MAP kinase inhibitor, etc.), steroid drug (e.g., dexamethasone, hexestrol, cortisone acetate, etc.), sexual hormone or its derivatives (e.g., progesterone, estradiol, estradiol benzoate, etc.), parathyroid hormone (PTH), calcium receptor antagonist and the like.

The above-described other active ingredient and the compound of the present invention or a salt thereof may be used in combination by mixing them according to a method known per se and formulating into one pharmaceutical composition (e.g., tablet, powder, granule, capsule (including soft capsule), liquid, injection, suppository, sustained release preparation, etc.). Alternatively, they may be formulated into separate preparations and administered to a same subject simultaneously or separately at time interval(s).

The medicine of the present invention can be used in combination therapy with other therapeutic methods, without being limited in the type of drug. For example, in case of cerebrovascular disorder, the medicine can be used in combination with hypothermia or brain hypothermia, cerebral thrombectomy, cerebral embolectomy or the like, and in case of neurodegenerative disease such as Alzheimer's disease or Parkinson's disease, the medicine can be used in combination with a therapeutic method such as neural stem cell transplantation, without being limited to the mentioned examples.

Dosage of the compound of the present invention may vary depending on subject of administration, disease to be treated, symptoms, administration route or the like. For example, for treatment and/or prevention of cerebrovascular disorder in an adult, typically about 0.01 to 20 mg/kg of body weight, preferably about 0.1 to 10 mg/kg of body weight, more preferably about 0.1 to 5 mg/kg of body weight of the compound of the present invention as active ingredient is administered conveniently in the form of an injectable preparation about 1 to 5 times daily, and preferably about 1 to 3 times daily. In the case of other parenteral administration and oral administration, dosage equivalent to the above-described amount for injection can be administered. When symptoms are particularly severe, the dosage may be increased in accordance with the symptoms.

Hereinafter, the present invention will be illustrated in more detail with reference to Examples, Reference Examples and Experimental Examples.

Example 1

N-1,2-Benzisoxazol-3-yl-4-(3-phenyl-1,2,4-thiadiazol-5-yl)piperazine-1-carboxamide (1) 1,2-Benzisoxazol-3-amine To a solution of acetohydroxamic acid (10.0 g, 133 mmol) in N,N-dimethylformamide (150 ml) was added potassium tert-butoxide (14.9 g, 133 mmol), and the mixture was stirred at room temperature for 30 minutes. 2-Fluorobenzonitrile (18.0 g, 133 mmol) was added thereto, followed by stirring at room temperature for 5 hours. The reaction mixture was poured to water and extracted with ethyl acetate. The extract was washed with water and dried over anhydrous magnesium sulfate, and the solvent was distilled off under reduced pressure. The residue was recrystallized from hexane to give 4.80 g (27.0%) of the desired product as a solid.
$^1$H-NMR (CDCl$_3$) δ; 4.43 (2H, br s), 7.23-7.28 (1H, m), 7.43 (1H, d, J=9.3 Hz), 7.50-7.56 (2H, m).

(2) Bis(2,2,2-trichloroethyl) 1,2-benzisoxazol-3-ylimidodicarbonate

To a solution of 1,2-benzisoxazol-3-amine (4.00 g, 29.8 mmol) and pyridine (7.25 ml, 89.6 mmol) in tetrahydrofuran (100 ml) was added under ice-cooling, 2,2,2-trichloroethyl chloroformate (8.20 ml, 59.6 mmol), and the mixture was stirred under ice-cooling for 1 hour and at room temperature for 20 minutes. The reaction mixture was poured to water and extracted with ethyl acetate. The extract was washed with water and dried over anhydrous magnesium sulfate, and the solvent was distilled off under reduced pressure. To the residue was added hexane to give 13.3 g (91.7%) of the desired product as a solid.
$^1$H-NMR (CDCl$_3$) δ; 4.82 (4H, s), 7.36-7.44 (1H, m), 7.59-7.65 (3H, m).

(3) tert-Butyl 4-[(1,2-benzisoxazol-3-ylamino)carbonyl]piperazine-1-carboxylate

A solution of bis(2,2,2-trichloroethyl) 1,2-benzisoxazol-3-ylimidodicarbonate (3.00 g, 6.19 mmol), diisopropylethylamine (1.08 ml, 6.19 mmol) and 1-(tert-butoxycarbonyl)piperazine (2.30 g, 12.4 mmol) in dimethyl sulfoxide (20 ml) was stirred at 70° C. for 2 hours. The reaction mixture was poured to water and extracted with ethyl acetate. The extract was washed with water and dried over anhydrous magnesium sulfate, and the solvent was distilled off under reduced pressure. The residue was crystallized from hexane, which was purified by silica gel column chromatography (hexane:ethyl acetate=1:1), and then recrystallized from a mixed solvent of hexane and ethyl acetate to give 710 mg (33.2%) of the desired product.
$^1$H-NMR (CDCl$_3$) δ; 1.50 (9H, s), 3.56-3.66 (8H, m), 7.27-7.32 (1H, m), 7.46-7.58 (2H, m), 8.05 (1H, d, J=8.4 Hz), 8.73 (1H, s).

(4) N-1,2-Benzisoxazol-3-ylpiperazine-1-carboxamide trifluoroacetate

A solution of tert-butyl 4-[(1,2-benzisoxazol-3-ylamino)carbonyl]piperazine-1-carboxylate (16.5 g, 47.6 mmol) in trifluoroacetic acid (200 ml) was stirred at room temperature for 2 hours, and then the solvent was distilled off under reduced pressure. The residue was recrystallized from a mixed solvent of methanol and diethyl ether to give 16.3 g (95.3%) of the desired product.
$^1$H-NMR (DMSO-d$_6$) δ; 3.18-3.22 (4H, m), 3.72-3.75 (4H, m), 7.30-7.35 (1H, m), 7.59-7.67 (2H, m), 7.86 (1H, d, J=8.4 Hz), 8.99 (2H, br s), 10.11 (1H, s).

(5) N-1,2-Benzisoxazol-3-yl-4-(3-phenyl-1,2,4-thiadiazol-5-yl)piperazine-1-carboxamide To a solution of 5-chloro-3-phenyl-1,2,4-thiadiazole (109 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 148 mg (52.3%) of the desired product. mp 234-235° C.
$^1$H-NMR (DMSO-d$_6$) δ; 3.64-3.75 (8H, m), 7.22-7.29 (1H, m), 7.41-7.44 (3H, m), 7.51-7.61 (2H, m), 7.80 (1H, d, J=8.0 Hz), 8.05-8.09 (2H, m), 10.06 (1H, s).

Example 2

N-1,2-Benzisoxazol-3-yl-4-[3-(4-fluorophenyl)-1,2,4-thiadiazol-5-yl]piperazine-1-carboxamide To a solution of 5-chloro-3-(4-fluorophenyl)-1,2,4-thiadiazole (119 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 114 mg (48.5%) of the desired product.
$^1$H-NMR (DMSO-$d_6$) δ; 3.70-3.73 (8H, m), 7.29-7.35 (3H, m), 7.61-7.64 (2H, m), 7.86 (1H, d, J=7.8 Hz), 8.15-8.19 (2H, m), 10.11 (1H, s).

Example 3

N-1,2-Benzisoxazol-3-yl-4-[3-(3-fluorophenyl)-1,2,4-thiadiazol-5-yl]piperazine-1-carboxamide To a solution of 5-chloro-3-(3-fluorophenyl)-1,2,4-thiadiazole (119 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 132 mg (56.2%) of the desired product.
$^1$H-NMR (DMSO-$d_6$) δ; 3.71-3.73 (8H, m), 7.30-7.37 (2H, m), 7.51-7.67 (3H, m), 7.83-7.88 (2H, m), 7.97 (1H, d, J=7.8 Hz), 10.11 (1H, s).

Example 4

N-1,2-Benzisoxazol-3-yl-4-[3-(2-fluorophenyl)-1,2,4-thiadiazol-5-yl]piperazine-1-carboxamide To a solution of 5-chloro-3-(2-fluorophenyl)-1,2,4-thiadiazole (119 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the desired product as a solid was separated by filtration, which was then recrystallized from a mixed solvent of ethyl acetate and tetrahydrofuran. Yield: 96.0 mg (40.9%).
$^1$H-NMR (DMSO-$d_6$) δ; 3.69-3.75 (8H, m), 7.29-7.36 (3H, m), 7.50-7.64 (3H, m), 7.86 (1H, d, J=7.8 Hz), 8.02-8.07 (1H, m), 10.11 (1H, s).

Example 5

N-1,2-Benzisoxazol-3-yl-4-[3-(4-chlorophenyl)-1,2,4-thiadiazol-5-yl]piperazine-1-carboxamide To a solution of 5-chloro-3-(4-chlorophenyl)-1,2,4-thiadiazole (179 mg, 0.555 mmol) and N-1,2-benzisoxazol-3-ylpiperazine-1-carboxamide trifluoroacetate (200 mg, 0.555 mmol) in dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 85.0 mg (34.7%) of the desired product.
$^1$H-NMR (DMSO-$d_6$) δ; 3.70-3.73 (8H, m), 7.30-7.35 (1H, m), 7.56 (2H, d, J=7.2 Hz), 7.62-7.67 (2H, m), 7.86 (1H, d, J=7.8 Hz), 8.13 (2H, d, J=7.2 Hz), 10.11 (1H, s).

Example 6

N-1,2-Benzisoxazol-3-yl-4-[3-(4-methylphenyl)-1,2,4-thiadiazol-5-yl]piperazine-1-carboxamide To a solution of 5-chloro-3-(4-methylphenyl)-1,2,4-thiadiazole (117 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 91.0 mg (39.1%) of the desired product.
$^1$H-NMR (DMSO-$d_6$) δ; 2.36 (3H, s), 3.69-3.79 (8H, m), 7.28-7.34 (3H, m), 7.59-7.67 (2H, m), 7.86 (1H, d, J=8.1 Hz), 8.02 (2H, d, J=8.1 Hz), 10.11 (1H, s).

Example 7

N-1,2-Benzisoxazol-3-yl-4-{3-[4-(trifluoromethyl)phenyl]-1,2,4-thiadiazol-5-yl}piperazine-1-carboxamide To a solution of 5-chloro-3-(4-trifluoromethylphenyl)-1,2,4-thiadiazole (147 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 97.0 mg (36.9%) of the desired product.
$^1$H-NMR (DMSO-$d_6$) δ; 3.72-3.74 (8H, m), 7.30-7.35 (1H, m), 7.59-7.67 (2H, m), 7.86-7.88 (3H, m), 8.33 (2H, d, J=8.1 Hz), 10.12 (1H, s).

Example 8

N-1,2-Benzisoxazol-3-yl-4-[3-(phenoxymethyl)-1,2,4-thiadiazol-5-yl]piperazine-1-carboxamide To a solution of 5-chloro-3-(phenoxymethyl)-1,2,4-thiadiazole (126 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 151 mg (61.7%) of the desired product.
$^1$H-NMR (DMSO-$d_6$) δ; 3.60-3.70 (8H, m), 5.04 (2H, s), 6.92-7.01 (3H, m), 7.25-7.33 (3H, m), 7.57-7.63 (2H, m), 7.84 (1H, d, J=8.1 Hz), 10.07 (1H, s).

Example 9

N-1,2-Benzisoxazol-3-yl-4-(3-isopropyl-1,2,4-thiadiazol-5-yl)piperazine-1-carboxamide To a solution of 5-chloro-3-isopropyl-1,2,4-thiadiazole (90.3 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 42.0 mg (20.3%) of the desired product. mp 178-179° C.

$^1$H-NMR (DMSO-$d_6$) δ; 1.23 (6H, d, J=7.5 Hz), 2.90-2.99 (1H, m), 3.56-3.58 (4H, m), 3.67-3.70 (4H, m), 7.29-7.34 (1H, m), 7.58-7.64 (2H, m), 7.85 (1H, d, J=7.5 Hz), 10.07 (1H, s).

Example 10

N-1,2-Benzisoxazol-3-yl-4-[3-(2-thienyl)-1,2,4-thiadiazol-5-yl]piperazine-1-carboxamide To a solution of 5-chloro-3-(2-thienyl)-1,2,4-thiadiazole (119 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 128 mg (55.9%) of the desired product.

$^1$H-NMR (DMSO-$d_6$) δ; 3.67-3.71 (4H, m), 3.81-3.85 (4H, m), 7.08-7.11 (1H, m), 7.24-7.29 (1H, m), 7.39-7.55 (3H, m), 7.74-7.75 (1H, m), 7.96 (1H, d, J=7.8 Hz), 9.78 (1H, s).

Example 11

N-1,2-Benzisoxazol-3-yl-4-[3-(3-thienyl)-1,2,4-thiadiazol-5-yl]piperazine-1-carboxamide To a solution of 5-chloro-3-(3-thienyl)-1,2,4-thiadiazole (119 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 100 mg (43.7%) of the desired product.

$^1$H-NMR (DMSO-$d_6$) δ; 3.68-3.72 (8H, m), 7.29-7.34 (1H, m), 7.62-7.66 (4H, m), 7.86 (1H, d, J=8.1 Hz), 8.11-8.12 (1H, m), 10.10 (1H, s).

Example 12

N-1,2-Benzisoxazol-3-yl-4-[3-(3-furyl)-1,2,4-thiadiazol-5-yl]piperazine-1-carboxamide To a solution of 5-chloro-3-(3-furyl)-1,2,4-thiadiazole (104 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 44.0 mg (20.0%) of the desired product.

$^1$H-NMR (DMSO-$d_6$) δ; 3.64-3.73 (8H, m), 6.89 (1H, d, J=2.1 Hz), 7.30-7.34 (1H, m), 7.58-7.67 (2H, m), 7.77-7.78 (1H, m), 7.86 (1H, d, J=7.8 Hz), 8.22-8.23 (1H, m), 10.09 (1H, s).

Example 13

N-1,2-Benzisoxazol-3-yl-4-(3-pyridin-4-yl-1,2,4-thiadiazol-5-yl)piperazine-1-carboxamide To a solution of 4-(5-chloro-1,2,4-thiadiazol-3-yl)pyridine (104 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 50.0 mg (22.1%) of the desired product.

$^1$H-NMR (DMSO-$d_6$) δ; 3.72-3.74 (8H, m), 7.32 (1H, t, J=6.9 Hz), 7.59-7.67 (2H, m), 7.86 (1H, d, J=7.8 Hz), 8.01 (2H, d, J=5.4 Hz), 8.72 (2H, d, J=5.4 Hz), 10.11 (1H, s).

Example 14

N-1,2-Benzisoxazol-3-yl-4-(3-pyridin-3-yl-1,2,4-thiadiazol-5-yl)piperazine-1-carboxamide To a solution of 3-(5-chloro-1,2,4-thiadiazol-3-yl)pyridine (104 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the desired product as a solid was separated by filtration, which was purified by silica gel column chromatography (ethyl acetate) to give the desired product as a solid. The resulting solid was recrystallized from a mixed solvent of ethyl acetate, tetrahydrofuran and hexane to yield 55.7 mg (24.6%) of the desired product.

$^1$H-NMR (DMSO-$d_6$) δ; 3.72-3.74 (8H, m), 7.30-7.35 (1H, m), 7.51-7.54 (1H, m), 7.61-7.67 (2H, m), 7.85-7.88 (1H, m), 8.43 (1H, d, J=7.5 Hz), 8.67-8.68 (1H, m), 9.27-9.28 (1H, m), 10.11 (1H, s).

Example 15

N-1,2-Benzisoxazol-3-yl-4-(3-pyridin-2-yl-1,2,4-thiadiazol-5-yl)piperazine-1-carboxamide To a solution of 2-(5-chloro-1,2,4-thiadiazol-3-yl)pyridine (104 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 2 hours. The reaction mixture was poured to water, and the precipitated solid was separated by filtration, which was recrystallized from a mixed solvent of ethyl acetate and tetrahydrofuran to give 55.7 mg (24.6%) of the desired product. mp 222-223° C.

¹H-NMR (DMSO-d₆) δ; 3.71-3.74 (8H, m), 7.30-7.34 (1H, m), 7.47-7.51 (1H, m), 7.59-7.67 (2H, m), 7.86 (1H, d, J=7.8 Hz), 7.91-7.96 (1H, m), 8.16 (1H, d, J=7.5 Hz), 8.68-8.69 (1H, m), 10.11 (1H, s).

Example 16

N-1,2-Benzisoxazol-3-yl-4-(3-morpholin-4-yl-1,2,4-thiadiazol-5-yl)piperazine-1-carboxamide To a solution of 4-(5-chloro-1,2,4-thiadiazol-3-yl)morpholine (114 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 1 hour. The reaction mixture was poured to water, and the precipitated solid was separated by filtration, which was recrystallized from a mixed solvent of methanol, ethyl acetate and tetrahydrofuran to give 89.4 mg (38.7%) of the desired product.

¹H-NMR (DMSO-d₆) δ; 3.56-3.59 (8H, s), 3.72-3.79 (8H, m), 7.23-7.28 (1H, m), 7.45-7.55 (2H, m), 7.92 (1H, d, J=8.4 Hz), 9.91 (1H, s).

Example 17

N-1,2-Benzisoxazol-3-yl-4-(3-piperidin-1-yl-1,2,4-thiadiazol-5-yl)piperazine-1-carboxamide To a solution of 1-(5-chloro-1,2,4-thiadiazol-3-yl)piperidine (114 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 1 hour. The reaction mixture was poured to water and extracted with ethyl acetate. The extract was washed with water and dried over anhydrous magnesium sulfate. The solvent was distilled off under reduced pressure, and the residue was purified by silica gel column chromatography (hexane: ethyl acetate=1:1) to give the desired product as a solid. The resulting solid was recrystallized from a mixed solvent of ethyl acetate, tetrahydrofuran and hexane to yield 44.0 mg (10.7%) of the desired product. mp 214-215° C.

¹H-NMR (CDCl₃) δ; 1.59-1.62 (6H, m), 3.60-3.63 (8H, s), 3.79-3.82 (4H, m), 7.29-7.34 (1H, m), 7.49-7.60 (2H, m), 8.05 (1H, d, J=8.1 Hz), 8.69 (1H, s).

Example 18

N-1,2-Benzisoxazol-3-yl-4-[3-(4-benzylpiperazin-1-yl)-1,2,4-thiadiazol-5-yl]piperazine-1-carboxamide To a solution of 1-benzyl-4-(5-chloro-1,2,4-thiadiazol-3-yl)piperazine (500 mg, 1.70 mmol) and N-1,2-benzisoxazol-3-ylpiperazine-1-carboxamide trifluoroacetate (612 mg, 1.70 mmol) in N,N-dimethylformamide (5 ml) was added triethylamine (1.18 ml, 8.50 mmol) at room temperature, and the mixture was stirred at room temperature for 0.5 hour. The reaction mixture was poured to water and extracted with ethyl acetate. The extract was washed with water and dried over anhydrous magnesium sulfate. The solvent was distilled off under reduced pressure, and the residue was recrystallized from a mixed solvent of ethyl acetate and hexane to give 347 mg (40.5%) of the desired product.

¹H-NMR (CDCl₃) δ; 2.50-2.53 (4H, m), 3.55 (2H, s), 3.58-3.66 (8H, m), 3.78-3.82 (4H, m), 7.26-7.35 (6H, m), 7.48-7.57 (2H, m), 8.05 (1H, d, J=8.1 Hz), 8.67 (1H, s).

Example 19 tert-Butyl 4-(5-{4-[(1,2-benzisoxazol-3-ylamino)carbonyl]piperazin-1-yl}-1,2,4-thiadiazol-3-yl)piperazine-1-carboxylate To a solution of tert-butyl 4-(5-chloro-1,2,4-thiadiazol-3-yl)piperazine-1-carboxylate (169 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 5 minutes. The reaction mixture was poured to water and the desired product as a solid was separated by filtration, which was recrystallized from a mixed solvent of ethyl acetate and tetrahydrofuran to give 126 mg (44.1%) of the desired product.

¹H-NMR (DMSO-d₆) δ; 1.48 (9H, s), 3.48-3.50 (4H, m), 3.60-3.64 (8H, m), 3.79-3.83 (4H, m), 7.28-7.34 (1H, m), 7.49-7.60 (2H, m), 8.05 (1H, d, J=8.1 Hz), 8.68 (1H, s).

Example 20

N-1,2-Benzisoxazol-3-yl-4-(3-piperazin-1-yl-1,2,4-thiadiazol-5-yl)piperazine-1-carboxamide dihydrochloride To a solution of tert-butyl 4-(5-{4-[(1,2-benzisoxazol-3-ylamino)carbonyl]piperazin-1-yl}-1,2,4-thiadiazol-3-yl)piperazine-1-carboxylate (87.0 mg, 0.169 mmol) in tetrahydrofuran (5 ml) and methanol (3 ml) was added a solution of 4 N hydrogen chloride in ethyl acetate (8 ml), and the mixture was stirred at room temperature for 4 hours. The solvent was distilled off under reduced pressure. The residue was recrystallized from a mixed solvent of methanol and diethyl ether to give 50.0 mg (65.6%) of the desired product.

¹H-NMR (DMSO-d₆) δ; 3.13 (4H, br s), 3.53 (4H, br s), 3.70 (8H, br s), 4.03 (1H, br s), 7.29-7.34 (1H, m), 7.58-7.66 (2H, m), 7.85 (1H, d, J=8.1 Hz), 9.21 (2H, br s), 10.09 (1H, s).

The structural formulae of Compounds obtained in Examples 1 to 20 are shown in Table 1.

TABLE 1

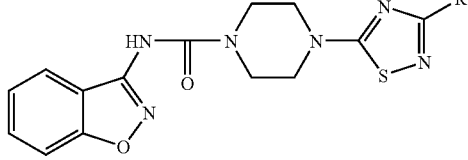

| Example No. | R |
|---|---|
| 1 | 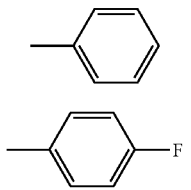 |
| 2 | 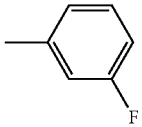 |
| 3 | 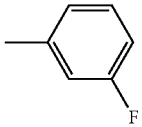 |

TABLE 1-continued

![structure: benzisoxazole-NH-C(O)-N-piperazine-N-thiadiazole-R]

| Example No. | R |
|---|---|
| 4 | 2-fluoro-3-methylphenyl (methyl/F on benzene) |
| 5 | 4-chlorophenyl |
| 6 | 4-methylphenyl |
| 7 | 4-(trifluoromethyl)phenyl |
| 8 | -CH₂-O-phenyl (phenoxymethyl / -OCH₂- linker to phenyl) |
| 9 | isopropyl (CH(CH₃)₂) |
| 10 | 2-thienyl |
| 11 | 3-thienyl |
| 12 | 3-furyl |
| 13 | 4-pyridyl |
| 14 | 3-pyridyl |
| 15 | 2-pyridyl |
| 16 | morpholino |

TABLE 1-continued

![structure: benzisoxazole-NH-C(O)-N-piperazine-N-thiadiazole-R]

| Example No. | R |
|---|---|
| 17 | piperidino |
| 18 | 4-benzylpiperazin-1-yl |
| 19 | 4-(tert-butoxycarbonyl)piperazin-1-yl |
| 20 | piperazin-1-yl |

Example 21

N-1,2-Benzisoxazol-3-yl-4-(4-phenyl-1,3-thiazol-2-yl)piperazine-1-carboxamide

(1) tert-Butyl 4-(4-phenyl-1,3-thiazol-2-yl)piperazine-1-carboxylate

A mixture of 2-chloro-4-phenyl-1,3-thiazole (1.16 g, 5.92 mmol), 1-(tert-butoxycarbonyl)-piperazine (3.30 g, 17.8 mmol), potassium carbonate (817 mg, 5.92 mmol) and N,N-dimethylformamide (20 ml) was stirred at 120° C. for 2 hours, poured to water, which was extracted with ethyl acetate. The extract was washed with water, dried over anhydrous magnesium sulfate, and the solvent was distilled off under reduced pressure. The residue was purified by silica gel column chromatography (hexane:ethyl acetate=7:3) to give the desired product as a solid. The resulting solid was recrystallized from a mixed solvent of hexane and ethyl acetate to yield 1.43 g (70.1%) of the desired product.

$^1$H-NMR (CDCl$_3$) δ; 1.49 (9H, s), 3.51-3.59 (8H, m), 6.79 (1H, s), 7.27-7.39 (3H, m), 7.80-7.83 (2H, m).

(2) 1-(4-Phenyl-1,3-thiazol-2-yl)piperazine dihydrochloride

To a solution of tert-butyl 4-(4-phenyl-1,3-thiazol-2-yl)piperazine-1-carboxylate (1.25 g, 3.62 mmol) in ethyl acetate (20 ml) was added a solution of 4 N hydrogen chloride in ethyl acetate (20 ml), and the mixture was stirred at room temperature for 1 hour. To the reaction mixture was added diethyl ether (30 ml), and the desired product as a solid was separated by filtration, which was washed with diethyl ether to yield 1.06 g (92.2%) of the desired product.

¹H-NMR (DMSO-d₆) δ; 3.24 (4H, br s), 3.72-3.75 (4H, m), 7.30-7.43 (4H, m), 7.87 (2H, d, J=8.1 Hz), 8.50 (1H, br s), 9.57 (2H, br s).

(3) N-1,2-Benzisoxazol-3-yl-4-(4-phenyl-1,3-thiazol-2-yl)piperazine-1-carboxamide A mixture of 1-(4-Phenyl-1,3-thiazol-2-yl)piperazine (330 mg, 0.673 mmol), bis(2,2,2-trichloroethyl) 1,2-benzisoxazol-3-ylimidodicarbonate (326 mg, 0.673 mmol), diisopropylethylamine (0.117 ml, 0.673 mmol) and dimethylsulfoxide (5 ml) was stirred at 70° C. for 2 hours. The reaction mixture was poured to water and extracted with ethyl acetate. The extract was washed with water and dried over anhydrous magnesium sulfate. The solvent was distilled off under reduced pressure. The residue was purified by silica gel column chromatography (hexane: ethyl acetate=1:1) to give the desired product as a solid. The resulting solid was recrystallized from a mixed solvent of tetrahydrofuran, ethyl acetate and hexane to yield 115 mg (42.1%) of the desired product.

¹H-NMR (DMSO-d₆) δ; 3.58-3.60 (4H, m), 3.62-3.72 (4H, m), 7.27-7.43 (5H, m), 7.58-7.66 (2H, m), 7.85-7.89 (3H, m), 10.07 (1H, s).

Example 22

N-1,2-Benzisoxazol-3-yl-4-(3-phenyl-1,2,4-oxadiazol-5-yl)piperazine-1-carboxamide To a solution of 5-chloro-3-phenyl-1,2,4-oxadiazole (99.9 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.389 ml, 2.78 mmol) at room temperature, and the mixture was stirred at room temperature for 5 minutes. The reaction mixture was poured to water, and the desired product as a solid was separated by filtration. The resulting solid was recrystallized from a mixed solvent of ethyl acetate and tetrahydrofuran to give 157 mg (72.4%) of the desired product. mp 215-216° C.

¹H-NMR (DMSO-d₆) δ; 3.72 (8H, s), 7.30-7.35 (1H, m), 7.49-7.67 (5H, m), 7.85-7.94 (3H, m), 10.09 (1H, s).

Example 23

N-1,2-Benzisoxazol-3-yl-4-(4-phenyl-1,3-oxazol-2-yl)piperazine-1-carboxamide

(1) tert-Butyl 4-(4-phenyl-1,3-oxazol-2-yl)piperazine-1-carboxylate

A solution of tert-butyl piperazine-1-carboxylate (1.21 g, 6.51 mmol) and 2-chloro-4-phenyl-1,3-oxazole (390 mg, 2.17 mmol) in xylene (50 ml) was stirred at 155° C. for 12 hours. The solvent was distilled off under reduced pressure. The residue was poured to water, and extracted with ethyl acetate. The extract was washed with water and dried over anhydrous magnesium sulfate. The solvent was distilled off under reduced pressure. The residue was purified by silica gel column chromatography (hexane: ethyl acetate=9:1) to give 260 mg (12.1%) of the desired product as a solid.

¹H-NMR (CDCl₃) δ; 1.49 (9H, s), 3.54 (8H, s), 7.26-7.39 (3H, m), 7.51 (1H, s), 7.67 (2H, d, J=8.7 Hz).

(2) 1-(4-Phenyl-1,3-oxazol-2-yl)piperazine

To a solution of tert-butyl 4-(4-phenyl-1,3-oxazol-2-yl)piperazine-1-carboxylate (590 mg, 1.79 mmol) in tetrahydrofuran (4 ml) and methanol (4 ml) was added a solution of 4 N hydrogen chloride in ethyl acetate (4 ml), and the mixture was stirred at room temperature for 1 hour. The solvent was distilled off under reduced pressure. The residue was poured to an aqueous 1 N sodium hydroxide solution (10 ml) and extracted with chloroform. The extract was washed with water and dried over anhydrous magnesium sulfate. The solvent was distilled off under reduced pressure to give 370 mg (90.0%) of the desired product as an oil.

¹H-NMR (CDCl₃) δ; 2.95-2.98 (4H, m), 3.52-3.55 (4H, m), 7.25-7.27 (1H, m), 7.32-7.38 (2H, m), 7.49 (1H, s), 7.65 (2H, d, J=6.9 Hz).

(3) N-1,2-benzisoxazol-3-yl-4-(4-phenyl-1,3-oxazol-2-yl)piperazine-1-carboxamide A mixture of 1-(4-Phenyl-1,3-oxazol-2-yl)piperazine (391 mg, 0.807 mmol), bis(2,2,2-trichloroethyl) 1,2-benzisoxazol-3-ylimidodicarbonate (370 mg, 1.61 mmol), diisopropylethylamine (0.141 ml, 0.807 mmol) and dimethylsulfoxide (5 ml) was stirred at 70° C. for 2 hours. The reaction mixture was poured to water and extracted with ethyl acetate. The extract was washed with water and dried over anhydrous magnesium sulfate. The solvent was distilled off under reduced pressure. The residue was purified by silica gel column chromatography (hexane:ethyl acetate=2:1) to give the desired product as a solid. The resulting solid was recrystallized from a mixed solvent of ethyl acetate and hexane to give 44.0 mg (14.1%) of the desired product. mp 171-172° C.

¹H-NMR (CDCl₃) δ; 3.72-3.80 (8H, m), 7.28-7.41 (4H, m), 7.49-7.59 (3H, m), 7.68 (2H, d, J=7.2 Hz), 8.07 (1H, d, J=8.1 Hz), 8.47 (1H, br s).

The structural formulae of Compounds obtained in Examples 21 to 23 are shown in Table 2.

TABLE 2

| Example No. | X | Y |
|---|---|---|
| 21 | S | C |
| 22 | O | N |
| 23 | O | C |

Example 24

N-1,2-Benzisoxazol-3-yl-1-(3-phenyl-1,2,4-thiadiazol-5-yl)piperidine-4-carboxamide

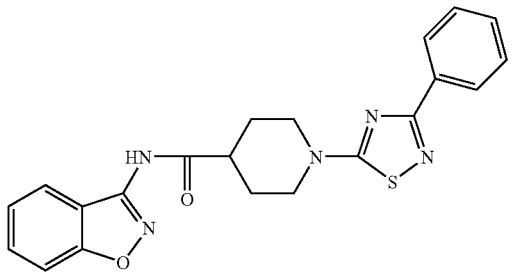

To a solution of 1-(3-phenyl-1,2,4-thiadiazol-5-yl)piperidine-4-carboxylic acid (289 mg, 1.00 mmol) and N,N-dimethylformamide (0.010 ml) in tetrahydrofuran (5 ml) was added in water-bath, oxalyl chloride (0.174 ml, 2.00 mmol), and the mixture was stirred at room temperature for 1 hour. The solvent was distilled off under reduced pressure. The residue was added to a solution of 1,2-benzisoxazol-3-amine (134 mg, 1.00 mmol) in pyridine (0.404 ml, 5.00 mmol) under ice-cooling, followed by stirring at room temperature for 1 hour. The solvent was distilled off under reduced pressure. The residue was poured to water and extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give the desired product as a solid. The resulting solid was recrystallized from a mixed solvent of hexane and ethyl acetate to give 60.3 mg (14.9%) of the desired product.

$^1$H-NMR (CDCl$_3$) δ; 2.05-2.22 (4H, m), 2.88 (1H, br s), 3.36-3.45 (2H, m), 4.11-4.18 (2H, m), 7.32-7.63 (6H, m), 8.19-8.27 (3H, m), 9.46 (1H, br s).

Example 25

N-Phenyl-4-(3-phenyl-1,2,4-thiadiazol-5-yl)piperazine-1-carboxamide

To a solution of 1-(3-phenyl-1,2,4-thiadiazol-5-yl)piperazine (1.00 g, 4.06 mmol) and triethylamine (0.565 ml, 4.06 mmol) in tetrahydrofuran (20 ml) was added, under ice-cooling, phenyl isocyanate (0.529 ml, 4.87 mmol), and the mixture was stirred at room temperature for 3 hours. To the reaction mixture was added diisopropyl ether (40 ml), and the solid was separated by filtration. The resulting solid was recrystallized from a mixed solvent of hexane and ethyl acetate to give 1.19 g (80.4%) of the desired product as a solid.

$^1$H-NMR (CDCl$_3$) δ; 3.70 (8H, s), 6.43 (1H, s), 7.06-7.11 (1H, m), 7.29-7.46 (7H, m), 8.17-8.21 (2H, m).

Example 26

N-(4-Fluorophenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 4-fluorophenyl isocyanate (0.139 ml, 1.22 mmol), and the mixture was stirred at room temperature for 3 hours. The solvent was distilled off under reduced pressure, and the residue was recrystallized from a mixed solvent of hexane and ethyl acetate to give 265 mg (85.2%) of the desired product as a solid.

$^1$H-NMR (CDCl$_3$) δ; 3.71 (8H, s), 6.36 (1H, s), 6.99-7.05 (2H, m), 7.26-7.34 (2H, m), 7.43-7.45 (3H, m), 8.18-8.21 (2H, m).

Example 27

N-(3-Fluorophenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3-fluorophenyl isocyanate (0.139 ml, 1.22 mmol), and the mixture was stirred at room temperature for 3 hours. The solvent was distilled off under reduced pressure, and the residue was recrystallized from a mixed solvent of hexane and ethyl acetate to give 187 mg (60.1%) of the desired product as a solid.

$^1$H-NMR (CDCl$_3$) δ; 3.71 (8H, s), 6.49 (1H, s), 6.75-6.81 (1H, m), 7.01-7.04 (1H, m), 7.21-7.34 (2H, m), 7.42-7.46 (3H, m), 8.18-8.21 (2H, m).

Example 28

N-(2-Fluorophenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2-fluorophenyl isocyanate (0.139 ml, 1.22 mmol), and the mixture was stirred at room temperature for 3 hours. The solvent was distilled off under reduced pressure, and the residue was recrystallized from ethyl acetate to give 146 mg (46.9%) of the desired product as a solid.

$^1$H-NMR (CDCl$_3$) δ; 3.73 (8H, s), 6.63 (1H, s), 6.98-7.16 (3H, m), 7.42-7.46 (3H, m), 8.04-8.10 (1H, m), 8.17-8.22 (2H, m).

Example 29

N-(4-Chlorophenyl)-4-(3-phenyl-1,2,4-thiadiazol-5-yl)piperazine-1-carboxamide

To a solvent of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 4-chlorophenyl isocyanate (0.188 mg, 1.22 mmol), and the mixture was stirred at room temperature for 1 hour. The solvent was distilled off under reduced pressure, and the residue was recrystallized from a mixed solvent of hexane and ethyl acetate to give 310 mg (95.4%) of the desired product as a solid.

$^1$H-NMR (CDCl$_3$) δ; 3.70 (8H, s), 6.44 (1H, s), 7.29-7.34 (4H, m), 7.43-7.46 (3H, m), 8.18-8.21 (2H, m).

Example 30

N-(4-Methylphenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 4-tolyl isocyanate (0.154 ml, 1.22 mmol), and the mixture was stirred at room temperature for 1 hour. The solvent was distilled off under reduced pressure, and the residue was recrystallized from a mixed solvent of hexane and ethyl acetate to give 298 mg (96.8%) of the desired product as a solid.

$^1$H-NMR (CDCl$_3$) δ; 2.31 (3H, s), 3.68 (8H, s), 6.31 (1H, s), 7.11 (2H, d, J=8.8 Hz), 7.23 (2H, d, J=8.8 Hz), 7.42-7.46 (3H, m), 8.17-8.22 (2H, m).

Example 31

4-(3-Phenyl-1,2,4-thiadiazol-5-yl)-N-[4-(trifluoromethyl)phenyl]piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 4-trifluoromethylphenyl isocyanate (0.184 ml, 1.22 mmol), and the mixture was stirred at room temperature for 1 hour. The solvent was distilled off under reduced pressure, and the residue was recrystallized from a mixed solvent of hexane and ethyl acetate to give 248 mg (70.5%) of the desired product as a solid.

$^1$H-NMR (CDCl$_3$) δ; 3.73 (8H, s), 6.57 (1H, s), 7.43-7.46 (3H, m), 7.50 (2H, d, J=9.0 Hz), 7.57 (2H, d, J=9.0 Hz), 8.18-8.21 (2H, m).

Example 32

N-(4-tert-Butylphenyl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 4-tert-butylphenyl isocyanate (0.214 ml, 1.22 mmol), and the mixture was stirred at room temperature for 1 hour. The solvent was distilled off under reduced pressure, and the residue was recrystallized from a mixed solvent of hexane and ethyl acetate to give 235 mg (68.7%) of the desired product as a solid.

$^1$H-NMR (CDCl$_3$) δ; 1.30 (9H, s), 3.70 (8H, s), 6.34 (1H, s), 7.27 (2H, d, J=8.7 Hz), 7.34 (2H, d, J=8.7 Hz), 7.42-7.46 (3H, m), 8.18-8.21 (2H, m).

Example 33

N-(4-Methoxyphenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 4-methoxyphenyl isocyanate (0.158 ml, 1.22 mmol), and the mixture was stirred at room temperature for 2 hours. To the resulting solution was added hexane (4 ml) and the solid was separated by filtration, which was recrystallized from a mixed solvent of tetrahydrofuran and ethyl acetate to give 180 mg (56.1%) of the desired product as a solid.

$^1$H-NMR (CDCl$_3$) δ; 3.69 (8H, s), 3.79 (3H, s), 6.31 (1H, s), 6.87 (2H, d, J=8.7 Hz), 7.24 (2H, d, J=8.7 Hz), 7.42-7.46 (3H, m), 8.18-8.21 (2H, m).

Example 34

N-(2,3-Dihydro-1-benzofuran-5-yl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2,3-dihydrobenzo[b]furan-5-isocyanate (197 mg, 1.22 mmol), and the mixture was stirred at room temperature for 1 hour. The solvent was distilled off under reduced pressure, and the residue was recrystallized from a mixed solvent of hexane and ethyl acetate to give 268 mg (81.0%) of the desired product as a solid.

$^1$H-NMR (CDCl$_3$) δ; 3.20 (2H, t, J=8.8 Hz), 3.69 (8H, s), 4.57 (2H, t, J=8.8 Hz), 6.26 (1H, s), 6.71 (1H, d, J=8.4 Hz), 6.90 (1H, s), 7.26-7.30 (1H, m), 7.41-7.45 (3H, m), 8.17-8.22 (2H, m).

Example 35

4-(3-Phenyl-1,2,4-thiadiazol-5-yl)-N-2-thienylpiperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2-thienyl isocyanate (0.153 ml, 1.22 mmol), and the mixture was stirred at room temperature for 1 hour. The solvent was distilled off under reduced pressure, and the residue was recrystallized from a mixed solvent of hexane and ethyl acetate to give 257 mg (85.1%) of the desired product as a solid.

$^1$H-NMR (CDCl$_3$) δ; 3.71 (8H, s), 6.59-6.61 (1H, m), 6.81-6.90 (2H, m), 7.06 (1H, s), 7.42-7.45 (3H, m), 8.17-8.22 (2H, m).

Example 36

N-(6-Fluoro-1,2-benzisoxazol-3-yl)-4-(3-phenyl-1,2,4-thiadiazol-5-yl)piperazine-1-carboxamide (1) Bis(2,2,2-trichloroethyl) 6-fluoro-1,2-benzisoxazol-3-yl)imidodicarbonate To a solution of 6-fluoro-1,2-benzisoxazol-3-amine (2.00 g, 13.1 mmol) and pyridine (4.24 ml, 52.4 mmol) in tetrahydrofuran (40 ml) was added, under ice-cooling, 2,2,2-trichloroethyl chlorocarbonate (4.51 ml, 32.8 mmol), and the mixture was stirred at room temperature for 2 hours. The reaction mixture was poured to water and extracted with ethyl acetate. The extract was washed with water and dried over anhydrous magnesium sulfate. The solvent was distilled off under reduced pressure, and the residue was purified by silica gel column chromatography (hexane: ethyl acetate=1:1) to give 6.00 g (91.5%) of the desired product as an oil.

$^1$H-NMR (CDCl$_3$) δ; 4.83 (4H, s), 7.15-7.22 (1H, m), 7.33-7.37 (1H, m), 7.58-7.62 (1H, m).

(2) N-(6-Fluoro-1,2-benzisoxazol-3-yl)-4-(3-phenyl-1,2,4-thiadiazol-5-yl)piperazine-1-carboxamide A mixture of 1-(3-phenyl-1,2,4-thiadiazol-5-yl)piperazine (492 mg, 2.00 mmol), bis(2,2,2-trichloroethyl) (6-fluoro-1,2-benzisoxazol-3-yl)imidodicarbonate (502 mg, 1.00 mmol), diisopropylethylamine (0.174 ml, 1.00 mmol) and dimethyl sulfoxide (5 ml) was stirred at 70° C. for 5 hours. The reaction mixture was poured to water and extracted with ethyl acetate. The extract was washed with water and dried over anhydrous magnesium sulfate. The solvent was distilled off under reduced pressure, and the residue was recrystallized from a mixed solvent of tetrahydrofuran and ethyl acetate to yield 136 mg (32.1%) of the desired product.

$^1$H-NMR (DMSO-d$_6$) δ; 3.69-3.73 (8H, m), 7.19-7.25 (1H, m), 7.46-7.48 (3H, m), 7.60-7.63 (1H, m), 7.89-7.93 (1H, m), 8.11-8.13 (2H, m), 10.17 (1H, s).

Example 37

N-(4-Methoxy-1,2-benzisoxazol-3-yl)-4-(3-phenyl-1,2,4-thiadiazol-5-yl)piperazine-1-carboxamide (1) Bis(2,2,2-trichloroethyl) (4-methoxy-1,2-benzisoxazol-3-yl)imidodicarbonate To a solution of 4-methoxy-1,2-benzisoxazol-3-amine (4.00 g, 24.4 mmol) and pyridine (7.89 ml, 97.6 mmol) in tetrahydrofuran (80 ml) was added, under ice-cooling, 2,2,2-trichloroethyl chlorocarbonate (8.41 ml, 61.0 mmol), and the mixture was stirred at room temperature for 2 hours. The reaction mixture was poured to water and extracted with ethyl acetate. The extract was washed with water and dried over anhydrous magnesium sulfate. The solvent was distilled off under reduced pressure, and hexane was added to the residue. The precipitated powder was separated by filtration to give 11.1 g (87.4%) of the desired product.

$^1$H-NMR (CDCl$_3$) δ; 3.87 (3H, s), 4.81 (4H, s), 6.64 (1H, d, J=8.1 Hz), 7.17 (1H, d, J=8.4 Hz), 7.47-7.53 (1H, m).

(2) N-(4-Methoxy-1,2-benzisoxazol-3-yl)-4-(3-phenyl-1,2,4-thiadiazol-5-yl)piperazine-1-carboxamide A mixture of 1-(3-phenyl-1,2,4-thiadiazol-5-yl)piperazine (492 mg, 2.00 mmol), bis(2,2,2-trichloroethyl) (4-methoxy-1,2-benzisoxazol-3-yl)imidodicarbonate (515 mg, 1.00 mmol), diisopropylethylamine (0.350 ml, 2.00 mmol) and dimethyl sulfoxide (10 ml) was stirred at 70° C. for 5 hours. The reaction mixture was poured to water and extracted with ethyl acetate. The extract was washed with water and dried over anhydrous magnesium sulfate. The solvent was distilled off under reduced pressure, and the residue was recrystallized from ethyl acetate to yield 325 mg (74.5%) of the desired product.

$^1$H-NMR (DMSO-d$_6$) δ; 3.68 (8H, s), 3.84 (3H, s), 6.79 (1H, d, J=7.8 Hz), 7.18 (1H, d, J=8.4 Hz), 7.46-7.56 (4H, m), 8.10-8.14 (2H, m), 9.47 (1H, s).

Example 38

N-Isoxazolo[5,4-b]pyridin-3-yl-4-(3-phenyl-1,2,4-thiadiazol-5-yl)piperazine-1-carboxamide (1) Bis(2,2,2-trichloroethyl) isoxazolo[5,4-b]pyridin-3-ylimidodicarbonate To a solution of isoxazolo[5,4-b]pyridin-3-ylamine (2.00 g, 14.8 mmol) and pyridine (4.79 ml, 59.2 mmol) in tetrahydrofuran (40 ml) was added, under ice-cooling, 2,2,2-trichloroethyl chlorocarbonate (5.11 ml, 37.1 mmol), and the mixture was stirred at room temperature for 2 hours. The reaction mixture was poured to water and extracted with ethyl acetate. The extract was washed with water and dried over anhydrous magnesium sulfate. The solvent was distilled off under reduced pressure, and hexane was added to the residue. The precipitated solid was separated by filtration to yield 4.23 g (58.8%) of the desired product.

$^1$H-NMR (CDCl$_3$) δ; 4.83 (4H, s), 7.43-7.47 (1H, m), 8.06-8.09 (1H, m), 8.70-8.73 (1H, m).

(2) N-Isoxazolo[5,4-b]pyridin-3-yl-4-(3-phenyl-1,2,4-thiadiazol-5-yl)piperazine-1-carboxamide A mixture of 1-(3-phenyl-1,2,4-thiadiazol-5-yl)piperazine (738 mg, 3.00 mmol), bis(2,2,2-trichloroethyl) isoxazolo[5,4-b]pyridin-3-ylimidodicarbonate (486 mg, 1.00 mmol), diisopropylethylamine (0.348 ml, 2.00 mmol) and dimethyl sulfoxide (5 ml) was stirred at 70° C. for 5 hours. The reaction mixture was poured to water and extracted with ethyl acetate. The extract was washed with water and dried over anhydrous magnesium sulfate. The solvent was distilled off under reduced pressure, and the residue was recrystallized from tetrahydrofuran to yield 240 mg (59.0%) of the desired product.

$^1$H-NMR (DMSO-d$_6$) δ; 3.77 (8H, s), 6.30-6.35 (1H, m), 7.46-7.49 (3H, m), 7.57-7.60 (1H, m), 8.08-8.13 (3H, m), 12.05 (1H, s).

Example 39

N-(2-Methoxyphenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2-methoxyphenyl isocyanate (0.162 ml, 1.22 mmol) at room temperature, and the mixture was stirred at room temperature for 1 hour. The solvent was distilled off under reduced pressure, and the residue was recrystallized from a mixed solvent of hexane and ethyl acetate to give 219 mg (68.2%) of the desired product as a solid.

$^1$H-NMR (CDCl$_3$) δ; 3.73 (8H, s), 3.90 (3H, s), 6.86-7.01 (3H, m), 7.15 (1H, br s), 7.41-7.46 (3H, m), 8.11-8.21 (3H, m).

Example 40

N-(3-Methoxyphenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3-methoxyphenyl isocyanate (0.160 ml, 1.22 mmol) at room temperature, and the mixture was stirred at room temperature for 1 hour. The solvent was distilled off under reduced pressure. The residue was purified by silica gel column chromatography (hexane:ethyl acetate=1:1) and recrystallized from a mixed solvent of hexane and ethyl acetate to give 133 mg (41.4%) of the desired product as a solid.

$^1$H-NMR (CDCl$_3$) δ; 3.70 (8H, s), 3.81 (3H, s), 6.40 (1H, br s), 6.62-6.65 (1H, m), 6.84-6.87 (1H, m), 7.10-7.12 (1H, m), 7.18-7.23 (1H, m), 7.42-7.45 (3H, m), 8.18-8.21 (2H, m).

Example 41

N-(2-Chlorophenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2-chlorophenyl isocyanate (0.147 ml, 1.22 mmol) at room temperature, and the mixture was stirred at room temperature for 1 hour. The solvent was distilled off under reduced pressure, and the residue was recrystallized from ethyl acetate to give 167 mg (51.5%) of the desired product as a solid.

$^1$H-NMR (CDCl$_3$) δ; 3.75 (8H, s), 6.97-7.03 (1H, m), 7.05 (1H, br s), 7.25-7.31 (1H, m), 7.35-7.38 (1H, m), 7.41-7.46 (3H, m), 8.16-8.22 (3H, m).

Example 42

N-(3-Chlorophenyl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3-chlorophenyl isocyanate (0.148 ml, 1.22 mmol) at room temperature, and the mixture was stirred at room temperature for 1 hour. The solvent was distilled off under reduced pressure, and the residue was recrystallized from a mixed solvent of hexane and ethyl acetate to give 100 mg (30.9%) of the desired product as a solid.

$^1$H-NMR (CDCl$_3$) δ; 3.71 (8H, s), 6.42 (1H, br s), 7.04-7.07 (1H, m), 7.22-7.24 (2H, m), 7.43-7.48 (4H, m), 8.18-8.21 (2H, m).

Example 43

N-(2-Methylphenyl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2-methylphenyl isocyanate (0.150 ml, 1.22 mmol) at room temperature, and the mixture was stirred at room temperature for 1 hour. The solvent was distilled off under reduced pressure, and the residue was recrystallized from a mixed solvent of hexane and tetrahydrofuran to give 158 mg (51.1%) of the desired product as a solid.

$^1$H-NMR (CDCl$_3$) δ; 2.27 (3H, s), 3.71 (8H, s), 6.16 (1H, br s), 7.06-7.09 (1H, m), 7.19-7.21 (2H, m), 7.42-7.44 (3H, m), 7.56-7.58 (1H, m), 8.18-8.21 (2H, m).

Example 44

N-(3-Methylphenyl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3-methylphenyl isocyanate (0.152 ml, 1.22 mmol) at room temperature, and the mixture was stirred at room temperature for 1 hour. The solvent was distilled off under reduced pressure, and the residue was recrystallized from a mixed solvent of hexane and tetrahydrofuran to give 120 mg (38.8%) of the desired product as a solid.

$^1$H-NMR (CDCl$_3$) δ; 2.34 (3H, s), 3.70 (8H, s), 6.34 (1H, br s), 6.89-6.91 (1H, m), 7.11-7.23 (3H, m), 7.42-7.44 (3H, m), 8.18-8.21 (2H, m).

Example 45

4-(3-Phenyl-1,2,4-thiadiazol-5-yl)-N-[2-(trifluoromethyl)phenyl]piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2-trifluoromethylphenyl isocyanate (0.169 ml, 1.22 mmol) at room temperature, and the mixture was stirred at room temperature for 1 hour. The solvent was distilled off under reduced pressure, and the residue was recrystallized from a mixed solvent of hexane and tetrahydrofuran to give 148 mg (42.1%) of the desired product as a solid.

$^1$H-NMR (CDCl$_3$) δ; 3.73 (8H, s), 6.81 (1H, br s), 7.16-7.21 (1H, m), 7.41-7.45 (3H, m), 7.53-7.61 (2H, m), 8.05-8.08 (1H, m), 8.16-8.22 (2H, m).

Example 46

4-(3-Phenyl-1,2,4-thiadiazol-5-yl)-N-[3-(trifluoromethyl)phenyl]piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3-trifluoromethylphenyl isocyanate (0.170 ml, 1.22 mmol) at room temperature, and the mixture was stirred at room temperature for 1 hour. The solvent was distilled off under reduced pressure, and the residue was recrystallized from a mixed solvent of hexane and tetrahydrofuran to give 55.4 mg (15.7%) of the desired product as a solid.

$^1$H-NMR (CDCl$_3$) δ; 3.71 (8H, s), 6.60 (1H, br s), 7.31-7.34 (1H, m), 7.40-7.44 (4H, m), 7.56-7.59 (1H, m), 7.66 (1H, br s), 8.17-8.21 (2H, m).

Example 47

N-(2-Bromophenyl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2-bromophenyl isocyanate (0.150 ml, 1.22 mmol) at room temperature, and the mixture was stirred at room temperature for 1 hour. The solvent was distilled off under reduced pressure, and the residue was recrystallized from a mixed solvent of hexane and ethyl acetate to give 241 mg (66.8%) of the desired product as a solid.

$^1$H-NMR (CDCl$_3$) δ; 3.76 (8H, s), 6.91-6.97 (1H, m), 7.07 (1H, br s), 7.29-7.35 (1H, m), 7.41-7.46 (3H, m), 7.51-7.54 (1H, m), 8.16-8.22 (3H, m).

Example 48

N-[3-(Methylthio)phenyl]-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3-methylthiophenyl isocyanate (0.168 ml, 1.22 mmol) at room temperature, and the mixture was stirred at room temperature for 1 hour. The solvent was distilled off under reduced pressure. The residue was recrystallized from a mixed solvent of hexane and ethyl acetate to give 168 mg (50.3%) of the desired product as a solid.

$^1$H-NMR (CDCl$_3$) δ; 2.48 (3H, s), 3.69 (8H, s), 6.43 (1H, br s), 6.95-6.98 (1H, m), 7.07-7.11 (1H, m), 7.19-7.25 (1H, m), 7.35-7.36 (1H, m), 7.41-7.46 (3H, m), 8.17-8.21 (2H, m).

Example 49

N-(4-Cyanophenyl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (6 ml) was added 4-cyanophenyl isocyanate (176 mg, 1.22 mmol) at room temperature, and the mixture was stirred at room temperature for 1 hour. The solvent was distilled off under reduced pressure. The residue was recrystallized from a mixed solvent of hexane and tetrahydrofuran to give 160 mg (50.6%) of the desired product as a solid.

$^1$H-NMR (CDCl$_3$) δ; 3.67 (4H, br s), 3.75 (4H, br s), 7.42 (3H, br s), 7.53-7.56 (2H, m), 7.64-7.67 (2H, m), 8.18 (2H, br s), 8.74 (1H, br s).

Example 50

N-(4-Acetylphenyl)-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 4-acetylphenyl isocyanate (196 mg, 1.22 mmol) at room temperature, and the mixture was stirred at room temperature for 1 hour. The solvent was distilled off under reduced pressure. The residue was recrystallized from a mixed solvent of hexane and ethyl acetate to give 278 mg (84.0%) of the desired product as a solid.

$^1$H-NMR (CDCl$_3$) δ; 2.58 (3H, s), 3.73 (8H, s), 6.72 (1H, br s), 7.43-7.50 (5H, m), 7.92-7.95 (2H, m), 8.18-8.21 (2H, m).

Example 51

4-(3-Phenyl-1,2,4-thiadiazol-5-yl)-N-pyridin-3-ylpiperazine-1-carboxamide (1) Bis(2,2,2-trichloroethyl)pyridin-3-ylimidodicarbonate To a solution of 3-aminopyridine (1.00 g, 10.6 mmol) and pyridine (2.58 ml, 31.9 mmol) in tetrahydrofuran (35 ml) was added, under ice-cooling, 2,2,2-trichloroethyl chloroformate (2.94 ml, 21.2 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 1.82 g (38.5%) of the desired product as a solid.

$^1$H-NMR (CDCl$_3$) δ; 4.80 (4H, s), 7.39-7.44 (1H, m), 7.63-7.68 (1H, m), 8.59-8.60 (1H, m), 8.64-8.66 (1H, m).

(2) 4-(3-Phenyl-1,2,4-thiadiazol-5-yl)-N-pyridin-3-ylpiperazine-1-carboxamide

A mixed solution of bis(2,2,2-trichloroethyl)pyridin-3-ylimidodicarbonate (271 mg, 0.610 mmol), 1-(3-phenyl-1,2,4-thiadiazol-5-yl)piperazine (200 mg, 0.812 mmol) and diisopropylethylamine (0.211 ml, 1.22 mmol) in dimethyl sulfoxide (2 ml) was stirred at 70° C. for 3 hours and further stirred at 80° C. for 1 hour. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give 106 mg (47.5%) of the desired product as a solid.

$^1$H-NMR (CDCl$_3$) δ; 3.72 (8H, br s), 6.84 (1H, br s), 7.25-7.28 (1H, m), 7.40-7.44 (3H, m), 7.95-7.99 (1H, m), 8.16-8.20 (2H, m), 8.29-8.30 (1H, m), 8.45-8.46 (1H, m).

Example 52

4-(3-Phenyl-1,2,4-thiadiazol-5-yl)-N-quinolin-2-ylpiperazine-1-carboxamide (1) 2,2,2-Trichloroethyl quinolin-2-ylcarbamate To a solution of 2-aminoquinoline (1.00 g, 6.94 mmol) and pyridine (0.673 ml, 8.32 mmol) in tetrahydrofuran (23 ml) was added, under ice-cooling, 2,2,2-trichloroethyl chloroformate (1.15 ml, 8.32 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 908 mg (40.9%) of the desired product as a solid was separated by filtration.

$^1$H-NMR (DMSO-d$_6$) δ; 5.01 (2H, s), 7.47-7.54 (1H, m), 7.68-8.05 (4H, m), 8.33-8.41 (1H, m), 11.02 (1H, br s).

(2) 4-(3-Phenyl-1,2,4-thiadiazol-5-yl)-N-quinolin-2-ylpiperazine-1-carboxamide

A mixed solution of 2,2,2-trichloroethyl quinolin-2-ylcarbamate (236 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and ethyl acetate to give 142 mg (46.0%) of the desired product as a solid.

$^1$H-NMR (DMSO-d$_6$) δ; 3.67 (4H, br s), 3.73 (4H, br s), 7.40-7.48 (4H, m), 7.63-7.68 (1H, m), 7.75-7.78 (1H, m), 7.86 (1H, d, J=7.8 Hz), 7.99 (1H, br s), 8.10-8.13 (2H, m), 8.23 (1H, d, J=8.7 Hz), 9.82 (1H, br s).

Example 53

Methyl 5-({[4-(3-phenyl-1,2,4-thiadiazol-5-yl)piperazin-1-yl]carbonyl}amino)-2-furancarboxylate (1) Methyl 5-{[(2,2,2-trichloroethoxy)carbonyl]amino}-2-furoate To a solution of methyl 5-amino-2-furancarboxylate (1.00 g, 7.09 mmol) and pyridine (1.72 ml, 21.3 mmol) in tetrahydrofuran (24 ml) was added, under ice-cooling, 2,2,2-trichloroethyl chloroformate (1.96 ml, 14.2 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 662 mg (29.6%) of the desired product as a solid was separated by filtration.

$^1$H-NMR (CDCl$_3$) δ; 3.87 (3H, s), 4.84 (2H, s), 6.33 (1H br s), 7.17-7.19 (1H, m), 7.83 (1H, br s).

(2) Methyl 5-({[4-(3-phenyl-1,2,4-thiadiazol-5-yl)piperazin-1-yl]carbonyl}amino)-2-furancarboxylate A mixed solution of methyl 5-{[(2,2,2-trichloroethoxy)carbonyl]amino}-2-furancarboxylate (321 mg, 1.01 mmol), 1-(3-phenyl-1,2,4-thiadiazol-5-yl)piperazine (200 mg, 0.812 mmol) and diisopropylethylamine (0.177 ml, 1.01 mmol) in dimethyl sulfoxide (3.4 ml) was stirred at 70° C. for 5 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 71.7 mg (17.1%) of the desired product as a solid.

$^1$H-NMR (DMSO-$d_6$) δ; 3.65 (4H, br s), 3.71 (4H, br s), 3.78 (3H, s), 6.24-6.25 (1H, m), 7.18-7.20 (1H, m), 7.41-7.44 (3H, m), 8.11-8.16 (2H, m), 10.36 (1H, s).

Example 54

N-1H-Benzimidazol-2-yl-4-(3-phenyl-1,2,4-thiadiazol-5-yl)piperazine-1-carboxamide

(1) 2,2,2-Trichloroethyl 1H-benzimidazol-2-ylcarbamate

To a solution of 2-aminobenzimidazole (1.00 g, 7.51 mmol) and pyridine (0.714 ml, 9.01 mmol) in tetrahydrofuran (25 ml) was added, under ice-cooling, 2,2,2-trichloroethyl chloroformate (1.25 ml, 9.01 mmol), and the mixture was stirred at room temperature for 1 hour and half. Water was poured to the reaction mixture, and 1.27 g (54.6%) of the desired product as a solid was separated by filtration.

$^1$H-NMR (DMSO-$d_6$) δ; 5.31 (2H, s), 6.99-7.05 (1H, m), 7.14-7.24 (2H, m), 7.32 (2H, br s), 7.78 (1H, d, J=7.5 Hz).

(2) N-1H-Benzimidazol-2-yl-4-(3-phenyl-1,2,4-thiadiazol-5-yl)piperazine-1-carboxamide A mixed solution of 2,2,2-trichloroethyl 1H-benzimidazol-2-ylcarbamate (228 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3.5 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column-chromatography (hexane:ethyl acetate=2:8) and recrystallized from a mixed solvent of hexane and tetrahydrofuran to give 35.6 mg (11.9%) of the desired product as a solid.

$^1$H-NMR (DMSO-$d_6$) δ; 3.61 (4H, br s), 3.78 (4H, br s), 7.03-7.06 (2H, m), 7.25-7.28 (2H, m), 7.47-7.49 (3H, m), 8.10-8.14 (2H, m), 11.68 (1H, br s).

Example 55

N-(1-Methyl-1H-benzimidazol-2-yl)-4-(3-phenyl-1,2,4-thiadiazol-5-yl)piperazine-1-carboxamide

(1) 2,2,2-Trichloroethyl (1-methyl-1H-benzimidazol-2-yl)carbamate

To a solution of 1-methyl-1H-benzimidazol-2-amine (1.00 g, 6.79 mmol) and pyridine (0.646 ml, 8.15 mmol) in tetrahydrofuran (23 ml) was added, under ice-cooling, 2,2,2-trichloroethyl chloroformate (1.13 ml, 8.15 mmol), and the mixture was stirred at room temperature for 1.5 hour. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 546 mg (24.9%) of the desired product as a solid was separated by filtration.

$^1$H-NMR (CDCl$_3$) δ; 3.67 (3H, s), 4.89 (2H, s), 7.24-7.28 (5H, m).

(2) N-(1-Methyl-1H-benzimidazol-2-yl)-4-(3-phenyl-1,2,4-thiadiazol-5-yl)piperazine-1-carboxamide A mixed solution of 2,2,2-trichloroethyl (1-methyl-1H-benzimidazol-2-yl)carbamate (238 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours. Water was poured to the reaction mixture, and 145 mg (46.8%) of the desired product as a solid was separated by filtration.

$^1$H-NMR (DMSO-$d_6$) δ; 3.54 (3H, s), 3.65 (4H, br s), 3.89 (4H, br s), 7.04-7.46 (7H, m), 8.11-8.19 (2H, m), 11.99 (1H, s).

Example 56

N-1,3-Benzothiazol-2-yl-4-(3-phenyl-1,2,4-thiadiazol-5-yl)piperazine-1-carboxamide

(1) 2,2,2-Trichloroethyl 1,3-benzothiazol-2-ylcarbamate

To a solution of 2-aminobenzothiazole (1.00 g, 6.66 mmol) and pyridine (0.633 ml, 7.99 mmol) in tetrahydrofuran (22 ml) was added, under ice-cooling, 2,2,2-trichloroethyl chloroformate (1.11 ml, 7.99 mmol), and the mixture was stirred at room temperature for 1 hour. Water was poured to the reaction mixture, and 1.19 g (54.7%) of the desired product as a solid was separated by filtration.

$^1$H-NMR (DMSO-$d_6$) δ; 5.06 (2H, s), 7.31 (1H, t, J=7.8 Hz), 7.44 (1H, t, J=7.8 Hz), 7.72 (1H, d, J=7.8 Hz), 7.97 (1H, d, J=7.8 Hz).

(2) N-1,3-Benzothiazol-2-yl-4-(3-phenyl-1,2,4-thiadiazol-5-yl)piperazine-1-carboxamide A mixed solution of 2,2,2-trichloroethyl 1,3-benzothiazol-2-ylcarbamate (240 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 81.4 mg (26.1%) of the desired product as a solid.

$^1$H-NMR (CDCl$_3$) δ; 3.65-3.69 (4H, m), 3.84 (4H, br s), 7.22-7.27 (2H, m), 7.34-7.44 (5H, m), 7.67 (1H, br s), 8.15-8.19 (2H, m).

Example 57

N-(3-Cyanophenyl)-4-(3-phenyl-1,2,4-thiadiazol-5-yl)-piperazine carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3-cyanophenyl isocyanate (176 mg, 1.22 mmol) at room temperature, and the mixture was stirred at room temperature for 1 hour. The solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 204 mg (64.4%) of the desired product as a solid.

$^1$H-NMR (CDCl$_3$) δ; 3.72 (8H, s), 6.65 (1H, br s), 7.34-7.45 (5H, m), 7.62-7.65 (1H, m), 7.75 (1H, br s), 8.18-8.21 (2H, m).

Example 58

4-(3-Phenyl-1,2,4-thiadiazol-5-yl)-N-(2,2,4,4-tetrafluoro-4H-1,3-benzodioxin-6-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 6-isocyanato-2,2,4,4-tetrafluoro-1,3-benzodioxene (303.4 mg, 1.22 mmol) at room temperature, and the mixture was stirred at room temperature for 1 hour. The solvent was distilled off under reduced pressure. The residue was recrystallized from a mixed solvent of hexane and tetrahydrofuran to give 279 mg (69.3%) of the desired product as a solid.

$^1$H-NMR (CDCl$_3$+DMSO-d$_6$) δ; 3.67-3.70 (4H, m), 3.75-3.79 (4H, m), 7.01 (1H, d, J=9.0 Hz), 7.42-7.45 (3H, m), 7.77-7.81 (1H, m), 7.91-7.92 (1H, m), 8.16-8.19 (2H, m), 8.85 (1H, s).

Example 59

N-2-Naphthyl-4-(3-phenyl-1,2,4-thiadiazol-5-yl)piperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2-naphthyl isocyanate (206 mg, 1.22 mmol) at room temperature, and the mixture was stirred at room temperature for 1 hour. The solvent was distilled off under reduced pressure. The residue was recrystallized from a mixed solvent of hexane and tetrahydrofuran to give 176 mg (52.2%) of the desired product as a solid.

$^1$H-NMR (CDCl$_3$+DMSO-d$_6$) δ; 3.68-3.70 (4H, m), 3.77-3.81 (4H, m), 7.31-7.46 (5H, m), 7.56-7.60 (1H, m), 7.71-7.76 (3H, m), 8.03 (1H, br s), 8.16-8.19 (2H, m), 8.56 (1H, br s).

Example 60

N-(2,6-Dichloropyridin-4-yl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 2,6-dichloropyridin-4-isocyanate (230 mg, 1.22 mmol) at room temperature, and the mixture was stirred at room temperature for 1 hour. The solvent was distilled off under reduced pressure. The residue was recrystallized from a mixed solvent of hexane and tetrahydrofuran to give 287 mg (81.1%) of the desired product as a solid.

$^1$H-NMR (DMSO-d$_6$) δ; 3.66-3.77 (8H, m), 7.41-7.44 (3H, m), 7.57 (2H, s), 8.16-8.19 (2H, m), 9.10 (1H, br s).

Example 61

4-(3-Phenyl-1,2,4-thiadiazol-5-yl)-N-quinolin-3-ylpiperazine-1-carboxamide (1) Bis(2,2,2-trichloroethyl) quinolin-3-ylimidodicarbonate To a solution of 3-aminoquinoline (1.00 g, 6.94 mmol) and pyridine (1.68 ml, 20.8 mmol) in tetrahydrofuran (23 ml) was added, under ice-cooling, 2,2,2-trichloroethyl chloroformate (1.92 ml, 13.9 mmol), and the mixture was stirred at room temperature for 1.5 hour. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 2.46 g (71.7%) of the desired product as a solid was separated by filtration.

$^1$H-NMR (CDCl$_3$) δ; 4.82 (4H, s), 7.59-7.67 (2H, m), 7.76-7.83 (2H, m), 8.12-8.14 (1H, m), 8.83-8.84 (1H, m).

(2) 4-(3-Phenyl-1,2,4-thiadiazol-5-yl)-N-quinolin-3-ylpiperazine-1-carboxamide

A mixed solution of bis(2,2,2-trichloroethyl) quinolin-3-ylimidodicarbonate (301.4 mg, 0.610 mmol), 1-(3-phenyl-1,2,4-thiadiazol-5-yl)piperazine (200 mg, 0.812 mmol) and diisopropylethylamine (0.106 ml, 0.610 mmol) in dimethyl sulfoxide (2 ml) was stirred at 70° C. for 5 hours and then stirred at 80° C. for 1 hour and half. Water was poured to the reaction mixture, and the resulting solution was extracted with ethyl acetate. The extract was washed with water and dried over anhydrous magnesium sulfate, and the solvent was distilled off under reduced pressure. Chloroform was poured to the residue, and 110 mg (43.2%) of the desired product as a solid was separated by filtration.

$^1$H-NMR (CDCl$_3$+DMSO-d$_6$) δ; 3.69-3.74 (4H, m), 3.78-3.84 (4H, m), 7.38-7.57 (5H, m), 7.74-7.77 (1H, m), 7.97-8.00 (1H, m), 8.16-8.20 (2H, m), 8.54-8.55 (1H, m), 8.74 (1H, br s), 8.91-8.92 (1H, m).

Example 62

Methyl 3-({[4-(3-phenyl-1,2,4-thiadiazol-5-yl)piperazin-1-yl]carbonyl}amino)benzoate To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added methyl-3- isocyanatobenzoate (216 mg, 1.22 mmol) at room temperature, and the mixture was stirred at room temperature for 1 hour. The solvent was distilled off under reduced pressure. The residue was recrystallized from a mixed solvent of hexane and ethyl acetate to give 102 mg (29.7%) of the desired product as a solid.

$^1$H-NMR (CDCl$_3$) δ; 3.71 (8H, s), 3.91 (3H, s), 6.60 (1H, br s), 7.37-7.46 (4H, m), 7.71-7.77 (2H, m), 7.91-7.92 (1H, m), 8.18-8.21 (2H, m).

Example 63

Methyl 2-({[4-(3-phenyl-1,2,4-thiadiazol-5-yl)piperazin-1-yl]carbonyl}amino)benzoate To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added methyl-2-isocyanatobenzoate (216 ml, 1.22 mmol) at room temperature, and the mixture was stirred at room temperature for 1 hour. The solvent was distilled off under reduced pressure. The residue was recrystallized from a mixed solvent of hexane and tetrahydrofuran to give 239 mg (69.5%) of the desired product as a solid.

$^1$H-NMR (CDCl$_3$) δ; 3.71-3.76 (4H, m), 3.80-3.86 (4H, m), 3.93 (3H, s), 6.98-7.03 (1H, m), 7.40-7.44 (3H, m), 7.50-7.56 (1H, m), 8.00-8.03 (1H, m), 8.17-8.20 (2H, m), 8.52-8.56 (1H, m).

Example 64

N-(3,4-Dimethoxyphenyl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3,4-dimethoxyphenyl isocyanate (0.182 ml, 1.22 mmol) at room temperature, and the mixture was stirred at room temperature for 1 hour. The solvent was distilled off under reduced pressure, and the residue was recrystallized from tetrahydrofuran to give 64.6 mg (18.7%) of the desired product as a solid.

$^1$H-NMR (CDCl$_3$) δ; 3.70 (8H, br s), 3.86 (3H, s), 3.88 (3H, s), 6.34 (1H, br s), 6.75-6.82 (2H, m), 7.15 (1H, br s), 7.43 (3H, br s), 8.20 (2H, br s).

Example 65

4-(3-Phenyl-1,2,4-thiadiazol-5-yl)-N-3-thienylpiperazine-1-carboxamide

To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3-thienyl isocyanate (0.152 ml, 1.22 mmol) at room temperature, and the mixture was stirred at room temperature for 1 hour. The solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 50.0 mg (16.6%) of the desired product.

$^1$H-NMR (CDCl$_3$) δ; 3.70 (8H, s), 6.55 (1H, br s), 6.91-6.95 (1H, m), 7.22-7.34 (1H, m), 7.40-7.45 (4H, m), 8.17-8.21 (2H, m).

Example 66

4-(3-Phenyl-1,2,4-thiadiazol-5-yl)-N-(5-pyridin-3-yl-1,3,4-oxadiazol-2-yl)piperazine-1-carboxamide (1) 2,2,2-Trichloroethyl (5-pyridin-3-yl-1,3,4-oxadiazol-2-yl)carbamate To a solution of 5-pyridin-3-yl-1,3,4-oxadiazol-2-ylamine (1.00 g, 6.17 mmol) and pyridine (1.47 ml, 18.5 mmol) in tetrahydrofuran (20 ml) was added, under ice-cooling, 2,2,2-trichloroethyl chloroformate (1.70 ml, 12.3 mmol), and the mixture was stirred at room temperature for 1.5 hour. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 1.13 g (54.5%) of the desired product as a solid was separated by filtration.

$^1$H-NMR (DMSO-d$_6$) δ; 5.03 (2H, s), 7.39 (1H, br s), 7.61-7.67 (1H, m), 8.26-8.30 (1H, m), 8.78-8.80 (1H, m), 9.09 (1H, br s).

(2) 4-(3-Phenyl-1,2,4-thiadiazol-5-yl)-N-(5-pyridin-3-yl-1,3,4-oxadiazol-2-yl)piperazine-1-carboxamide A mixed solution of 2,2,2-trichloroethyl (5-pyridin-3-yl-1,3,4-oxadiazol-2-yl)carbamate (249 mg, 0.738 mmol), 1-(3-phenyl-1,2,4-thiadiazol-5-yl)piperazine (200 mg, 0.812 mmol) and diisopropylethylamine (0.129 ml, 0.728 mmol) in dimethyl sulfoxide (2.5 ml) was stirred at 70° C. for 3 hours and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and crystals were separated by filtration, which was recrystallized from a mixed solvent of hexane and tetrahydrofuran to give 110 mg (34.2%) of the desired product as a solid.

$^1$H-NMR (CDCl$_3$) δ; 3.67 (4H, br s), 3.87-4.01 (4H, m), 7.42-7.50 (4H, m), 8.19-8.25 (3H, m), 8.79-8.82 (1H, m), 9.20-9.21 (1H, m).

Example 67

N-(5-Ethyl-1,3,4-oxadiazol-2-yl)-4-(3-phenyl-1,2,4-thiadiazol-5-yl)piperazine-1-carboxamide (1) 2,2,2-Trichloroethyl (5-ethyl-1,3,4-oxadiazol-2-yl)carbamate To a solution of 5-ethyl-1,3,4-oxadiazol-2-ylamine (1.00 g, 8.84 mmol) and pyridine (2.10 ml, 26.5 mmol) in tetrahydrofuran (29 ml) was added, under ice-cooling, 2,2,2-trichloroethyl chloroformate (2.45 ml, 17.7 mmol), and the mixture was stirred at room temperature for 1.5 hour. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) to give 763 mg (29.9%) of the desired product as a solid.

$^1$H-NMR (CDCl$_3$) δ; 1.38 (3H, t, J=7.8 Hz), 2.85 (2H, q, J=7.8 Hz), 4.87 (2H, s).

(2) N-(5-ethyl-1,3,4-oxadiazol-2-yl)-4-(3-phenyl-1,2,4-thiadiazol-5-yl)piperazine-1-carboxamide A mixed solution of 2,2,2-trichloroethyl (5-ethyl-1,3,4-oxadiazol-2-yl)carbamate (213 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours and half. Water was poured to the reaction mixture, and the resulting solution was extracted with ethyl acetate. The extract was washed with water and dried over anhydrous magnesium sulfate, and the solvent was distilled off under reduced pressure. Chloroform was poured to the residue, and 140 mg (49.1%) of the desired product as a solid was separated by filtration.

$^1$H-NMR (CDCl$_3$) δ; 1.35 (3H, t, J=7.5 Hz), 2.72 (2H, q, J=7.5 Hz), 3.63 (4H, br s), 3.81 (2H, br s), 3.95 (2H, br s), 7.41-7.43 (3H, m), 8.18-8.20 (2H, m).

Example 68

4-(3-Phenyl-1,2,4-thiadiazol-5-yl)-N-[3-(trifluoromethoxy)phenyl]piperazine-1-carboxamide To a solution of 3-trifluoromethoxy benzoate (206 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1 hour and half. The resulting mixture was cooled to room temperature, 1-(3-Phenyl-1,2,4-thiadiazol-5-yl)piperazine (172 mg, 0.700 mmol) was added thereto, and the mixture was stirred at room temperature for 2 hours and half. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and ethyl acetate to give 118 mg (37.6%) of the desired product as a solid.

$^1$H-NMR (CDCl$_3$) δ; 3.70 (8H, s), 6.69 (1H, br s), 6.98-7.00 (1H, m), 7.23-7.31 (3H, m), 7.41-7.46 (3H, m), 8.18-8.21 (2H, m).

Example 69

N-[3-(Difluoromethoxy)phenyl]-4-(3-phenyl-1,2,4-thiadiazol-5-yl)piperazine-1-carboxamide To a solution of 3-difluoromethoxy benzoate (188 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1 hour and half. The resulting mixture was cooled to room temperature, 1-(3-phenyl-1,2,4-thiadiazol-5-yl)piperazine (172 mg, 0.700 mmol) was added thereto, and the mixture was stirred at room temperature for 2.5 hours. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and ethyl acetate to give 112 mg (37.0%) of the desired product as a solid.

$^1$H-NMR (CDCl$_3$) δ; 3.71 (8H, s), 6.47 (1H, br s), 6.82-6.84 (1H, m), 7.14-7.16 (2H, m), 7.26-7.31 (2H, m), 7.43-7.45 (3H, m), 8.18-8.21 (2H, m).

Example 70

4-(3-Phenyl-1,2,4-thiadiazol-5-yl)-N-[3-(1,1,2,2-tetrafluoroethyl)phenyl]piperazine-1-carboxamide To a solution of 3-(1,1,2,2-tetrafluoroethoxy)benzoic acid (238 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1 hour and half. The resulting mixture was cooled to room temperature, 1-(3-phenyl-1,2,4-thiadiazol-5-yl)piperazine (172 mg, 0.70 mmol) was added thereto, and the mixture was stirred at room temperature for 2 hours and half. Water was poured to the reaction mixture, and the resulting solution was extracted with ethyl acetate. The extracts were washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and ethyl acetate to give 105 mg (31.2%) of the desired product as a solid.

$^1$H-NMR (CDCl$_3$+DMSO-d) δ; 3.67-3.68 (4H, m), 3.73-3.75 (4H, m), 5.98-6.34 (1H, m), 6.83 (1H, d, J=7.5 Hz), 7.23-7.29 (1H, m), 7.42-7.43 (4H, m), 7.52 (1H, br s), 8.15-8.23 (2H, m), 8.72 (1H, br s).

Example 71

N-1H-1,2,3-Benzotriazol-5-yl-4-(3-phenyl-1,2,4-thiadiazol-5-yl)piperazine-1-carboxamide

(1) Bis(2,2,2-trichloroethyl) 1H-1,2,3-benzotriazol-5-ylimidodicarbonate

To a solution of 5-aminobenzotriazol (1.00 g, 7.45 mmol) and pyridine (0.71 ml, 8.95 mmol) in tetrahydrofuran (25 ml) was added, under ice-cooling, 2,2,2-trichloroethyl chloroformate (1.24 ml, 8.95 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to yield 442 mg (19.1%) of the desired product.

$^1$H-NMR (CDCl$_3$) δ; 4.87 (2H, s), 5.23 (2H, s), 7.32 (1H, br s), 7.42-7.48 (1H, m), 8.08-8.13 (1H, m), 8.49-8.50 (1H, m).

(2) N-1H-1,2,3-Benzotriazol-5-yl-4-(3-phenyl-1,2,4-thiadiazol-5-yl)piperazine-1-carboxamide A mixed solution of bis(2,2,2-trichloroethyl) 1H-1,2,3-benzotriazol-5-ylcarbamate dicarbonate (295 mg, 0.610 mmol), 1-(3-phenyl-1,2,4-thiadiazol-5-yl)piperazine (300 mg, 1.22 mmol) and diisopropylethylamine (0.212 ml, 1.22 mmol) in dimethyl sulfoxide (2 ml) was stirred at 70° C. for 3 hours and half. After water was poured to the reaction mixture, a crystal was separated by filtration with ethyl acetate and recrystallized from a mixed solvent of hexane and tetrahydrofuran to give 112 mg (45.4%) of the desired product as a solid. mp 271-272° C.
$^1$H-NMR (DMSO-d$_6$) δ; 3.66-3.70 (8H, m), 7.44-7.51 (4H, m), 7.85 (1H, d, J=9.0 Hz), 8.12-8.15 (3H, m), 8.98 (1H, s).

Example 72

N-1,3-Benzodioxol-5-yl-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 3,4-(methylenedioxy)phenyl isocyanate (199 mg, 1.22 mmol) at room temperature, and the mixture was stirred at room temperature for 1 hour. The solvent was distilled off under reduced pressure. The residue was recrystallized from a mixed solvent of hexane and tetrahydrofuran to give 239 mg (71.9%) of the desired product as a solid.
$^1$H-NMR (CDCl$_3$) δ; 3.67 (8H, s), 5.93 (2H, s), 6.33 (1H, br s), 6.62-6.65 (1H, m), 6.71-6.74 (1H, m), 7.00-7.02 (1H, m), 7.41-7.44 (3H, m), 8.16-8.19 (2H, m).

Example 73

N-(2,3-Dihydro-1,4-benzodioxin-6-yl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 6-isocyanato-1,4-benzodioxan (167 ml, 1.22 mmol) at room temperature, and the mixture was stirred at room temperature for 1 hour. The solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 161 mg (46.9%) of the desired product as a solid.
$^1$H-NMR (CDCl$_3$) δ; 3.67 (8H, s), 4.23 (4H, s), 6.30 (1H, br s), 6.77-6.82 (2H, m), 6.93 (1H, d, J=2.1 Hz), 7.42-7.44 (3H, m), 8.18-8.21 (2H, m).

Example 74

N-[3-(Dimethylamino)phenyl]-4-(3-phenyl-1,2,4-thiadiazol-5-yl)piperazine-1-carboxamide To a solution of 3-dimethylaminobenzoic acid (165 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1 hour and half. The resulting mixture was cooled to room temperature, 1-(3-phenyl-1,2,4-thiadiazol-5-yl)piperazine (172 mg, 0.700 mmol) was added thereto, and the mixture was stirred at room temperature for 2 hours and half. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 140 mg (42.1%) of the desired product as a solid.
$^1$H-NMR (CDCl$_3$) δ; 2.95 (6H, s), 3.68 (8H, s), 6.40 (1H, br s), 6.45-6.49 (1H, m), 6.58-6.62 (1H, m), 6.90 (1H, br s), 7.16 (1H, t, J=8.1 Hz), 7.42-7.46 (3H, m), 8.18-8.21 (2H, m).

Example 75

N-1H-Indol-3-yl-4-(3-phenyl-1,2,4-thiadiazol-5-yl)piperazine-1-carboxamide

To a solution of indole-3-carboxylic acid (162 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1.5 hour. The resulting mixture was cooled to room temperature, 1-(3-phenyl-1,2,4-thiadiazol-5-yl)piperazine (172 mg, 0.700 mmol) was added thereto, and the mixture was stirred at room temperature for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 90 mg (27.3%) of the desired product as a solid.
$^1$H-NMR (CDCl$_3$+DMSO-d$_6$) δ; 3.69-3.73 (4H, s), 3.78-3.81 (4H, m), 7.02 (1H, t, J=7.8 Hz), 7.11 (1H, t, J=7.8 Hz), 7.32-7.36 (1H, m), 7.41-7.45 (4H, m), 7.67 (1H, s), 8.17-8.20 (3H, m).

Example 76

N-(Isoquinolin-4-yl)-4-(3-phenyl-1,2,4-thiadiazol-5-yl)piperazine-1-carboxamide (1) 2,2,2-Trichloroethyl isoquinolin-4-ylcarbamate To a solution of 3-aminoisoquinoline (1.00 g, 6.94 mmol) and pyridine (0.660 ml, 8.32 mmol) in tetrahydrofuran (23 ml) was added, under ice-cooling, 2,2,2-trichloroethyl chloroformate (1.15 ml, 8.32 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 2.03 g (91.7%) of the desired product as a solid was separated by filtration.
$^1$H-NMR (DMSO-d$_6$) δ; 5.01 (2H, s), 7.54 (1H, t, J=7.8 Hz), 7.72 (1H, t, J=7.8 Hz), 7.91 (1H, d, J=7.8 Hz), 8.06 (1H, d, J=8.1 Hz), 8.17 (1H, s), 9.15 (1H, s).

(2) N-(Isoquinolin-4-yl)-4-(3-phenyl-1,2,4-thiadiazol-5-yl)piperazine-1-carboxamide A mixed solution of 2,2,2-trichloroethyl isoquinolin-4-ylcarbamate (236 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 87.7 mg (28.5%) of the desired product as a solid.

$^1$H-NMR (CDCl$_3$) δ; 3.74-3.81 (8H, br s), 7.38 (1H, br s), 7.43-7.48 (4H, m), 7.64 (1H, t, J=7.8 Hz), 7.80 (1H, d, J=8.4 Hz), 7.88 (1H, d, J=8.4 Hz), 8.19-8.22 (2H, m), 8.37 (1H, br s), 8.95 (1H, br s).

Example 77

N-(5-Chloro-1,3-benzoxazol-2-yl)-4-(3-phenyl-1,2,4-thiadiazol-5-yl)piperazine-1-carboxamide (1) 2,2,2-Trichloroethyl (5-chloro-1,3-benzoxazol-2-yl)carbamate To a solution of 2-amino-5-chlorobenzoxazole (1.00 g, 5.39 mmol) and pyridine (0.564 ml, 7.12 mmol) in tetrahydrofuran (20 ml) was added, under ice-cooling, 2,2,2-trichloroethyl chloroformate (0.850 ml, 7.12 mmol), and the mixture was stirred at room temperature for 2 hours and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 394 mg (19.3%) of the desired product as a solid was separated by filtration.

$^1$H-NMR (CDCl$_3$+DMSO-d$_6$) δ; 4.92 (2H, s), 7.17-7.21 (1H, m), 7.37 (1H, d, J=8.4 Hz), 7.55 (1H, br s).

(2) N-(5-Chloro-1,3-benzoxazol-2-yl)-4-(3-phenyl-1,2,4-thiadiazol-5-yl)piperazine-1-carboxamide A mixed solution of 2,2,2-trichloroethyl (5-chloro-1,3-benzoxazol-2-yl)carbamate (254 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and ethyl acetate to give 79.2 mg (24.3%) of the desired product as a solid.

$^1$H-NMR (CDCl$_3$) δ; 3.66 (4H, br s), 3.84 (2H, br s), 4.03 (2H, br s), 7.15-7.31 (3H, m), 7.41-7.47 (3H, m), 8.17-8.22 (2H, m), 11.46 (1H, br s).

Example 78

N-(1-Methyl-1H-indol-3-yl)-4-(3-phenyl-1,2,4-thiadiazol-5-yl)piperazine-1-carboxamide To a solution of 1-methylindole-3-carboxylic acid (175 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1 hour and half. The resulting mixture was cooled to room temperature, 1-(3-phenyl-1,2,4-thiadiazol-5-yl)piperazine (172 mg, 0.700 mmol) was added thereto, and the mixture was stirred at room temperature for 2.5 hours. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 52.4 mg (17.9%) of the desired product as a solid.

$^1$H-NMR (CDCl$_3$) δ; 3.66-3.74 (8H, m), 3.76 (3H, s), 6.37 (1H, br s), 7.08-7.13 (1H, m), 7.20-7.31 (3H, m), 7.36 (1H, s), 7.40-7.48 (3H, m), 8.17-8.20 (2H, m).

Example 79

3-({[4-(3-Phenyl-1,2,4-thiadiazol-5-yl)piperazin-1-yl]carbonyl}amino)phenyl acetate To a solution of 3-acetoxybenzoic acid (180 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1.5 hour. The resulting mixture was cooled to room temperature, 1-(3-phenyl-1,2,4-thiadiazol-5-yl)piperazine (172 mg, 0.700 mmol) was added thereto, and the mixture was stirred at room temperature for 2 hours and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 66 mg (22.3%) of the desired product as a solid.

$^1$H-NMR (CDCl$_3$) δ; 2.29 (3H, s), 3.68 (8H, s), 6.55 (1H, br s), 6.77-6.81 (1H, m), 7.12-7.16 (1H, m), 7.26-7.32 (2H, m), 7.41-7.46 (3H, m), 8.17-8.22 (2H, m).

Example 80

N-(5-Morpholin-4-yl-1,3,4-oxadiazol-2-yl)-4-(3-phenyl-1,2,4-thiadiazol-5-yl)piperazine-1-carboxamide (1) 2,2,2-Trichloroethyl (5-morpholin-4-yl-1,3,4-oxadiazol-2-yl)carbamate To a solution of 5-morpholin-4-yl-1,3,4-oxadiazol-2-ylamine (1.00 g, 5.88 mmol) and pyridine (0.570 ml, 7.05 mmol) in tetrahydrofuran (20 ml) was added, under ice-cooling, 2,2,2-trichloroethyl chloroformate (0.976 ml, 7.05 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to yield 269 mg (13.3%) of the desired product as a solid.

$^1$H-NMR (CDCl$_3$) δ; 3.45-3.48 (4H, m), 3.78-3.81 (4H, m), 4.82 (2H s).

(2) N-(5-Morpholin-4-yl-1,3,4-oxadiazol-2-yl)-4-(3-phenyl-1,2,4-thiadiazol-5-yl)piperazine-1-carboxamide A mixed solution of 2,2,2-trichloroethyl (5-morpholin-4-yl-1,3,4-oxadiazol-2-yl)carbamate (269 mg, 0.777 mmol), 1-(3-phenyl-1,2,4-thiadiazol-5-yl)piperazine (211 mg, 0.854 mmol) and diisopropylethylamine (0.149 ml, 0.854 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 31 mg (9.0%) of the desired product as a solid.

$^1$H-NMR (CDCl$_3$) δ; 3.13 (4H, br s), 3.75-4.08 (12H, m), 7.37-7.45 (3H, m), 8.15-8.19 (2H, m), 10.76 (1H, s).

Example 81

N-1H-Indol-5-yl-4-(3-phenyl-1,2,4-thiadiazol-5-yl)piperazine-1-carboxamide (1) 2,2,2-Trichloroethyl 1H-indol-5-ylcarbamate To a solution of 5-aminoindole (1.00 g, 7.57 mmol) and pyridine (0.720 ml, 9.08 mmol) in tetrahydrofuran (25 ml) was added, under ice-cooling, 2,2,2-trichloroethyl chloroformate (1.26 ml, 9.08 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 334 mg (14.3%) of the desired product as a solid.

$^1$H-NMR (CDCl$_3$) δ; 4.84 (2H, s), 6.51-6.53 (1H, m), 6.84 (1H, br s), 7.15-7.36 (3H, m), 7.73 (1H, br s), 8.13 (1H, br s).

(2) N-1H-Indol-5-yl-4-(3-phenyl-1,2,4-thiadiazol-5-yl)piperazine-1-carboxamide

A mixed solution of 2,2,2-trichloroethyl 1H-indol-5-ylcarbamate (227 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours, and then stirred at 70° C. for 18 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane: ethyl acetate=1:1) and recrystallized from a mixed solvent of hexane and tetrahydrofuran to give 71.3 mg (23.9%) of the desired product as a solid.

$^1$H-NMR (CDCl$_3$+DMSO-d$_6$) δ; 3.69 (4H, br s), 3.75 (4H, br s), 6.35 (1H, br s), 7.10-7.17 (2H, m), 7.28-7.31 (1H, m), 7.40-7.43 (3H, m), 7.60 (1H, br s), 8.14-8.17 (2H, m), 8.27 (1H, br s), 10.43 (1H, br s).

Example 82

4-(3-Phenyl-1,2,4-thiadiazol-5-yl)-N-pyridin-2-ylpiperazine-1-carboxamide (1) 2,2,2-Trichloroethyl pyridin-2-ylcarbamate To a solution of 2-aminopyridine (1.00 g, 10.6 mmol) and pyridine (1.01 ml, 12.7 mmol) in tetrahydrofuran (35 ml) was added, under ice-cooling, 2,2,2-trichloroethyl chloroformate (1.76 ml, 12.7 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 1.77 g (61.6%) of the desired product as a solid was separated by filtration.

$^1$H-NMR (CDCl$_3$) δ; 4.90 (2H, s), 7.02-7.06 (1H, m), 7.72-7.79 (1H, m), 8.05-8.08 (1H, m), 8.54-8.57 (1H, m), 10.76 (1H, br s).

(2) 4-(3-Phenyl-1,2,4-thiadiazol-5-yl)-N-pyridin-2-ylpiperazine-1-carboxamide

A mixed solution of 2,2,2-trichloroethyl pyridin-2-ylcarbamate (270 mg, 0.610 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=3:7) and recrystallized from a mixed solvent of hexane and tetrahydrofuran to give 124 mg (55.4%) of the desired product as a solid.

$^1$H-NMR (CDCl$_3$) δ; 3.69-3.72 (8H, m), 6.96-7.00 (1H, m), 7.39-7.44 (4H, m), 7.64-7.70 (1H, m), 7.99 (1H, d, J=8.1 Hz), 8.16-8.21 (3H, m).

Example 83

4-(3-Phenyl-1,2,4-thiadiazol-5-yl)-N-pyridin-4-ylpiperazine-1-carboxamide (1) 2,2,2-Trichloroethyl pyridin-4-ylcarbamate To a solution of 4-aminopyridine (1.00 g, 10.6 mmol) and pyridine (1.01 ml, 12.7 mmol) in tetrahydrofuran (35 ml) was added, under ice-cooling, 2,2,2-trichloroethyl chloroformate (1.76 ml, 12.7 mmol), and the mixture was stirred at room temperature for 2 hours. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 1.05 g (36.6%) of the desired product as a solid was separated by filtration.

$^1$H-NMR (CDCl$_3$) δ; 4.84 (2H, s), 7.38-7.40 (2H, m), 7.43 (1H, br s), 8.51-8.53 (2H, m).

(2) 4-(3-Phenyl-1,2,4-thiadiazol-5-yl)-N-pyridin-4-ylpiperazine-1-carboxamide A mixed solution of 2,2,2-trichloroethyl pyridin-4-ylcarbamate (271 mg, 0.610 mmol), 1-(3-phenyl-1,2,4-thiadiazol-5-yl)piperazine (200 mg, 0.812 mmol) and diisopropylethylamine (0.129 ml, 0.610 mmol) in dimethyl sulfoxide (2.5 ml) was stirred at 80° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (methanol ethyl acetate=1:1) and recrystallized from a mixed solvent of hexane and tetrahydrofuran to give 98.3 mg (44.1%) of the desired product as a solid.

$^1$H-NMR (CDCl$_3$) δ; 3.73 (8H, s), 6.70 (1H, br s), 7.34 (2H, d, J=6.3 Hz), 7.41-7.43 (3H, m), 8.16-8.19 (2H, m), 8.45 (2H, d, J=5.7 Hz).

Example 84

N-1-Benzothien-3-yl-4-(3-phenyl-1,2,4-thiadiazol-5-yl)piperazine-1-carboxamide To a solution of 1-benzothiophene-3-carboxylic acid (178 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1 hour and half. The resulting mixture was cooled to room temperature, 1-(3-phenyl-1,2,4-thiadiazol-5-yl)piperazine (172 mg, 0.700 mmol) was added thereto, and the mixture was stirred at room temperature for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 99.8 mg (33.8%) of the desired product as a solid.

$^1$H-NMR (CDCl$_3$) δ; 3.71-3.77 (8H, m), 6.73 (1H, br s), 7.37-7.45 (5H, m), 7.53-7.57 (1H, m), 7.67 (1H, s), 7.83-7.86 (1H, m), 8.17-8.20 (2H, m).

Example 85

4-(3-Phenyl-1,2,4-thiadiazol-5-yl)-N-pyridin-3-ylpiperazine-1-carboxamide hydrochloride To a solution of 4-(3-phenyl-1,2,4-thiadiazol-5-yl)-N-pyridin-3-ylpiperazine-1-carboxamide (1.37 g, 3.73 mmol) in tetrahydrofuran (500 ml) was added a solution of 4 N hydrogen chloride in ethyl acetate (100 ml) at room temperature, and the mixture was stirred at room temperature for 5 hours. The solvent was distilled off under reduced pressure, and the residue was recrystallized from a mixed solvent of diethyl ether and methanol to give 1.38 g (92.1%) of the desired product as a solid. mp 204-205° C.

$^1$H-NMR (CDCl$_3$+DMSO-d$_6$) δ; 3.41 (1H, br s), 3.68-3.71 (4H, m), 3.82-3.86 (4H, m), 7.40-7.44 (3H, m), 7.85-7.90 (1H, m), 8.11-8.16 (2H, m), 8.43 (1H, d, J=5.4 Hz), 8.69-8.73 (1H, m), 9.29-9.30 (1H, m), 10.06 (1H, s).

Example 86

N-1H-Indazol-3-yl-4-(3-phenyl-1,2,4-thiadiazol-5-yl)piperazine-1-carboxamide

(1) Bis(2,2,2-trichloroethyl) 1H-indazol-3-ylimidodicarbonate

To a solution of 3-aminoindazole (1.00 g, 7.51 mmol) and pyridine (1.82 ml, 22.5 mmol) in tetrahydrofuran (25 ml) was added, under ice-cooling, 2,2,2-trichloroethyl chloroformate (2.08 ml, 15.0 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 2.16 g (59.5%) of the desired product as a solid was separated by filtration.

$^1$H-NMR (CDCl$_3$) δ; 4.91 (2H, s), 5.14 (2H, s), 7.33-7.39 (1H, m), 7.56-7.61 (1H, m), 8.10 (1H, d, J=8.1 Hz), 8.21 (1H, d, J=8.7 Hz), 10.45 (1H, br s).

(2) N-1H-Indazol-3-yl-4-(3-phenyl-1,2,4-thiadiazol-5-yl)piperazine-1-carboxamide A mixed solution of bis(2,2,2-trichloroethyl) 1H-indazol-3-ylimidodicarbonate (295 mg, 0.61 mmol), 1-(3-phenyl-1,2,4-thiadiazol-5-yl)piperazine (300 mg, 1.22 mmol) and diisopropylethylamine (0.106 ml, 0.610 mmol) in dimethyl sulfoxide (2.5 ml) was stirred at 80° C. for 5 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (100% ethyl acetate, followed by ethyl acetate:methanol=1:1) and recrystallized from a mixed solvent of hexane and tetrahydrofuran to give 30.2 mg (12.2%) of the desired product as a solid.

$^1$H-NMR (CDCl$_3$+DMSO-d$_6$) δ; 3.72 (4H, br s), 3.82 (4H, br s), 7.06 (1H, t, J=6.6 Hz), 7.30 (1H, t, J=6.6 Hz), 7.38-7.49 (4H, m), 7.78 (1H, d, J=8.1 Hz), 8.16-8.19 (2H, m), 8.75 (1H, br s), 11.76 (1H, br s).

Example 87

N-[3-(Hydroxymethyl)phenyl]-4-(3-phenyl-1,2,4-thiadiazol-5-yl)piperazine-1-carboxamide Under a nitrogen gas stream, to a solution of methyl 3-({[4-(3-phenyl-1,2,4-thiadiazol-5-yl)piperazin-1-yl]carbonyl}amino)benzoate (300 mg, 0.710 mmol) in tetrahydrofuran (7.0 ml) was added, under ice-cooling, a 1.5 M solution of diisobutylaluminum hydride in toluene (4.7 ml, 7.10 mmol), and the mixture was stirred at room temperature for 2 hours. An aqueous saturated ammonium chloride solution was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 42 mg (15.0%) of the desired product as a solid.

$^1$H-NMR (CDCl$_3$+DMSO-d$_6$) δ; 3.66-3.74 (8H, m), 4.53 (2H, d, J=6.0 Hz), 4.95 (1H, t, J=6.0 Hz), 6.95 (1H, d, J=7.5

Hz), 7.19 (1H, t, J=7.5 Hz), 7.39 (1H, d, J=7.5 Hz), 7.40-7.46 (3H, m), 7.46 (1H, s), 8.14-8.17 (2H, m), 8.58 (1H, br s).

Example 88

N-Isoxazol-3-yl-4-(3-phenyl-1,2,4-thiadiazol-5-yl)piperazine-1-carboxamide (1) 2,2,2-Trichloroethyl isoxazol-3-ylcarbamate To a solution of 3-aminoisoxazole (0.878 ml, 11.9 mmol) and pyridine (1.13 ml, 14.3 mmol) in tetrahydrofuran (30 ml) was added, under ice-cooling, 2,2,2-trichloroethyl chloroformate (1.97 ml, 14.3 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate:hexane=1:1) to give 2.91 g (94.1%) of the desired product as a solid.
$^1$H-NMR (CDCl$_3$) δ; 4.85 (2H, s), 6.91 (1H, br s), 8.29 (1H, d, J=2.1 Hz), 8.59 (1H, br s).

(2) N-Isoxazol-3-yl-4-(3-phenyl-1,2,4-thiadiazol-5-yl)piperazine-1-carboxamide

A mixed solution of 2,2,2-trichloroethyl isoxazol-3-ylcarbamate (192 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate:hexane=1:1) and recrystallized from a mixed solvent of hexane and tetrahydrofuran to give 49.5 mg (18.8%) of the desired product as a solid.
$^1$H NMR (CDCl$_3$) δ; 3.72-3.83 (8H, m), 7.05 (1H, d, J=1.5 Hz), 7.43-7.45 (3H, m), 8.19-8.22 (2H, m), 8.29 (1H, d, J=1.5 Hz), 9.05 (1H, br s).

Example 89

N-(3-Hydroxyphenyl)-4-(3-phenyl-1,2,4-thiadiazol-5-yl)piperazine-1-carboxamide

To a solution of 3-({[4-(3-phenyl-1,2,4-thiadiazol-5-yl)piperazin-1-yl]carbonyl}amino)phenyl acetate (635 mg, 1.50 mmol) in methanol/tetrahydrofuran (2:1) (60 ml) was added an aqueous 1 N sodium hydroxide solution (1.5 ml), and the mixture was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 360 mg (62.9%) of the desired product as a solid.
$^1$H-NMR (CDCl$_3$+DMSO-d$_6$) δ; 3.66-3.71 (8H, m), 6.37-6.40 (1H, m), 6.86-6.89 (1H, m), 6.99 (1H, t, J=7.8 Hz), 7.04 (1H, m), 7.42-7.44 (3H, m), 8.13-8.16 (2H, m), 8.50 (1H, s), 9.04 (1H, s).

Example 90

N-(2-Methoxypyridin-3-yl)-4-(3-phenyl-1,2,4-thiadiazol-5-yl)piperazine-1-carboxamide To a solution of 2-methoxynicotinic acid (153 mg, 1.00 mmol) and triethylamine (0.293 ml, 2.10 mmol) in toluene (10 ml) was added diphenylphosphoryl azide (0.226 ml, 1.05 mmol) at room temperature, and the mixture was stirred at room temperature for 30 minutes, followed by elevating the temperature to 90° C. and stirring for 1 hour and half. The resulting mixture was cooled to room temperature, 1-(3-phenyl-1,2,4-thiadiazol-5-yl)piperazine (172 mg, 0.70 mmol) was added thereto, and the mixture was stirred at room temperature for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 60.2 mg (21.7%) of the desired product as a solid.
$^1$H-NMR (CDCl$_3$) δ; 3.73 (8H, s), 4.04 (3H, s), 6.88-6.93 (1H, m), 7.03 (1H, br s), 7.42-7.46 (3H, m), 7.80-7.82 (1H, m), 8.18-8.21 (2H, m), 8.36-8.39 (1H, m).

Example 91

N-1,3-Benzothiazol-6-yl-4-(3-phenyl-1,2,4-thiadiazol-5-yl)piperazine-1-carboxamide (1) 2,2,2-Trichloroethyl 1,3-benzothiazol-6-ylcarbamate To a solution of 6-amino-1,3-benzothiazole (1.00 g, 6.66 mmol) and pyridine (0.633 ml, 7.99 mmol) in tetrahydrofuran (22 ml) was added, under ice-cooling, 2,2,2-trichloroethyl chloroformate (1.11 ml, 7.99 mmol), and the mixture was stirred at room temperature for 1.5 hour. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 1.45 g (66.7%) of the desired product as a solid was separated by filtration.
$^1$H-NMR (CDCl$_3$) δ; 4.87 (2H, s), 7.11 (1H, br s), 7.35 (1H, dd, J=2.1, 8.7 Hz), 8.08 (1H, d, J=9.0 Hz), 8.34 (1H, br s), 8.93 (1H, s).

(2) N-1,3-Benzothiazol-6-yl-4-(3-phenyl-1,2,4-thiadiazol-5-yl)piperazine-1-carboxamide A mixed solution of 2,2,2-trichloroethyl 1,3-benzothiazol-6-ylcarbamate (240 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 80° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate:hexane=1:1) and recrystallized from a mixed solvent of hexane and ethyl acetate to give 63.2 mg (20.3%) of the desired product as a solid.

¹H-NMR (CDCl₃) δ; 3.73 (8H, s), 6.34 (1H, br s), 7.25-7.29 (1H, m), 7.42-7.45 (3H, m), 8.03 (1H, d, J=9.0 Hz), 8.17-8.20 (2H, m), 8.27-8.28 (1H, m), 8.89 (1H, s).
The structural formulae of Compounds obtained in Examples 25 to 91 are shown in Table 3.
TABLE 3
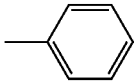
| Example No. | R |
|---|---|
| 25 |  |
| 26 | 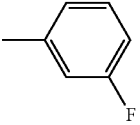 |
| 27 | 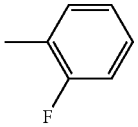 |
| 28 |  |
| 29 | 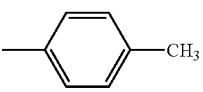 |
| 30 | 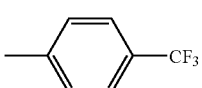 |
| 31 | 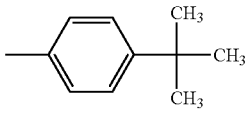 |
| 32 | 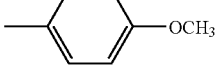 |
| 33 | 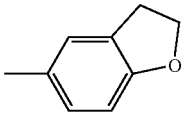 |
| 34 | 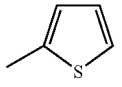 |
| 35 | 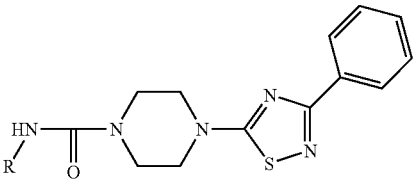 |
TABLE 3-continued
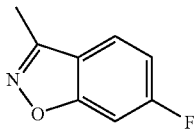
| Example No. | R |
|---|---|
| 36 | 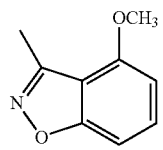 |
| 37 | 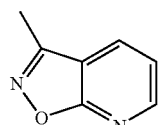 |
| 38 | 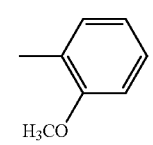 |
| 39 | 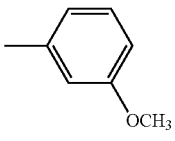 |
| 40 | 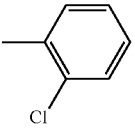 |
| 41 | 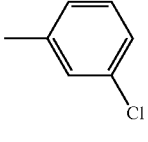 |
| 42 | 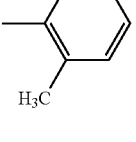 |
| 43 | 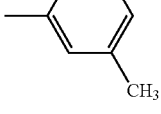 |
| 44 | |

TABLE 3-continued
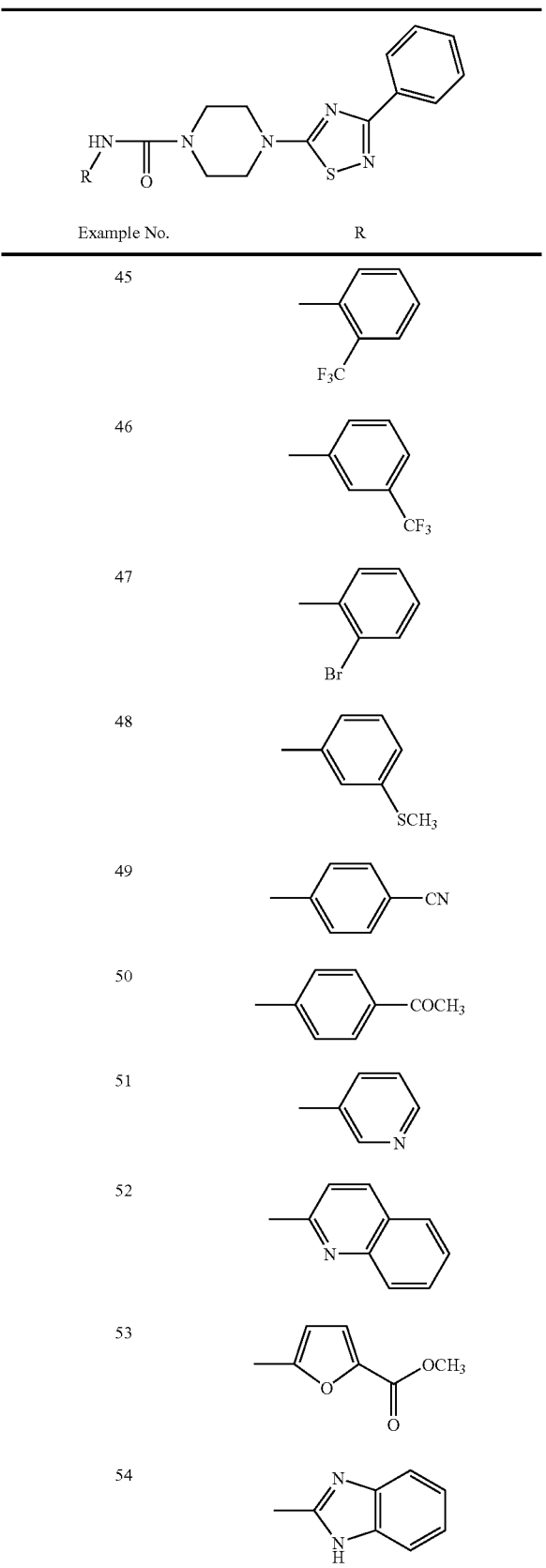
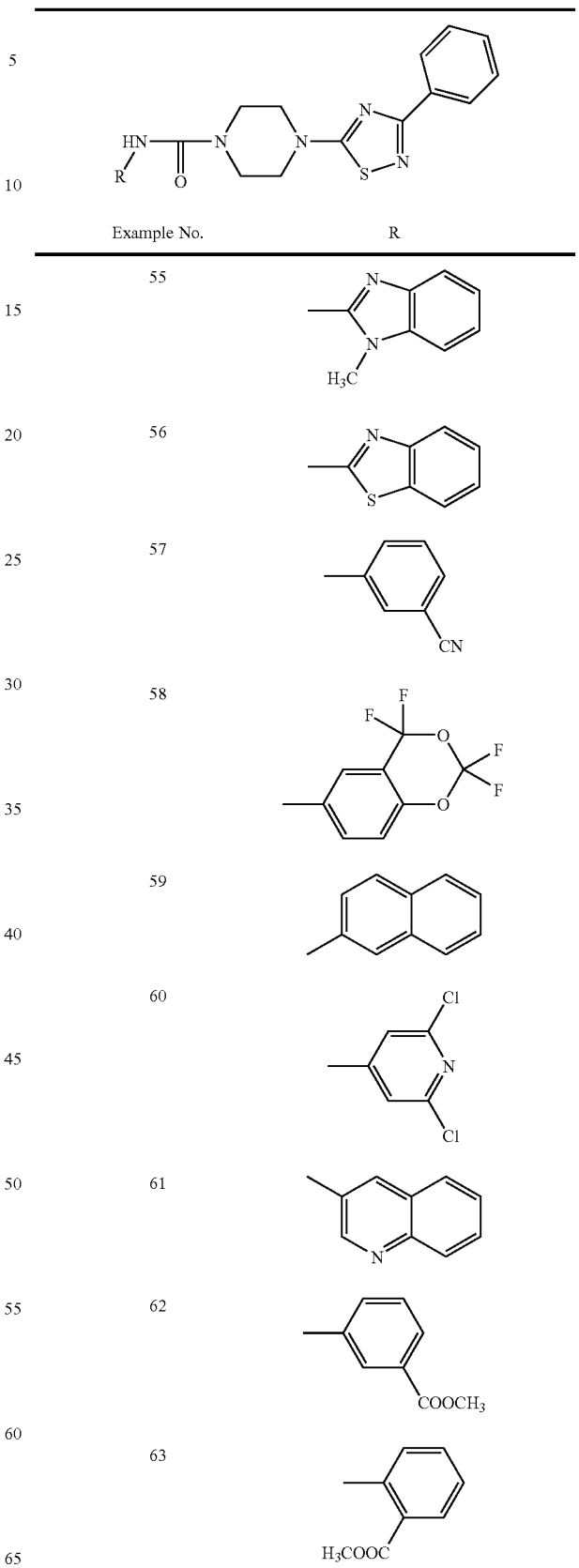

TABLE 3-continued

[Structure: R-NH-C(=O)-N(piperazine)-N-[1,3,4-thiadiazole with 3-phenyl substituent]]

| Example No. | R |
|---|---|
| 64 | 3,4-dimethoxyphenyl (—OCH₃, —OCH₃) |
| 65 | 3-thienyl |
| 66 | 5-methyl-2-(pyridin-3-yl)-1,3,4-oxadiazole |
| 67 | 5-methyl-2-ethyl-1,3,4-oxadiazole (CH₂CH₃) |
| 68 | 3-(trifluoromethoxy)phenyl (OCF₃) |
| 69 | 3-(difluoromethoxy)phenyl (OCF₂H) |
| 70 | 3-(OCF₂CF₂H)phenyl |
| 71 | 1H-benzotriazol-5-yl |
| 72 | 1,3-benzodioxol-5-yl |
| 73 | 2,3-dihydro-1,4-benzodioxin-6-yl |
| 74 | 3-(N,N-dimethylamino)phenyl |
| 75 | 3-methyl-1H-indol-? |
| 76 | 4-methylisoquinolinyl |
| 77 | 5-chloro-2-methylbenzoxazol-? |
| 78 | 1,3-dimethyl-1H-indol-? |
| 79 | 3-(acetyloxy)phenyl (OCOCH₃) |
| 80 | 5-methyl-2-morpholino-1,3,4-oxadiazole |
| 81 | 5-methyl-1H-indol-? |
| 82 | 2-methylpyridin-? |

TABLE 3-continued

[Structure: HN(R)-C(=O)-N(piperazine)-N-[1,2,4-thiadiazol-5-yl with 3-phenyl substituent]]

| Example No. | R |
|---|---|
| 83 | 4-methylpyridin-yl (pyridine with methyl) |
| 84 | 3-methylbenzothiophen-yl |
| 85 | 3-methylpyridin-yl · HCl |
| 86 | 3-methyl-1H-indazol-yl |
| 87 | 3-methylbenzyl alcohol (methylphenyl-CH₂OH) |
| 88 | 3-methylisoxazol-yl |
| 89 | 3-methylphenol (methylphenyl-OH) |
| 90 | 3-methyl-2-methoxypyridinyl (H₃CO) |
| 91 | methylbenzothiazol-yl |

Example 92

N-Pyridin-3-yl-4-(3-pyridin-2-yl-1,2,4-thiadiazol-5-yl)piperazine-1-carboxamide (1) 1-(3-Pyridin-2-yl-1,2,4-thiadiazol-5-yl)piperazine To a solution of 2-(5-chloro-1,2,4-thiadiazol-3-yl)pyridine (3.96 g, 20.0 mmol) and 1-tert-butoxycarbonyl-piperazine (3.73 g, 20.0 mmol) in dimethylformamide (40 ml) was added triethylamine (11.2 ml, 80.0 mmol), and the mixture was stirred at room temperature for 1 hour. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give 6.35 g (91.2%) of tert-butyl 4-(3-pyridin-2-yl-1,2,4-thiadiazol-5-yl)piperazine-1-carboxylate as a solid.

tert-Butyl 4-(3-pyridin-2-yl-1,2,4-thiadiazol-5-yl)piperazine-1-carboxylate (6.35 g, 17.0 mmol) was dissolved in tetrahydrofuran (100 ml), and a solution of 4 N hydrogen chloride in ethyl acetate (50 ml) was added thereto, followed by stirring at room temperature for 5 hours. Hexane (250 ml) was poured to the reaction mixture, and a solid was separated by filtration. The obtained solid was dissolved in an aqueous saturated sodium hydrogen carbonate solution, followed by stirring at room temperature for 2 hours. Water was poured to the reaction mixture, and the resulting solution was extracted with a mixed solution of ethyl acetate/tetrahydrofuran (1:1). The extract was washed with water and dried over anhydrous magnesium sulfate, and the solvent was distilled off under reduced pressure. Hexane was added to the residue, and 2.79 g (67.0%) of the desired product as a solid was separated by filtration.

$^1$H-NMR (CDCl$_3$) δ; 2.98-3.04 (4H, m), 3.58-3.64 (4H, m), 7.29-7.36 (1H, m), 7.74-7.83 (1H, m), 8.22 (1H, d, J=8.0 Hz), 8.73-8.76 (1H, m).

(2) N-Pyridin-3-yl-4-(3-pyridin-2-yl-1,2,4-thiadiazol-5-yl)piperazine-1-carboxamide A mixed solution of 2,2,2-trichloroethyl pyridin-3-ylcarbamate (297 mg, 1.10 mmol), 1-(3-pyridin-2-yl-1,2,4-thiadiazol-5-yl)piperazine (300 mg, 1.21 mmol) and diisopropylethylamine (0.211 ml, 1.21 mmol) in dimethyl sulfoxide (2.5 ml) was stirred at 80° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate:hexane=1:1, followed by ethyl acetate:methanol=9:1) and recrystallized from a mixed solvent of hexane and tetrahydrofuran to give 156 mg (38.5%) of the desired product as a solid.

$^1$H-NMR (CDCl$_3$) δ; 3.64-3.77 (8H, m), 7.20-7.25 (1H, m), 7.33-7.38 (1H, m), 7.79-7.85 (1H, m), 7.95-7.99 (2H, m), 8.24-8.27 (2H, m), 8.49-8.50 (1H, m), 8.69-8.71 (1H, m).

Example 93

4-[3-(3-Furyl)-1,2,4-thiadiazol-5-yl]-N-pyridin-3-ylpiperazine-1-carboxamide (1) 1-[3-(3-Furyl)-1,2,4-thiadiazol-5-yl]piperazine To a solution of 5-chloro-3-(3-furyl)-1,2,4-thiadiazole (2.98 g, 16.0 mmol) and 1-(tert-butoxycarbonyl)-piperazine (2.97 g, 16.0 mmol) in dimethylformamide (30 ml) was added triethylamine (8.9 ml, 63.9 mmol), and the mixture was stirred at room temperature for 1 hour. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give 3.30 g (61.4%) of tert-butyl 4-[3-(3-furyl)-1,2,4-thiadiazol-5-yl]piperazine-1-carboxylate as a solid.

tert-Butyl 4-[3-(3-furyl)-1,2,4-thiadiazol-5-yl]piperazine-1-carboxylate (3.30 g, 9.81 mmol) was dissolved in ethyl acetate (50 ml), and a solution of 4 N hydrogen chloride in ethyl acetate (25 ml) was added thereto, followed by stirring at room temperature for 18 hours. Hexane (120 ml) was poured to the reaction mixture, and a solid was separated by filtration. The obtained solid was dissolved in an aqueous saturated sodium hydrogen carbonate solution, followed by stirring at room temperature for 2 hours. Water was poured to the reaction mixture, and the resulting solution was extracted with a mixed solution of ethyl acetate/tetrahydrofuran (1:1). The extract was washed with water and dried over anhydrous magnesium sulfate, and the solvent was distilled off under reduced pressure. Hexane was added to the residue, and 1.30 g (56.0%) of the desired product as a solid was separated by filtration.

$^1$H-NMR (CDCl$_3$) δ; 2.98-3.01 (4H, m), 3.52-3.56 (4H, m), 6.90 (1H, br s), 7.42 (1H, br s), 8.01 (1H, br s).

(2) 4-[3-(3-Furyl)-1,2,4-thiadiazol-5-yl]-N-pyridin-3-ylpiperazine-1-carboxamide A mixed solution of 2,2,2-trichloroethyl pyridin-3-ylcarbamate (311 mg, 1.15 mmol), 1-[3-(3-furyl)-1,2,4-thiadiazol-5-yl]piperazine (300 mg, 1.27 mmol) and diisopropylethylamine (0.221 ml, 1.27 mmol) in dimethyl sulfoxide (3.8 ml) was stirred at 80° C. for 1 hour and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 117 mg (28.3%) of the desired product as a solid.

$^1$H-NMR (CDCl$_3$+DMSO-d$_6$) δ; 3.63-3.66 (4H, m), 3.74-3.78 (4H, m), 6.91-6.92 (1H, m), 7.21-7.25 (1H, m), 7.45-7.47 (1H, m), 7.99-8.04 (2H, m), 8.24-8.26 (1H, m), 8.44 (1H, br s), 8.62 (1H, br s).

Example 94

4-(4-Phenyl-1,3-thiazol-2-yl)-N-pyridin-3-ylpiperazine-1-carboxamide

(1) 1-(4-Phenyl-1,3-thiazol-2-yl)piperazine

A solution of 2-chloro-4-phenyl-1,3-thiazole (1.54 mg, 7.87 mmol), 1-(tert-butoxycarbonyl)-piperazine (4.40 g, 23.6 mmol) and potassium carbonate (1.09 g, 7.87 mmol) in dimethylformamide (26 ml) was stirred at 120° C. for 2 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give 691 mg (25.4%) of tert-butyl 4-(4-phenyl-1,3-thiazol-2-yl)piperazine-1-carboxylate as a solid.

tert-Butyl 4-(4-phenyl-1,3-thiazol-2-yl)piperazine-1-carboxylate (691 mg, 2.00 mmol) was dissolved in ethyl acetate (50 ml), and a solution of 4 N hydrogen chloride in ethyl acetate (11 ml) was added thereto, followed by stirring at room temperature for 1 hour and half. Diethyl ether (20 ml) was poured to the reaction mixture, and a solid was separated by filtration, which was dissolved in an aqueous 1 N sodium hydroxide solution (7 ml). Water was poured to the reaction mixture, and the resulting solution was extracted with chloroform. The extract was washed with water and dried over anhydrous magnesium sulfate. The solvent was distilled off under reduced pressure to give 396 mg (80.8%) of the desired product as an oil.

$^1$H-NMR (CDCl$_3$) δ; 2.99-3.03 (4H, m), 3.51-3.54 (4H, m), 6.76 (1H, s), 7.25-7.28 (1H, m), 7.36 (2H, t, J=7.8 Hz), 7.81-7.84 (2H, m).

(2) 4-(4-Phenyl-1,3-thiazol-2-yl)-N-pyridin-3-ylpiperazine-1-carboxamide

A mixed solution of bis(2,2,2-trichloroethyl)pyridin-3-ylimidodicarbonate (359 mg, 0.810 mmol), 1-(4-phenyl-1,3-thiazol-2-yl)piperazine (396 mg, 1.62 mmol) and diisopropylethylamine (0.281 ml, 1.62 mmol) in dimethyl sulfoxide (2.7 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (100% ethyl acetate) and recrystallized from a mixed solvent of hexane and tetrahydrofuran to give 82.0 mg (27.8%) of the desired product as a solid. mp 74-75° C.

$^1$H-NMR (CDCl$_3$) δ; 3.63-3.73 (8H, m), 6.65 (1H, br s), 6.83 (1H, s), 7.24-7.41 (4H, m), 7.82-7.85 (2H, m), 7.97-8.01 (1H, m), 8.29-8.31 (1H, m), 8.46-8.47 (1H, m).

The structural formulae of Compound obtained in Examples 92 to 94 are shown in Table 4.

TABLE 4

| Example No. | R |
|---|---|
| 92 | 3-(2-pyridyl)-5-methyl-1,2,4-thiadiazol-3-yl |
| 93 | 3-(3-furyl)-5-methyl-1,2,4-thiadiazol-3-yl |

TABLE 4-continued

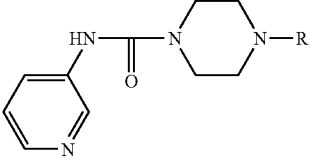

| Example No. | R |
|---|---|
| 94 | 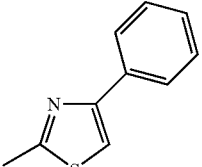 |

Example 95

Benzyl 4-[(1,2-benzisoxazol-3-ylamino)carbonyl]piperazine-1-carboxylate

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added benzyl chloroformate (0.120 ml, 0.833 mmol) under ice-cooling, and the mixture was stirred at room temperature for 2 hours. The reaction mixture was poured to water and extracted with ethyl acetate. The extract was washed with water and dried over anhydrous magnesium sulfate, and the solvent was distilled off under reduced pressure. The residue was recrystallized from a mixed solvent of hexane and ethyl acetate to yield 152 mg (72.0%) of the desired product. mp 137-138° C.

$^1$H-NMR (CDCl$_3$) δ; 3.66 (8H, br s), 5.18 (2H, s), 7.27-7.40 (6H, m), 7.46 (1H, d, J=8.4 Hz), 7.52-7.58 (1H, m), 8.05 (1H, d, J=8.7 Hz), 8.72 (1H, s).

Example 96

3-Fluorobenzyl 4-[(1,2-benzisoxazol-3-ylamino)carbonyl]piperazine-1-carboxylate

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added 3-fluorobenzyl chloroformate (157 mg, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of hexane and ethyl acetate to give 132 mg (59.7%) of the desired product as a solid.

$^1$H-NMR (CDCl$_3$) δ; 3.66 (8H, br s), 5.16 (2H, s), 6.99-7.15 (3H, m), 7.25-7.37 (2H, m), 7.45-7.57 (2H, m), 8.03 (1H, d, J=8.1 Hz), 8.90 (1H, s).

Example 97

Isopropyl 4-[(1,2-benzisoxazol-3-ylamino)carbonyl]piperazine-1-carboxylate

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added isopropyl chloroformate (0.102 ml, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of hexane and ethyl acetate to give 90.0 mg (48.9%) of the desired product as a solid.

$^1$H-NMR (CDCl$_3$) δ; 1.28 (6H, d, J=6.3 Hz), 3.62-3.67 (8H, m), 4.92-5.01 (1H, m), 7.26-7.32 (1H, m), 7.47 (1H, d, J=8.4 Hz), 7.49-7.57 (1H, m), 8.04 (1H, d, J=9.3 Hz), 8.59 (1H, s).

Example 98

Isobutyl 4-[(1,2-benzisoxazol-3-ylamino)carbonyl]piperazine-1-carboxylate

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added isobutyl chloroformate (0.108 ml, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of hexane and ethyl acetate to give 95.0 mg (49.5%) of the desired product as a solid.

$^1$H-NMR (CDCl$_3$) δ; 0.96 (6H, d, J=6.6 Hz), 1.93-2.02 (1H, m), 3.65-3.66 (8H, m), 3.92 (2H, d, J=6.6 Hz), 7.26-7.33 (1H, m), 7.48 (1H, d, J=8.4 Hz), 7.53-7.59 (1H, m), 8.05 (1H, d, J=7.5 Hz), 8.61 (1H, s).

Example 99

Cyclopentyl 4-[(1,2-benzisoxazol-3-ylamino)carbonyl]piperazine-1-carboxylate

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added cyclopentyl chloroformate (124 mg, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of hexane and ethyl acetate to give 135 mg (67.8%) of the desired product as a solid.

$^1$H-NMR (CDCl$_3$) δ; 1.59-1.90 (8H, m), 3.60-3.65 (8H, m), 5.14-5.18 (1H, m), 7.27-7.33 (1H, m), 7.47-7.58 (2H, m), 8.05 (1H, d, J=8.1 Hz), 8.68 (1H, s).

Example 100

N-1,2-Benzisoxazol-3-yl-4-benzoylpiperazine-1-carboxamide

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added benzoyl chloride (0.0970 ml, 0.833 mmol) under ice-cooling, and the mixture was stirred at room temperature for 3 hours. The reaction mixture was poured to water and extracted with ethyl acetate. The extract was washed with water, and the solvent was distilled off under reduced pressure. The residue was recrystallized from a mixed solvent of hexane and ethyl acetate to give 134 mg (69.0%) of the desired product as a solid.

¹H-NMR (CDCl₃) δ; 3.60-3.95 (8H, m), 7.28-7.33 (1H, m), 7.43-7.48 (6H, m), 7.53-7.59 (1H, m), 8.03 (1H, d, J=8.4 Hz), 8.92 (1H, s).

Example 101

N-1,2-Benzisoxazol-3-yl-4-(pyridin-2-ylcarbonyl)piperazine-1-carboxamide

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added picolinoyl chloride hydrochloride (148 mg, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of hexane and ethyl acetate to give 53.0 mg (27.2%) of the desired product as a solid.

¹H-NMR (CDCl₃) δ; 3.73 (2H, br s), 3.82 (4H, br s), 3.95 (2H, br s), 7.26-7.55 (4H, m), 7.74 (1H, d, J=7.8 Hz), 7.82-7.87 (1H, m), 8.06 (1H, d, J=8.4 Hz), 8.61-8.63 (2H, m).

Example 102

N-1,2-Benzisoxazol-3-yl-4-(2-furoyl)piperazine-1-carboxamide

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added 2-furoyl chloride (0.0821 ml, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of hexane and ethyl acetate to give 100 mg (52.9%) of the desired product as a solid.

¹H-NMR (CDCl₃) δ; 2.17-2.22 (4H, m), 2.35-2.38 (4H, m), 4.92-4.95 (1H, m), 5.49-5.51 (1H, m), 5.68-5.75 (1H, m), 5.86-6.01 (3H, m), 6.47 (1H, d, J=8.0 Hz), 7.32 (1H, s).

Example 103

N-1,2-Benzisoxazol-3-yl-4-(3-phenylpropanoyl)piperazine-1-carboxamide

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added 3-phenylpropionyl chloride (0.124 ml, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of hexane and ethyl acetate to give 142 mg (67.6%) of the desired product as a solid.

¹H-NMR (CDCl₃) δ; 2.69 (2H, t, J=8.2 Hz), 3.02 (2H, t, J=8.2 Hz), 3.50 (4H, br s), 3.63-3.66 (2H, m), 3.76-3.78 (2H, m), 7.20-7.33 (6H, m), 7.48 (1H, d, J=8.4 Hz), 7.53-7.59 (1H, m), 8.03 (1H, d, J=8.4 Hz), 8.70 (1H, s).

Example 104

N-1,2-Benzisoxazol-3-yl-4-(cyclohexylcarbonyl)piperazine-1-carboxamide

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added cyclohexanecarbonyl chloride (0.111 ml, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of hexane and ethyl acetate to give 160 mg (80.8%) of the desired product as a solid.

¹H-NMR (CDCl₃) δ; 1.24-1.83 (10H, m), 2.47-2.54 (1H, m), 3.69-3.76 (8H, m), 7.28-7.33 (1H, m), 7.48 (1H, d, J=8.1 Hz), 7.54-7.59 (1H, m), 8.05 (1H, d, J=8.4 Hz), 8.71 (1H, s).

Example 105

N-1,2-Benzisoxazol-3-yl-N'-benzylpiperazine-1,4-dicarboxamide

To a solution of N-1,2-benzisoxazol-3-ylpiperazine-1-carboxamide trifluoroacetate (200 mg, 0.555 mmol) and triethylamine (0.309 ml, 2.22 mmol) in tetrahydrofuran (4 ml) was added benzyl isocyanate (0.103 ml, 0.833 mmol) under ice-cooling, and the mixture was stirred at room temperature for 1 hour. The reaction mixture was poured to water and extracted with ethyl acetate. The extract was washed with water, and the solvent was distilled off under reduced pressure. The residue was recrystallized from a mixed solvent of tetrahydrofuran and ethyl acetate to give 157 mg (74.8%) of the desired product as a solid.

¹H-NMR (CDCl₃) δ; 3.41-3.53 (8H, m), 4.23-4.28 (3H, m), 7.11-7.33 (6H, m), 7.59-7.62 (2H, m), 8.13 (1H, d, J=8.2 Hz), 9.91 (1H, s).

The structural formulae of Compounds obtained in Examples 95 to 105 are shown in Table 5.

TABLE 5

| Example No. | R |
|---|---|
| 95 | benzyl-O- (−OCH₂C₆H₅) |

TABLE 5-continued

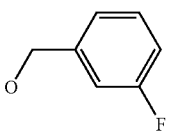

| Example No. | R |
|---|---|
| 96 | 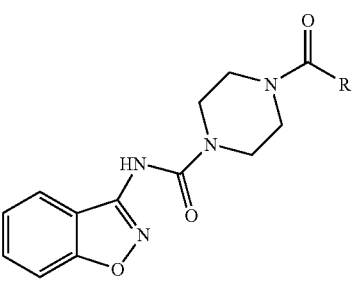 |
| 97 | OCH(CH₃)₂ |
| 98 | OCH₂CH(CH₃)₂ |
| 99 | 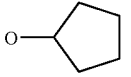 |
| 100 | 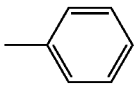 |
| 101 | 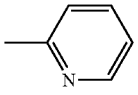 |
| 102 | 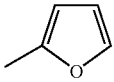 |
| 103 | 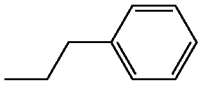 |
| 104 | 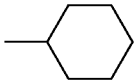 |
| 105 | 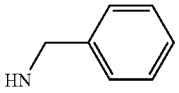 |

Example 106

N-1,2-Benzisoxazol-3-yl-4-(3-phenyl-1,2,4-thiadiazol-5-yl)piperazine-1-carboxamide hydrochloride

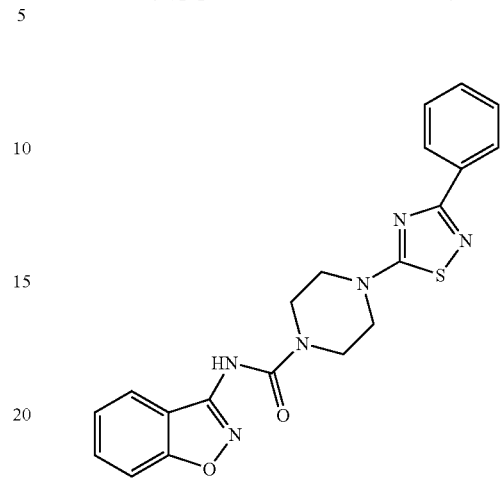

To a solution of N-1,2-benzisoxazol-3-yl-4-(3-phenyl-1,2,4-thiadiazol-5-yl)piperazine-1-carboxamide (2.00 g, 4.92 mmol) in tetrahydrofuran (500 ml) was added a solution of 4 N hydrogen chloride in ethyl acetate (100 ml), and the mixture was stirred at room temperature for 5 hours and concentrated. Diethyl ether was added to the residue, and the desired product as a solid was separated by filtration.

Yield: 2.00 g (91.7%).

Elementary Analysis Calculated for ($C_{20}H_{19}N_6O_2SCl$): C, 54.23; H, 4.32; N, 18.97; Cl, 8.00.

Found: C, 54.35; H, 4.48; N, 18.69; Cl, 7.99.

Example 107 tert-Butyl [1-(5-{4-[(1,2-benzisoxazol-3-ylamino)carbonyl]piperazin-1-yl}-1,2,4-thiadiazol-3-yl)piperidin-4-yl]carbamate (1) tert-Butyl {1-[amino(imino)methyl]piperidin-4-yl}carbamate hydrochloride To a solution of 4-(N-tert-butoxycarbonylamino)piperidine (5.00 g, 25.0 mmol) and 1H-pyrazole-1-carboximidamide (3.66 g, 25.0 mmol) in acetonitrile (30 ml) was added triethylamine (3.48 ml, 25.0 mmol), and the mixture was stirred at 60° C. for 12 hours. After the reaction mixture was cooled to room temperature, a crystal was separated by filtration and washed with acetonitrile and diethyl ether to yield 6.31 g (90.4%) of the desired product.

¹H-NMR (DMSO-d₆) δ; 1.27-1.38 (11H, m), 1.75-1.78 (2H, m), 3.03-3.10 (2H, m), 3.51 (1H, br s), 3.75-3.79 (2H, m), 6.93 (1H, d, J=7.2 Hz), 7.50 (4H, br s).

(2) tert-Butyl [1-(5-chloro-1,2,4-thiadiazol-3-yl)piperidin-4-yl]carbamate

To a solution of tert-butyl {1-[amino(imino)methyl]piperidin-4-yl}carbamate hydrochloride (1.50 g, 5.38 mmol) and perchloromethyl mercaptan (0.578 ml, 5.38 mmol) in dichloromethane (20 ml) was added dropwise a solution of sodium hydroxide (0.861 g, 21.5 mmol) in water (2.5 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=4:1) to give 590 mg (34.3%) of the desired product as a solid.

$^1$H-NMR (CDCl$_3$) δ; 1.35-1.45 (11H, m), 2.00-2.04 (2H, m), 3.06-3.16 (2H, m), 3.66 (1H, br s), 4.27-4.31 (2H, m), 4.45 (1H, br s).

(3) tert-Butyl [1-(5-{4-[(1,2-benzisoxazol-3-ylamino)carbonyl]piperazin-1-yl}-1,2,4-thiadiazol-3-yl)piperidin-4-yl]carbamate To a solution of tert-butyl [1-(5-chloro-1,2,4-thiadiazol-3-yl)piperidin-4-yl]carbamate (442 mg, 1.39 mmol) and N-1,2-benzisoxazol-3-ylpiperazine-1-carboxamide trifluoroacetate (500 mg, 1.39 mmol) in dimethylformamide (5 ml) was added triethylamine (0.969 ml, 6.95 mmol) at room temperature, and the mixture was stirred at room temperature for 30 minutes. The reaction mixture was poured to water, and a solid was separated by filtration, which was recrystallized from a mixed solvent of ethyl acetate and tetrahydrofuran to give 335 mg (45.6%) of the desired product as a solid.

$^1$H-NMR (DMSO-d$_6$) δ; 1.30-1.38 (11H, m), 1.71-1.75 (2H, m), 2.87-2.95 (2H, m), 3.49 (5H, br s), 3.66 (4H, br s), 4.11-4.15 (2H, m), 6.82 (1H, d, J=8.7 Hz), 7.27-7.32 (1H, m), 7.56-7.64 (2H, m), 7.83 (1H, d, J=7.2 Hz), 10.05 (1H, s).

Example 108

4-[3-(4-Aminopiperidin-1-yl)-1,2,4-thiadiazol-5-yl]-N-1,2-benzisoxazol-3-ylpiperazine-1-carboxamide dihydrochloride To a solution of tert-butyl [1-(5-{4-[(1,2-benzisoxazol-3-ylamino)carbonyl]piperazin-1-yl}-1,2,4-thiadiazol-3-yl)piperidin-4-yl]carbamate (200 mg, 0.378 mmol) in tetrahydrofuran (10 ml) and methanol (10 ml) was added a solution of 4 N hydrogen chloride in ethyl acetate (10 ml), and the mixture was stirred at room temperature for 5 hours. The solvent was distilled off under reduced pressure, and the residue was recrystallized from a mixed solvent of methanol and diethyl ether to give 181 mg (95.5%) of the desired product as a solid.

$^1$H-NMR (DMSO-d$_6$) δ; 1.45-1.55 (2H, m), 1.91-1.95 (2H, m), 2.88-2.97 (2H, m), 3.20 (1H, br s), 3.51 (4H, br s), 3.68 (4H, br s), 4.14 (1H, br s), 4.21-4.25 (2H, m), 7.28-7.33 (1H, m), 7.57-7.65 (2H, m), 7.84 (1H, d, J=7.8 Hz), 8.14 (3H, br s), 10.08 (1H, s).

Example 109

N-1,2-Benzisoxazol-3-yl-4-(3-pyrrolidin-1-yl-1,2,4-thiadiazol-5-yl)piperazine-1-carboxamide (1) Pyrrolidine-1-carboximidamide hydrochloride To a solution of pyrrolidine (5.00 g, 70.3 mmol) and 1H-pyrazole-1-carboximidamide (10.3 g, 70.3 mmol) in acetonitrile (30 ml) was added triethylamine (9.79 ml, 70.3 mmol), and the mixture was stirred at 60° C. for 12 hours. After cooling to room temperature, a solid was separated by filtration and washed with acetonitrile and diethyl ether to give 7.36 g (70.1%) of the desired product.

$^1$H-NMR (DMSO-d$_6$) δ 1.87-1.92 (4H, m), 3.29-3.34 (4H, m), 7.30 (4H, br s).

(2) 5-Chloro-3-pyrrolidin-1-yl-1,2,4-thiadiazole

To a solution of pyrrolidine-1-carboximidamide hydrochloride (1.50 g, 10.0 mmol) and perchloromethyl mercaptan (1.08 ml, 10.0 mmol) in dichloromethane (20 ml) was added dropwise a solution of sodium hydroxide (1.60 g, 40.0 mmol) in water (4 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=4:1) to give 590 mg (31.0%) of the desired product as an oil.

$^1$H-NMR (CDCl$_3$) δ; 1.96-2.01 (4H, m), 3.55-3.60 (4H, m).

(3) N-1,2-Benzisoxazol-3-yl-4-(3-pyrrolidin-1-yl-1,2,4-thiadiazol-5-yl)piperazine-1-carboxamide To a solution of 5-chloro-3-pyrrolidin-1-yl-1,2,4-thiadiazole (158 mg, 0.833 mmol) and N-1,2-benzisoxazol-3-ylpiperazine-1-carboxamide trifluoroacetate (300 mg, 0.833 mmol) in N,N-dimethylformamide (3 ml) was added triethylamine (0.581 ml, 4.17 mmol) at room temperature, and the mixture was stirred at room temperature for 30 minutes. The reaction mixture was poured to water and extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give the desired product as a solid. The resulting solid was recrystallized from a mixed solvent of hexane and ethyl acetate to give 28.5 mg (8.58%) of the desired product.

$^1$H-NMR (DMSO-d$_6$) δ; 1.94-1.98 (4H, m), 3.52-3.64 (8H, m), 3.80-3.84 (4H, m), 7.26-7.35 (1H, m), 7.46-7.60 (2H, m), 8.05 (1H, d, J=7.8 Hz), 9.22 (1H, s).

Example 110

N-1,2-Benzisoxazol-3-yl-4-[3-(4-hydroxypiperidin-1-yl)-1,2,4-thiadiazol-5-yl]piperazine-1-carboxamide (1) 4-Hydroxypiperidine-1-carboximidamide hydrochloride To a solution of 4-hydroxypiperidine (5.00 g, 49.4 mmol) and 1H-pyrazole-1-carboximidamide (7.25 g, 49.4 mmol) in acetonitrile (30 ml) was added triethylamine (6.89 ml, 49.4 mmol), and the mixture was stirred at 60° C. for 12 hours. The solvent was distilled off under reduced pressure to give the desired product quantitatively as an oil.

$^1$H-NMR (CDCl$_3$) δ; 1.29-1.45 (2H, m), 1.72-1.80 (2H, m), 3.12-3.26 (2H, m), 3.37 (1H, br s), 3.58-3.74 (2H, m), 4.90 (1H, br s), 7.56 (4H, br s).

(2) 1-(5-Chloro-1,2,4-thiadiazol-3-yl)piperidin-4-ol

To a solution of 4-hydroxypiperidine-1-carboximidamide hydrochloride (1.80 g, 10.0 mmol) and perchloromethyl mercaptan (2.15 ml, 20.0 mmol) in dichloromethane (50 ml) was added dropwise a solution of sodium hydroxide (3.20 g, 80.0 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=1:1) to give 350 mg (12.7%) of the desired product as a solid.

$^1$H-NMR (CDCl$_3$) δ; 1.53-1.65 (3H, m), 1.92-2.00 (2H, m), 3.27-3.36 (2H, m), 3.88-3.96 (1H, m), 4.08-4.16 (2H, m).

(3) N-1,2-Benzisoxazol-3-yl-4-[3-(4-hydroxypiperidin-1-yl)-1,2,4-thiadiazol-5-yl]piperazine-1-carboxamide To a solution of 1-(5-chloro-1,2,4-thiadiazol-3-yl)piperidin-4-ol (153 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.387 ml, 2.78 mmol) at room temperature, and the mixture was stirred at room temperature for 1 hour. The reaction mixture was poured to water, and a solid was separated by filtration and washed with water, which was recrystallized from a mixed solvent of tetrahydrofuran and ethyl acetate to give 79.0 mg (33.2%) of the desired product as a solid.

$^1$H-NMR (DMSO-d$_6$) δ; 1.32-1.35 (2H, m), 1.73 (2H, br s), 3.08-3.12 (2H, m), 3.49 (4H, br s), 3.66 (5H, br s), 3.92-3.96 (2H, m), 4.68 (1H, d, J=3.9 Hz), 7.27-7.33 (1H, m), 7.57-7.62 (2H, m), 7.83 (1H, d, J=7.8 Hz), 10.05 (1H, s).

Example 111

Ethyl 1-(5-{4-[(1,2-benzisoxazol-3-ylamino)carbonyl]piperazin-1-yl}-1,2,4-thiadiazol-3-yl)piperidine-4-carboxylate

(1) Ethyl 1-[amino(imino)methyl]piperidine-4-carboxylate hydrochloride

To a solution of ethyl isonipecotate (5.00 g, 31.8 mmol) and 1H-pyrazole-1-carboximidamide (4.66 g, 31.8 mmol) in acetonitrile (30 ml) was added triethylamine (4.43 ml, 31.8 mmol), and the mixture was stirred at 60° C. for 12 hours. The solvent was distilled off under reduced pressure to give the desired product quantitatively as an oil.

$^1$H-NMR (CDCl$_3$) δ; 1.23 (3H, t, J=6.9 Hz), 1.66-1.78 (2H, m), 1.95-1.99 (2H, m), 2.52-2.59 (1H, m), 3.14-3.22 (2H, m), 3.93-3.98 (2H, m), 4.10 (2H, q, J=6.9 Hz), 7.33 (4H, br s).

(2) Ethyl 1-(5-chloro-1,2,4-thiadiazol-3-yl)piperidine-4-carboxylate

To a solution of ethyl 1-[amino(imino)methyl]piperidine-4-carboxylate hydrochloride (1.50 g, 6.36 mmol) and perchloromethyl mercaptan (1.37 ml, 12.7 mmol) in dichloromethane (40 ml) was added dropwise a solution of sodium hydroxide (2.04 g, 50.9 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=4:1) to give 1.10 g (62.9%) of the desired product as an oil.

$^1$H-NMR (CDCl$_3$) δ; 1.27 (3H, t, J=7.5 Hz), 1.73-2.03 (4H, m), 2.46-2.57 (1H, m), 3.04-3.18 (2H, m), 4.16 (2H, q, J=7.5 Hz), 4.24-4.33 (2H, m).

(3) Ethyl 1-(5-{4-[(1,2-benzisoxazol-3-ylamino)carbonyl]piperazin-1-yl}-1,2,4-thiadiazol-3-yl)piperidine-4-carboxylate To a solution of tert-butyl 1-(5-chloro-1,2,4-thiadiazol-3-yl)piperidin-4-yl]carbamate (153 mg, 0.555 mmol) and N-1,2-benzisoxazol-3-ylpiperazine-1-carboxamide trifluoroacetate (200 mg, 0.555 mmol) in N,N-dimethylformamide (2 ml) was added triethylamine (0.387 ml, 2.78 mmol) at room temperature, and the mixture was stirred at room temperature for 30 minutes. The reaction mixture was poured to water and extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give 30.0 mg (11.2%) of the desired product as a solid.

$^1$H-NMR (DMSO-d$_6$) δ; 1.19 (3H, t, J=7.2 Hz), 1.46-1.56 (2H, m), 1.82-1.86 (2H, m), 2.49-2.56 (1H, m), 2.92-2.56 (2H, m), 3.49 (4H, br s), 3.65-3.68 (4H, m), 4.01-4.14 (4H, m), 7.27-7.33 (1H, m), 7.56-7.64 (2H, m), 7.83 (1H, d, J=8.1 Hz), 10.05 (1H, s).

Example 112

1-(5-{4-[(1,2-Benzisoxazol-3-ylamino)carbonyl]piperazin-1-yl}-1,2,4-thiadiazol-3-yl)piperidine-4-carboxylic acid A mixed solution of ethyl 1-(5-{4-[(1,2-benzisoxazol-3-ylamino)carbonyl]piperazin-1-yl}-1,2,4-thiadiazol-3-yl)piperidine-4-carboxylate (60.0 mg, 0.124 mmol), an aqueous 1 N sodium hydroxide solution (0.992 ml, 0.992 mmol), tetrahydrofuran (3 ml) and ethanol (3 ml) was stirred at 80° C. for 5 hours. The solvent was distilled off under reduced pressure. The residue was adjusted to pH 3 by addition of an aqueous 1 N sodium hydroxide solution. A solid was separated by filtration and washed with water to give 17.0 mg (30.0%) of the desired product.

$^1$H-NMR (DMSO-d$_6$) δ; 1.48-1.56 (2H, m), 1.81-1.85 (2H, m), 2.42 (1H, br s), 2.90-2.97 (2H, m), 3.50 (4H, br s), 3.65-3.68 (4H, m), 4.09-4.13 (2H, m), 7.27-7.32 (1H, m), 7.56-7.64 (2H, m), 7.83 (1H, d, J=7.8 Hz), 10.05 (1H, s), 12.20 (1H, br s).

Example 113

4-{3-[4-(Aminocarbonyl)piperidin-1-yl]-1,2,4-thiadiazol-5-yl}-N-1,2-benzisoxazol-3-ylpiperazine-1-carboxamide A solution of 1-(5-{4-[(1,2-benzisoxazol-3-ylamino)carbonyl]piperazin-1-yl}-1,2,4-thiadiazol-3-yl)piperidine-4-carboxylic acid (70.0 mg, 0.153 mmol), 1-hydroxybenzotriazole (23.4 mg, 0.153 mmol) and 1-(3-dimethylaminopropyl)-3-ethylcarbodiimide hydrochloride (44.1 mg, 0.230 mmol) in N,N-dimethylformamide (2 ml) was stirred at room temperature for 1 hour. 25% Ammonia water (33.8 mg, 0.497 mmol) was added thereto under ice-cooling, and the resulting mixture was stirred at room temperature for 0.5 hour. The reaction mixture was poured to water, and a solid was separated by filtration, which was recrystallized from a mixed solvent of tetrahydrofuran, ethyl acetate and hexane to give 52.3 mg (74.9%) of the desired product as a solid.

$^1$H-NMR (DMSO-d$_6$) δ; 1.43-1.54 (2H, m), 1.69-1.72 (2H, m), 2.23-2.30 (1H, m), 2.80-2.88 (2H, m), 3.50 (4H, br s), 3.67 (4H, br s), 4.18-4.23 (2H, m), 6.77 (1H, br s), 7.27-7.33 (2H, m), 7.56-7.64 (2H, m), 7.83 (1H, d, J=8.1 Hz), 10.05 (1H, s).

Example 114 tert-Butyl [2-({[1-(5-{4-[(1,2-benzisoxazol-3-ylamino)carbonyl]piperazin-1-yl}-1,2,4-thiadiazol-3-yl)piperidin-4-yl]carbonyl}amino)ethyl]carbamate A solution of 1-(5-{4-[(1,2-benzisoxazol-3-ylamino)carbonyl]piperazin-1-yl}-1,2,4-thiadiazol-3-yl)piperidine-4-carboxylic acid (100 mg, 0.219 mmol), 1-hydroxybenzotriazole (29.6 mg, 0.219 mmol), 1-(3-dimethylaminopropyl)-3-ethylcarbodiimide hydrochloride (84.0 mg, 0.438 mmol) and tert-butyl N-(2-aminoethyl)carbamate (35.0 mg, 0.219 mmol) in N,N-dimethylformamide (2 ml) was stirred at room temperature for 12 hours. The reaction mixture was poured to water, and a solid was separated by filtration, which was recrystallized from a mixed solvent of tetrahydrofuran, ethyl acetate and hexane to give 111 mg (84.7%) of the desired product as a solid.

$^1$H-NMR (DMSO-$d_6$) δ; 1.37 (9H, s), 1.44-1.55 (2H, m), 1.67-1.70 (2H, m), 2.27 (1H, br s), 2.81-3.06 (6H, m), 3.50 (4H, br s), 3.67 (4H, br s), 4.19-4.23 (2H, m), 6.78 (1H, br s), 7.28-7.33 (1H, m), 7.56-7.65 (2H, m), 7.79 (1H, br s), 7.84 (1H, d, J=7.2 Hz), 10.07 (1H, br s).

Example 115

4-[3-(4-{[(2-Aminoethyl)amino]carbonyl}piperidin-1-yl)-1,2,4-thiadiazol-5-yl]-N-1,2-benzisoxazol-3-ylpiperazine-1-carboxamide dihydrochloride A solution of tert-butyl [2-({[1-(5-{4-[(1,2-benzisoxazol-3-ylamino)carbonyl]piperazin-1-yl}-1,2,4-thiadiazol-3-yl)piperidin-4-yl]carbonyl}amino)ethyl]carbamate (70.0 mg, 0.117 mmol) and a solution of 2 N hydrogen chloride in methanol (10 ml) in tetrahydrofuran (10 ml) was stirred at room temperature for 12 hours. The solvent was distilled off under reduced pressure, and the residue was recrystallized from a mixed solvent of methanol and diethyl ether to give 61.0 mg (91.0%) of the desired product as a solid.

$^1$H-NMR (DMSO-$d_6$) δ; 1.46-1.57 (2H, m), 1.73-1.77 (2H, m), 2.32 (1H, br s), 2.73-2.90 (4H, m), 3.26-3.32 (3H, m), 3.50 (4H, br s), 3.61 (4H, br s), 4.20-4.25 (2H, m), 7.28-7.34 (1H, m), 7.58-7.66 (2H, m), 7.85 (1H, d, J=7.8 Hz), 7.96 (3H, br s), 8.11 (1H, t, J=5.7 Hz), 10.08 (1H, s).

Example 116 tert-Butyl {2-[4-(5-{4-[(1,2-benzisoxazol-3-ylamino)carbonyl]piperazin-1-yl}-1,2,4-thiadiazol-3-yl)piperazin-1-yl]-2-oxoethyl}carbamate A solution of N-1,2-benzisoxazol-3-yl-4-(3-piperazin-1-yl-1,2,4-thiadiazol-5-yl)piperazine-1-carboxamide (100 mg, 0.241 mmol), 1-hydroxybenzotriazole (32.5 mg, 0.241 mmol), 1-(3-dimethylaminopropyl)-3-ethylcarbodiimide hydrochloride (92.5 mg, 0.482 mmol) and N-(tert-butoxycarbonyl)glycine (42.3 mg, 0.241 mmol) in N,N-dimethylformamide (2 ml) was stirred at room temperature for 12 hours. The reaction mixture was poured to water, and a solid was separated by filtration, which was recrystallized from a mixed solvent of tetrahydrofuran, ethyl acetate and hexane to give 102 mg (73.9%) of the desired product as a solid.

$^1$H-NMR (DMSO-$d_6$) δ; 1.38 (9H, s), 3.50 (12H, br s), 3.68 (4H, br s), 3.81 (2H, d, J=6.0 Hz), 6.76 (1H, br s), 7.28-7.33 (1H, m), 7.52-7.62 (2H, m), 7.84 (1H, d, J=7.8 Hz), 10.09 (1H, br s).

Example 117

N-1,2-Benzisoxazol-3-yl-4-[3-(4-glycylpiperazin-1-yl)-1,2,4-thiadiazol-5-yl]piperazine-1-carboxamide dihydrochloride A solution of tert-butyl {2-[4-(5-{4-[(1,2-benzisoxazol-3-ylamino)carbonyl]piperazin-1-yl}-1,2,4-thiadiazol-3-yl)piperazin-1-yl]-2-oxoethyl}carbamate (70.0 mg, 0.122 mmol) and a solution of 2 N hydrogen chloride in methanol (5 ml) in tetrahydrofuran (5 ml) was stirred at room temperature for 12 hours. The solvent was distilled off under reduced pressure, and the residue was recrystallized from a mixed solvent of methanol and diethyl ether to give 60.0 mg (90.4%) of the desired product as a solid.

$^1$H-NMR (DMSO-$d_6$) δ; 3.46-3.56 (13H, m), 3.69 (4H, br s), 3.90 (2H, d, J=5.7 Hz), 7.29-7.34 (1H, m), 7.58-7.66 (2H, m), 7.85 (1H, d, J=8.1 Hz), 8.15 (3H, br s), 10.09 (1H, s).

The structural formulae of Compounds obtained in Examples 107 to 117 are shown in Table 6.

TABLE 6

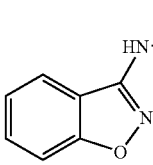

| Example No. | R |
|---|---|
| 107 | 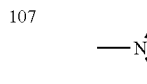 |
| 108 | 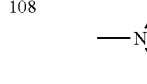 |
| 109 | 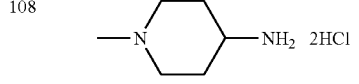 |
| 110 | 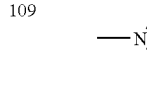 |
| 111 | 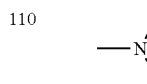 |
| 112 |  |
| 113 |  |

TABLE 6-continued

[Structure: benzisoxazole-NH-C(O)-N(piperazine)N-thiadiazole-R]

| Example No. | R |
|---|---|
| 114 | —N(piperidine)—CONH(CH₂)₂NHCOOC(CH₃)₃ |
| 115 | —N(piperidine)—CONH(CH₂)₂NH₂ 2HCl |
| 116 | —N(piperazine)N—COCH₂NHCOOC(CH₃)₃ |
| 117 | —N(piperazine)N—COCH₂NH₂ 2HCl |

Example 118

N-(3-Methylisoxazol-5-yl)-4-(3-phenyl-1,2,4-thiadiazol-5-yl)piperazine-1-carboxamide

(1) 2,2,2-Trichloroethyl (3-methylisoxazol-5-yl)carbamate

To a solution of 3-methyl-5-aminoisoxazole (1.00 g, 10.2 mmol) and pyridine (0.97 ml, 12.2 mmol) in tetrahydrofuran (34 ml) was added 2,2,2-trichloroethyl chloroformate (1.69 ml, 12.2 mmol) under ice-cooling, and the mixture was stirred at room temperature for 3 hours and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=7:3) to give 718 mg (26%) of the desired product as a solid.

$^1$H-NMR (CDCl$_3$) δ; 2.28 (3H, s), 4.86 (2H, s), 6.04 (1H, s), 8.33 (1H, br s).

(2) N-(3-Methylisoxazol-5-yl)-4-(3-phenyl-1,2,4-thiadiazol-5-yl)piperazine-1-carboxamide A mixed solution of 2,2,2-trichloroethyl (3-methylisoxazol-5-yl)carbamate (302 mg, 1.11 mmol), 1-(3-phenyl-1,2,4-thiadiazol-5-yl)piperazine (300 mg, 1.33 mmol) and diisopropylethylamine (0.212 ml, 1.33 mmol) in dimethyl sulfoxide (3.7 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 167 mg (40.6%) of the desired product as a solid.

$^1$H NMR (CDCl$_3$+DMSO-d$_6$) δ; 2.22 (3H, s), 3.64-3.78 (8H, m), 5.98 (1H, s), 7.40-7.44 (3H, m), 8.13-8.19 (2H, m), 10.29 (1H, br s).

Example 119

N-Pyridin-4-yl-4-(3-pyridin-2-yl-1,2,4-thiadiazol-5-yl)piperazine-1-carboxamide

A mixed solution of 2,2,2-trichloroethyl pyridin-4-ylcarbamate (198 mg, 0.735 mmol), 1-(3-pyridin-2-yl-1,2,4-thiadiazol-5-yl)piperazine (200 mg, 0.809 mmol) and diisopropylethylamine (0.139 ml, 0.809 mmol) in dimethyl sulfoxide (2.5 ml) was stirred at 80° C. for 3 hours. Water was poured to the reaction mixture, and the resulting solution was extracted with a mixed solution of ethyl acetate/tetrahydrofuran (1:1). The extract was washed with water and dried over anhydrous magnesium sulfate, and the solvent was distilled off under reduced pressure. The residue was purified by silica gel column chromatography (ethyl acetate:methanol=9:1) and recrystallized from a mixed solvent of hexane and tetrahydrofuran to give 62.1 mg (23.0%) of the desired product as a solid.

$^1$H-NMR (CDCl$_3$) δ; 3.59-3.62 (4H, m), 3.70-3.73 (4H, m), 7.33-7.39 (3H, m), 7.78-7.84 (1H, m), 8.25 (1H, d, J=7.8 Hz), 8.32-8.37 (3H, m), 8.67-8.68 (1H, m).

Example 120

4-[3-(3-Furyl)-1,2,4-thiadiazol-5-yl]-N-pyridin-4-ylpiperazine-1-carboxamide

A mixed solution of 2,2,2-trichloroethyl pyridin-4-ylcarbamate (207 mg, 0.770 mmol), 1-[3-(3-furyl)-1,2,4-thiadiazol-5-yl]piperazine (200 mg, 0.846 mmol) and diisopropylethylamine (0.134 ml, 0.846 mmol) in dimethyl sulfoxide (2.5 ml) was stirred at 80° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 84.5 mg (30.8%) of the desired product as a solid.

$^1$H-NMR (CDCl$_3$) δ; 3.61-3.65 (4H, m), 3.72-3.76 (4H, m), 6.87-6.88 (1H, m), 7.47-7.50 (3H, m), 8.02-8.03 (1H, m), 8.33 (2H, d, J=6.3 Hz), 8.95 (1H, br s).

Example 121

N-(1,1-Dioxido-1-benzothien-6-yl)-4-(3-phenyl-1,2,4-thiadiazol-5-yl)piperazine-1-carboxamide

(1) 2,2,2-Trichloroethyl (1,1-dioxido-1-benzothien-6-yl)carbamate

To a solution of 1-benzothiophen-6-amine 1,1-dioxide (1.00 g, 5.52 mmol) and pyridine (0.525 ml, 6.62 mmol) in tetrahydrofuran (18 ml) was added, under ice-cooling, 2,2,2-trichloroethyl chloroformate (0.916 ml, 6.62 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 1.71 g (87.1%) of the desired product as a solid was separated by filtration.

$^1$H-NMR (CDCl$_3$) δ; 4.85 (2H, s), 6.67 (1H, d, J=6.9 Hz), 7.18-7.21 (1H, m), 7.31-7.34 (2H, m), 7.62-7.66 (1H, m), 7.87-7.88 (1H, m).

(2) N-(1,1-Dioxido-1-benzothien-6-yl)-4-(3-phenyl-1,2,4-thiadiazol-5-yl)piperazine-1-carboxamide A mixed solution of 2,2,2-trichloroethyl (1,1-dioxido-1-benzothien-6-yl)carbamate (263 mg, 0.738 mmol), 1-(3-phenyl-1,2,4-thiadiazol-5-yl)piperazine (200 mg, 0.811 mmol) and diisopropylethylamine (0.129 ml, 0.811 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 106 mg (31.7%) of the desired product as a solid.

$^1$H NMR (CDCl$_3$+DMSO-d$_6$) δ; 3.69-3.78 (8H, m), 6.67 (1H, d, J=6.6 Hz), 7.24 (1H, d, J=6.6 Hz), 7.29 (1H, d, J=8.4 Hz), 7.41-7.43 (3H, m), 7.79-7.82 (1H, br s), 8.15-8.18 (2H, m), 8.97 (1H, br s).

Example 122

N-Pyridin-3-yl-4-[3-(2-thienyl)-1,2,4-thiadiazol-5-yl]piperazine-1-carboxamide (1) tert-Butyl 4-[3-(2-thienyl)-1,2,4-thiadiazol-5-yl]piperazine-1-carboxylate To a solution of 5-chloro-3-(2-thienyl)-1,2,4-thiadiazole (4.80 g, 23.7 mmol) and tert-butyl piperazine-1-carboxylate (4.41 g, 23.7 mmol) in dimethylformamide (50 ml) was added triethylamine (13.2 ml, 94.7 mmol) at room temperature, and the mixture was stirred at room temperature for 1 hour. Water was poured to the reaction mixture, and the resulting solution was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give 4.33 g (51.9%) of the desired product as a solid.

$^1$H-NMR (DMSO-d$_6$) δ; 1.49 (9H, s), 3.59 (8H, s), 7.08 (1H, dd, J=3.6, 5.2 Hz), 7.38 (1H, dd, J=1.4, 5.2 Hz), 7.73 (1H, dd, J=1.4, 3.6 Hz).

(2) 1-[3-(2-Thienyl)-1,2,4-thiadiazol-5-yl]piperazine

To a solution of tert-butyl 4-[3-(2-thienyl)-1,2,4-thiadiazol-5-yl]piperazine-1-carboxylate (4.30 g, 12.2 mmol) in ethyl acetate (70 ml) was added a solution of 4 N hydrochloric acid in ethyl acetate (35 ml), and the mixture was stirred at room temperature for 18 hours and half. Hexane (150 ml) was poured to the reaction mixture, and a solid was separated by filtration. The obtained solid was dissolved in an aqueous saturated sodium hydrogen carbonate solution, followed by stirring at room temperature for 2 hours. Water was poured to the reaction mixture, and the resulting solution was extracted with a mixed solution of ethyl acetate/tetrahydrofuran (1:1). The extract was washed with water and dried over anhydrous magnesium sulfate, and the solvent was distilled off under reduced pressure. Hexane was poured to the residue, and 2.31 g (75.0%) of the desired product as a solid was separated by filtration.

$^1$H-NMR (CDCl$_3$) δ; 3.00-3.03 (4H, m), 3.55-3.60 (4H, m), 7.06-7.10 (1H, m), 7.36-7.39 (1H, m), 7.72-7.74 (1H, m).

(3) N-Pyridin-3-yl-4-[3-(2-thienyl)-1,2,4-thiadiazol-5-yl]piperazine-1-carboxamide A mixed solution of 2,2,2-trichloroethyl pyridin-3-ylcarbamate (235 mg, 0.872 mmol), 1-[3-(2-thienyl)-1,2,4-thiadiazol-5-yl]piperazine (200 mg, 0.793 mmol) and diisopropylethylamine (0.152 ml, 0.872 mmol) in dimethyl sulfoxide (2.5 ml) was stirred at 80° C. for 3 hours. Water was poured to the reaction mixture, and the resulting solution was extracted with ethyl acetate. The extract was washed with water, and the solvent was distilled off under reduced pressure. The residue was purified by silica gel column chromatography (ethyl acetate) and recrystallized from a mixed solvent of hexane and tetrahydrofuran to give 109 mg (37.1%) of the desired product as a solid.

$^1$H-NMR (CDCl$_3$) δ; 3.63-3.66 (4H, s), 3.74-3.77 (4H, m), 7.07-7.10 (1H, m), 7.20-7.24 (1H, m), 7.37-7.39 (1H, m), 7.72-7.74 (1H, m), 7.99-8.02 (1H, m), 8.23-8.25 (1H, m), 8.33 (1H, br s), 8.59 (1H, d, J=2.4 Hz).

Example 123

N-Pyridin-3-yl-4-[3-(3-thienyl)-1,2,4-thiadiazol-5-yl]piperazine-1-carboxamide (1) tert-Butyl 4-[3-(3-thienyl)-1,2,4-thiadiazol-5-yl]piperazine-1-carboxylate To a solution of 5-chloro-3-(3-thienyl)-1,2,4-thiadiazole (2.47 g, 12.2 mmol) and tert-butyl piperazine-1-carboxylate (2.27 g, 12.2 mmol) in dimethylformamide (25 ml) was added triethylamine (6.8 ml, 48.8 mmol) at room temperature, and the mixture was stirred at room temperature for 1 hour. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give 3.72 g (86.5%) of the desired product as a solid.

$^1$H-NMR (DMSO-d$_6$) δ; 1.49 (9H, s), 3.56-3.62 (8H, m), 7.26-7.34 (1H, m), 7.68-7.70 (1H, m), 7.99-8.01 (1H, m).

(2) 1-[3-(3-Thienyl)-1,2,4-thiadiazol-5-yl]piperazine

To a solution of tert-butyl 4-[3-(3-thienyl)-1,2,4-thiadiazol-5-yl]piperazine-1-carboxylate (3.70 g, 10.5 mmol) in ethyl acetate (60 ml) was added a solution of 4 N hydrochloric acid in ethyl acetate (30 ml), and the mixture was stirred at room temperature for 22 hours. Hexane (200 ml) was poured to the reaction mixture, and a solid was separated by filtration. The obtained solid was dissolved in an aqueous saturated sodium hydrogen carbonate solution, followed by stirring at room temperature for 2 hours. Water was poured to the reaction mixture, and 1.86 g (70.4%) of the desired product as a solid was separated by filtration.

$^1$H-NMR (CDCl$_3$) δ; 2.98-3.01 (4H, m), 3.55-3.58 (4H, m), 7.37 (1H, dd, J=3.0, 5.1 Hz), 7.65 (1H, dd, J=0.9, 4.8 Hz), 7.98 (1H, dd, J=1.2, 3.0 Hz).

(3) N-Pyridin-3-yl-4-[3-(3-thienyl)-1,2,4-thiadiazol-5-yl]piperazine-1-carboxamide A mixed solution of 2,2,2-trichloroethyl pyridin-3-ylcarbamate (235 mg, 0.872 mmol), 1-[3-(3-thienyl)-1,2,4-thiadiazol-5-yl]piperazine (200 mg, 0.793 mmol) and diisopropylethylamine (0.152 ml, 0.872 mmol) in dimethyl sulfoxide (2.5 ml) was stirred at 80° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 98.2 mg (33.3%) of the desired product as a solid.

$^1$H-NMR (CDCl$_3$) δ; 3.63-3.67 (4H, s), 3.74-3.77 (4H, m), 7.20-7.24 (1H, m), 7.32-7.35 (1H, m), 7.67-7.69 (1H, m), 7.99-8.02 (2H, m), 8.24 (1H, d, J=3.6 Hz), 8.43 (1H, br s), 8.61 (1H, d, J=2.1 Hz).

Example 124

N-Pyridin-4-yl-4-[3-(2-thienyl)-1,2,4-thiadiazol-5-yl]piperazine-1-carboxamide A mixed solution of 2,2,2-trichloroethyl pyridin-4-ylcarbamate (235 mg, 0.872 mmol), 1-[3-(2-thienyl)-1,2,4-thiadiazol-5-yl]piperazine (200 mg, 0.793 mmol) and diisopropylethylamine (0.152 ml, 0.872 mmol) in dimethyl sulfoxide (2.5 ml) was stirred at 80° C. for 3.5 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate, followed by methanol:ethyl acetate=1:9) and recrystallized from a mixed solvent of hexane and ethyl acetate to give 54.9 mg (18.6%) of the desired product as a solid.

$^1$H-NMR (CDCl$_3$) δ; 3.71 (8H, s), 6.89 (1H, br s), 7.07-7.10 (1H, m), 7.34-7.39 (3H, m), 7.73-7.74 (1H, m), 8.43-8.45 (2H, m).

Example 125

N-Pyridin-4-yl-4-[3-(3-thienyl)-1,2,4-thiadiazol-5-yl]piperazine-1-carboxamide A mixed solution of 2,2,2-trichloroethyl pyridin-4-ylcarbamate (235 mg, 0.872 mmol), 1-[3-(3-thienyl)-1,2,4-thiadiazol-5-yl]piperazine (200 mg, 0.793 mmol) and diisopropylethylamine (0.152 ml, 0.872 mmol) in dimethyl sulfoxide (2.5 ml) was stirred at 80° C. for 3 hours and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate, followed by methanol:ethyl acetate=1:9) and recrystallized from a mixed solvent of hexane and tetrahydrofuran to give 38.4 mg (13.0%) of the desired product as a solid.

$^1$H-NMR (CDCl$_3$) δ; 3.66-3.75 (8H, m), 7.00 (1H, br s), 7.32-7.37 (3H, m), 7.67-7.70 (1H, m), 7.99-8.01 (1H, m), 8.43-8.45 (2H, m).

Example 126

4-(3-Phenyl-1,2,4-thiadiazol-5-yl)-N-[2-(trifluoromethyl)-1H-benzimidazol-5-yl]piperazine-1-carboxamide

(1) 2,2,2-Trichloroethyl [2-(trifluoromethyl)-1H-benzimidazol-5-yl]carbamate To a solution of 2-(trifluoromethyl)-1H-benzimidazol-5-amine (1.00 g, 4.97 mmol) and pyridine (0.473 ml, 5.97 mmol) in tetrahydrofuran (17 ml) was added, under ice-cooling, 2,2,2-trichloroethyl chloroformate (0.826 ml, 5.97 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=7:3) to give 1.28 g (68.5%) of the desired product as a solid.

$^1$H-NMR (CDCl$_3$) δ; 4.84 (2H, s), 7.09-7.13 (1H, m), 7.33 (1H, br s), 7.60 (1H, d, J=8.7 Hz), 8.01 (1H, br s), 11.17 (1H, br s).

(2) 4-(3-Phenyl-1,2,4-thiadiazol-5-yl)-N-[2-(trifluoromethyl)-1H-benzimidazol-5-yl]piperazine-1-carboxamide A mixed solution of 2,2,2-trichloroethyl [2-(trifluoromethyl)-1H-benzimidazol-5-yl]carbamate (278 mg, 0.738 mmol), 1-(3-phenyl-1,2,4-thiadiazol-5-yl)piperazine (200 mg, 0.811 mmol) and diisopropylethylamine (0.129 ml, 0.738 mmol) in dimethyl sulfoxide (2.5 ml) was stirred at 70° C. for 3 hours and half. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane: ethyl acetate=1:1) and recrystallized from a mixed solvent of hexane and tetrahydrofuran to give 115 mg (32.8%) of the desired product as a solid.

$^1$H NMR (DMSO-d$_6$) δ; 3.68-3.77 (8H, s), 7.42-7.44 (4H, m), 7.57 (1H, br s), 7.94 (1H, br s), 8.15-8.18 (2H, m), 8.66 (1H, br s), 13.25 (1H, br s).

Example 127

4-(4-Phenyl-1,3-thiazol-2-yl)-N-pyridin-4-ylpiperazine-1-carboxamide

A mixed solution of 2,2,2-trichloroethyl pyridin-4-ylcarbamate (360 mg, 1.33 mmol), 1-(4-phenyl-1,3-thiazol-2-yl)piperazine (360 mg, 1.47 mmol) and diisopropylethylamine (0.256 ml, 1.47 mmol) in dimethyl sulfoxide (4.4 ml) was stirred at 70° C. for 8 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give 93.7 mg (19.2%) of the desired product as a solid.

$^1$H-NMR (CDCl$_3$) δ; 3.62-3.72 (8H, m), 6.83 (1H, s), 6.95 (1H, s), 7.29-7.41 (5H, m), 7.82 (2H, d, J=7.2 Hz), 8.44 (2H, d, J=6.3 Hz).

Example 128

N-(1,1-Dioxido-1-benzothien-6-yl)-4-[3-(2-thienyl)-1,2,4-thiadiazol-5-yl]piperazine-1-carboxamide A mixed solution of 2,2,2-trichloroethyl (1,1-dioxido-1-benzothien-6-yl)carbamate (257 mg, 0.720 mmol), 1-[3-(2-thienyl)-1,2,4-thiadiazol-5-yl]piperazine (200 mg, 0.792 mmol) and diisopropylethylamine (0.129 ml, 0.720 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. Chloroform was added to the residue, and 69.6 mg (21.0%) of the desired product as a solid was separated by filtration.

$^1$H NMR (DMSO-$d_6$) δ; 3.65-3.77 (8H, s), 6.82 (1H, d, J=6.9 Hz), 7.08-7.11 (1H, m), 7.32-7.36 (2H, m), 7.45-7.47 (1H, m), 7.69-7.74 (2H, m), 8.02 (1H, s), 9.10 (1H, s).

Example 129

N-(3,5-Dimethylisoxazol-4-yl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2.5 ml) was added 3,5-dimethylisoxazol-4-yl isocyanate (168 mg, 1.22 mmol) at room temperature, and the mixture was stirred at room temperature for 1 hour. The solvent was distilled off under reduced pressure. The residue was purified by silica gel column chromatography (hexane:ethyl acetate=1:1) and recrystallized from a mixed solvent of hexane and ethyl acetate to give 214 mg (68.6%) of the desired product as a solid.

$^1$H-NMR (CDCl$_3$) δ; 2.16 (3H, s), 2.30 (3H, s), 3.68 (8H, s), 5.98 (1H, br s), 7.40-7.44 (3H, m), 8.16-8.19 (2H, m).

Example 130

N-(5-Methyl-3-phenylisoxazol-4-yl)-4-(3-phenyl-1,2,4-thiadiazol-5-yl)piperazine-1-carboxamide To a solution of 1-(3-phenyl-1,2,4-thiadiazol-5-yl)piperazine (200 mg, 0.812 mmol) and triethylamine (0.113 ml, 0.812 mmol) in tetrahydrofuran (2 ml) was added 5-methyl-3-phenyl-4-isoxazolyl isocyanate (244 mg, 1.22 mmol) at room temperature, and the mixture was stirred at room temperature for 1 hour. The solvent was distilled off under reduced pressure. The residue was purified by silica gel column chromatography (hexane:ethyl acetate=1:1) and recrystallized from a mixed solvent of hexane and ethyl acetate to give 229 mg (63.3%) of the desired product as a solid.

$^1$H-NMR (CDCl$_3$) δ; 2.38 (3H, s), 3.61 (8H, s), 5.98 (1H, br s), 7.42-7.43 (6H, m), 7.60-7.62 (2H, m), 8.16-8.17 (2H, m).

Example 131

N-(3,4-Dimethylisoxazol-5-yl)-4-(3-phenyl-1,2,4-thiadiazol-5-yl)piperazine-1-carboxamide (1) 2,2,2-Trichloroethyl (3,4-dimethylisoxazol-5-yl)carbamate To a solution of 5-amino-3,4-dimethylisoxazole (1.00 g, 8.92 mmol) and pyridine (0.873 ml, 10.7 mmol) in tetrahydrofuran (30 ml) was added, under ice-cooling, 2,2,2-trichloroethyl chloroformate (1.48 ml, 10.7 mmol), and the mixture was stirred at room temperature for 1 hour. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give 1.61 g (62.9%) of the desired product as an oil.

$^1$H-NMR (CDCl$_3$) δ; 1.92 (3H, s), 2.22 (3H, s), 4.82 (2H, s), 7.40 (1H, br s).

(2) N-(3,4-Dimethylisoxazol-5-yl)-4-(3-phenyl-1,2,4-thiadiazol-5-yl)piperazine-1-carboxamide A mixed solution of 2,2,2-trichloroethyl (3,4-dimethylisoxazol-5-yl)carbamate (212 mg, 0.738 mmol), 1-(3-phenyl-1,2,4-thiadiazol-5-yl)piperazine (200 mg, 0.812 mmol) and diisopropylethylamine (0.141 ml, 0.812 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give 126 mg (44.3%) of the desired product as a solid.

$^1$H-NMR (DMSO-$d_6$) δ; 1.86 (3H, s), 2.19 (3H, s), 3.65-3.68 (4H, m), 3.73-3.76 (4H, m), 7.40-7.44 (3H, m), 8.15-8.18 (2H, m), 9.24 (1H, s).

Example 132

N-(3-Methylisoxazol-5-yl)-4-(4-phenyl-1,3-thiazol-2-yl)piperazine-1-carboxamide

A mixed solution of 2,2,2-trichloroethyl (3-methylisoxazol-5-yl)carbamate (245 mg, 0.897 mmol), 1-(4-phenyl-1,3-thiazol-2-yl)piperazine (200 mg, 0.815 mmol) and diisopropylethylamine (0.156 ml, 0.897 mmol) in dimethyl sulfoxide (2.5 ml) was stirred at 70° C. for 3 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 135 mg (44.9%) of the desired product as a solid.

$^1$H-NMR (CDCl$_3$) δ; 2.26 (3H, m), 3.67 (8H, br s), 6.05 (1H, s), 6.82 (1H, s), 7.28-7.40 (3H, m), 7.81-7.83 (2H, m).

Example 133

N-1H-Benzimidazol-5-yl-4-(3-phenyl-1,2,4-thiadiazol-5-yl)piperazine-1-carboxamide (1) 2,2,2-Trichloroethyl 1H-benzimidazol-5-ylcarbamate To a solution of 1H-benzimidazol-5-amine (1.00 g, 7.51 mmol) and pyridine (0.73 ml, 9.01 mmol) in tetrahydrofuran (25 ml) was added, under ice-cooling, 2,2,2-trichloroethyl chloroformate (1.25 ml, 9.01 mmol), and the mixture was stirred at room temperature for 1.5 hour. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 1.49 g (64.4%) of the desired product as a solid was separated by filtration.

¹H-NMR (CDCl₃) δ; 5.22 (2H, s), 7.27-7.29 (1H, m), 7.90-8.01 (2H, m), 8.06 (1H, br s), 8.56 (1H, s), 10.16 (1H, br s).

(2) N-1H-Benzimidazol-5-yl-4-(3-phenyl-1,2,4-thiadiazol-5-yl)piperazine-1-carboxamide A mixed solution of 2,2,2-trichloroethyl 1H-benzimidazol-5-ylcarbamate (313 mg, 1.01 mmol), 1-(3-phenyl-1,2,4-thiadiazol-5-yl)piperazine (300 mg, 1.22 mmol) and diisopropylethylamine (0.212 ml, 1.22 mmol) in dimethyl sulfoxide (2.5 ml) was stirred at 70° C. for 1 day. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 20.2 mg (5.0%) of the desired product as a solid.

¹H-NMR (CDCl₃) δ; 3.70-3.75 (8H, m), 7.17 (1H, d, J=9.6 Hz), 7.31-7.53 (5H, m), 7.83 (1H, s), 8.13-8.16 (2H, m), 8.60 (1H, s), 12.10 (1H, br s).

Example 134

N-[6-(4-Methylpiperazin-1-yl)pyridin-3-yl]-4-(3-phenyl-1,2,4-thiadiazol-5-yl)piperazine-1-carboxamide (1) 2,2,2-Trichloroethyl [6-(4-methylpiperazin-1-yl)pyridin-3-yl]carbamate To a solution of 6-(4-methylpiperazin-1-yl)pyridine-3-amine (1.00 g, 5.20 mmol) and pyridine (0.509 ml, 6.24 mmol) in tetrahydrofuran (17 ml) was added, under ice-cooling, 2,2,2-trichloroethyl chloroformate (0.509 ml, 6.24 mmol), and the mixture was stirred at room temperature for 1 hour and half. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 349 mg (18.2%) of the desired product as a solid was separated by filtration.

¹H-NMR (CDCl₃+DMSO-d₆) δ; 2.50 (3H, s), 2.76 (4H, br s), 3.59 (4H, br s), 4.83 (2H, s), 6.70 (1H, d, J=9.0 Hz), 7.73-7.76 (1H, m), 8.29 (1H br s), 9.72 (1H, s).

(2) N-[6-(4-Methylpiperazin-1-yl)pyridin-3-yl]-4-(3-phenyl-1,2,4-thiadiazol-5-yl)piperazine-1-carboxamide A mixed solution of 2,2,2-trichloroethyl [6-(4-methylpiperazin-1-yl)pyridin-3-yl]carbamate (271 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 1 day. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and tetrahydrofuran to give 35.4 mg (10.3%) of the desired product as a solid.

¹H-NMR (CDCl₃) δ; 2.35 (3H, s), 2.51-2.54 (4H, m), 3.50-3.53 (4H, m), 3.70 (8H, s), 6.23 (1H, br s), 6.65 (1H, d, J=9.0 Hz), 7.41-7.43 (3H, m), 7.64-7.67 (1H, m), 8.01-8.02 (1H, m), 8.17-8.18 (2H, m).

Example 135

N-[6-(Acetylamino)pyridin-3-yl]-4-(3-phenyl-1,2,4-thiadiazol-5-yl)piperazine-1-carboxamide (1) 2,2,2-Trichloroethyl [6-(acetylamino)pyridin-3-yl]carbamate To a solution of N-(5-aminopyridin-2-yl)acetamide (1.00 g, 6.62 mmol) and pyridine (0.647 ml, 7.94 mmol) in tetrahydrofuran (22 ml) was added, under ice-cooling, 2,2,2-trichloroethyl chloroformate (1.10 ml, 7.94 mmol), and the mixture was stirred at room temperature for 2 hours. Water was poured to the reaction mixture, and the resulting solution was extracted with ethyl acetate. The extract was washed with water and dried over anhydrous magnesium sulfate, and the solvent was distilled off under reduced pressure. Hexane was poured to the residue, and 1.47 g (68.1%) of the desired product as a solid was separated by filtration.

¹H-NMR (CDCl₃+DMSO-d₆) δ; 2.15 (3H, s), 4.84 (2H, s), 7.85 (1H, br d, J=9.0 Hz), 8.07 (1H, d, J=9.0 Hz), 8.48 (1H, br s), 9.88 (1H, br s), 9.96 (1H, br s).

(2) N-[6-(Acetylamino)pyridin-3-yl]-4-(3-phenyl-1,2,4-thiadiazol-5-yl)piperazine-1-carboxamide A mixed solution of 2,2,2-trichloroethyl [6-(acetylamino)pyridin-3-yl]carbamate (241 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 15 hours. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 148 mg (47.5%) of the desired product as a solid.

¹H-NMR (CDCl₃+DMSO-d₆) δ; 2.11 (3H, s), 3.65-3.73 (8H, m), 7.39-7.44 (3H, m), 7.45-7.79 (1H, m), 8.02 (1H, br s), 8.12-8.16 (2H, m), 8.42 (1H, d, J=2.7 Hz), 8.70 (1H, s), 10.18 (1H, s).

Example 136

N-(6-Aminopyridin-3-yl)-4-(3-phenyl-1,2,4-thiadiazol-5-yl)piperazine-1-carboxamide (1) 2,2,2-Trichloroethyl (6-aminopyridin-3-yl)carbamate To a solution of 2,5-diaminopyridine (1.00 g, 9.16 mmol) and pyridine (0.889 ml, 11.0 mmol) in tetrahydrofuran (30 ml) was added, under ice-cooling, 2,2,2-trichloroethyl chloroformate (1.52 ml, 11.0 mmol), and the mixture was stirred at room temperature for 1 hour. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) to give 471 mg (18.1%) of the desired product as a solid.

$^1$H-NMR (CDCl$_3$) δ; 4.46 (2H, br s), 4.81 (2H, s), 6.51 (1H, d, J=8.7 Hz), 7.17 (1H, br s), 7.66 (1H, br d, J=7.8 Hz), 8.01-8.02 (1H, m).

(2) N-(6-Aminopyridin-3-yl)-4-(3-phenyl-1,2,4-thiadiazol-5-yl)piperazine-1-carboxamide A mixed solution of 2,2,2-trichloroethyl (6-aminopyridin-3-yl)carbamate (210 mg, 0.738 mmol), 1-(3-phenyl-1,2,4-thiadiazol-5-yl)piperazine (200 mg, 0.812 mmol) and diisopropylethylamine (0.129 ml, 0.738 mmol) in dimethyl sulfoxide (2.5 ml) was stirred at 70° C. for 3 days. Water was poured to the reaction mixture, and the resulting solution was extracted with ethyl acetate. The extract was washed with water and dried over anhydrous magnesium sulfate, and the solvent was distilled off under reduced pressure. The residue was purified by high performance liquid chromatography (YMC HPLC Column eluted with 10% to 100% Liquid A; Liquid A: a 0.1% solution of trifluoroacetic acid in acetonitrile; Liquid B: an aqueous 0.1% trifluoroacetic acid solution) and recrystallized from a mixed solvent of hexane and ethyl acetate to give 90.8 mg (32.3%) of the desired product as a solid.

$^1$H-NMR (CDCl$_3$) δ; 3.62 (8H, s), 5.68 (2H, br s), 6.40 (1H, d, J=8.8 Hz), 7.39-7.49 (4H, m), 7.90-7.91 (1H, m), 8.10-8.15 (2H, m), 8.38 (1H, br s).

Example 137

N-Methyl-4-(3-phenyl-1,2,4-thiadiazol-5-yl)-N-pyridin-3-ylpiperazine-1-carboxamide Under a nitrogen gas stream, to a solution of 4-(3-phenyl-1,2,4-thiadiazol-5-yl)-N-pyridin-3-ylpiperazine-1-carboxamide (100 mg, 0.273 mmol) in dimethylformamide (1.0 ml) was added, under ice-cooling, sodium hydride (13.1 mg, 0.327 mmol), and the mixture was stirred at room temperature for 30 minutes. Methyl iodide (0.020 ml, 0.327 mmol) was added thereto under ice-cooling, and the mixture was stirred at 0° C. for 30 minutes, followed by stirring at room temperature for 2 hours and half. An aqueous saturated ammonium chloride solution was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give 43.0 mg (41.4%) of the desired product as a solid.

$^1$H-NMR (CDCl$_3$) δ; 3.30 (3H, s), 3.38-3.41 (4H, m), 3.45-3.48 (4H, m), 7.31-7.35 (1H, m), 7.38-7.42 (3H, m), 7.49-7.53 (1H, m), 8.13-8.16 (2H, m), 8.41-8.43 (1H, m), 8.51 (1H, d, J=2.7 Hz).

Example 138 tert-Butyl 3-({[4-(3-phenyl-1,2,4-thiadiazol-5-yl)piperazin-1-yl]carbonyl}amino)piperidine-1-carboxylate (1) tert-Butyl 3-{[(2,2,2-trichloroethoxy)carbonyl]amino}piperidine-1-carboxylate To a solution of tert-butyl 3-aminopiperidine-1-carboxylate (1.00 g, 4.99 mmol) and pyridine (489 ml, 5.99 mmol) in tetrahydrofuran (16 ml) was added, under ice-cooling, 2,2,2-trichloroethyl chloroformate (0.829 ml, 5.99 mmol), and the mixture was stirred at room temperature for 1 hour. Water was poured to the reaction mixture, and the resulting solution was extracted with ethyl acetate. The extract was introduced to water and dried over anhydrous magnesium sulfate. The solvent was distilled off under reduced pressure to give 867 mg (46.2%) of the desired product as an oil.

$^1$H-NMR (CDCl$_3$) δ; 1.46 (9H, s), 1.48-1.69 (3H, m), 1.85-1.89 (1H, m), 3.28-3.37 (3H, m), 3.58-3.63 (1H, m), 3.68-3.76 (1H, m), 4.69 (1H, d, J=12.0 Hz), 4.75 (1H, d, J=12.0 Hz), 5.13 (1H, d, J=6.0 Hz).

(2) tert-Butyl 3-({[4-(3-phenyl-1,2,4-thiadiazol-5-yl)piperazin-1-yl]carbonyl}amino)piperidine-1-carboxylate A mixed solution of tert-butyl 3-{[(2,2,2-trichloroethoxy)carbonyl]amino}piperidine-1-carboxylate (555 mg, 1.48 mmol), 1-(3-phenyl-1,2,4-thiadiazol-5-yl)piperazine (400 mg, 1.62 mmol) and diisopropylethylamine (0.257 ml, 1.48 mmol) in dimethyl sulfoxide (4.9 ml) was stirred at 70° C. for 4 days. Water was poured to the reaction mixture, and the resulting solution was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give 90.9 mg (13.0%) of the desired product as a solid.

$^1$H-NMR (CDCl$_3$) δ; 1.43-1.79 (4H, m), 1.48 (9H, s), 2.99-3.64 (13H, m), 3.87-3.88 (1H, m), 7.39-7.45 (3H, m), 8.16-8.19 (2H, m).

The structural formulae of Compounds obtained in Examples 118 to 138 are shown in Table 7.

TABLE 7

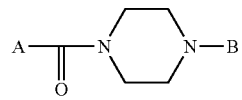

| Example No. | A | B |
| --- | --- | --- |
| 118 | 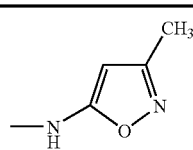 | 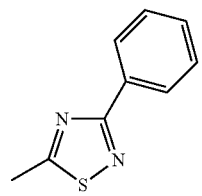 |

TABLE 7-continued
| Example No. | A | B |
|---|---|---|
| 119 | 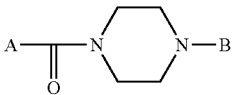 | 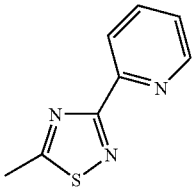 |
| 120 | 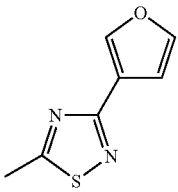 | 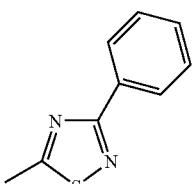 |
| 121 | 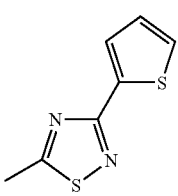 | 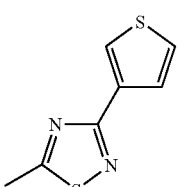 |
| 122 | 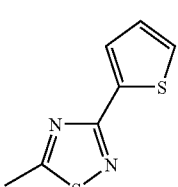 | 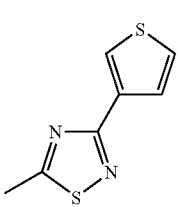 |
| 123 | | |
| 124 | | |
| 125 | | |

TABLE 7-continued

| Example No. | A | B |
|---|---|---|
| 126 | 6-(methylamino)-2-(trifluoromethyl)-1H-benzimidazole | 5-methyl-3-phenyl-1,2,4-thiadiazole |
| 127 | 4-(methylamino)pyridine | 2-methyl-4-phenylthiazole |
| 128 | 6-(methylamino)-1-benzothiophene 1,1-dioxide | 5-methyl-3-(thiophen-2-yl)-1,2,4-thiadiazole |
| 129 | 4-(methylamino)-3,5-dimethylisoxazole | 5-methyl-3-phenyl-1,2,4-thiadiazole |
| 130 | 4-(methylamino)-5-methyl-3-phenylisoxazole | 5-methyl-3-phenyl-1,2,4-thiadiazole |
| 131 | 5-(methylamino)-3,4-dimethylisoxazole | 5-methyl-3-phenyl-1,2,4-thiadiazole |
| 132 | 5-(methylamino)-3-methylisoxazole | 2-methyl-4-phenylthiazole |

TABLE 7-continued
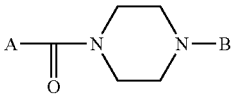
| Example No. | A | B |
|---|---|---|
| 133 | 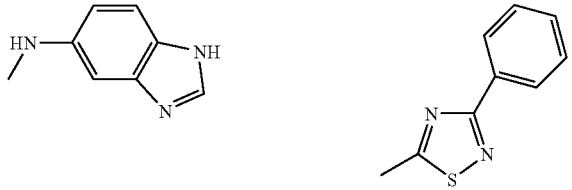 | 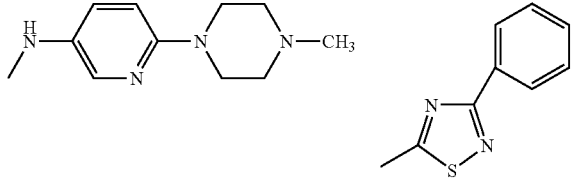 |
| 134 | 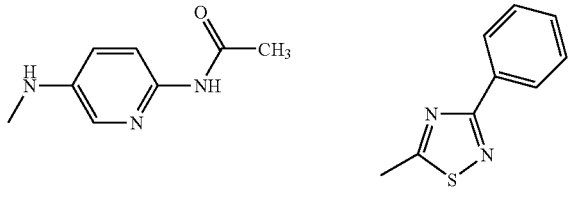 | 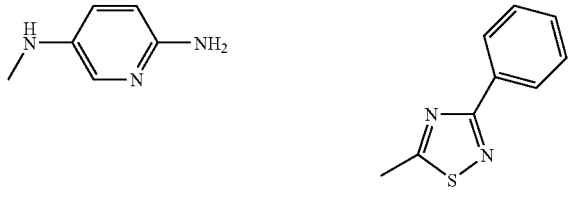 |
| 135 | 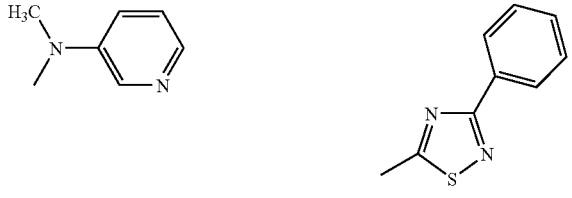 | 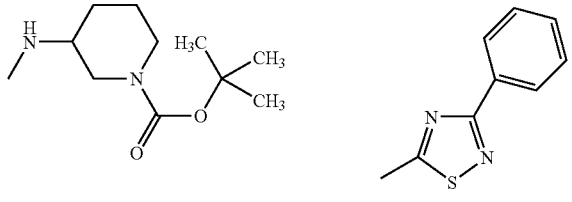 |
| 136 | | |
| 137 | | |
| 138 | | |

Example 139

N-1,2-Benzisoxazol-3-yl-3-methyl-4-(3-phenyl-1,2,4-thiadiazol-5-yl)piperazine-1-carboxamide

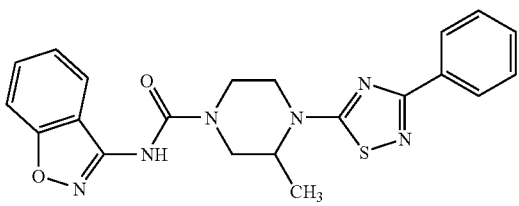

(1) tert-Butyl 3-methyl-4-(3-phenyl-1,2,4-thiadiazol-5-yl)piperazine-1-carboxylate To a solution of 1-tert-butoxycarbonyl-3-methylpiperazine (5.00 g, 24.0 mmol) and 4-tert-butoxycarbonylaminopiperidine (5.20 g, 26.4 mmol) in dimethylformamide (100 ml) was added triethylamine (3.35 ml, 24.0 mmol) at room temperature and the mixture was stirred at room temperature for 3 hours and at 70° C. for 1 hour. The reaction mixture was poured into water and the mixture was extracted with ethyl acetate. The extract was washed with water and dried over anhydrous magnesium sulfate. The solvent was distilled off under reduced pressure. The residue was recrystallized from a mixed solvent of ethyl acetate and hexane to obtain the desired product (6.75 g, 78.0%) as a solid.

$^1$H-NMR (CDCl$_3$) δ; 1.31 (3H, d, J=6.6 Hz), 1.50 (9H, s), 3.04 (1H, br s), 3.21 (1H, br s), 3.43-3.52 (1H, m), 3.74-3.79 (1H, m), 3.98-4.35 (3H, m), 7.40-7.44 (3H, m), 8.17-8.20 (2H, m).

(2) 2-Methyl-1-(3-phenyl-1,2,4-thiadiazol-5-yl)piperazine hydrochloride

To tert-butyl 3-methyl-4-(3-phenyl-1,2,4-thiadiazol-5-yl)piperazine-1-carboxylate (6.70 g, 18.6 mmol) was added a solution of 2N hydrogen chloride in methanol (400 ml) and the mixture was stirred at room temperature for 12 hours, and the solvent was distilled off under reduced pressure. The residue was recrystallized from a mixed solvent of ether and methanol to obtain the desired product (4.54 g, 82.2%) as a solid.

$^1$H-NMR (DMSO-d$_6$) δ; 1.43 (3H, d, J=6.6 Hz), 3.10-3.17 (1H, m), 3.29-3.33 (3H, m), 3.59-3.68 (1H, m), 3.92-3.96 (1H, m), 4.36 (1H, br s), 7.47-7.49 (3H, m), 8.09-8.12 (2H, m), 9.47 (2H, br s).

(3) 2-Methyl-1-(3-phenyl-1,2,4-thiadiazol-5-yl)piperazine

To 2-methyl-1-(3-phenyl-1,2,4-thiadiazol-5-yl)piperazine hydrochloride (500 mg, 1.68 mmol) was added an aqueous 1N sodium hydroxide solution (10 ml) and the mixture was extracted with chloroform. The extract was dried over anhydrous magnesium sulfate and the solvent was distilled off under reduced pressure to obtain the desired product (438 mg, 100%) as oil.

$^1$H-NMR (CDCl$_3$) δ; 1.40 (3H, d, J=6.3 Hz), 2.87-2.96 (2H, m), 3.07-3.14 (2H, m), 3.39-3.49 (1H, m), 3.71-3.74 (1H, m), 4.03 (1H, br s), 7.39-7.46 (3H, m), 8.16-8.20 (2H, m).

(4) N-1,2-Benzisoxazol-3-yl-3-methyl-4-(3-phenyl-1,2,4-thiadiazol-5-yl)piperazine-1-carboxamide A solution of 2-methyl-1-(3-phenyl-1,2,4-thiadiazol-5-yl)piperazine (390 mg, 1.50 mmol), bis(2,2,2-trichloroethyl) 1,2-benzisoxazol-3-ylimidodicarbonate (363 mg, 0.750 mmol), diisopropylethylamine (0.131 ml, 0.750 mmol) and dimethylsulfoxide (10 ml) was stirred at 70° C. for 2 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (hexane:ethyl acetate=1:1) to obtain the desired product as a solid. This was recrystallized from a mixed solvent of ethyl acetate and hexane to obtain the desired product (220 mg, 69.8%) as a solid.

$^1$H-NMR (DMSO-d$_6$) δ; 1.31 (3H, d, J=6.9 Hz), 3.22-3.42 (2H, m), 3.57-3.65 (1H, m), 3.80-3.90 (1H, m), 4.13-4.29 (3H, m), 7.31-7.35 (1H, m), 7.47-7.50 (3H, m), 7.59-7.67 (2H, m), 7.84 (1H, d, J=8.1 Hz), 8.11-8.15 (2H, m), 10.10 (1H, s).

Example 140

N-1,2-Benzisoxazol-3-yl-4-(4-phenyl-2-thienyl)piperazine-1-carboxamide

(1) Ethyl 4-(4-phenyl-2-thienyl)piperazine-1-carboxylate

To a solution of 3-phenylthiophene (5.00 g, 32.0 mmol) in acetic acid (65 ml) was added dropwise a solution of bromine (5.00 g, 32.0 mmol) in acetic acid (50 ml) and the mixture was heated under reflux for 5 hours. After cooling to room temperature, the reaction mixture was poured into water and the mixture was extracted with ether. The extract was washed with aqueous saturated sodium bicarbonate solution and dried over anhydrous magnesium sulfate, and the solvent was distilled off under reduced pressure. The residue was purified by silica gel column chromatography (hexane:ethyl acetate=9:1) to obtain a mixture of 2-bromo-4-phenylthiophene and 2-bromo-3-phenylthiophene (6.00 g, 80.4%) as an oil.

A solution of the mixture of 2-bromo-4-phenylthiophene and 2-bromo-3-phenylthiophene (6.00 g, 25.0 mmol), 1-ethoxycarbonylpiperazine (3.96 g, 25.0 mmol), sodium tert-butoxide (3.48 g, 36.2 mmol), 2,2'-bis(diphenylphosphino)-1,1'-binaphthyl (468 mg, 0.750 mmol) and tris(dibenzylideneacetone)dipalladium (0) (544 mg, 0.594 mmol) in toluene (50 ml) was stirred at 100° C. for 48 hours. Insolubles were filtered off and the filtrate was concentrated. The residue was purified by silica gel column chromatography (hexane: ethyl acetate=9:1) to obtain ethyl 4-(4-phenyl-2-thienyl)piperazine-1-carboxylate (365 mg, 4.61%) as an oil.

$^1$H-NMR (CDCl$_3$) δ; 1.29 (3H, t, J=7.2 Hz), 3.14-3.17 (4H, m), 3.63-3.67 (4H, m), 4.17 (2H, q, J=7.2 Hz), 6.47 (1H, d, J=1.8 Hz), 6.78 (1H, d, J=1.8 Hz), 7.26-7.30 (1H, m), 7.34-7.40 (2H, m), 7.52-7.56 (2H, m).

(2) 1-(4-Phenyl-2-thienyl)piperazine

A solution of ethyl 4-(4-phenyl-2-thienyl)piperazine-1-carboxylate (350 mg, 1.11 mmol), an aqueous 8N sodium hydroxide solution (5 ml) and ethanol (10 ml) was stirred at 100° C. for 3 hours, and the solvent was distilled off under reduced pressure. The residue was poured into water and the mixture was extracted with chloroform. The extract was dried over anhydrous magnesium sulfate and the solvent was distilled off under reduced pressure to obtain the desired product (240 mg, 88.9%) as an oil.

$^1$H-NMR (CDCl$_3$) δ; 3.03-3.06 (4H, m), 3.15-3.18 (4H, m), 6.42 (1H, d, J=1.8 Hz), 6.74 (1H, d, J=1.8 Hz), 7.26-7.29 (1H, m), 7.34-7.39 (2H, m), 7.54-7.56 (2H, m).

(3) N-1,2-Benzisoxazol-3-yl-4-(4-phenyl-2-thienyl) piperazine-1-carboxamide

A solution of 1-(4-phenyl-2-thienyl)piperazine (240 mg, 0.984 mmol), bis(2,2,2-trichloroethyl) 1,2-benzisoxazol-3-ylimidodicarbonate (239 mg, 0.492 mmol), diisopropylethylamine (0.0857 ml, 0.492 mmol) and dimethylsulfoxide (3 ml) was stirred at 70° C. for 2 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (hexane:ethyl acetate=1:1) to obtain the desired product as a solid. This was recrystallized from a mixed solvent of ethyl acetate and hexane to obtain the desired product (42.5 mg, 21.4%) as a solid.

$^1$H-NMR (DMSO-d$_6$) δ; 3.23 (4H, br s), 3.71 (4H, br s), 6.72 (1H, s), 7.11 (1H, s), 7.24-7.41 (4H, m), 7.58-7.67 (4H, m), 7.84 (1H, d, J=8.1 Hz), 10.04 (1H, s).

Example 141

N-(3,4-Dimethylisoxazol-5-yl)-4-[3-(3-fluorophenyl)-1,2,4-thiadiazol-5-yl]piperazine-1-carboxamide (1) tert-Butyl 4-{[(3,4-dimethylisoxazol-5-yl)amino] carbonyl}piperazine-1-carboxylate A solution of 1-(tert-butoxycarbonyl)piperazine (5.00 g, 26.8 mmol), 2,2,2-trichloroethyl (3,4-dimethylisoxazol-5-yl)carbamate (3.85 g, 13.4 mmol), disopropylethylamine (2.33 ml, 13.4 mmol) and dimethylsulfoxide (50 ml) was stirred at 70° C. for 2 hours, the reaction mixture was poured into water, and the mixture was extracted with ethyl acetate. The extract was washed with water and dried over anhydrous magnesium sulfate. The solvent was distilled off under reduced pressure. The residue was recrystallized from a mixed solvent of ethyl acetate and hexane to obtain the desired product (1.80 g, 41.4%) as a solid.

$^1$H-NMR (DMSO-d$_6$) δ; 1.48 (9H, s), 1.87 (3H, s), 2.19 (3H, s), 3.49 (8H, s), 6.81 (1H, br s).

(2) N-(3,4-Dimethylisoxazol-5-yl)piperazine-1-carboxamide trifluoroacetate

A mixture of tert-butyl 4-{[3,4-dimethylisoxazol-5-yl) amino]carbonyl}piperazine-1-carboxylate (1.00 g, 3.08 mmol) and trifluoroacetic acid (20 ml) was stirred at room temperature for 2 hours, and the solvent was distilled off under reduced pressure to obtain the desired product (1.00 g, 96.2%) as an oil.

$^1$H-NMR (CDCl$_3$) δ; 1.76 (3H, s), 2.13 (3H, s), 3.17 (4H, br s), 3.63 (4H, br s), 8.89 (2H, br s), 9.38 (1H, br s).

(3) N-(3,4-dimethylisoxazol-5-yl)-4-[3-(3-fluorophenyl)-1,2,4-thiadiazol-5-yl]piperazine-1-carboxamide A solution of N-(3,4-dimethylisoxazol-5-yl)piperazine-1-carboxamide trifluoroacetate (300 mg, 0.887 mmol), 5-chloro-3-(3-fluorophenyl)-1,2,4-thiadiazole (190 mg, 0.887 mmol), triethylamine (0.618 ml, 4.43 mmol) and N,N-dimethylformamide (3 ml) was stirred at room temperature for 2 hours and the reaction mixture was poured into water. A solid was collected by filtration and recrystallized from a mixed solvent of tetrahydrofuran and ethyl acetate to obtain the desired product (160 mg, 44.8%) as a solid.

$^1$H-NMR (CDCl$_3$) δ; 1.88 (3H, s), 2.20 (3H, s), 3.66-3.75 (8H, m), 7.08-7.15 (1H, m), 7.36-7.44 (1H, m), 7.86-7.91 (1H, m), 7.96-8.00 (1H, m), 9.05 (1H, s).

Example 142

4-(3-Phenyl-1,2,4-thiadiazol-5-yl)-N-pyrimidin-5-ylpiperazine-1-carboxamide (1) Pyrimidine-5-amine A mixture of 5-amino-4,6-dichloropyrimidine (2.00 g, 12.2 mmol), ether (240 ml), sodium hydroxide (8 g), water (32 ml) and 10% palladium-carbon (160 mg) was stirred under a hydrogen atmosphere at room temperature for 3 days, insolubles were filtered off and an organic layer was separated. The organic layer was dried over anhydrous magnesium sulfate and the solvent was distilled off under reduced pressure to obtain the desired product (370 mg, 31.9%) as a solid.

$^1$H-NMR (CDCl$_3$) δ; 3.75 (2H, br s), 8.21 (2H, s), 8.66 (1H, s).

(2) 2,2,2-Trichloroethyl pyrimidin-5-ylcarbamate

To a solution of pyrimidine-5-amine (100 mg, 1.05 mmol) and pyridine (0.255 ml, 3.15 mmol) in tetrahydrofuran (3 ml) was added 2,2,2-trichloroethyl chloroformate (0.217 ml, 1.58 mmol) with ice-cooling, the mixture was stirred for 30 minutes with ice-cooling, the reaction mixture was poured into ice-water and the mixture was extracted with ethyl acetate. The extract was washed with water and dried over anhydrous magnesium sulfate and the solvent was distilled off under reduced pressure. The residue was purified by silica gel column chromatography (hexane: ethyl acetate=1:1) to obtain the desired product (100 mg, 35.2%) as a solid.

$^1$H-NMR (CDCl$_3$) δ; 4.87 (2H, s), 7.60 (1H, br s), 8.95 (2H, s), 9.02 (1H, s).

(3) 4-(3-Phenyl-1,2,4-thiadiazol-5-yl)-N-pyrimidin-5-ylpiperazine-1-carboxamide

A solution of 2,2,2-trichloroethyl pyrimidin-5-ylcarbamate (100 mg, 0.369 mmol), 1-(3-phenyl-1,2,4-thiadiazol-5-yl)piperazine (87.4 mg, 0.369 mmol), diisopropylethylamine (0.0643 ml, 0.369 mmol) and dimethylsulfoxide (2 ml) was stirred at 70° C. for 2.5 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of tetrahydrofuran, ethyl acetate and hexane to obtain the desired product (26.3 mg, 19.5%) as a solid.

$^1$H-NMR (DMSO-d$_6$) δ; 3.69 (8H, br s), 7.47-7.49 (3H, m), 8.11-8.14 (2H, m), 8.79 (1H, s), 8.90 (2H, s), 9.12 (1H, s).

Example 143

N-(6-Methoxypyridin-3-yl)-4-(3-phenyl-1,2,4-thiadiazol-5-yl)piperazine-1-carboxamide (1) 2,2,2-Trichloroethyl (6-methoxypyridin-3-yl)carbamate To a solution of 5-amino-2-methoxypyridine (1.00 g, 8.06 mmol) and pyridine (1.96 ml, 24.2 mmol) in tetrahydrofuran (20 ml) was added 2,2,2-trichloroethyl chloroformate (1.67 ml, 12.1 mmol) with ice-cooling, the mixture was stirred for 30 minutes with ice-cooling, the reaction mixture was poured into ice-water and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) to obtain the desired product (2.30 g, 95.4%) as a solid.

$^1$H-NMR (CDCl$_3$) δ; 3.92 (3H, s), 4.82 (2H, s), 6.75 (1H, d, J=8.7 Hz), 6.80 (1H, br s), 7.81 (1H, dd, J=8.7, 2.7 Hz), 8.11 (1H, d, J=2.7 Hz).

(2) N-(6-Methoxypyridin-3-yl)-4-(3-phenyl-1,2,4-thiadiazol-5-yl)piperazine-1-carboxamide A solution of 2,2,2-trichloroethyl (6-methoxypyridin-3-yl) carbamate (300 mg, 1.00 mmol), 1-(3-phenyl-1,2,4-thiadiazol-5-yl)piperazine (246 mg, 1.00 mmol), diisopropylethylamine (0.174 ml, 1.00 mmol) and dimethylsulfoxide (5 ml) was stirred at 70° C. for 5 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of tetrahydrofuran, ethyl acetate and hexane to obtain the desired product (84.0 mg, 21.2%) as a solid.

$^1$H-NMR (DMSO-d$_6$) δ; 3.65 (8H, br s), 3.80 (3H, s), 6.75 (1H, d, J=9.0 Hz), 7.47-7.49 (3H, m), 7.76 (1H, dd, J=9.0, 2.7 Hz), 8.10-8.14 (2H, m), 8.19 (1H, d, J=2.7 Hz), 8.71 (1H, s).

Example 144

N-(4-Ethoxypyrimidin-5-yl)-4-(3-phenyl-1,2,4-thiadiazol-5-yl)piperazine-1-carboxamide

(4) 4-Ethoxypyrimidine-5-amine

A mixture of 5-amino-4,6-dichloropyrimidine (5.00 g, 30.5 mmol), tetrahydrofuran (100 ml), sodium hydroxide (2.44 g, 61.0 mmol), ethanol (100 ml) and 10% palladium-carbon (500 mg) was stirred under a hydrogen atmosphere at room temperature for 1 day, insolubles were filtered off and an organic layer was separated. The organic layer was dried over anhydrous magnesium sulfate and the solvent was distilled off under reduced pressure to obtain the desired product (4.00 g, 94.3%) as an oil.

$^1$H-NMR (CDCl$_3$) δ; 1.43 (3H, t, J=6.9 Hz), 3.75 (2H, br s), 4.48 (2H, q, J=6.9 Hz), 7.92 (1H, s), 8.24 (1H, s).

(2) 2,2,2-Trichloroethyl (4-ethoxyprimidin-5-yl)carbamate

To a solution of 4-ethoxypyrimidine-5-amine (1.00 g, 7.19 mmol) and pyridine (1.74 ml, 21.6 mmol) in tetrahydrofuran (20 ml) was added 2,2,2-trichloroethyl chloroformate (1.49 ml, 10.8 mmol) with ice-cooling, the mixture was stirred for 30 minutes with ice-cooling, the reaction mixture was poured into ice-water and the mixture was extracted with ethyl acetate. The extract was washed with water and dried over anhydrous magnesium sulfate and the solvent was distilled off under reduced pressure. The residue was recrystallized from a mixed solvent of ethyl acetate and hexane to obtain the desired product (1.73 g, 76.5%) as a solid.

$^1$H-NMR (CDCl$_3$) δ; 1.48 (3H, t, J=7.2 Hz), 4.55 (2H, q, J=7.2 Hz), 4.87 (2H, s), 7.15 (1H, br s), 8.51 (1H, s), 9.20 (1H, br s).

(3) N-(4-Ethoxypyrimidin-5-yl)-4-(3-phenyl-1,2,4-thiadiazol-5-yl)piperazine-1-carboxamide A solution of 2,2,2-trichloroethyl (4-ethoxypyrimidin-5-yl)carbamate (315 mg, 1.00 mmol), 1-(3-phenyl-1,2,4-thiadiazol-5-yl)piperazine (246 mg, 1.00 mmol), diisopropylethylamine (0.174 ml, 1.00 mmol) and dimethylsulfoxide (5 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of tetrahydrofuran, ethyl acetate and hexane to obtain the desired product (290 mg, 70.6%) as a solid.

$^1$H-NMR (DMSO-d$_6$) δ; 1.36 (3H, t, J=7.2 Hz), 3.65 (8H, br s), 4.44 (2H, q, J=7.2 Hz), 7.47-7.49 (3H, m), 8.10-8.14 (2H, m), 8.26 (1H, s), 8.50 (1H, s), 8.65 (1H, s).

Example 145

N-(3-Phenylisoxazol-5-yl)-4-(3-phenyl-1,2,4-thiadiazol-5-yl)piperazine-1-carboxamide

(1) 3-Phenylisoxazole-5-amine

A mixture of 3-oxo-3-phenylpropanenitrile (5.00 g, 34.4 mmol), hydroxylamine sulfate (3.10 g, 18.9 mmol), ethanol (35 ml) and an aqueous solution (35 ml) of sodium hydroxide (1.66 g, 41.4 mmol) was stirred at 80° C. for 24 hours. After cooling to room temperature, the reaction mixture was adjusted to pH=11 by addition of an aqueous 8N sodium hydroxide solution and then extracted with chloroform. The extract was washed with water and dried over anhydrous magnesium sulfate. The solvent was distilled off under reduced pressure and the residue was purified by silica gel column chromatography (hexane:ethyl acetate=1:1) to obtain the desired product (1.09 g, 19.8%) as a solid.

$^1$H-NMR (CDCl$_3$) δ; 4.00 (2H, br s), 6.09 (1H, s), 7.41-7.46 (3H, m), 7.70-7.73 (2H, m).

(2) 2,2,2-Trichloroethyl (3-phenylisoxazol-5-yl)carbamate

To a solution of 3-phenylisoxazole-5-amine (420 mg, 2.62 mmol) and pyridine (0.636 ml, 7.87 mmol) in tetrahydrofuran (5 ml) was added 2,2,2-trichloroethyl chloroformate (0.542 ml, 3.93 mmol) with ice-cooling, the mixture was stirred for 30 minutes with ice-cooling, the reaction mixture was poured into ice-water and the mixture was extracted with ethyl acetate. The extract was washed with water and dried over anhydrous magnesium sulfate and the solvent was distilled off under reduced pressure to obtain the desired product (750 mg, 85.3%) as a solid.

$^1$H-NMR (CDCl$_3$) δ; 4.88 (2H, s), 7.09 (1H, br s), 7.45-7.52 (3H, m), 7.77-7.81 (2H, m), 8.15 (1H, br s).

(3) N-(3-Phenylisoxazol-5-yl)-4-(3-phenyl-1,2,4-thiadiazol-5-yl)piperazine-1-carboxamide A solution of 2,2,2-trichloroethyl (3-phenylisoxazol-5-yl) carbamate (336 mg, 1.00 mmol), 1-(3-phenyl-1,2,4-thiadiazol-5-yl)piperazine (246 mg, 1.00 mmol) diisopropylethylamine (0.174 ml, 1.00 mmol) and dimethylsulfoxide (5 ml) was stirred at 70° C. for 12 hours, the reaction mixture was poured into water and a solid was collected by filtration. This was recrystallized from a mixed solvent of tetrahydrofuran and ethyl acetate to obtain the desired product (310 mg, 71.8%) as a solid.

$^1$H-NMR (DMSO-d$_6$) δ; 3.58-3.71 (8H, m), 7.23 (1H, s), 7.47-7.55 (6H, m), 7.84-7.87 (2H, m), 8.11-8.14 (2H, m), 10.04 (1H, s).

Example 146

4-[3-(3-Fluorophenyl)-1,2,4-thiadiazol-5-yl]-N-pyridin-3-ylpiperazine-1-carboxamide (1) 2,2,2-Trichloroethyl pyridin-3-ylcarbamante To a solution of 3-aminopyridine (11.4 g, 120 mmol) and pyridine (29.1 ml, 360 mmol) in tetrahydrofuran (200 ml) was added 2,2,2-trichloroethyl chloroformate (25.0 ml, 181 mmol) with ice-cooling, the mixture was stirred for 2 hours with ice-cooling, the reaction mixture was poured into ice-water and the mixture was extracted with ethyl acetate. The extract was washed with water and dried over anhydrous magnesium sulfate and the solvent was distilled off under reduced pressure to obtain the desired product (29.0 g, 89.8%) as a solid.
$^1$H-NMR (CDCl$_3$) δ; 4.85 (2H, s), 7.27 (1H, br s), 7.29-7.33 (1H, m), 8.01-8.04 (1H, m), 8.37-8.40 (1H, m), 8.56-8.57 (1H, m).

(2) tert-Butyl 4-[(pyridin-3-ylamino)carbonyl]piperazine-1-carboxylate

A solution of 2,2,2-trichloroethyl pyridin-3-ylcarbamate (15.0 g, 55.7 mmol), 1-(tert-butoxycarbonyl)piperazine (15.5 g, 83.5 mmol), diisopropylethylamine (9.70 ml, 55.7 mmol) and dimethylsulfoxide (300 ml) was stirred at 70° C. for 12 hours, the reaction mixture was poured into water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate to obtain the desired product (5.74 g, 33.6%) as a solid.
$^1$H-NMR (CDCl$_3$) δ; 1.49 (9H, s), 3.52 (8H, s), 6.63 (1H, s), 7.22-7.26 (1H, m), 7.95-7.99 (1H, m), 8.27-8.30 (1H, m), 8.43-8.44 (1H, m).

(3) N-Pyridin-3-ylpiperazine-1-carboxamide 2 trifluoroacetate

A mixture of tert-butyl 4-[(pyridin-3-ylamino)carbonyl]piperazine-1-carboxylate (5.50 g, 18.0 mmol) and trifluoroacetic acid (200 ml) was stirred at room temperature for 4 hours and the solvent was distilled off under reduced pressure. The residue was recrystallized from a mixed solvent of methanol and ether to obtain the desired product (7.31 g, 93.8%) as a solid.
$^1$H-NMR (DMSO-d$_6$) δ; 3.17 (4H, br s), 3.68-3.71 (4H, m), 7.62-7.67 (1H, m), 8.18 (1H, d, J=9.0 Hz), 8.36-8.38 (1H, m), 8.87 (1H, d, J=2.1 Hz), 9.03 (3H, br s), 9.40 (1H, s).

(4) 4-[3-(3-Fluorophenyl)-1,2,4-thiadiazol-5-yl]-N-pyridin-3-ylpiperazine-1-carboxamide A solution of N-pyridin-3-ylpiperazine-1-carboxamide 2 trifluoroacetate (300 mg, 0.691 mmol), 5-chloro-3-(3-fluorophenyl)-1,2,4-thiadiazole (149 mg, 0.691 mmol), triethylamine (0.482 ml, 3.46 mmol) and N,N-dimethylformamide (6 ml) was stirred at room temperature for 2 hours, the reaction mixture was poured into water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate to obtain the desired product (118 mg, 44.4%) as a solid.
$^1$H-NMR (DMSO-d$_6$) δ; 3.67 (8H, br s), 7.27-7.37 (2H, m), 7.50-7.58 (1H, m), 7.81-7.91 (2H, m), 7.96 (1H, d, J=8.1 Hz), 8.16-8.18 (1H, m), 8.65 (1H, d, J=2.4 Hz), 8.92 (1H, s).

Example 147

4-(3-Phenyl-1,2,4-thiadiazol-5-yl)-N-pyridazin-3-ylpiperazine-1-carboxamide (1) Pyridazine-3-amine A mixture of 6-chloropyridazine-3-amine (5.00 g, 38.6 mmol), tetrahydrofuran (240 ml), sodium hydroxide (8.00 g, 200 mmol), water (32 ml) and 10% palladium-carbon (500 mg) was stirred under a hydrogen atmosphere at room temperature for 2 days, insolubles were filtered off and the filtrate was concentrated. The residue was dissolved in methanol (100 ml), insolubles were filtered off and the filtrate was concentrated to obtain the desired product as a solid quantitatively.
$^1$H-NMR (DMSO-d$_6$) δ; 2.51 (2H, br s), 6.46-6.49 (1H, m), 6.93-6.97 (1H, m), 8.06-8.08 (1H, m).

(2) 2,2,2-Trichloroethyl pyridazin-3-ylcarbamate

To a solution of pyridazine-3-amine (2.00 g, 21.0 mmol) and pyridine (5.10 ml, 63.1 mmol) in tetrahydrofuran (100 ml) was added 2,2,2-trichloroethyl chloroformate (4.34 ml, 31.5 mmol) with ice-cooling, the mixture was stirred for 50 minutes with ice-cooling, the reaction mixture was poured into ice-water and the mixture was extracted with ethyl acetate. The extract was washed with water and dried over anhydrous magnesium sulfate and the solvent was distilled off under reduced pressure. The residue was purified by silica gel column chromatography (ethyl acetate) to obtain the desired product (530 mg, 9.3%) as a solid.
$^1$H-NMR (CDCl$_3$) δ; 4.87 (2H, s), 7.52 (1H, dd, J=8.7, 5.1 Hz), 8.25 (1H, dd, J=1.5, 8.7 Hz), 8.31 (1H, br s), 8.95 (1H, dd, J=1.5, 5.1 Hz).

(3) 4-(3-Phenyl-1,2,4-thiadiazol-5-yl)-N-pyridazin-3-ylpiperazine-1-carboxamide

A solution of 2,2,2-trichloroethyl pyridazin-3-ylcarbamate (200 mg, 0.793 mmol), 1-(3-phenyl-1,2,4-thiadiazol-5-yl)piperazine (182 mg, 0.739 mmol), diisopropylethylamine (0.129 ml, 0.739 mmol) and dimethylsulfoxide (3 ml) was stirred at 70° C. for 12 hours, the reaction mixture was poured into water and a solid was collected by filtration. This was recrystallized from ethyl acetate to obtain the desired product (117 mg, 43.0%) as a solid. mp 185-186° C.
$^1$H-NMR (DMSO-d$_6$) δ; 3.65-3.73 (8H, m), 7.46-7.50 (3H, m), 7.59 (1H, dd, J=9.0, 5.4 Hz), 8.01 (1H, dd, J=1.5, 9.0 Hz), 8.11-8.14 (2H, m), 8.86 (1H, dd, J=5.4, 1.5 Hz), 10.11 (1H, br s).

Example 148

4-(3-Phenyl-1,2,4-thiadiazol-5-yl)-N-pyrazin-2-ylpiperazine-1-carboxamide (1) 2,2,2-Trichloroethyl pyrazin-2-ylcarbamate To a solution of aminopyrazine (2.00 g, 21.0 mmol) and pyridine (5.10 ml, 63.1 mmol) in tetrahydrofuran was added 2,2,2-trichloroethyl chloroformate (4.34 ml, 31.5 mmol) with ice-cooling, the mixture was stirred for 2 hours with ice-cooling, the reaction mixture was poured into ice-water and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) to obtain the desired product (193 mg, 3.4%) as a solid.

$^1$H-NMR (CDCl$_3$) δ; 4.90 (2H, s), 8.34-8.39 (2H, m), 8.61 (1H, br s), 9.38 (1H, d, J=1.2 Hz).

(2) 4-(3-Phenyl-1,2,4-thiadiazol-5-yl)-N-pyrazin-2-ylpiperazine-1-carboxamide A solution of 2,2,2-trichloroethyl pyrazin-2-ylcarbamate (150 mg, 0.556 mmol), 1-(3-phenyl-1,2,4-thiadiazol-5-yl) piperazine (137 mg, 0.556 mmol), diisopropylethylamine (0.0968 ml, 0.556 mmol) and dimethylsulfoxide (3 ml) was stirred at 70° C. for 12 hours, the reaction mixture was poured into water and a solid was collected by filtration and washed with water. This was recrystallized from a mixed solvent of tetrahydrofuran and ethyl acetate to obtain the desired product (74.3 mg, 36.4%) as a solid.

$^1$H-NMR (DMSO-d$_6$) δ; 3.60-3.71 (8H, m), 7.47-7.50 (3H, m), 8.10-8.14 (2H, m), 8.23-8.24 (1H, m), 8.31-8.33 (1H, m), 9.04-9.05 (1H, m), 9.76 (1H, br s).

Example 149

N-(3,4-Dimethylisoxazol-5-yl)-4-[3-(2-fluorophenyl)-1,2,4-thiadiazol-5-yl]piperazine-1-carboxamide A solution of N-(3,4-dimethylisoxazol-5-yl)piperazine-1-carboxamide trifluoroacetate (297 mg, 0.707 mmol), 5-chloro-3-(2-fluorophenyl)-1,2,4-thiadiazole (152 mg, 0.707 mmol), triethylamine (0.491 ml, 3.53 mmol) and N,N-dimethylformamide (3 ml) was stirred at room temperature for 0.5 hours, the reaction mixture was poured into water and the mixture was extracted with ethyl acetate. The extract was washed with water and dried over anhydrous magnesium sulfate and the solvent was distilled off under reduced pressure. The residue was recrystallized from a mixed solvent of tetrahydrofuran and ethyl acetate to obtain the desired product (44.0 mg, 15.5%) as a solid.

$^1$H-NMR (DMSO-d$_6$) δ; 1.76 (3H, s), 2.13 (3H, s), 3.63 (8H, br s), 7.28-7.35 (2H, m), 7.49-7.56 (1H, m), 8.00-8.06 (1H, m), 9.34 (1H, s).

Example 150

N-(3,4-Dimethylisoxazol-5-yl)-4-[3-(4-fluorophenyl)-1,2,4-thiadiazol-5-yl]piperazine-1-carboxamide A solution of N-(3,4-dimethylisoxazol-5-yl)piperazine-1-carboxamide trifluoroacetate (210 mg, 0.621 mmol), 5-chloro-3-(4-fluorophenyl)-1,2,4-thiadiazole (133 mg, 0.621 mmol), triethylamine (0.432 ml, 3.11 mmol) and N,N-dimethylformamide (3 ml) was stirred at room temperature for 0.5 hours and the reaction mixture was poured into water. A solid was collected by filtration and recrystallized from a mixed solvent of tetrahydrofuran and ethyl acetate to obtain the desired product (49.5 mg, 19.8%) as a solid.

$^1$H-NMR (DMSO-d$_6$) δ; 1.77 (3H, s), 2.13 (3H, s), 3.64 (8H, s), 7.28-7.34 (2H, m), 8.13-8.18 (2H, m), 9.34 (1H, s).

Example 151

4-(3-Phenyl-1,2,4-thiadiazol-5-yl)-N-pyridazin-4-ylpiperazine-1-carboxamide

(1) Pyridazine-4-amine

A mixture of 3,6-dichloropyridazine-4-amine (5.00 g, 18.2 mmol), tetrahydrofuran (100 ml), sodium hydroxide (8.00 g, 200 mmol), water (32 ml) and 10% palladium-carbon (500 mg) was stirred under a hydrogen atmosphere at room temperature for 2 days, insolubles were filtered off and the filtrate was concentrated. The residue was dissolved in methanol (100 ml), insolubles were filtered off and the filtrate was concentrated to obtain the desired product quantitatively as a solid.

$^1$H-NMR (DMSO-d$_6$) δ; 2.51 (2H, br s), 6.00 (1H, br s), 7.81-7.85 (1H, m), 7.98-8.00 (1H, m).

(2) 2,2,2-Trichloroethyl pyridazin-4-ylcarbamate

To a solution of pyridazine-4-amine (1.73 g, 18.2 mmol) and pyridine (4.41 ml, 54.6 mmol) in tetrahydrofuran (100 ml) was added 2,2,2-trichloroethyl chloroformate (3.76 ml, 27.3 mmol) was added, the mixture was stirred for 1.5 hours with ice-cooling, the reaction mixture was poured into ice-water and the mixture was extracted with ethyl acetate. The extract was washed with water and dried over anhydrous magnesium sulfate and the solvent was distilled off under reduced pressure to obtain the desired product (218 mg, 4.4%) as a solid.

$^1$H-NMR (DMSO-d$_6$) δ; 5.02 (2H, s), 7.78-7.81 (1H, m), 9.03-9.05 (1H, m), 9.25-9.27 (1H, m), 10.95 (1H, br s).

(3) 4-(3-Phenyl-1,2,4-thiadiazol-5-yl)-N-pyridazin-4-ylpiperazine-1-carboxamide A solution of 2,2,2-trichloroethyl pyridazin-4-ylcarbamate (100 mg, 0.370 mmol), 1-(3-phenyl-1,2,4-thiadiazol-5-yl) piperazine (88.9 mg, 0.370 mmol), diisopropylethylamine (0.0645 ml, 0.370 mmol) and dimethylsulfoxide (2 ml) was stirred at 70° C. for 12 hours, the reaction mixture was poured into water and the mixture was extracted with ethyl acetate. The extract was washed with water and dried over anhydrous magnesium sulfate and the solvent was distilled off under reduced pressure. The residue was recrystallized from ethyl acetate to obtain the desired product (55.0 mg, 40.4%) as a solid.

$^1$H-NMR (DMSO-d$_6$) δ; 3.68-3.70 (8H, m), 7.46-7.50 (3H, m), 7.77-7.80 (1H, m), 8.11-8.15 (2H, m), 8.90-8.93 (1H, m), 9.29-9.31 (1H, m), 9.41 (1H, br s).

Example 152

N-(4-Ethoxypyrimidin-5-yl)-4-(4-phenyl-1,3-thiazol-2-yl)piperazine-1-carboxamide A solution of 2,2,2-trichloroethyl (4-ethoxypyrimidin-5-yl)carbamate (315 mg, 1.00 mmol), 1-(4-phenyl-1,3-thiazol-2-yl)piperazine (245 mg, 1.00 mmol), diisopropylethylamine (0.174 ml, 1.00 mmol) and dimethylsulfoxide (5 ml) was stirred at 70° C. for 12 hours, the reaction mixture was poured into water and the mixture was extracted with ethyl acetate. The extract was washed with water and dried over anhydrous magnesium sulfate and the solvent was distilled off under reduced pressure. The residue was recrystallized from a mixed solvent of ethyl acetate and hexane to obtain the desired product (177 mg, 43.2%) as a solid.

$^1$H-NMR (DMSO-d$_6$) δ; 1.36 (3H, t, J=7.2 Hz), 3.54-3.63 (8H, m), 4.45 (2H, q, J=7.2 Hz), 7.27-7.42 (4H, m), 7.86-7.89 (2H, m), 8.20 (1H, s), 8.49 (1H, d, J=2.1 Hz), 8.65 (1H, d, J=2.1 Hz).

Example 153

4-(4-Phenyl-1,3-thiazol-2-yl)-N-pyrimidin-5-ylpiperazine-1-carboxamide

A solution of 2,2,2-trichloroethyl pyrimidin-5-ylcarbamate (263 mg, 0.972 mmol), 1-(4-phenyl-1,3-thiazol-2-yl)piperazine (238 mg, 0.972 mmol), diisopropylethylamine (0.169 ml, 0.972 mmol) and dimethylsulfoxide (3 ml) was stirred at 70° C. for 12 hours, the reaction mixture was poured into water and the mixture was extracted with ethyl acetate. The extract was washed with water and dried over anhydrous magnesium sulfate and the solvent was distilled off under reduced pressure. The residue was recrystallized from ethyl acetate to obtain the desired product (97.4 mg, 27.4%) as a solid.

$^1$H-NMR (DMSO-$d_6$) δ; 3.54-3.69 (8H, m), 7.27-7.43 (4H, m), 7.86-7.89 (2H, m), 8.79 (1H, s), 8.91 (2H, s), 9.09 (1H, s).

Example 154

4-(4-Phenyl-1,3-thiazol-2-yl)-N-pyridazin-4-ylpiperazine-1-carboxamide

A solution of 2,2,2-trichloroethyl pyridazin-4-ylcarbamate (100 mg, 0.370 mmol), 1-(4-phenyl-1,3-thiazol-2-yl)piperazine (90.7 mg, 0.370 mmol), diisopropylethylamine (0.0645 ml, 0.370 mmol) and dimethylsulfoxide (2 ml) was stirred at 70° C. for 12 hours, the reaction mixture was poured into water and the mixture was extracted with ethyl acetate. The extract was washed with water and dried over anhydrous magnesium sulfate and the solvent was distilled off under reduced pressure. The residue was recrystallized from ethyl acetate to obtain the desired product (80.4 mg, 59.1%) as a solid.

$^1$H-NMR (DMSO-$d_6$) δ; 3.55-3.68 (8H, m), 7.27-7.42 (4H, m), 7.77-7.79 (1H, m), 7.86-7.88 (2H, m), 8.90 (1H, d, J=6.0 Hz), 9.30 (1H, d, J=2.4 Hz), 9.39 (1H, br s).

Example 155

N-{6-[Acetyl(methyl)amino]pyridin-3-yl]-4-(3-phenyl-1,2,4-thiadiazol-5-yl)piperazine-1-carboxamide (1) N-(5-Nitropyridin-2-yl)acetamide To a solution of 2-amino-5-nitropyridine (13.9 g, 100 mmol) and pyridine (24 ml, 300 mmol) in tetrahydrofuran (300 ml) was added dropwise acetyl chloride (10.7 ml, 150 mmol) with ice-cooling, the mixture was stirred at room temperature for 1 hour. To the mixture was added dropwise acetyl chloride (10.7 ml, 150 mmol) and the mixture was stirred at room temperature for 1 hour. The reaction mixture was poured into ice-water and the desired product (14.5 g, 80.1%) as a solid was collected by filtration.

$^1$H-NMR (DMSO-$d_6$) δ; 2.17 (3H, s), 8.28 (1H, d, J=9.1 Hz), 8.59 (1H, dd, J=2.7, 9.1 Hz), 9.16 (1H, d, J=2.7 Hz), 11.23 (1H, s).

(2) N-Methyl-N-(5-nitorpyridin-2-yl)acetamide

To a solution of N-(5-nitropyridin-2-yl)acetamide (2.00 g, 1.10 mmol) in N,N-dimethylformamide (40 ml) was added sodium hydride (60%, 663 mg, 16.6 mmol) with ice-cooling, the mixture was stirred at room temperature for 40 minutes and to the mixture was added iodomethane (1.33 ml, 16.6 mmol) with ice-cooling. The mixture was stirred at room temperature for 30 minutes, the reaction mixture was poured into ice-water and the mixture was extracted with ethyl acetate. The extract was washed and dried over anhydrous magnesium sulfate and the solvent was distilled off under reduced pressure. The residue was recrystallized from a mixed solvent of hexane and ethyl acetate to obtain the desired product (1.40 g, 65.1%) as a solid.

$^1$H-NMR (CDCl$_3$) δ; 2.40 (3H, s), 3.57 (3H, s), 7.99 (1H, d, J=9.0 Hz), 8.44 (1H, dd, J=3.0, 9.0 Hz), 9.25 (1H, d, J=3.0 Hz).

(3) N-5-(Aminopyridin-2-yl)-N-methylacetamide

A mixture of N-methyl-N-(5-nitropyridin-2-yl)acetamide (1.30 g, 6.66 mmol), 10% palladium-carbon (130 mg), tetrahydrofuran (10 ml) and methanol (10 ml) was stirred under a hydrogen atmosphere for 12 hours and insolubles were filtered off. The filtrate was concentrated to obtain the desired product (1.00 g, 90.9%) as an oil.

$^1$H-NMR (CDCl$_3$) δ; 1.93 (3H, s), 3.27 (3H, s), 3.82 (2H, br s), 6.96-7.07 (2H, m), 7.96 (1H, d, J=2.7 Hz).

(4) 2,2,2-Trichloroethyl {6-[acetyl(methyl)amino]pyridin-3-yl}carbamate

To a solution of N-(5-aminopyridin-2-yl)-N-methylacetamide (1.00 g, 6.06 mmol) and pyridine (1.47 ml, 18.2 mmol) in tetrahydrofuran (20 ml) was added 2,2,2-trichloroethyl chloroformate (1.25 ml, 9.09 mmol) with ice-cooling, the mixture was stirred for 0.5 hour with ice-cooling, the reaction mixture was poured into ice-water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate to obtain the desired product (1.08 g, 52.4%) as a solid.

$^1$H-NMR (CDCl$_3$) δ; 2.09 (3H, s), 3.36 (3H, s), 4.85 (2H, s), 7.16-7.35 (2H, m), 8.05 (1H, br s), 8.45 (1H, d, J=2.4 Hz).

(5) N-{6-[Acetyl(methyl)amino]pyridin-3-yl]-4-(3-phenyl-1,2,4-thiadiazol-5-yl)piperazine-1-carboxamide A solution of 2,2,2-trichloroethyl {6-[acetyl(methyl)amino]pyridin-3-yl}carbamate (200 mg, 0.587 mmol), 1-(3-phenyl-1,2,4-thiadiazol-5-yl)piperazine (145 mg, 0.587 mmol), diisopropylethylamine (0.102 ml, 0.587 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from a mixed solvent of ethyl acetate and hexane to obtain the desired product (101 mg, 39.3%) as a solid.

$^1$H-NMR (DMSO-$d_6$) δ; 1.93 (3H, s), 3.19 (3H, s), 3.68 (8H, br s), 7.37 (1H, d, J=9.0 Hz), 7.47-7.49 (3H, m), 7.96 (1H, dd, J=9.0, 2.4 Hz), 8.11-8.14 (2H, m), 8.55 (1H, d, J=2.4 Hz), 9.03 (1H, s).

Example 156

N-{6-[Acetyl(methyl)amino]pyridin-3-yl]-4-(4-phenyl-1,3-thiazol-2-yl)piperazine-1-carboxamide A solution of 2,2,2-trichloroethyl {6-[acetyl(methyl)amino]pyridin-3-yl}carbamate (200 mg, 0.587 mmol), 1-(4-phenyl-1,3-thiazol-2-yl)piperazine (144 mg, 0.587 mmol), diisopropylethylamine (0.102 ml, 0.587 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from a mixed solvent of ethyl acetate and hexane to obtain the desired product (114 mg, 44.5%) as a solid.
$^1$H-NMR (DMSO-d$_6$) δ; 1.92 (3H, s), 3.19 (3H, s), 3.54-3.56 (4H, m), 3.65-3.66 (4H, m), 7.26-7.42 (5H, m), 7.86 (2H, d, J=7.2 Hz), 7.95-7.99 (1H, m), 8.55 (1H, d, J=2.1 Hz), 9.00 (1H, s).

Example 157

N-(1-Methyl-1H-pyrazol-5-yl]-4-(4-phenyl-1,3-thiazol-2-yl)piperazine-1-carboxamide (1) Bis(2,2,2-trichloroethyl) (1-methyl-1H-pyrazol-5-yl)imidodicarbonate To a solution of 1-methyl-1H-pyrazole-5-amine (10.0 g, 103 mmol) and pyridine (25.0 ml, 309 mmol) in tetrahydrofuran (200 ml) was added 2,2,2-trichloroethyl chloroformate (21.3 ml, 155 mmol) with ice-cooling, the mixture was stirred for 0.5 hour with ice-cooling, the reaction mixture was poured into ice-water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate to obtain the desired product (15.0 g, 32.5%) as a solid.
$^1$H-NMR (CDCl$_3$) δ; 3.80 (3H, s), 4.83 (4H, s), 6.26 (1H, d, J=2.4 Hz), 7.50 (1H, d, J=2.4 Hz).

(2) N-(1-Methyl-1H-pyrazol-5-yl]-4-(4-phenyl-1,3-thiazol-2-yl)piperazine-1-carboxamide A solution of bis(2,2,2-trichloroethyl) (1-methyl-1H-pyrazol-5-yl)imidodicarbonate (200 mg, 0.447 mmol), 1-(4-phenyl-1,3-thiazol-2-yl)piperazine (180 mg, 0.734 mmol), diisopropylethylamine (0.129 ml, 0.734 mmol) and dimethylsulfoxide (2 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from a mixed solvent of ethyl acetate and hexane to obtain the desired product (54.8 mg, 33.2%) as a solid.
$^1$H-NMR (DMSO-d$_6$) δ; 3.52-3.54 (4H, m), 3.60-3.62 (7H, m), 6.01 (1H, d, J=1.8 Hz), 7.26-7.41 (5H, m), 7.86-7.89 (2H, m), 8.68 (1H, s).

Example 158

N-[4-(Acetylamino)phenyl]-4-(3-phenyl-1,2,4-thiadiazol-5-yl)piperazine-1-carboxamide (1) 2,2,2-Trochloroethyl [4-(acetylamino)phenyl]carbamate To a solution of 4-aminoacetoanilide (15.0 g, 100 mmol) and pyridine (24.3 ml, 300 mmol) in tetrahydrofuran (300 ml) was added 2,2,2-trichloroethyl chloroformate (20.7 ml, 150 mmol) with ice-cooling, the mixture was stirred for 1 hour with ice-cooling, the reaction mixture was poured into ice-water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate to obtain the desired product (27.3 g, 84.0%) as a solid.
$^1$H-NMR (CDCl$_3$) δ; 2.13 (3H, s), 4.83 (2H, s), 7.43-7.53 (4H, m), 9.05 (2H, br s).

(2) N-[4-(Acetylamino)phenyl]-4-(3-phenyl-1,2,4-thiadiazol-5-yl)piperazine-1-carboxamide A solution of 2,2,2-trichloroethyl [4-(acetylamino)phenyl]carbamate (200 mg, 0.614 mmol), 1-(3-phenyl-1,2,4-thiadiazol-5-yl)piperazine (151 mg, 0.614 mmol), diisopropylethylamine (0.107 ml, 0.614 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from ethyl acetate to obtain the desired product (25.0 mg, 9.6%) as a solid.
$^1$H-NMR (DMSO-d$_6$) δ; 2.01 (3H, s), 3.64 (8H, br s), 7.34-7.49 (7H, m), 8.11-8.14 (2H, m), 8.64 (1H, s), 9.81 (1H, s).

Example 159

N-[4-(Acetylamino)phenyl]-4-(4-phenyl-1,3-thiazol-2-yl)piperazine-1-carboxamide

A solution of 2,2,2-trichloroethyl [4-(acetylamino)phenyl]carbamate (200 mg, 0.614 mmol), 1-(4-phenyl-1,3-thiazol-2-yl)piperazine (150 mg, 0.614 mmol), diisopropylethylamine (0.107 ml, 0.614 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from ethyl acetate to obtain the desired product (38.0 mg, 14.7%) as a solid.
$^1$H-NMR (DMSO-d$_6$) δ; 2.01 (3H, s), 3.51 (4H, br s), 3.62 (4H, br s), 7.29-7.46 (8H, m), 7.80-7.89 (2H, m), 8.60 (1H, s), 9.80 (1H, s).

Example 160

4-[3-(2-Fluorophenyl)-1,2,4-thiadiazol-5-yl]-N-pyridin-3-ylpiperazine-1-carboxamide A solution of N-pyridin-3-ylpiperazine-1-carboxamide 2 trifluoroacetate (300 mg, 0.691 mmol), 5-chloro-3-(2-fluorophenyl)-1,2,4-thiadiazole (149 mg, 0.691 mmol), triethylamine (0.482 ml, 3.46 mmol) and N,N-dimethylformamide (6 ml) was stirred at room temperature for 15 minutes, the reaction mixture was poured into water and the mixture was extracted with ethyl acetate. The extract was washed with water and dried over anhydrous magnesium sulfate. The solvent was distilled off under reduced pressure. The residue was recrystallized from ethyl acetate to obtain the desired product (170 mg, 44.4%) as a solid.
$^1$H-NMR (DMSO-d$_6$) δ; 3.66 (8H, br s), 7.27-7.35 (3H, m), 7.50-7.54 (1H, m), 7.87-7.91 (1H, m), 8.00-8.06 (1H, m), 8.16-8.18 (1H, m), 8.65 (1H, d, J=2.4 Hz), 8.90 (1H, s).

Example 161

4-[3-(4-Fluorophenyl)-1,2,4-thiadiazol-5-yl]-N-pyridin-3-ylpiperazine-1-carboxamide A solution of N-pyridin-3-ylpiperazine-1-carboxamide 2 trifluoroacetate (300 mg, 0.691 mmol), 5-chloro-3-(4-fluorophenyl)-1,2,4-thiadiazole (149 mg, 0.691 mmol), triethylamine (0.482 ml, 3.46 mmol) and N,N-dimethylformamide (6 ml) was stirred at room temperature for 15 minutes, the reaction mixture was poured into water and the mixture was extracted with ethyl acetate. The extract was washed with water and dried over anhydrous magnesium sulfate. The solvent was distilled off under reduced pressure. The residue was recrystallized from ethyl acetate to obtain the desired product (149 mg, 56.0%) as a solid.

$^1$H-NMR (DMSO-d$_6$) δ; 3.67 (8H, br s), 7.27-7.34 (3H, m), 7.87-7.91 (1H, m), 8.14-8.18 (3H, m), 8.65 (1H, d, J=2.7 Hz), 8.91 (1H, s).

Example 162

N-[2-(Acetylamino)pyrimidin-5-yl]-4-(4-phenyl-1,3-thiazol-2-yl)piperazine-1-carboxamide (1) N-(5-Nitropyrimidin-2-yl)acetamide To a solution of 2-amino-5-nitropyrimidine (3.00 g, 21.4 mmol), 4-dimethylaminopyridine (2.61 g, 21.4 mmol) and pyridine (10.4 ml, 128 mmol) in acetonitrile (100 ml) was added acetyl chloride (3.04 ml, 42.8 mmol), the mixture was stirred at 100° C. for 1 hour. To the mixture was added acetyl chloride (2.00 ml, 28.1 mmol) and the mixture was stirred at 100° C. for 12 hours. The reaction mixture was poured into ice-water and the mixture was extracted with ethyl acetate. The extract was washed with water and dried over anhydrous magnesium sulfate. The solvent was distilled off under reduced pressure and the residue was recrystallized from a mixed solvent of hexane and ethyl acetate to obtain the desired product (1.22 g, 31.3%) as a solid.

$^1$H-NMR (CDCl$_3$) δ; 2.59 (3H, s), 8.88 (1H, br s), 9.36 (2H, s).

(2) N-5-(Aminopyrimidin-2-yl)acetamide

A mixture of N-(5-nitropyrimidin-2-yl)acetamide (620 g, 3.40 mmol), 10% palladium-carbon (100 mg), tetrahydrofuran (10 ml) and methanol (10 ml) was stirred under a hydrogen atmosphere for 12 hours. Insolubles were filtered off and the filtrate was concentrated to obtain the desired product (460 mg, 89.0%) as a solid.

$^1$H-NMR (DMSO-d$_6$) δ; 2.03 (3H, s), 2.86 (1H, br s), 5.28 (2H, s), 7.99 (2H, s).

(3) 2,2,2-Trichloroethyl [2-(acetylamino)pyrimidin-5-yl]carbamate

To a solution of N-(5-aminopyrimidin-2-yl)acetamide (450 mg, 2.96 mmol) and pyridine (0.718 ml, 8.87 mmol) in tetrahydrofuran (10 ml) was added 2,2,2-trichloroethyl chloroformate (0.612 ml, 4.44 mmol) with ice-cooling, the mixture was stirred for 1 hour with ice-cooling and then at room temperature for 2 hours, the reaction mixture was poured into ice-water and the mixture was extracted with ethyl acetate. The extract was washed with water and dried over anhydrous magnesium sulfate and the solvent was distilled off under reduced pressure to obtain the desired product (88.3 mg, 9.1%) as a solid.

$^1$H-NMR (CDCl$_3$) δ; 2.46 (3H, s), 4.85 (2H, s), 8.30 (1H, br s), 8.76 (2H, s).

(4) N-[2-(Acetylamino)pyrimidin-5-yl]-4-(4-phenyl-1,3-thiazol-2-yl)piperazine-1-carboxamide A solution of 2,2,2-trichloroethyl [2-(acetylamino)pyrimidin-5-yl]carbamate (60.0 mg, 0.187 mmol), 1-(4-phenyl-1,3-thiazol-2-yl)piperazine (44.9 mg, 0.183 mmol), diisopropylethylamine (0.0319 ml, 0.183 mmol) and dimethylsulfoxide (2 ml) was stirred at 80° C. for 4 hours, the reaction mixture was poured into water and the mixture was extracted with ethyl acetate. The extract was washed with water and dried over anhydrous magnesium sulfate. The solvent was distilled off under reduced pressure. The residue was recrystallized from a mixed solvent of tetrahydrofuran, ethyl acetate and hexane to obtain the desired product (31.0 mg, 40.0%) as a solid.

$^1$H-NMR (DMSO-d$_6$) δ; 2.12 (3H, s), 3.54 (4H, br s), 3.66 (4H, br s), 7.29-7.42 (4H, m), 7.86 (2H, d, J=8.4 Hz), 8.71 (2H, s), 8.94 (1H, s), 10.42 (1H, s).

Example 163

4-(4-Phenyl-1,3-thiazol-2-yl)-N-pyridazin-3-ylpiperazine-1-carboxamide

A solution of 2,2,2-trichloroethyl pyridazin-3-ylcarbamate (200 mg, 0.793 mmol), 1-(4-phenyl-1,3-thiazol-2-yl)piperazine (181 mg, 0.739 mmol), diisopropylethylamine (0.129 ml, 0.739 mmol) and dimethylsulfoxide (3 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from ethyl acetate to obtain the desired product (120 mg, 44.3%) as a solid.

$^1$H-NMR (DMSO-d$_6$) δ; 3.52-3.56 (4H, m), 3.68-3.71 (4H, m), 7.26-7.42 (4H, m), 7.56-7.61 (1H, m), 7.86-7.89 (2H, m), 7.99-8.02 (1H, m), 8.85-8.86 (1H, m), 10.03 (1H, s).

Example 164

N-Isoxazol-5-yl-4-(4-phenyl-1,3-thiazol-2-yl)piperazine-1-carboxamide (1) Propiolamide Methyl propiolate (25 ml, 281 mmol) was added dropwise to conc. aqueous ammonia (25 ml, 281 mmol) at 30° C. and the mixture was stirred at −30° C. for 20 minutes. The solvent was distilled off under reduced pressure, ether (200 ml) was added to the residue, the mixture was filtered and the filtrate was concentrated to obtain the desired product (18.5 g, 95.4%) as a solid.

$^1$H-NMR (DMSO-d$_6$) δ; 4.08 (1H, s), 7.62 (1H, br s), 8.08 (1H, br s).

(2) Propiolonitrile

A mixture of phosphorus pentaoxide (23.5 g, 165 mmol) and propiolamide (5.40 g, 78 mmol) was heated at 180° C. for 30 minutes and the desired product thus produced was trapped at 70° C. to obtain the desired product (1.54 g, 38.7%) as a liquid.

(3) Isoxazole-5-amine

A mixture of propiolonitrile (1.54 g, 30.2 mmol), hydroxylamine hydrochloride (2.10 g, 30.2 mmol), an aqueous 10% sodium hydroxide solution (12.1 ml, 30.2 mmol) and methanol (12 ml) was stirred at 30° C. for 12 hours. The reaction mixture was extracted with ethyl acetate. The extract was dried over anhydrous magnesium sulfate and the solvent was distilled off under reduced pressure. The residue was purified by silica gel column chromatography (ethyl acetate) to obtain the desired product (760 mg, 29.9%) as a solid.

$^1$H-NMR (CDCl$_3$) δ; 4.51 (2H, br s), 5.11 (2H, d, J=2.1 Hz), 7.96 (2H, d, J=2.1 Hz).

(4) 2,2,2-Trichloroethyl isoxazol-5-ylcarbamate

To a solution of isoxazole-5-amine (740 mg, 8.80 mmol) and pyridine (2.14 ml, 26.4 mmol) in tetrahydrofuran (10 ml) was added 2,2,2-trichloroethyl chloroformate (1.82 ml, 13.2 mmol) with ice-cooling and the mixture was stirred for 40 minutes with ice-cooling. To the mixture was further added 2,2,2-trichloroethyl chloroformate (1.82 ml, 13.2 mmol) with ice-cooling and the mixture was stirred for 30 minutes with ice-cooling, the reaction mixture was poured into ice-water and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) to obtain the desired product (1.23 g, 53.9%) as a solid.

$^1$H-NMR (CDCl$_3$) δ; 4.87 (2H, s), 6.20 (1H, d, J=2.1 Hz), 8.00 (1H, br s), 8.18 (1H, d, J=2.1 Hz).

(5) N-Isoxazol-5-yl-4-(4-phenyl-1,3-thiazol-2-yl)piperazine-1-carboxamide

A solution of 2,2,2-trichloroethyl isoxazol-5-ylcarbamate (200 mg, 0.771 mmol), 1-(4-phenyl-1,3-thiazol-2-yl)piperazine (189 mg, 0.771 mmol), diisopropylethylamine (0.134 ml, 0.771 mmol) and dimethylsulfoxide (7 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of ethyl acetate and hexane to obtain the desired product (98.8 mg, 36.1%) as a solid.

$^1$H-NMR (DMSO-d$_6$) δ; 3.51 (4H, br s), 3.64 (4H, br s), 6.05 (1H, d, J=1.8 Hz), 7.26-7.42 (4H, m), 7.85-7.88 (2H, m), 8.35 (1H, d, J=1.8 Hz), 10.51 (1H, s).

Example 165

N-Isoxazol-5-yl-4-(3-phenyl-1,2,4-thiadiazol-5-yl)piperazine-1-carboxamide

A solution of 2,2,2-trichloroethyl isoxazol-5-ylcarbamate (200 mg, 0.771 mmol), 1-(3-phenyl-1,2,4-thiadiazol-5-yl)piperazine (190 mg, 0.771 mmol), diisopropylethylamine (0.134 ml, 0.771 mmol) and dimethylsulfoxide (7 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of tetrahydrofuran, ethyl acetate and hexane to obtain the desired product (61.5 mg, 22.4%) as a solid.

$^1$H-NMR (DMSO-d$_6$) δ; 3.65-3.67 (8H, m), 6.05 (1H, d, J=2.1 Hz), 7.46-7.50 (3H, m), 8.10-8.13 (2H, m), 8.36 (1H, d, J=2.1 Hz), 10.55 (1H, s).

Example 166

4-(4-Phenyl-1,3-thiazol-2-yl)-N-pyrazin-2-ylpiperazine-1-carboxamide

A solution of 2,2,2-trichloroethyl pyrazin-2-ylcarbamate (200 mg, 0.545 mmol), 1-(4-phenyl-1,3-thiazol-2-yl)piperazine (181 mg, 0.739 mmol), diisopropylethylamine (0.129 ml, 0.739 mmol) and dimethylsulfoxide (4 ml) was stirred at 70° C. for 12 hours, the reaction mixture was poured into water and a solid was collected by filtration and washed with water. This was recrystallized from a mixed solvent of hexane and ethyl acetate to obtain the desired product (190 mg, 95.4%) as a solid. mp 134-135° C.

$^1$H-NMR (DMSO-d$_6$) δ; 3.54 (4H, br s), 3.68 (4H, br s), 7.29-7.42 (4H, m), 7.86-7.88 (2H, m), 8.23 (1H, s), 8.32 (1H, s), 9.05 (1H, s), 9.71 (1H, s).

Example 167

N-[4-(1H-Imidazol-1-yl)phenyl]-4-(4-phenyl-1,3-thiazol-2-yl)piperazine-1-carboxamide (1) 2,2,2-Trichloroethyl [4-(1H-imidazol-1-yl)phenyl]carbamate To a solution of 4-(1H-imidazol-1-yl)aniline (1.00 g, 6.28 mmol) and pyridine (1.52 ml, 18.8 mmol) in tetrahydrofuran (20 ml) was added 2,2,2-trichloroethyl chloroformate (1.30 ml, 9.42 mmol) with ice-cooling, the mixture was stirred for 1 hour with ice-cooling, the reaction mixture was poured into ice-water and the mixture was extracted with ethyl acetate. The extract was washed with water and dried over anhydrous magnesium sulfate and the solvent was distilled off under reduced pressure to obtain the desired product (1.83 g, 87.1%) as a solid.

$^1$H-NMR (CDCl$_3$) δ; 4.96 (2H, s), 7.09 (1H, s), 7.58-7.68 (5H, m), 8.17 (1H, s), 10.32 (1H, s).

(2) N-[4-(1H-Imidazol-1-yl)phenyl]-4-(4-phenyl-1,3-thiazol-2-yl)piperazine-1-carboxamide A solution of 2,2,2-trichloroethyl [4-(1H-imidazol-1-yl)phenyl]carbamate (200 mg, 0.598 mmol), 1-(4-phenyl-1,3-thiazol-2-yl)piperazine (147 mg, 0.598 mmol), diisopropylethylamine (0.104 ml, 0.598 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of ethyl acetate and hexane to obtain the desired product (91.0 mg, 35.4%) as a solid.

$^1$H-NMR (CDCl$_3$) δ; 3.64-3.73 (8H, m), 6.76 (1H, s), 6.83 (1H, s), 7.19-7.42 (7H, m), 7.48-7.52 (2H, m), 7.80-7.85 (3H, m).

Example 168

N-[4-(1H-Imidazol-1-yl)phenyl]-4-(3-phenyl-1,2,4-thiadiazol-5-yl)piperazine-1-carboxamide A solution of 2,2,2-trichloroethyl [4-(1H-imidazol-1-yl)phenyl]carbamate (200 mg, 0.598 mmol), 1-(3-phenyl-1,2,4-thiadiazol-5-yl)piperazine (147 mg, 0.598 mmol), diisopropylethylamine (0.104 ml, 0.598 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of tetrahydrofuran, ethyl acetate and hexane to obtain the desired product (71.0 mg, 35.4%) as a solid.

$^1$H-NMR (DMSO-d$_6$) δ; 3.67 (8H, s), 7.08 (1H, s), 7.46-7.66 (8H, m), 8.11-8.16 (3H, m), 8.88 (1H, s).

Example 169

N-(2-Oxo-2,3-dihydro-1H-indol-5-yl)-4-(4-phenyl-1,3-thiazol-2-yl)piperazine-1-carboxamide (1) 2,2,2-Trichloroethyl (2-oxo-2,3-dihydro-1H-indol-5-yl)carbamate To a solution of 5-amino-1,3-dihydro-2H-indol-2-one (1.00 g, 6.75 mmol) and pyridine (1.64 ml, 20.3 mmol) in N,N-dimethylacetamide (6 ml) and tetrahydrofuran (50 ml) was added 2,2,2-trichloroethyl chloroformate (1.40 ml, 10.2 mmol) with ice-cooling, the mixture was stirred for 1 hour with ice-cooling, the reaction mixture was poured into water and the mixture was extracted with ethyl acetate. The extract was washed with water and dried over anhydrous magnesium sulfate and the solvent was distilled off under reduced pressure to obtain the desired product (1.90 g, 87.2%) as a solid.

$^1$H-NMR (DMSO-d$_6$) δ; 3.46 (2H, s), 4.92 (2H, s), 6.74 (1H, d, J=8.1 Hz), 7.27 (1H, d, J=8.1 Hz), 7.38 (1H, s), 9.96 (1H, s), 10.29 (1H, s).

(2) N-(2-Oxo-2,3-dihydro-1H-indol-5-yl)-4-(4-phenyl-1,3-thiazol-2-yl)piperazine-1-carboxamide A solution of 2,2,2-trichloroethyl (2-oxo-2,3-dihydro-1H-indol-5-yl)carbamate (200 mg, 0.618 mmol), 1-(4-phenyl-1,3-thiazol-2-yl)piperazine (152 mg, 0.618 mmol), diisopropylethylamine (0.108 ml, 0.618 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of ethyl acetate and hexane to obtain the desired product (18.0 mg, 6.9%) as a solid.

$^1$H-NMR (DMSO-d$_6$) δ; 3.44 (2H, s), 3.52 (4H, br s), 3.61 (4H, br s), 6.69 (1H, d, J=8.4 Hz), 7.19 (1H, d, J=8.4 Hz), 7.27-7.42 (5H, m), 7.86 (2H, d, J=8.4 Hz), 8.52 (1H, s), 10.23 (1H, s).

Example 170

N-(2-Oxo-2,3-dihydro-1H-indol-5-yl)-4-(3-phenyl-1,2,4-thiazol-2-yl)piperazine-1-carboxamide A solution of 2,2,2-trichloroethyl (2-oxo-2,3-dihydro-1H-indol-5-yl)carbamate (200 mg, 0.618 mmol), 1-(3-phenyl-1,2,4-thiadiazol-5-yl)piperazine (152 mg, 0.618 mmol), diisopropylethylamine (0.108 ml, 0.618 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of ethyl acetate and hexane to obtain the desired product (91.0 mg, 35.0%) as a solid.

$^1$H-NMR (DMSO-d$_6$) δ; 3.44 (2H, s), 3.63 (8H, s), 6.70 (1H, d, J=8.1 Hz), 7.19 (1H, d, J=8.1 Hz), 7.34 (1H, s), 7.47-7.49 (3H, m), 8.10-8.13 (2H, m), 8.55 (1H, s), 10.23 (1H, s).

Example 171

N-[2-(Acetylamino)pyrimidin-5-yl]-4-(3-phenyl-1,2,4-thiadiazol-5-yl)piperazine-1-carboxamide A solution of 2,2,2-trichloroethyl [2-acetylamino)pyrimidin-5-yl)carbamate (200 mg, 0.611 mmol), 1-(3-phenyl-1,2,4-thiadiazol-5-yl)piperazine (150 mg, 0.611 mmol), diisopropylethylamine (0.106 ml, 0.611 mmol) and dimethylsulfoxide (4 ml) was stirred at 80° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from a mixed solvent of tetrahydrofuran and methanol to obtain the desired product (168 mg, 64.9%) as a solid.

$^1$H-NMR (DMSO-d$_6$) δ; 2.13 (3H, s), 3.68 (8H, br s), 7.49-7.492 (3H, m), 8.11-8.14 (2H, m), 8.71 (2H, s), 8.94 (1H, s), 10.42 (1H, s).

Example 172

N-{4-[Acetyl(methyl)amino]phenyl}-4-(4-phenyl-1,3-thiazol-2-yl)piperazine-1-carboxamide (1) N-Methyl-N-(4-nitrophenyl)acetamide To a solution of N-methyl-4-nitroaniline (5.00 g, 32.9 mmol) and pyridine (7.97 ml, 98.6 mmol) in tetrahydrofuran (100 ml) was added acetyl chloride (3.51 ml, 49.4 mmol) with ice-cooling, the mixture was stirred for 3 hours with ice-cooling, the reaction mixture was poured into ice-water and the desired product (2.60 g, 40.7%) as a solid was collected by filtration.

$^1$H-NMR (CDCl$_3$) δ; 2.03 (3H, s), 3.35 (3H, s), 7.40 (2H, d, J=8.7 Hz), 8.29 (2H, d, J=8.7 Hz).

(2) N-(4-Aminophenyl)-4-methylacetamide

A solution of N-methyl-N-(4-nitrophenyl)acetamide (2.40 g, 12.4 mmol), 10% palladium-carbon (300 mg) and methanol (100 ml) was stirred under a hydrogen atmosphere for 12 hours. Insolubles were filtered off and the filtrate was concentrated to obtain the desired product (1.79 g, 88.2%) as an oil.

$^1$H-NMR (CDCl$_3$) δ; 1.85 (3H, s), 3.20 (3H, s), 3.77 (2H, s), 6.68 (2H, d, J=8.4 Hz), 6.95 (2H, d, J=8.4 Hz).

(3) 2,2,2-Trichloroethyl {4-[acetyl(methyl)amino]phenyl}carbamate

To a solution of N-(4-aminophenyl)-N-methylacetamide (1.78 g, 10.8 mmol) and pyridine (2.63 ml, 32.5 mmol) in tetrahydrofuran (60 ml) was added 2,2,2-trichloroethyl chloroformate (2.23 ml, 16.2 mmol) with ice-cooling, the mixture was stirred for 2 hours with ice-cooling, the reaction mixture was poured into ice-water and the mixture was extracted with ethyl acetate. The extract was washed with water and dried over anhydrous magnesium sulfate and the solvent was distilled off under reduced pressure. To the residue was added hexane and the desired product (3.17 g, 86.4%) as a solid was collected by filtration.

$^1$H-NMR (CDCl$_3$) δ; 1.88 (3H, s), 3.25 (3H, s), 4.84 (2H, s), 7.17 (2H, d, J=8.4 Hz), 7.22 (1H, br s), 7.50 (2H, d, J=8.4 Hz).

(4) N-{4-[Acetyl(methyl)amino]phenyl}-4-(4-phenyl-1,3-thiazol-2-yl)piperazine-1-carboxamide A solution of 2,2,2-trichloroethyl {4-[acetyl(methyl)amino]phenyl}carbamate (200 mg, 0.589 mmol), 1-(4-phenyl-1,3-thiazol-2-yl)piperazine (144 mg, 0.589 mmol), diisopropylethylamine (0.103 ml, 0.589 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from a mixed solvent of ethyl acetate and hexane to obtain the desired product (80.0 mg, 31.3%) as a solid.

$^1$H-NMR (DMSO-d$_6$) δ; 1.75 (3H, s), 3.11 (3H, s), 3.55 (4H, br s), 3.63 (4H, br s), 7.19 (2H, d, J=8.4 Hz), 7.29-7.42 (4H, m), 7.53 (2H, d, J=8.4 Hz), 7.87 (2H, d, J=6.4 Hz), 8.81 (1H, br s).

Example 173

N-{4-[Acetyl(methyl)amino]phenyl}-4-(3-phenyl-1,2,4-thiadiazol-5-yl)piperazine-1-carboxamide A solution of 2,2,2-trichloroethyl {4-[acetyl(methyl)amino]phenyl}carbamate (200 mg, 0.589 mmol), 1-(3-phenyl-1,2,4-thiadiazol-5-yl)piperazine (145 mg, 0.589 mmol), diisopropylethylamine (0.103 ml, 0.589 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of ethyl acetate and hexane to obtain the desired product (47.3 mg, 18.3%) as a solid.

$^1$H-NMR (DMSO-d$_6$) δ; 1.75 (3H, s), 3.11 (3H, s), 3.66 (8H, br s), 7.20 (2H, d, J=8.1 Hz), 7.47-7.54 (5H, m), 8.11-8.14 (2H, m), 8.34 (1H, br s).

Example 174

N-[3-(Acetylamino)phenyl]-4-(3-phenyl-1,2,4-thiadiazol-5-yl)piperazine-1-carboxamide (1) 2,2,2-Trichloroethyl 3-[(acetylamino)phenyl}carbamate To a solution of 3-acetamidoaniline (5.00 g, 33.3 mmol) and pyridine (8.08 ml, 99.9 mmol) in tetrahydrofuran (100 ml) was added 2,2,2-trichloroethyl chloroformate (6.89 ml, 50.0 mmol) with ice-cooling, the mixture was stirred for 1 hour with ice-cooling and then at room temperature for 2 hour, the reaction mixture was poured into ice-water and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) to obtain the desired product (9.04 g, 83.7%) as an oil.

$^1$H-NMR (CDCl$_3$) δ; 2.18 (3H, s), 4.81 (2H, s), 7.18-7.32 (5H, m), 7.75 (1H, s).

(2) N-[3-(Acetylamino)phenyl]-4-(3-phenyl-1,2,4-thiadiazol-5-yl)piperazine-1-carboxamide A solution of 2,2,2-trichloroethyl [3-(acetylamino)phenyl]carbamate (200 mg, 0.614 mmol), 1-(3-phenyl-1,2,4-thiadiazol-5-yl)piperazine (151 mg, 0.614 mmol), diisopropylethylamine (0.107 ml, 0.614 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product. This was recrystallized from a mixed solvent of ethyl acetate and hexane to obtain the desired product (107 mg, 41.3%) as a solid.

$^1$H-NMR (DMSO-d$_6$) δ; 2.02 (3H, s), 3.64 (8H, br s), 7.14 (3H, s), 7.47-7.49 (3H, m), 7.79 (1H, s), 8.10-8.14 (2H, m), 8.72 (1H, s), 9.85 (1H, s).

Example 175

N-[3-(Acetylamino)phenyl]-4-(4-phenyl-1,3-thiazol-2-yl)piperazine-1-carboxamide

A solution of 2,2,2-trichloroethyl [3-(acetylamino)phenyl]carbamate (200 mg, 0.614 mmol), 1-(4-phenyl-1,3-thiazol-2-yl)piperazine (150 mg, 0.614 mmol), diisopropylethylamine (0.107 ml, 0.614 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from chloroform to obtain the desired product (87.0 mg, 33.6%) as a solid.

$^1$H-NMR (DMSO-d$_6$) δ; 2.02 (3H, s), 3.52 (4H, br s), 3.63 (4H, br s), 7.14 (3H, s), 7.29-7.42 (4H, m), 7.79 (1H, br s), 7.86-7.89 (2H, m), 8.69 (1H, s), 9.85 (1H, s).

Example 176

N-[4-(2-Oxopropyl)phenyl]-4-(3-phenyl-1,2,4-thiadiazol-5-yl)piperazine-1-carboxamide (1) 1-(4-Aminophenyl)acetone A solution of 1-(4-nitrophenyl)acetone (2.00 g, 11.2 mmol), 10% palladium-carbon (200 mg), methanol (20 ml) and tetrahydrofuran (10 ml) was stirred under a hydrogen atmosphere for 12 hours. Insolubles were filtered off to obtain the desired product (1.13 g, 67.6%) as an oil.

¹H-NMR (CDCl₃) δ; 2.04 (3H, s), 3.49 (2H, s), 4.97 (2H, s), 6.49 (2H, d, J=8.4 Hz), 6.83 (2H, d, J=8.4 Hz).

(2) 2,2,2-Trichloroethyl [4-(2-oxopropyl)phenyl]carbamate

To a solution of 1-(4-aminophenyl)acetone (1.13 g, 7.57 mmol) and pyridine (1.84 ml, 22.7 mmol) in tetrahydrofuran (50 ml) was added 2,2,2-trichloroethyl chloroformate (1.57 ml, 11.4 mmol) with ice-cooling, and the mixture was stirred for 1 hour with ice-cooling and then at room temperature for 1 hour, the reaction mixture was poured into ice-water and the mixture was extracted with ethyl acetate. The extract was washed with water and dried over anhydrous magnesium sulfate and the solvent was distilled off under reduced pressure. The residue was purified by silica gel column chromatography (hexane: ethyl acetate=1:1) to obtain the desired product (1.44 g, 58.4%) as an oil.

¹H-NMR (CDCl₃) δ; 2.16 (3H, s), 3.67 (2H, s), 4.82 (2H, s), 6.91 (1H, br s), 7.17 (2H, d, J=8.4 Hz), 7.39 (2H, d, J=8.4 Hz).

(3) N-[4-(2-Oxopropyl)phenyl]-4-(3-phenyl-1,2,4-thiadiazol-5-yl)piperazine-1-carboxamide A solution of 2,2,2-trichloroethyl [4-(2-oxopropyl)phenyl]carbamate (200 mg, 0.616 mmol), 1-(3-phenyl-1,2,4-thiadiazol-5-yl)piperazine (152 mg, 0.616 mmol), diisopropylethylamine (0.107 ml, 0.616 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of ethyl acetate and hexane to obtain the desired product (45.2 mg, 17.4%) as a solid.

¹H-NMR (DMSO-d₆) δ; 2.10 (3H, s), 3.64-3.66 (10H, m), 7.06 (2H, d, J=8.4 Hz), 7.40 (2H, d, J=8.4 Hz), 8.47-8.49 (3H, m), 8.11-8.14 (2H, m), 8.68 (1H, s).

Example 177

N-[4-(2-Oxopropyl)phenyl]-4-(4-phenyl-1,3-thiazol-2-yl)piperazine-1-carboxamide

A solution of 2,2,2-trichloroethyl [4-(2-oxopropyl)phenyl]carbamate (200 mg, 0.616 mmol), 1-(4-phenyl-1,3-thiazol-2-yl)piperazine (151 mg, 0.616 mmol), diisopropylethylamine (0.107 ml, 0.616 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of ethyl acetate and hexane to obtain the desired product (47.0 mg, 18.2%) as a solid.

¹H-NMR (DMSO-d₆) δ; 2.10 (3H, s), 3.52 (4H, br s), 3.62 (4H, br s), 3.66 (2H, s), 7.06 (2H, d, J=8.7 Hz), 7.29-7.42 (6H, m), 7.87 (2H, d, J=8.4 Hz), 8.64 (1H, s).

Example 178

N-(4-Chloro-3-methylisoxazol-5-yl)-4-(4-phenyl-1,3-thiazol-2-yl)piperazine-1-carboxamide (1) 4-Chloro-3-methylisoxazole-5-amine To a solution of 3-methylisoxazole-5-amine (5.00 g, 51.0 mmol) in dichloromethane (40 ml) was slowly added N-chlorosuccinimide (6.80 g, 51.0 mmol) with ice-cooling and the mixture was stirred for 1 hour with ice-cooling and then at room temperature for 2 hours. The reaction mixture was washed with an aqueous 1N sodium hydroxide solution and dried over anhydrous magnesium sulfate and the solvent was distilled off under reduced pressure. Hexane was added to the residue and the desired product (5.65 g, 83.6%) as a solid was collected by filtration.

¹H-NMR (CDCl₃) δ; 2.18 (3H, s), 4.54 (2H, br s).

(2) Bis(2,2,2-trichloroethyl) (4-chloro-3-methylisoxazol-5-yl)imidodicarbonate

To a solution of 4-chloro-3-methylisoxazole-5-amine (2.00 g, 15.1 mmol) and pyridine (3.66 ml, 45.3 mmol) in tetrahydrofuran (100 ml) was added 2,2,2-trichloroethyl chloroformate (3.13 ml, 22.7 mmol) with ice-cooling, and the mixture was stirred for 1 hour with ice-cooling. To the mixture was further added 2,2,2-trichloroethyl chloroformate (3.13 ml, 22.7 mmol) with ice-cooling and the mixture was stirred at room temperature for 1 hour. The reaction mixture was poured into ice-water and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) to obtain the desired product (3.47 g, 47.5%) as a solid.

¹H-NMR (CDCl₃) δ; 2.34 (3H, s), 4.85 (4H, s).

(3) N-(4-Chloro-3-methylisoxazol-5-yl)-4-(4-phenyl-1,3-thiazol-2-yl)piperazine-1-carboxamide A solution of bis(2,2,2-trichloroethyl) (4-chloro-3-methylisoxazol-5-yl)imidodicarbonate (200 mg, 0.418 mmol), 1-(4-phenyl-1,3-thiazol-2-yl)piperazine (204 mg, 0.836 mmol), diisopropylethylamine (0.144 ml, 0.836 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (hexane:ethyl acetate=1:1) to obtain the desired product as a solid. This was recrystallized from a mixed solvent of ethyl acetate and hexane to obtain the desired product (123 mg, 73.2%) as a solid.

¹H-NMR (DMSO-d₆) δ; 2.22 (3H, s), 3.54 (4H, br s), 3.63 (4H, br s), 7.26-7.42 (4H, m), 7.85-7.89 (2H, m), 9.79 (1H, s).

Example 179

N-(4-Chloro-3-methylisoxazol-5-yl)-4-(3-phenyl-1,2,4-thiadiazol-5-yl)piperazine-1-carboxamide A solution of bis(2,2,2-trichloroethyl) (4-chloro-3-methylisoxazol-5-yl)imidodicarbonate (200 mg, 0.418 mmol), 1-(3-phenyl-1,2,4-thiadiazol-5-yl)piperazine (203 mg, 0.836 mmol), diisopropylethylamine (0.144 ml, 0.836 mmol) and dimethylsulfoxide (4 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (hexane:ethyl acetate=1:1) to obtain the desired product as a solid. This was recrystallized from a mixed solvent of ethyl acetate and hexane to obtain the desired product (111 mg, 66.1%) as a solid.

$^1$H-NMR (DMSO-d$_6$) δ; 2.22 (3H, s), 3.65 (8H, s), 7.47-7.49 (3H, m), 8.11-8.14 (2H, m), 9.82 (1H, s).

Example 180

4-(3-Phenyl-1,2,4-thiadiazol-5-yl)-N-pyrimidin-2-ylpiperazine-1-carboxamide (1) 2,2,2-Trichloroethyl pyrimidin-2-ylcarbamate To a solution of pyrimidine-2-amine (2.00 g, 21.0 mmol) and pyridine (5.10 ml, 63.0 mmol) in N,N-dimethylacetamide (50 ml) was added 2,2,2-trichloroethyl chloroformate (4.34 ml, 31.5 mmol) with ice-cooling, and the mixture was stirred for 40 minutes with ice-cooling. The reaction mixture was poured into ice-water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate and the desired product (2.57 g, 45.2%) as a solid was collected by filtration.
$^1$H-NMR (CDCl$_3$) δ; 4.90 (2H, s), 7.05-7.09 (1H, m), 8.74-8.76 (2H, m), 9.74 (1H, br s).

(2) 4-(3-Phenyl-1,2,4-thiadiazol-5-yl)-N-pyrimidin-2-ylpiperazine-1-carboxamide

A solution of 2,2,2-trichloroethyl pyrimidin-2-ylcarbamate (200 mg, 0.739 mmol), 1-(3-phenyl-1,2,4-thiadiazol-5-yl)piperazine (182 mg, 0.739 mmol), diisopropylethylamine (0.258 ml, 1.48 mmol) and dimethylsulfoxide (3 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from ethyl acetate to obtain the desired product (138 mg, 51.1%) as a solid.
$^1$H-NMR (DMSO-d$_6$) δ; 3.64 (8H, s), 7.02-7.05 (1H, m), 7.46-7.48 (3H, m), 8.10-8.13 (2H, m), 8.55-8.57 (2H, m), 9.72 (1H, s).

Example 181

4-(4-Phenyl-1,3-thiazol-2-yl)-N-pyrimidin-2-ylpiperazine-1-carboxamide

A solution of 2,2,2-trichloroethyl pyrimidin-2-ylcarbamate (200 mg, 0.739 mmol), 1-(4-phenyl-1,3-thiazol-2-yl)piperazine (181 mg, 0.739 mmol), diisopropylethylamine (0.258 ml, 1.48 mmol) and dimethylsulfoxide (3 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was recrystallized from a mixed solvent of ethyl acetate and hexane to obtain the desired product (190 mg, 70.4%) as a solid.
$^1$H-NMR (DMSO-d$_6$) δ; 3.52 (4H, br s), 3.62 (4H, br s), 7.01-7.05 (1H, m), 7.26-7.42 (4H, m), 7.85-7.88 (2H, m), 8.55-8.56 (2H, m), 9.67 (1H, s).

Example 182

4-(4-Phenyl-1,3-thiazol-2-yl)-N-pyrimidin-4-ylpiperazine-1-carboxamide (1) 2,2,2-Trichloroethyl pyrimidin-4-ylcarbamate To a solution of pyrimidine-4-amine (1.00 g, 10.5 mmol) and pyridine (2.55 ml, 31.5 mmol) in N,N-dimethylacetamide (50 ml) was added 2,2,2-trichloroethyl chloroformate (2.55 ml, 31.5 mmol) with ice-cooling, and the mixture was stirred for 1 hour with ice-cooling. The reaction mixture was poured into ice-water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate and the desired product (1.97 g, 69.4%) as a solid was collected by filtration.
$^1$H-NMR (CDCl$_3$) δ; 4.91 (2H, s), 8.03 (1H, dd, J=5.7, 1.2 Hz), 8.68 (1H, d, J=5.7 Hz), 9.04 (1H, d, J=1.2 Hz), 9.81 (1H, br s).

(2) 4-(4-Phenyl-1,3-thiazol-2-yl)-N-pyrimidin-4-ylpiperazine-1-carboxamide

A solution of 2,2,2-trichloroethyl pyrimidin-4-ylcarbamate (200 mg, 0.739 mmol), 1-(4-phenyl-1,3-thiazol-2-yl)piperazine (181 mg, 0.739 mmol), diisopropylethylamine (0.258 ml, 1.48 mmol) and dimethylsulfoxide (3 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product. This was recrystallized from a mixed solvent of tetrahydrofuran, ethyl acetate and hexane to obtain the desired product (135 mg, 49.8%) as a solid.
$^1$H-NMR (DMSO-d$_6$) δ; 3.51-3.54 (4H, m), 3.65-3.68 (4H, m), 7.29-7.42 (4H, m), 7.78-7.88 (3H, m), 8.51 (1H, d, J=6.0 Hz), 8.79 (1H, s), 9.94 (1H, s).

Example 183

4-(3-Phenyl-1,2,4-thiadiazol-5-yl)-N-pyrimidin-4-ylpiperazine-1-carboxamide

A solution of 2,2,2-trichloroethyl pyrimidin-4-ylcarbamate (200 mg, 0.739 mmol), 1-(3-phenyl-1,2,4-thiadiazol-5-yl)piperazine (182 mg, 0.739 mmol), diisopropylethylamine (0.258 ml, 1.48 mmol) and dimethylsulfoxide (3 ml) was stirred at 70° C. for 12 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product. This was recrystallized from a mixed solvent of tetrahydrofuran, ethyl acetate and hexane to obtain the desired product (110 mg, 40.7%) as a solid.
$^1$H-NMR (DMSO-d$_6$) δ; 3.65-3.70 (8H, m), 7.47-7.49 (3H, m), 7.79-7.81 (1H, m), 8.10-8.14 (2H, m), 8.52 (1H, d, J=6.0 Hz), 8.78 (1H, s), 9.99 (1H, s).

Example 184

N-(1-Acetyl-2,3-dihydro-1H-indol-5-yl)-4-(4-phenyl-1,3-thiazol-2-yl)piperazine-1-carboxamide (1) 2,2,2-Trichloroethyl (1-acetyl-2,3-dihydro-1H-indol-5-yl)carbamate To a solution of 1-acetylindoline-5-amine (1.00 g, 5.67 mmol) and pyridine (1.38 ml, 17.0 mmol) in N,N-dimethylacetamide (20 ml) was added 2,2,2-trichloroethyl chloroformate (1.17 ml, 8.51 mmol) with ice-cooling, and the mixture was stirred for 2 hours with ice-cooling. The reaction mixture was poured into ice-water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate and the desired product (1.66 g, 83.4%) as a solid was collected by filtration.

$^1$H-NMR (CDCl$_3$) δ; 2.22 (3H, s), 3.21 (2H, t, J=8.4 Hz), 4.07 (2H, t, J=8.4 Hz), 4.82 (2H, s), 6.86 (1H, br s), 7.01 (1H, d, J=8.4 Hz), 7.50 (1H, br s), 8.15 (1H, d, J=8.4 Hz).

(2) N-(1-Acetyl-2,3-dihydro-1H-indol-5-yl)-4-(4-phenyl-1,3-thiazol-2-yl)piperazine-1-carboxamide A solution of 2,2,2-trichloroethyl (1-acetyl-2,3-dihydro-1H-indol-5-yl)carbamate (200 mg, 0.569 mmol), 1-(4-phenyl-1,3-thiazol-2-yl)piperazine (140 mg, 0.569 mmol), diisopropylethylamine (0.198 ml, 1.14 mmol) and dimethylsulfoxide (4 ml) was stirred at 70° C. for 48 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product. This was recrystallized from a mixed solvent of tetrahydrofuran, ethyl acetate and hexane to obtain the desired product (92.0 mg, 36.1%) as a solid.

$^1$H-NMR (DMSO-d$_6$) δ; 2.13 (3H, s), 3.10 (2H, t, J=8.7 Hz), 3.51 (4H, br s), 3.62 (4H, br s), 4.06 (2H, t, J=8.7 Hz), 7.14-7.17 (1H, m), 7.29-7.39 (5H, m), 7.86-7.92 (3H, m), 8.59 (1H, s).

Example 185

N-(1-Acetyl-2,3-dihydro-1H-indol-5-yl)-4-(3-phenyl-1,2,4-thiadiazol-5-yl)piperazine-1-carboxamide A solution of 2,2,2-trichloroethyl (1-acetyl-2,3-dihydro-1H-indol-5-yl)carbamate (200 mg, 0.569 mmol), 1-(3-phenyl-1,2,4-thiadiazol-5-yl)piperazine (140 mg, 0.569 mmol), diisopropylethylamine (0.198 ml, 1.14 mmol) and dimethylsulfoxide (4 ml) was stirred at 70° C. for 48 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product. This was recrystallized from a mixed solvent of tetrahydrofuran, ethyl acetate and hexane to obtain the desired product (110.0 mg, 43.1%) as a solid.

$^1$H-NMR (DMSO-d$_6$) δ; 2.13 (3H, s), 3.10 (2H, t, J=9.0 Hz), 3.63 (8H, br s), 4.06 (2H, t, J=9.0 Hz), 7.14-7.16 (1H, m), 7.40 (1H, s), 7.47-7.49 (4H, m), 7.90 (1H, d, J=8.7 Hz), 8.10-8.14 (2H, m), 8.62 (1H, s).

Example 186

4-(4-Phenyl-1,3-thiazol-2-yl)-N-[6-(trifluoromethyl)pyridin-3-yl]piperazine-1-carboxamide (1) 2,2,2-Trichloroethyl [6-(trifluoromethyl)pyridin-3-yl]carbamate To a solution of 6-(trifluoromethyl)pyridine-3-amine (1.00 g, 6.15 mmol) and pyridine (1.50 ml, 18.5 mmol) in N,N-dimethylacetamide (20 ml) was added 2,2,2-trichloroethyl chloroformate (1.17 ml, 8.51 mmol) with ice-cooling, and the mixture was stirred for 1 hour with ice-cooling. The reaction mixture was poured into ice-water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate and the desired product (1.83 g, 88.0%) as a solid was collected by filtration.

$^1$H-NMR (CDCl$_3$) δ; 4.86 (2H, s), 7.19 (1H, br s), 7.68-7.87 (2H, m), 8.71 (1H, br s).

(2) 4-(4-Phenyl-1,3-thiazol-2-yl)-N-[6-(trifluoromethyl)pyridin-3-yl]piperazine-1-carboxamide A solution of 2,2,2-trichloroethyl [6-(trifluoromethyl)pyridin-3-yl]carbamate (200 mg, 0.593 mmol), 1-(4-phenyl-1,3-thiazol-2-yl)piperazine (145 mg, 0.593 mmol), diisopropylethylamine (0.207 ml, 1.19 mmol) and dimethylsulfoxide (4 ml) was stirred at 70° C. for 48 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of tetrahydrofuran, ethyl acetate and hexane to obtain the desired product (110 mg, 42.8%) as a solid.

$^1$H-NMR (DMSO-d$_6$) δ; 3.55-3.57 (4H, m), 3.67-3.69 (4H, m), 7.29-7.42 (4H, m), 7.80 (1H, d, J=9.0 Hz), 7.86-7.89 (2H, m), 8.15-8.19 (1H, m), 8.83 (1H, d, J=2.7 Hz), 9.29 (1H, s).

Example 187

4-(3-Phenyl-1,2,4-thiadiazol-5-yl)-N-[6-(trifluoromethyl)pyridin-3-yl]piperazine-1-carboxamide A solution of 2,2,2-trichloroethyl [6-(trifluoromethyl)pyridin-3-yl]carbamate (200 mg, 0.593 mmol), 1-(3-phenyl-1,2,4-thiadiazol-5-yl)piperazine (146 mg, 0.593 mmol), diisopropylethylamine (0.207 ml, 1.19 mmol) and dimethylsulfoxide (4 ml) was stirred at 70° C. for 48 hours, the reaction mixture was poured into water and the mixture was extracted with ethyl acetate. The extract was washed with water and dried over anhydrous magnesium sulfate. The solvent was distilled off under reduced pressure. The residue was purified by silica gel column chromatography (ethyl acetate) to obtain the desired product as a solid. This was recrystallized from a mixed solvent of tetrahydrofuran, ethyl acetate and hexane to obtain the desired product (110 mg, 42.8%) as a solid.

$^1$H-NMR (DMSO-d$_6$) δ; 3.56-3.57 (4H, m), 3.67-3.69 (4H, m), 7.27-7.42 (3H, m), 7.80 (1H, d, J=8.4 Hz), 7.86-7.89 (2H, m), 8.15-8.19 (1H, m), 8.83 (1H, d, J=2.4 Hz), 9.29 (1H, s).

The structural formulas of the compounds obtained in Examples 140 to 187 are shown in Table 8.

TABLE 8
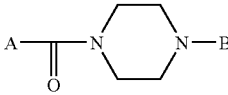
| Example No. | A | B |
|---|---|---|
| 140 | 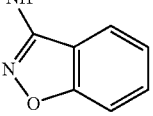 | 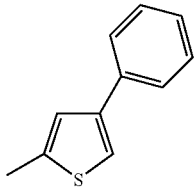 |
| 141 | 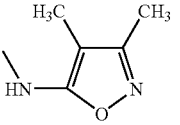 | 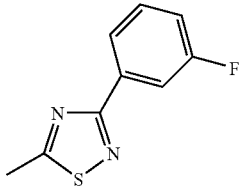 |
| 142 | 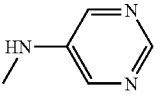 | 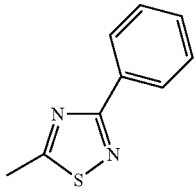 |
| 143 | 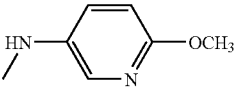 | 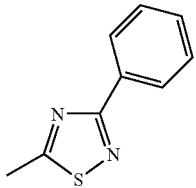 |
| 144 | 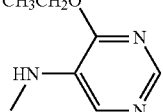 | 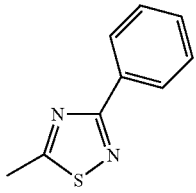 |
| 145 | 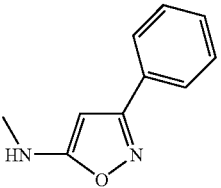 | 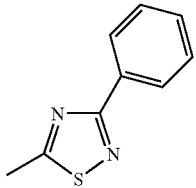 |
| 146 | 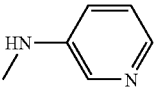 | 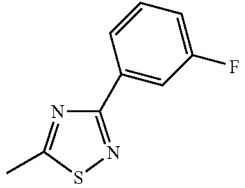 |

TABLE 8-continued
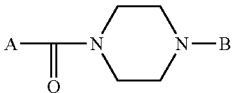
| Example No. | A | B |
|---|---|---|
| 147 | 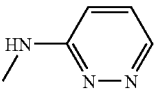 | 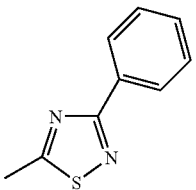 |
| 148 | 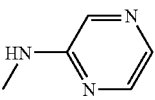 | 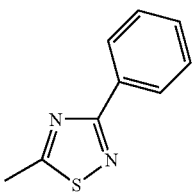 |
| 149 | 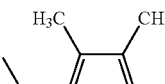 |  |
| 150 | 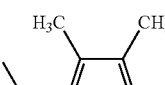 | 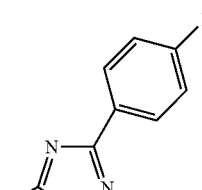 |
| 151 | 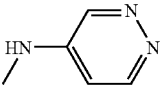 | 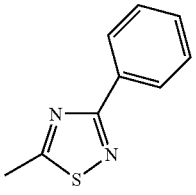 |
| 152 | 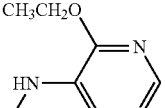 | 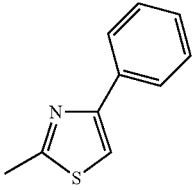 |
| 153 | 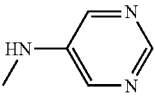 | 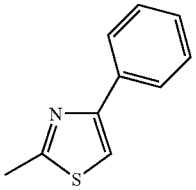 |

TABLE 8-continued
| Example No. | A | B |
|---|---|---|
| 154 | 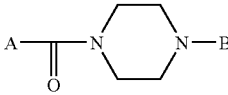 | 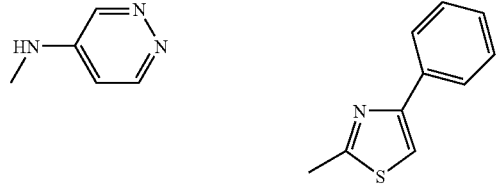 |
| 155 | 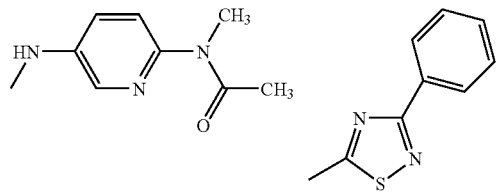 | 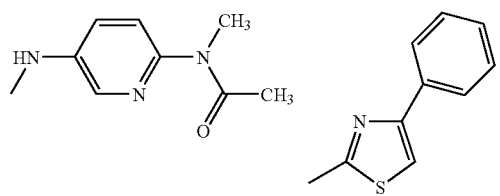 |
| 156 |  | 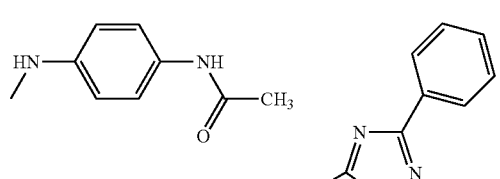 |
| 157 | 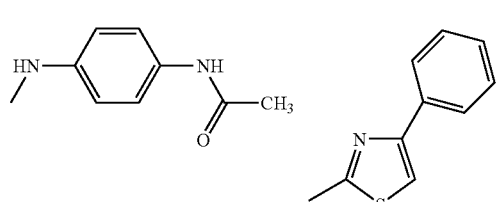 | 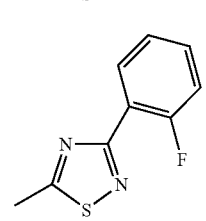 |
| 158 | | |
| 159 | | |
| 160 | | |

TABLE 8-continued

| Example No. | A | B |
|---|---|---|
| 161 | 3-(methylamino)pyridine | 3-(4-fluorophenyl)-5-methyl-1,2,4-thiadiazole |
| 162 | N-[5-(methylamino)pyrimidin-2-yl]acetamide | 2-methyl-4-phenylthiazole |
| 163 | 3-(methylamino)pyridazine | 2-methyl-4-phenylthiazole |
| 164 | 5-(methylamino)isoxazole | 2-methyl-4-phenylthiazole |
| 165 | 5-(methylamino)isoxazole | 5-methyl-3-phenyl-1,2,4-thiadiazole |
| 166 | 2-(methylamino)pyrazine | 2-methyl-4-phenylthiazole |
| 167 | 4-(1H-imidazol-1-yl)-N-methylaniline | 2-methyl-4-phenylthiazole |

TABLE 8-continued
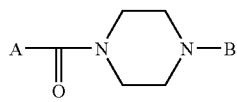
| Example No. | A | B |
|---|---|---|
| 168 | HN—⟨phenyl⟩—N(imidazole) | 3-phenyl-5-methyl-1,2,4-thiadiazole |
| 169 | HN—(5-indolin-2-one) | 4-phenyl-2-methyl-thiazole |
| 170 | HN—(5-indolin-2-one) | 3-phenyl-5-methyl-1,2,4-thiadiazole |
| 171 | HN—(pyrimidin-2-yl)NHC(O)CH₃ | 3-phenyl-5-methyl-1,2,4-thiadiazole |
| 172 | HN—⟨phenyl⟩—N(CH₃)C(O)CH₃ | 4-phenyl-2-methyl-thiazole |
| 173 | HN—⟨phenyl⟩—N(CH₃)C(O)CH₃ | 3-phenyl-5-methyl-1,2,4-thiadiazole |
| 174 | HN—⟨phenyl⟩—NHC(O)CH₃ | 3-phenyl-5-methyl-1,2,4-thiadiazole |

TABLE 8-continued

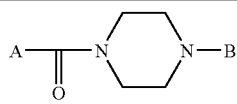

| Example No. | A | B |
|---|---|---|
| 175 | 3-(methylamino)-N-acetanilide derivative | 2-methyl-4-phenylthiazol-5-yl |
| 176 | 4-(methylamino)phenylacetone derivative | 5-methyl-3-phenyl-1,2,4-thiadiazol-2-yl |
| 177 | 4-(methylamino)phenylacetone derivative | 2-methyl-4-phenylthiazol-5-yl |
| 178 | 4-chloro-3-methyl-5-(methylamino)isoxazole | 2-methyl-4-phenylthiazol-5-yl |
| 179 | 4-chloro-3-methyl-5-(methylamino)isoxazole | 5-methyl-3-phenyl-1,2,4-thiadiazol-2-yl |
| 180 | 2-(methylamino)pyrimidine | 5-methyl-3-phenyl-1,2,4-thiadiazol-2-yl |
| 181 | 2-(methylamino)pyrimidine | 2-methyl-4-phenylthiazol-5-yl |

TABLE 8-continued

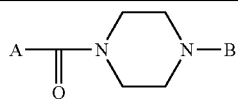

| Example No. | A | B |
|---|---|---|
| 182 | | |
| 183 | | |
| 184 | | |
| 185 | | |
| 186 | | |
| 187 | | |

Example 188

N-1,2-Benzisoxazol-3-yl-4-(4-phenyl-1,3-thiazol-2-yl)piperidine-1-carboxamide (1) tert-Butyl 4-(4-phenyl-1,3-thiazol-2-yl)piperidine-1-carboxylate A mixture of tert-butyl 4-(aminocarbonothioyl)piperidine-1-carboxylate (1.00 g, 7.24 mmol), 2-bromoacetophenone (1.58 g, 7.96 mmol), potassium carbonate (1.00 g, 7.24 mmol) and N,N-dimethylformamide (30 ml) was stirred at 110° C. for 1.5 hours. The reaction mixture was poured into water and the mixture was extracted with ethyl acetate. The extract was washed with water and dried over anhydrous magnesium sulfate and the solvent was distilled off under reduced pressure. The residue was purified by silica gel column chromatography (hexane: ethyl acetate=1:1) to obtain the desired product (1.38 g, 55.2%) as an oil.

$^1$H-NMR (CDCl$_3$) δ; 1.46 (9H, s), 1.69-1.86 (2H, m), 2.13-2.18 (2H, m), 2.88-2.96 (2H, m), 3.17-3.27 (1H, m), 4.19 (2H, br s), 7.29-7.51 (4H, m), 7.86-7.89 (2H, m).

(2) 4-(4-Phenyl-1,3-thiazol-2-yl)piperidine dihydrochloride

A solution of tert-butyl 4-(4-phenyl-1,3-thiazol-2-yl)piperidine-1-carboxylate (1.35 g, 3.92 mmol), 2N hydrogen chloride methanol (100 ml) and ethyl acetate (10 ml) was stirred at room temperature for 12 hours and the solvent was distilled off under reduced pressure. The residue was recrystallized from a mixed solution of methanol and ether to obtain the desired product (1.08 g, 98.2%) as a solid.

$^1$H-NMR (DMSO-d$_6$) δ; 1.91-2.07 (2H, m), 2.23-2.27 (2H, m), 2.99-3.11 (2H, m), 3.33-3.46 (3H, m), 6.50 (1H, br s), 7.32-7.47 (3H, m), 7.94-7.97 (2H, m), 8.05 (1H, s), 9.08 (1H, br s), 9.30 (1H, br s).

(3) 4-(4-Phenyl-1,3-thiazol-2-yl)piperidine

To 4-(4-phenyl-1,3-thiazol-2-yl)piperidine dihydrochloride (530 mg, 1.88 mmol) was added an aqueous 1N sodium hydroxide solution (10 ml) and the mixture was extracted with chloroform (50 ml). The extract was dried over anhydrous magnesium sulfate and the solvent was distilled off under reduced pressure to obtain the desired product (461 mg, 100%) as an oil.

$^1$H-NMR (CDCl$_3$) δ; 1.70-1.83 (2H, m), 2.14-2.19 (2H, m), 2.74-2.83 (2H, m), 3.15-3.24 (3H, m), 7.28-7.44 (4H, m), 7.86-7.90 (2H, m).

(4) N-1,2-Benzisoxazol-3-yl-4-(4-phenyl-1,3-thiazol-2-yl)piperidine-1-carboxamide A solution of bis(2,2,2-trichloroethyl) 1,2-benzisoxazol-3-ylimidodicarbonate (277 mg, 0.573 mmol), 4-(4-phenyl-1,3-thiazol-2-yl)piperidine (280 mg, 1.15 mmol) and diisopropylethylamine (0.0998 ml, 0.573 mmol) in dimethylsulfoxide (3 ml) was stirred at 70° C. for 12 hours, the reaction mixture was poured into water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate to obtain the desired product (110 mg, 47.4%) as a solid.

$^1$H-NMR (DMSO-d$_6$) δ; 1.71-1.82 (2H, m), 2.14-2.18 (2H, m), 3.09-3.16 (2H, m), 3.34-3.38 (1H, m), 4.24-4.29 (2H, m), 7.29-7.36 (2H, m), 7.42-7.47 (2H, m), 7.58-7.65 (2H, m), 7.84 (1H, d, J=7.8 Hz), 7.95-7.98 (2H, m), 8.02 (1H, s), 7.94 (1H, s).

Example 189

4-(4-Phenyl-1,3-thiazol-2-yl)-N-pyridin-3-ylpiperidine-1-carboxamide

A solution of 2,2,2-trichloroethyl pyridin-3-ylcarbamate (187 mg, 0.696 mmol), 4-(4-phenyl-1,3-thiazol-2-yl)piperidine (170 mg, 0.696 mmol), diisopropylethylamine (0.121 ml, 0.696 mmol) and dimethylsulfoxide (3 ml) was stirred at 70° C. for 12 hours, the reaction mixture was poured into water and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate to obtain the desired product (84.0 mg, 33.1%) as a solid.

$^1$H-NMR (DMSO-d$_6$) δ; 1.68-1.76 (2H, m), 2.12-2.16 (2H, m), 3.00-3.08 (2H, m), 3.30-3.08 (1H, m), 4.21-4.26 (2H, m), 7.24-7.46 (4H, m), 7.88-7.97 (3H, m), 8.01 (1H, s), 8.13-8.16 (1H, m), 8.64-8.65 (1H, m), 8.76 (1H, s).

Example 190

N-(3,4-Dimethylisoxazol-5-yl)-4-(4-phenyl-1,3-thiazol-2-yl)piperidine-1-carboxamide A solution of 2,2,2-trichloroethyl (3,4-dimethylisoxazol-5-yl)carbamate (200 mg, 1.02 mmol), 4-(4-phenyl-1,3-thiazol-2-yl)piperidine (250 mg, 1.02 mmol) and diisopropylethylamine (0.357 ml, 2.05 mmol) in dimethylsulfoxide (4 ml) was stirred at 70° C. for 12 hours, the reaction mixture was poured into water and the mixture was extracted with ethyl acetate. The extract was washed with water and dried over anhydrous magnesium sulfate and the solvent was distilled off under reduced pressure. The residue was purified by silica gel column chromatography (ethyl acetate) to obtain the desired product as a solid. This was recrystallized from a mixed solvent of tetrahydrofuran, ethyl acetate and hexane to obtain the desired product (201 mg, 51.5%) as a solid. mp 156-157° C.

$^1$H-NMR (DMSO-d$_6$) δ; 1.62-1.76 (5H, m), 2.10-2.13 (5H, m), 3.00-3.08 (2H, m), 3.30-3.37 (1H, m), 4.12-4.17 (2H, m), 7.31-7.46 (3H, m), 7.94-8.00 (3H, m), 9.17 (1H, s).

The structural formulas of the compounds obtained in Examples 188 to 190 are shown in Table 9.

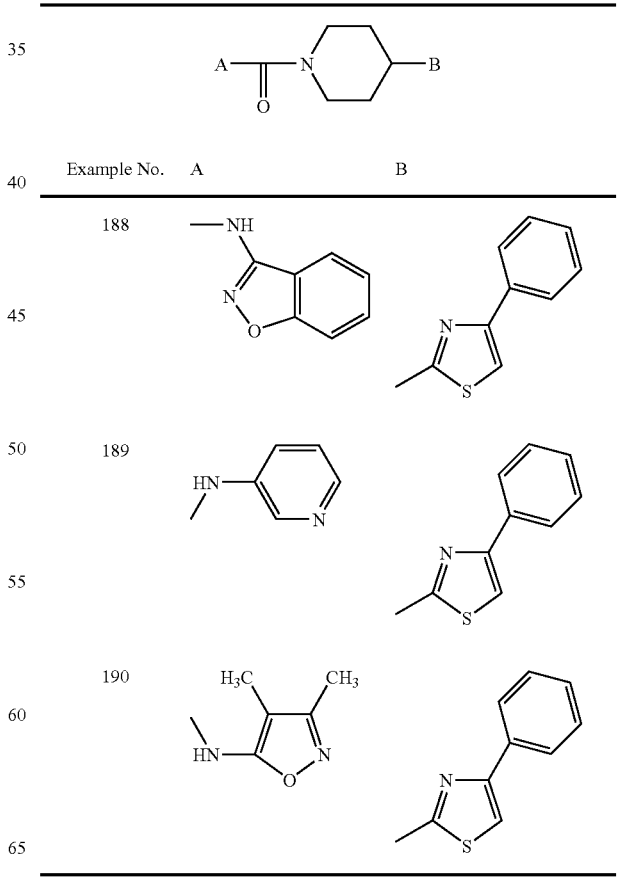

Example 191

4-(3-Phenyl-1,2,4-thiadiazol-5-yl)-N-1H-tetrazol-5-ylpiperazine-1-carboxamide (1) 2,2,2-Trichloroethyl 1H-tetrazol-5-ylcarbamate To a solution of 1H-tetrazole-5-amine (1.00 g, 11.8 mmol) and pyridine (1.15 ml, 14.1 mmol) in tetrahydrofuran (39 ml) was added 2,2,2-trichloroethyl chloroformate (1.95 ml, 14.1 mmol) with ice-cooling and the mixture was stirred at room temperature for 1 hour. Water was poured into the reaction mixture and the mixture was extracted with ethyl acetate. The extract was washed with water and dried over anhydrous magnesium sulfate and the solvent was distilled off under reduced pressure. To the residue was added hexane and a solid was collected by filtration to obtain the desired product (1.29 g, 42.1%).

$^1$H-NMR (CDCl$_3$+DMSO-d$_6$) δ; 4.93 (2H, s), 2.22 (3H, s), 5.91 (1H, br s), 12.13 (1H, br s).

(2) 4-(3-Phenyl-1,2,4-thiadiazol-5-yl)-N-1H-tetrazol-5-ylpiperazine-1-carboxamide A mixture of 2,2,2-trichloroethyl 1H-tetrazol-5-ylcarbamate (190 mg, 0.731 mmol), 1-(3-phenyl-1,2,4-thiadiazol-5-yl)piperazine (200 mg, 0.812 mmol) and diisopropylethylamine (0.141 ml, 0.812 mmol) in dimethylsulfoxide (2.5 ml) was stirred at 70° C. for 3 hours. Water was poured into the reaction mixture and a crystal was collected by filtration. They were recrystallized from a mixed solvent of hexane and tetrahydrofuran to obtain the desired product (72.9 mg, 27.9%) as a solid.

$^1$H-NMR (CDCl$_3$+DMSO-d$_6$) δ; 3.67-3.69 (4H, m), 3.76-3.83 (4H, m), 7.41-7.44 (3H, m), 8.13-8.17 (2H, m), 10.97 (1H, br s).

Example 192

N-(5-Methylisoxazol-3-yl)-4-(3-phenyl-1,2,4-thiadiazol-5-yl)piperazine-1-carboxamide (1) 2,2,2-Trichloroethyl (5-methylisoxazol-3-yl)carbamate To a solution of 5-methylisoxazole-3-amine (1.00 g, 10.2 mmol) and pyridine (0.998 ml, 12.2 mmol) in tetrahydrofuran (34 ml) was added 2,2,2-trichloroethyl chloroformate (1.69 ml, 12.2 mmol) with ice-cooling and the mixture was stirred at room temperature for 1 hour. Water was poured into the reaction mixture and the mixture was extracted with ethyl acetate. The extract was washed with water and dried over anhydrous magnesium sulfate and the solvent was distilled off under reduced pressure. Hexane was poured to the residue and a solid was collected by filtration to obtain the desired product (2.55 g, 91.4%).

$^1$H-NMR (CDCl$_3$) δ; 2.41 (3H, s), 4.84 (2H, s), 6.55 (1H, br s), 8.52 (1H, br s).

(2) N-(5-Methylisoxazol-3-yl)-4-(3-phenyl-1,2,4-thiadiazol-5-yl)piperazine-1-carboxamide A mixture of 2,2,2-trichloroethyl (5-methylisoxazol-3-yl)carbamate (200 mg, 0.731 mmol), 1-(3-phenyl-1,2,4-thiadiazol-5-yl)piperazine (200 mg, 0.812 mmol) and diisopropylethylamine (0.141 ml, 0.812 mmol) in dimethylsulfoxide (2.5 ml) was stirred at 70° C. for 3 hours. Water was poured into the reaction mixture and the mixture was extracted with ethyl acetate. The extract was washed with water and dried over anhydrous magnesium sulfate and the solvent was distilled off under reduced pressure. The residue was recrystallized from a mixed solvent of hexane and tetrahydrofuran to obtain the desired product (119 mg, 44.0%) as a solid.

$^1$H-NMR (CDCl$_3$+DMSO-d$_6$) δ; 2.37 (3H, s), 3.63-3.65 (4H, m), 3.73-3.77 (4H, m), 6.51 (1H, s), 7.41-7.44 (3H, m), 8.14-8.17 (2H, m), 9.72 (1H, s).

Example 193

4-(3-Phenyl-1,2,4-thiadiazol-5-yl)-N-1,3,4-thiadiazol-2-ylpiperazine-1-carboxamide (1) 2,2,2-Trichloroethyl 1,3,4-thiadiazol-2-ylcarbamate To a solution of 1,3,4-thiadiazole-2-amine (1.00 g, 9.89 mmol) and pyridine (0.968 ml, 11.9 mmol) in tetrahydrofuran (33 ml) was added 2,2,2-trichloroethyl chloroformate (1.64 ml, 11.9 mmol) with ice-cooling and the mixture was stirred at room temperature for 1 hour. Water was poured into the reaction mixture and the mixture was extracted with ethyl acetate. The extract was washed with water and dried over anhydrous magnesium sulfate and the solvent was distilled off under reduced pressure. Hexane was poured to the residue and a solid was collected by filtration to obtain the desired product (2.16 g, 79.1%).

$^1$H-NMR (CDCl$_3$) δ; 4.97 (1H, s), 8.85 (1H, s), 12.19 (1H, br s).

(2) 4-(3-Phenyl-1,2,4-thiadiazol-5-yl)-N-1,3,4-thiadiazol-2-ylpiperazine-1-carboxamide A mixture of 2,2,2-trichloroethyl 1,3,4-thiadiazol-2-ylcarbamate (247 mg, 0.893 mmol), 1-(3-phenyl-1,2,4-thiadiazol-5-yl)piperazine (200 mg, 0.812 mmol) and diisopropylethylamine (0.156 ml, 0.893 mmol) in dimethylsulfoxide (2.7 ml) was stirred at 70° C. for 18 hours. Water was poured into the reaction mixture and the mixture was extracted with ethyl acetate. The extract was washed with water and dried over anhydrous magnesium sulfate and the solvent was distilled off under reduced pressure. The residue was recrystallized from a mixed solvent of hexane and tetrahydrofuran to obtain the desired product (161 mg, 53.2%) as a solid.

$^1$H-NMR (CDCl$_3$+DMSO-d$_6$) δ; 3.57-3.60 (4H, m), 3.75-3.78 (4H, m), 7.31-7.38 (3H, m), 8.05-8.10 (2H, m), 8.64 (1H, s), 11.94 (1H, br s).

Example 194

N-(1-Methyl-1H-pyrazol-5-yl)-4-(3-phenyl-1,2,4-thiadiazol-5-yl)piperazine-1-carboxamide (1) 2,2,2-Trichloroethyl (1-methyl-1H-pyrazol-5-yl)carbamate To a solution of 1-methyl-1H-pyrazole-5-amine (1.00 g, 10.3 mmol) and pyridine (1.01 ml, 12.4 mmol) in tetrahydrofuran (34 ml) was added 2,2,2-trichloroethyl chloroformate (1.71 ml, 12.4 mmol) with ice-cooling and the mixture was stirred at room temperature for 1 hour. Water was added to the reaction mixture and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) to obtain the desired product (1.43 g, 50.8%) as an oil.

$^1$H-NMR (CDCl$_3$) δ; 3.78 (3H, s), 4.83 (2H, s), 6.21 (1H, br s), 7.15 (1H, br s), 7.43-7.44 (1H, m).

(2) N-(1-Methyl-1H-pyrazol-5-yl)-4-(3-phenyl-1,2,4-thiadiazol-5-yl)piperazine-1-carboxamide A mixture of 2,2,2-trichloroethyl (1-methyl-1H-pyrazol-5-yl)carbamate (243 mg, 0.893 mmol), 1-(3-phenyl-1,2,4-thiadiazol-5-yl)piperazine (200 mg, 0.812 mmol) and diisopropylethylamine (0.156 ml, 0.893 mmol) in dimethylsulfoxide (2.5 ml) was stirred at 70° C. for 15 hours. Water was poured into the reaction mixture and the mixture was extracted with ethyl acetate. The extract was washed with water and dried over anhydrous magnesium sulfate and the solvent was distilled off under reduced pressure. The residue was recrystallized from a mixed solvent of hexane and ethyl acetate to obtain the desired product (140 mg, 46.8%) as a solid.

$^1$H-NMR (CDCl$_3$+DMSO-d$_6$) δ; 3.58-3.67 (8H, m), 5.97-5.98 (1H, m), 7.27-7.28 (1H, m), 7.32-7.35 (3H, m), 8.06-8.10 (2H, m), 8.45 (1H, s).

Example 195

4-(3-Phenyl-1,2,4-thiadiazol-5-yl)-N-1H-pyrazol-3-ylpiperazine-1-carboxamide (1) Bis(2,2,2-trichloroethyl) 1H-pyrazol-5-ylimidodicarbonate To a solution of 1H-pyrazole-5-amine (1.00 g, 12.0 mmol) and pyridine (1.18 ml, 14.4 mmol) in tetrahydrofuran (40 ml) was added 2,2,2-trichloroethyl chloroformate (2.00 ml, 14.4 mmol) with ice-cooling and the mixture was stirred at room temperature for 1 hour and half. Water was poured into the reaction mixture and the mixture was extracted with ethyl acetate. The extract was washed with water and dried over anhydrous magnesium sulfate and the solvent was distilled off under reduced pressure. Hexane was poured to the residue and a solid was collected by filtration to obtain the desired product (1.25 g, 23.9%).

$^1$H-NMR (CDCl$_3$) δ; 4.84 (2H, s), 5.04 (2H, s), 6.92-6.93 (1H, m), 7.80 (1H, br s), 8.11 (1H, d, J=4.5 Hz).

(2) 4-(3-Phenyl-1,2,4-thiadiazol-5-yl)-N-1H-pyrazol-3-ylpiperazine-1-carboxamide A mixture of bis(2,2,2-trichloroethyl) 1H-pyrazol-5-ylimidodicarbonate (264 mg, 0.609 mmol), 1-(3-phenyl-1,2,4-thiadiazol-5-yl)piperazine (300 mg, 1.22 mmol) and diisopropylethylamine (0.106 ml, 0.609 mmol) in dimethylsulfoxide (4.0 ml) was stirred at 70° C. for 8 hours. Water was poured into the reaction mixture and the mixture was extracted with ethyl acetate. The extract was washed with water and dried over anhydrous magnesium sulfate and the solvent was distilled off under reduced pressure. The residue was purified by high performance liquid chromatography (YMC HPLC column, A solution 0.1% trifluoroacetic acid solution in acetonitrile, B solution 0.1% trifluoroacetic acid solution in water, eluted with 10% A solution to 100% A solution) and aqueous saturated sodium hydrogen carbonate solution was added thereto and the mixture was extracted with ethyl acetate. The extract was washed with water and dried over anhydrous magnesium sulfate and the solvent was distilled off under reduced pressure. The residue was recrystallized from a mixed solvent of hexane and tetrahydrofuran to obtain the desired product (22.7 mg, 10.5%) as a solid.

$^1$H-NMR (CDCl$_3$+DMSO-d$_6$) δ; 3.64 (4H, br s), 3.71 (4H, br s), 6.39 (1H, br s), 7.42 (4H, br s), 8.15 (2H, br s), 9.15 (1H, br s), 12.00 (1H, s).

Example 196

(1) 2,2,2-Trichloroethyl 1H-1,2,4-triazol-3-ylcarbamate

To a solution of 1H-1,2,4-triazole-3-amine (1.00 g, 11.9 mmol) and pyridine (1.16 ml, 14.3 mmol) in tetrahydrofuran (40 ml) was added 2,2,2-trichloroethyl chloroformate (1.97 ml, 14.3 mmol) with ice-cooling and the mixture was stirred at room temperature for 1 hour. Water was poured into the reaction mixture and the mixture was extracted with ethyl acetate. The extract was washed with water and dried over anhydrous magnesium sulfate and the solvent was distilled off under reduced pressure. The residue was purified by silica gel column chromatography (ethyl acetate) to obtain the desired product (1.38 g, 44.5%).

$^1$H-NMR (CDCl$_3$+DMSO-d$_6$) δ; 4.93 (2H, s), 7.08 (2H, br s), 7.37 (1H, s).

(2) 4-(3-Phenyl-1,2,4-thiadiazol-5-yl)-N-1H-1,2,4-triazol-3-ylpiperazine-1-carboxamide A mixture of 2,2,2-trichloroethyl 1H-1,2,4-triazol-3-ylcarbamate (265 mg, 0.609 mmol), 1-(3-phenyl-1,2,4-thiadiazol-5-yl)piperazine (300 mg, 1.22 mmol) and diisopropylethylamine (0.106 ml, 1.22 mmol) in dimethylsulfoxide (2.5 ml) was stirred at 70° C. for 8 hours. Water was poured into the reaction mixture. A crystal formed was collected by filtration and recrystallized from a mixed solvent of hexane and tetrahydrofuran to obtain the desired product (61.8 mg, 28.5%) as a solid.

$^1$H-NMR (CDCl$_3$+DMSO-d$_6$) δ; 3.65-3.68 (4H, m), 3.79-3.82 (4H, m), 7.41-7.43 (3H, m), 7.62 (1H, s), 8.15-8.18 (2H, m), 10.49 (1H, br s), 12.59 (1H, br s).

Example 197

N-[6-(Acetylamino)pyridin-3-yl]-4-(4-phenyl-1,3-thiazol-2-yl)piperazine-1-carboxamide A mixture of 2,2,2-trichloroethyl [6-(acetylamino)pyridin-3-yl]carbamate (293 mg, 0.897 mmol), 1-(4-phenyl-1,3-thiazol-2-yl)piperazine (200 mg, 0.815 mmol) and diisopropylethylamine (0.156 ml, 0.897 mmol) in dimethylsulfoxide (2.7 ml) was stirred at 70° C. for 15 hours. Water was poured into the reaction mixture and the mixture was extracted with ethyl acetate. The extract was washed with water and dried over anhydrous magnesium sulfate and the solvent was distilled off under reduced pressure. The residue was purified by silica gel column chromatography (ethyl acetate) and recrystallized from a mixed solvent of hexane and tetrahydrofuran to obtain the desired product (47.3 mg, 13.7%) as a solid.

$^1$H-NMR (CDCl$_3$+DMSO-d$_6$) δ; 2.13 (3H, m), 3.59-3.61 (4H, m), 3.70-3.72 (4H, m), 6.96 (1H, s), 7.28 (1H, d, J=7.2 Hz), 7.34-7.39 (2H, m), 7.78-7.86 (3H, m), 8.03 (1H, d, J=9.0 Hz), 8.44-8.45 (1H, m), 8.61 (1H, s), 10.07 (1H, s).

Example 198

N-(3,4-Dimethylisoxazol-5-yl)-4-(4-phenyl-1,3-thiazol-2-yl)piperazine-1-carboxamide A mixture of 2,2,2-trichloroethyl (3,4-dimethylisoxazol-5-yl)carbamate (258 mg, 0.897 mmol), 1-(4-phenyl-1,3-thiazol-2-yl)piperazine (200 mg, 0.815 mmol) and diisopropylethylamine (0.156 ml, 0.897 mmol) in dimethylsulfoxide (2.7 ml) was stirred at 70° C. for 3 hours. Water was poured into the reaction mixture and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) and recrystallized from a mixed solvent of hexane and tetrahydrofuran to obtain the desired product (43.1 mg, 13.8%) as a solid.

$^1$H-NMR (CDCl$_3$) δ; 1.89 (3H, s), 2.21 (3H, s), 3.66 (8H, s), 6.63 (1H, br s), 6.83 (1H, s), 7.29-7.31 (1H, m), 7.36-7.41 (2H, m), 7.82-7.84 (2H, m).

Example 199

N-(6-Chloropyridin-3-yl)-4-(3-phenyl-1,2,4-thiadiazol-5-yl)piperazine-1-carboxamide (1) 2,2,2-Trichloroethyl (6-chloropyridin-3-yl)carbamate To a solution of 6-chloropyridine-3-amine (1.00 g, 7.78 mmol) and pyridine (0.761 ml, 9.33 mmol) in tetrahydrofuran (25 ml) was added 2,2,2-trichloroethyl chloroformate (1.29 ml, 9.33 mmol) with ice-cooling and the mixture was stirred at room temperature for 1 hour. Water was poured into the reaction mixture and the mixture was extracted with ethyl acetate. The extract was washed with water and dried over anhydrous magnesium sulfate and the solvent was distilled off under reduced pressure. Hexane was poured to the residue and a solid was collected by filtration to obtain the desired product (2.17 g, 92.0%).

$^1$H-NMR (CDCl$_3$) δ; 4.84 (2H, s), 7.13 (1H, br s), 7.33 (1H, d, J=8.4 Hz), 7.98-8.02 (1H, m), 8.38 (1H, d, J=4.2 Hz).

(2) N-(6-Chloropyridin-3-yl)-4-(3-phenyl-1,2,4-thiadiazol-5-yl)piperazine-1-carboxamide A mixture of 2,2,2-trichloroethyl (6-chloropyridin-3-yl)carbamate (272 mg, 0.893 mmol), 1-(3-phenyl-1,2,4-thiadiazol-5-yl)piperazine (200 mg, 0.812 mmol) and diisopropylethylamine (0.156 ml, 0.893 mmol) in dimethylsulfoxide (2.7 ml) was stirred at 70° C. for 15 hours. Water was poured into the reaction mixture and the mixture was extracted with ethyl acetate. The extract was washed with water and dried over anhydrous magnesium sulfate and the solvent was distilled off under reduced pressure. The residue was recrystallized from a mixed solvent of hexane and tetrahydrofuran to obtain the desired product (165 mg, 50.7%) as a solid.

$^1$H-NMR (CDCl$_3$+DMSO-d$_6$) δ; 3.67 (8H, br s), 7.41 (1H, d, J=8.4 Hz), 7.47-7.49 (3H, m), 7.95-7.99 (1H, m), 8.11-8.14 (2H, m), 8.51 (1H, d, J=2.7 Hz), 9.05 (1H, s).

Example 200

N-(3-Methyl-1,2,4-thiadiazol-5-yl)-4-(3-phenyl-1,2,4-thiadiazol-5-yl)piperazine-1-carboxamide (1) 2,2,2-Trichloroethyl (3-methyl-1,2,4-thiadiazol-5-yl)carbamate To a solution of 3-methyl-1,2,4-thiadiazol-5-amine (1.00 g, 8.68 mmol) and pyridine (0.850 ml, 10.4 mmol) in tetrahydrofuran (30 ml) was added 2,2,2-trichloroethyl chloroformate (1.44 ml, 10.4 mmol) with ice-cooling and the mixture was stirred at room temperature for 4 hours. Water was added to the reaction mixture and the mixture was extracted with ethyl acetate. The extract was washed with water and dried over anhydrous magnesium sulfate and the solvent was distilled off under reduced pressure. Hexane was poured to the residue and a solid was collected by filtration to obtain the desired product (1.84 g, 72.8%).

$^1$H-NMR (CDCl$_3$) δ; 2.66 (3H, s), 4.99 (2H, s), 11.92 (1H, br s).

(2) N-(3-Methyl-1,2,4-thiadiazol-5-yl)-4-(3-phenyl-1,2,4-thiadiazol-5-yl)piperazine-1-carboxamide A mixture of 2,2,2-trichloroethyl (3-methyl-1,2,4-thiadiazol-5-yl)carbamate (260 mg, 0.893 mmol), 1-(3-phenyl-1,2,4-thiadiazol-5-yl)piperazine (200 mg, 0.812 mmol) and diisopropylethylamine (0.156 ml, 0.893 mmol) in dimethylsulfoxide (2.7 ml) was stirred at 70° C. for 15 hours. Water was poured into the reaction mixture and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) and recrystallized from a mixed solvent of hexane and ethyl acetate to obtain the desired product (116 mg, 36.8%) as a solid.

$^1$H-NMR (CDCl$_3$+DMSO-d$_6$) δ; 2.45 (3H, s), 3.68-3.69 (4H, m), 3.81-3.85 (4H, m), 7.41-7.43 (3H, m), 8.13-8.17 (2H, m), 11.80 (1H, br s).

Example 201

N-(3-Methylisothiazol-5-yl)-4-(3-phenyl-1,2,4-thiadiazol-5-yl)piperazine-1-carboxamide (1) 2,2,2-Trichloroethyl (3-methylisothiazol-5-yl)carbamate To a solution of 3-methylisothiazol-5-amine (1.00 g, 6.64 mmol) and pyridine (1.30 ml, 7.97 mmol) in tetrahydrofuran (22 ml) was added 2,2,2-trichloroethyl chloroformate (1.10 ml, 7.97 mmol) with ice-cooling and the mixture was stirred at room temperature for 3 hours. Water was poured into the reaction mixture and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=1:1) to obtain the desired product (767 mg, 39.9%) as a solid.

$^1$H-NMR (CDCl$_3$) δ; 2.41 (3H, s), 4.87 (2H, s), 6.59 (1H, s), 8.45 (1H, br s).

(2) N-(3-Methylisothiazol-5-yl)-4-(3-phenyl-1,2,4-thiadiazol-5-yl)piperazine-1-carboxamide A mixture of 2,2,2-trichloroethyl (3-methylisothiazol-5-yl)carbamate (259 mg, 0.893 mmol), 1-(3-phenyl-1,2,4-thiadiazol-5-yl)piperazine (200 mg, 0.812 mmol) and diisopropylethylamine (0.156 ml, 0.893 mmol) in dimethylsulfoxide (2.7 ml) was stirred at 70° C. for 20 hours. Water was poured into the reaction mixture and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=3:7) and recrystallized from a mixed solvent of hexane and tetrahydrofuran to obtain the desired product (92.7 mg, 29.5%) as a solid.

$^1$H-NMR (CDCl$_3$+DMSO-d$_6$) δ; 2.35 (3H, s), 3.68-3.69 (4H, m), 3.77-3.80 (4H, m), 6.61 (1H, s), 7.41-7.43 (3H, m), 8.14-8.17 (2H, m), 10.41 (1H, s).

Example 202

4-(4-Phenyl-1,3-thiazol-2-yl)-N-pyridin-3-ylpiperazine-1-carboxamide hydrochloride To a solution of 4-(4-phenyl-1,3-thiazol-2-yl)-N-pyridin-3-ylpiperazine-1-carboxamide (1.00 g, 2.74 mmol) in tetrahydrofuran (100 ml) was added a 4N solution of hydrogen chloride in ethyl acetate (20 ml) at room temperature. The mixture was stirred at room temperature for 2 hours and the solvent was distilled off under reduced pressure. The residue was recrystallized from a mixed solvent of diethyl ether and methanol to obtain the desired product (1.09 g, 99.0%) as a solid.

$^1$H-NMR (DMSO-$d_6$) δ; 3.56-3.59 (4H, m), 3.75-3.78 (4H, m), 7.26-7.42 (3H, m), 7.85-7.88 (2H, m), 7.97 (1H, dd, J=5.4, 8.7 Hz), 8.51 (1H, d, J=5.4 Hz), 8.70-8.74 (1H, m), 9.19-9.20 (1H, m), 10.24 (1H, s).

Example 203

N-(6-Cyanopyridin-3-yl)-4-(3-phenyl-1,2,4-thiadiazol-5-yl)piperazine-1-carboxamide

(1) 2,2,2-Trichloroethyl (6-cyanopyridin-3-yl)carbamate

To a solution of 5-cyanopyridine-2-carbonitrile (1.00 g, 8.39 mmol) and pyridine (0.821 ml, 10.1 mmol) in tetrahydrofuran (28 ml) was added 2,2,2-trichloroethyl chloroformate (1.39 ml, 10.1 mmol) with ice-cooling and the mixture was stirred at room temperature for 1 hour. Water was poured into the reaction mixture and the mixture was extracted with ethyl acetate. The extract was washed with water and dried over anhydrous magnesium sulfate and the solvent was distilled off under reduced pressure. To the residue was added hexane and a solid was collected by filtration to obtain the desired product (2.27 g, 92.0%).

$^1$H-NMR (CDCl$_3$) δ; 4.86 (2H, s), 7.36 (1H, br s), 7.70-7.73 (1H, m), 8.20-8.23 (1H, m), 8.63-8.65 (1H, m).

(2) N-(6-Cyanopyridin-3-yl)-4-(3-phenyl-1,2,4-thiadiazol-5-yl)piperazine-1-carboxamide A mixture of 2,2,2-trichloroethyl (6-cyanopyridin-3-yl)carbamate (263 mg, 0.893 mmol), 1-(3-phenyl-1,2,4-thiadiazol-5-yl)piperazine (200 mg, 0.812 mmol) and diisopropylethylamine (0.156 ml, 0.893 mmol) in dimethylsulfoxide (2.7 ml) was stirred at 70° C. for 3 hours. Water was poured into the reaction mixture and the mixture was extracted with ethyl acetate. The extract was washed with water and dried over anhydrous magnesium sulfate and the solvent was distilled off under reduced pressure. The residue was purified by silica gel column chromatography (hexane:ethyl acetate=3:7) and recrystallized from a mixed solvent of hexane and tetrahydrofuran to obtain the desired product (26.1 mg, 8.2%) as a solid.

$^1$H-NMR (CDCl$_3$+DMSO-$d_6$) δ; 3.69-3.70 (4H, m), 3.77-3.81 (4H, m), 7.42-7.44 (3H, m), 7.65 (1H, d, J=8.7. Hz), 8.15-8.22 (3H, m), 8.82 (1H, d, J=2.7 Hz), 9.25 (1H, s).

Example 204

N-(6-Chloroimidazo[1,2-b]pyridazin-2-yl)-4-(3-phenyl-1,2,4-thiadiazol-5-yl)piperazine-1-carboxamide

(1) 2,2,2-Trichloroethyl (6-chloroimidazo[1,2-b]pyridazin-2-yl)carbamate

To a solution of 6-chloroimidazo[1,2-b]pyridazine-2-amine (561 g, 3.3 mmol) in dimethylacetamide (11 ml) was added 2,2,2-trichloroethyl chloroformate (0.506 ml, 3.66 mmol) with ice-cooling, and the mixture was stirred at room temperature for 1 hour. Water was poured into the reaction solution, and a solid was separated by filtration, which was washed with water to give 724 mg (63.3%) of the desired product as a solid.

$^1$H-NMR (CDCl$_3$) δ; 4.96 (2H, s), 7.23 (1H, d, J=9.3 Hz), 7.97 (1H, d, J=9.3 Hz), 8.11 (1H, br s), 11.07 (1H, br s).

(2) N-(6-Chloroimidazo[1,2-b]pyridazin-2-yl)-4-(3-phenyl-1,2,4-thiadiazol-5-yl)piperazine-1-carboxamide A mixture of 2,2,2-trichloroethyl (6-chloroimidazo[1,2-b]pyridazin-2-yl)carbamate (700 mg, 2.04 mmol), 1-(3-phenyl-1,2,4-thiadiazol-5-yl)piperazine (456 mg, 1.85 mmol) and diisopropylethylamine (0.355 ml, 2.04 mmol) in dimethylsulfoxide (6.2 ml) was stirred at 70° C. for 1 day. Water was poured into the reaction solution, and the mixture was extracted with ethyl acetate. The extract was washed with water and dried over anhydrous magnesium sulfate, and the solvent was distilled off under reduced pressure. Hexane was added to the residue, and a solid was separated by filtration, which was recrystallized from a mixed solvent of hexane and tetrahydrofuran to give 380 mg (42.3%) of the desired product as a solid.

$^1$H-NMR (DMSO-$d_6$) δ; 2.45 (3H, s), 3.68-3.69 (4H, m), 3.81-3.85 (4H, m), 7.41-7.43 (3H, m), 8.13-8.17 (2H, m), 11.80 (1H, br s).

Example 205

N-[6-(Aminocarbonyl)pyridin-3-yl]-4-(3-phenyl-1,2,4-thiadiazol-5-yl)piperazine-1-carboxamide To a solution of N-(6-cyanopyridin-3-yl)-4-(3-phenyl-1,2,4-thiadiazol-5-yl)piperazine-1-carboxamide (100 mg, 0.255 mmol) in methanol/tetrahydrofuran (1:4) (15 ml) was added a 1N aqueous sodium hydroxide solution (2.56 ml, 2.55 mmol) at room temperature, and the mixture was stirred at 60° C. for 2 days. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 12.8 mg (12.2%) of the desired product as a solid.

$^1$H-NMR (CDCl$_3$+DMSO-$d_6$) δ; 3.69-3.70 (4H, m), 3.76-3.78 (4H, m), 7.22 (1H, br s), 7.42-7.44 (3H, m), 7.74 (1H, br s), 7.96-7.99 (1H, m), 8.05-8.09 (1H, m), 8.14-8.17 (2H, m), 8.73 (1H, d, J=2.4 Hz), 9.10 (1H, s).

Example 206

N-(3,4-Dimethylisoxazol-5-yl)-4-[3-(2-thienyl)-1,2,4-thiadiazol-5-yl]piperazine-1-carboxamide A mixture of 2,2,2-trichloroethyl (3,4-dimethylisoxazol-5-yl)carbamate (251 mg, 0.872 mmol), 1-[3-(2-thienyl)-1,2,4-thiadiazol-5-yl]piperazine (200 mg, 0.793 mmol) and diisopropylethylamine (0.152 ml, 0.872 mmol) in dimethylsulfoxide (2.5 ml) was stirred at 70° C. for 3.5 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) and recrystallized from a mixed solvent of hexane and tetrahydrofuran to give 106 mg (31.1%) of the desired product as a solid.

$^1$H-NMR (CDCl$_3$) δ; 1.89 (3H, s), 2.21 (3H, s), 3.69 (8H, s), 6.70 (1H, br s), 7.09 (1H, dd, J=3.6, 4.8 Hz), 7.39 (1H, dd, J=1.2, 4.8 Hz), 7.74 (1H, dd, J=1.2, 3.6 Hz).

Example 207

N-Imidazo[1,2-b]pyridazin-6-yl-4-(3-phenyl-1,2,4-thiadiazol-5-yl)piperazine-1-carboxamide (1) Imidazo[1,2-b]pyridazine-6-amine A solution of 6-chloroimidazo[1,2-b]pyridazine (5.00 g, 32.6 mmol) in a 25% aqueous ammonia water (50 ml) was stirred in a sealed tube at 180° C. for 8 hours, and the reaction solution was distilled off under reduced pressure. A form solid was separated by filtration, which was washed with water to give 2.94 g (67.3%) of the desired product as a solid.

$^1$H-NMR (DMSO-d$_6$) δ; 6.30 (2H, br s), 6.61 (1H, d, J=9.6 Hz), 7.38 (1H, s), 7.69-7.74 (2H, m).

(2) Bis(2,2,2-trichloroethyl) imidazo[1,2-b]pyridazin-6-ylimidodicarbonate

To a solution of imidazo[1,2-b]pyridazine-6-amine (1.00 g, 7.45 mmol) and 4-dimethylaminopyridine (2.73 g, 22.4 mmol) in tetrahydrofuran (75 ml) was added 2,2,2-trichloroethyl chloroformate (3.09 ml, 22.4 mmol) with ice-cooling, and the mixture was stirred at 60° C. for 15 hours. Water was poured into the reaction solution, and the mixture was extracted with ethyl acetate. The extract was washed with water and dried over anhydrous magnesium sulfate, and the solvent was distilled off under reduced pressure. Hexane was added to the residue, and a solid was collected by filtration to give 1.92 g (53.1%) of the desired product.

$^1$H-NMR (CDCl$_3$) δ; 4.84 (2H, s), 4.87 (2H, s), 7.73-7.74 (1H, m), 7.79-7.80 (1H, m), 7.89-7.98 (2H, m).

(3) N-Imidazo[1,2-b]pyridazin-6-yl-4-(3-phenyl-1,2,4-thiadiazol-5-yl)piperazine-1-carboxamide A mixture of bis(2,2,2-trichloroethyl) imidazo[1,2-b]pyridazin-6-ylimidodicarbonate (295 mg, 0.609 mmol), 1-(3-phenyl-1,2,4-thiadiazol-5-yl)piperazine (300 mg, 1.22 mmol) and diisopropylethylamine (0.106 ml, 0.609 mmol) in dimethylsulfoxide (2.0 ml) was stirred at 70° C. for 4 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 212 mg (85.7%) of the desired product as a solid.

$^1$H-NMR (CDCl$_3$) δ; 3.76 (8H, br s), 7.13 (1H, br s), 7.43-7.46 (3H, m), 7.68-7.69 (1H, s), 7.74-7.75 (1H, m), 7.84-7.94 (2H, m), 8.18-8.21 (2H, m).

Example 208

N-(4-Bromo-1-methyl-1H-pyrazol-5-yl)-4-(3-phenyl-1,2,4-thiadiazol-5-yl)piperazine-1-carboxamide (1) 2,2,2-Trichloroethyl (4-bromo-1-methyl-1H-pyrazol-5-yl)carbamate To a solution of 4-bromo-1-methyl-1H-pyrazol-5-amine (500 mg, 2.84 mmol) and pyridine (0.270 ml, 3.41 mmol) in tetrahydrofuran (9.5 ml) was added 2,2,2-trichloroethyl chloroformate (0.472 ml, 3.41 mmol) with ice-cooling, and the mixture was stirred at room temperature for 2 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give 289 mg (28.9%) of the desired product as an oil.

$^1$H-NMR (CDCl$_3$) δ; 3.82 (3H, s), 4.85 (2H, s), 6.56 (1H, br s), 7.47 (1H, s).

(2) N-(4-Bromo-1-methyl-1H-pyrazol-5-yl)-4-(3-phenyl-1,2,4-thiadiazol-5-yl)piperazine-1-carboxamide A mixture of 2,2,2-trichloroethyl (4-bromo-1-methyl-1H-pyrazol-5-yl)carbamate (289 mg, 0.822 mmol), 1-(3-phenyl-1,2,4-thiadiazol-5-yl)piperazine (184 mg, 0.747 mmol) and diisopropylethylamine (0.143 ml, 0.822 mmol) in dimethylsulfoxide (2.5 ml) was stirred at 70° C. for 15.5 hours. Water was poured into the reaction solution, and the mixture was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give 233 mg (69.7%) of the desired product as a solid.

$^1$H-NMR (CDCl$_3$+DMSO-d$_6$) δ; 3.69-3.71 (4H, m), 3.74 (3H, s), 3.75-3.79 (4H, m), 7.40-7.45 (4H, m), 8.16-8.19 (2H, m), 8.57 (1H, s).

Example 209

N-(3-tert-Butyl-1-methyl-1H-pyrazol-5-yl)-4-(3-phenyl-1,2,4-thiadiazol-5-yl)piperazine-1-carboxamide (1) 2,2,2-Trichloroethyl (3-tert-butyl-1-methyl-1H-pyrazol-5-yl)carbamate To a solution of 3-tert-butyl-1-methyl-1H-pyrazole-5-amine (500 g, 3.26 mmol) and pyridine (0.310 ml, 3.92 mmol) in tetrahydrofuran (11 ml) was added 2,2,2-trichloroethyl chloroformate (0.542 ml, 3.92 mmol) with ice-cooling, and the mixture was stirred at room temperature for 2 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane: ethyl acetate=1:1) to give 925 mg (86.5%) of the desired product as an oil.

$^1$H-NMR (CDCl$_3$) δ; 1.28 (9H, s), 3.72 (3H, s), 4.82 (2H, s), 6.08 (1H, s), 6.78 (1H, br s).

(2) N-(3-tert-Butyl-1-methyl-1H-pyrazol-5-yl)-4-(3-phenyl-1,2,4-thiadiazol-5-yl)piperazine-1-carboxamide A mixture of 2,2,2-trichloroethyl (3-tert-butyl-1-methyl-1H-pyrazol-5-yl)carbamate (294 mg, 0.895 mmol), 1-(3-phenyl-1,2,4-thiadiazol-5-yl)piperazine (200 mg, 0.812 mmol) and diisopropylethylamine (0.156 ml, 0.895 mmol) in dimethylsulfoxide (2.7 ml) was stirred at 70° C. for 15 hours. Water was poured into the reaction solution, and the mixture was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give 258 mg (74.8%) of the desired product as a solid.

$^1$H-NMR (CDCl$_3$+DMSO-d$_6$) δ; 1.28 (9H, s), 2.59 (3H, s), 3.69 (8H, s), 5.97 (1H, s), 6.41 (1H, br s), 7.42-7.43 (3H, m), 8.18-8.19 (2H, m).

Example 210

N-(1-Ethyl-1H-pyrazol-5-yl)-4-(3-phenyl-1,2,4-thiadiazol-5-yl)piperazine-1-carboxamide (1) 2,2,2-Trichloroethyl (1-ethyl-1H-pyrazol-5-yl)carbamate To a solution of 1-ethyl-1H-pyrazole-5-amine (500 mg, 4.50 mmol) and pyridine (0.440 ml, 5.40 mmol) in tetrahydrofuran (15 ml) was added 2,2,2-trichloroethyl chloroformate (0.747 ml, 5.40 mmol) with ice-cooling, and the mixture was stirred at room temperature for 1.5 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane: ethyl acetate=1:1) to give 646 mg (50.1%) of the desired product as an oil.

$^1$H-NMR (CDCl$_3$) δ; 1.40 (3H, t, J=7.2 Hz), 4.06 (2H, q, J=7.2 Hz), 4.82 (2H, s), 6.20-6.21 (1H, m), 7.45-7.46 (1H, m), 7.52 (1H, br s).

(2) N-(1-Ethyl-1H-pyrazol-5-yl)-4-(3-phenyl-1,2,4-thiadiazol-5-yl)piperazine-1-carboxamide A mixture of 2,2,2-trichloroethyl (3,4-dimethylisoxazol-5-yl)carbamate (256 mg, 0.893 mmol), 1-(3-phenyl-1,2,4-thiadiazol-5-yl)piperazine (200 mg, 0.812 g) and diisopropylethylamine (0.156 ml, 0.893 mmol) in dimethylsulfoxide (2.5 ml) was stirred at 70° C. for 5 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 115 mg (36.8%) of the desired product as a solid.

$^1$H-NMR (CDCl$_3$) δ; 1.44 (3H, t, J=7.0 Hz), 3.66 (8H, br s), 4.02 (2H, q, J=7.0 Hz), 6.08 (1H, br s), 6.39 (1H, br s), 7.42-7.47 (4H, m), 8.18-8.20 (2H, m).

Example 211

N-(1,3-Dimethyl-1H-pyrazol-5-yl)-4-(3-phenyl-1,2,4-thiadiazol-5-yl)piperazine-1-carboxamide (1) 2,2,2-Trichloroethyl (1,3-dimethyl-1H-pyrazol-5-yl)carbamate To a solution of 1,3-dimethyl-1H-pyrazol-5-amine (500 mg, 4.50 mmol) in dimethylacetamide (15 ml) was added 2,2,2-trichloroethyl chloroformate (0.747 ml, 5.40 mmol) with ice-cooling, and the mixture was stirred at 0° C. for 1 hour. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) to give 526 mg (40.8%) of the desired product as an oil.

$^1$H-NMR (CDCl$_3$) δ; 2.22 (3H, s), 3.71 (3H, s), 4.82 (2H, s), 6.01 (1H, s), 7.14 (1H, br s).

(2) N-(1,3-Dimethyl-1H-pyrazol-5-yl)-4-(3-phenyl-1,2,4-thiadiazol-5-yl)piperazine-1-carboxamide A mixture of 2,2,2-trichloroethyl (1,3-dimethyl-1H-pyrazol-5-yl)carbamate (256 mg, 0.893 mmol), 1-(3-phenyl-1,2,4-thiadiazol-5-yl)piperazine (200 mg, 0.812 mmol) and diisopropylethylamine (0.156 ml, 0.893 mmol) in dimethylsulfoxide (2.7 ml) was stirred at 70° C. for 15 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 146 mg (46.9%) of the desired product as a solid.

$^1$H-NMR (CDCl$_3$) δ; 2.23 (3H, s), 3.65-3.66 (8H, m), 3.66 (3H, s), 5.88 (1H, s), 6.46 (1H, br s), 7.41-7.46 (3H, m), 8.16-8.21 (2H, m).

Example 212

N-Imidazo[1,2-b]pyridazin-6-yl-4-(4-phenyl-1,3-thiazol-2-yl)piperazine-1-carboxamide A mixture of 2,2,2-trichloroethyl imidazo[1,2-b]pyridazin-6-ylcarbamate (198 mg, 0.408 mmol), 1-(4-phenyl-1,3-thiazol-2-yl)piperazine (200 mg, 0.815 mmol) and diisopropylethylamine (0.076 ml, 0.408 mmol) in dimethylsulfoxide (2.7 ml) was stirred at 70° C. for 15 hours. Water was poured into the reaction solution, and the mixture was exacted with ethyl acetate. The extract was washed with water and dried over anhydrous magnesium sulfate, and the solvent was distilled off under reduced pressure. The residue was recrystallized from a mixed solvent of hexane and tetrahydrofuran to give 110 mg (66.5%) of the desired product as a solid.

$^1$H-NMR (CDCl$_3$) δ; 3.66-3.76 (8H, m), 6.84 (1H, s), 7.16 (1H, s), 7.27-7.42 (3H, m), 7.68 (1H, s), 7.74 (1H, s), 7.83-7.93 (4H, m).

Example 213

N-(3,4-Dimethylisoxazol-5-yl)-4-(5-methyl-4-phenyl-1,3-thiazol-2-yl)piperazine-1-carboxamide (1) 1-Methyl-2-oxo-2-phenylethyl thiocyanate A solution of 2-bromopropiophenone (7.14 ml, 46.9 mmol) and potassium thiocyanate (4.56 g, 46.9 mmol) in ethanol (80 ml) was stirred at 80° C. for 3 hours. After cooling to room temperature, water was poured into the reaction solution, and the mixture was extracted with ethyl acetate. The extract was washed with water and dried over anhydrous magnesium sulfate, and the solvent was distilled off under reduced pressure to give 7.27 g (81.0%) of the desired product as an oil.

$^1$H-NMR (CDCl$_3$) δ; 1.87 (3H, d, J=7.2 Hz), 5.09 (1H, q, J=7.2 Hz), 7.51-7.57 (2H, m), 7.64-7.70 (1H, m), 7.92-7.96 (2H, m).

(2) 2-Bromo-5-methyl-4-phenyl-1,3-thiazole

A solution of 1-methyl-2-oxo-2-phenylethyl thiocyanate (1.00 g, 5.23 mmol) in 25% hydrogen bromide/acetic acid (10 ml) was stirred at 130° C. for 2 hours and at room temperature for 1 hour. Water was poured into the reaction solution, and the mixture was extracted with chloroform. The extract was washed with water and dried over anhydrous magnesium sulfate, and the solvent was distilled off under reduced pressure. The residue was purified by silica gel column chromatography (hexane:ethyl acetate=9:1) to give 971 mg (73.1%) of the desired product as an oil.

$^1$H-NMR (CDCl$_3$) δ; 2.53 (3H, s), 7.35-7.45 (3H, m), 7.59-7.63 (2H, m).

(3) tert-Butyl 4-(5-methyl-4-phenyl-1,3-thiazol-2-yl)piperazine-1-carboxylate

A solution of 2-bromo-5-methyl-4-phenyl-1,3-thiazole (9.56 g, 37.6 mmol), tert-butyl piperazine-1-carboxylate (14.8 g, 75.2 mmol) and potassium carbonate (5.20 g, 37.6 mmol) in dimethylformamide (125 ml) was stirred at 120° C. for 4 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give 2.45 g (18.1%) of the desired product as a solid.

$^1$H-NMR (CDCl$_3$) δ; 1.48 (9H, s), 3.42-3.47 (4H, m), 3.52-3.57 (4H, m), 7.26-7.36 (1H, m), 7.36-7.41 (2H, m), 7.58-7.62 (2H, m).

(4) 1-(5-Methyl-4-phenyl-1,3-thiazol-2-yl)piperazine

To a solution of N-(tert-butoxy)-4-(5-methyl-4-phenyl-1,3-thiazol-2-yl)piperazine-1-carboxamide (2.45 g, 6.82 mmol) in ethyl acetate (200 ml) was added a 4N hydrogen chloride solution in ethyl acetate (40 ml), and the mixture was stirred at room temperature for 18 hours. The solvent was distilled off under reduced pressure, and the residue was dissolved in water. The solution was neutralized with 1N sodium hydroxide, and the mixture was extracted with chloroform. The extract was washed with water and dried over anhydrous magnesium sulfate, and the solvent was distilled off under reduced pressure to give 1.51 g (85.6%) of the desired product as a solid.

$^1$H-NMR (CDCl$_3$) δ; 2.41 (3H, s), 2.95-3.00 (4H, m), 3.41-3.46 (4H, m), 7.23-7.42 (3H, m), 7.59-7.64 (2H, m).

(5) N-(3,4-Dimethylisoxazol-5-yl)-4-(5-methyl-4-phenyl-1,3-thiazol-2-yl)piperazine-1-carboxamide A mixture of 2,2,2-trichloroethyl (3,4-dimethylisoxazol-5-yl)carbamate (244 mg, 0.848 mmol), 1-(5-methyl-4-phenyl-1,3-thiazol-2-yl)piperazine (200 mg, 0.771 mmol) and diisopropylethylamine (0.148 ml, 0.848 mmol) in dimethylsulfoxide (2.6 ml) was stirred at 70° C. for 5 hours. Water was poured into the reaction solution, and the mixture was extracted with ethyl acetate. The extract was washed with water and dried anhydrous magnesium sulfate, and the solvent was distilled off under reduced pressure. The residue was recrystallized from a mixed solvent of hexane and ethyl acetate to give 186 mg (60.8%) of the desired product as a solid.

$^1$H-NMR (CDCl$_3$) δ; 1.88 (3H, s), 2.20 (3H, s), 2.43 (3H, s), 3.52-3.56 (4H, m), 3.62-3.65 (4H, m), 6.79 (1H, br s), 7.27-7.33 (1H, m), 7.38-7.43 (2H, m), 7.59-7.62 (2H, m).

Example 214

4-(5-Methyl-4-phenyl-1,3-thiazol-2-yl)-N-pyridin-3-ylpiperazine-1-carboxamide

A mixture of 2,2,2-trichloroethyl pyridin-3-ylcarbamate (229 mg, 0.848 mmol), 1-(5-methyl-4-phenyl-1,3-thiazol-2-yl)piperazine (200 mg, 0.771 mmol) and diisopropylethylamine (0.148 ml, 0.848 mmol) in dimethylsulfoxide (2.6 ml) was stirred at 70° C. for 5 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 68.4 mg (23.4%) of the desired product as a solid.

$^1$H-NMR (CDCl$_3$) δ; 2.44 (3H, s), 3.54-3.58 (4H, m), 3.64-3.68 (4H, m), 6.77 (1H, s), 7.23-7.33 (2H, m), 7.38-7.43 (2H, m), 7.58-7.62 (2H, m), 7.95-7.99 (1H, m), 8.28-8.30 (1H, m), 8.45-8.46 (1H, m).

Example 215

N-[6-(Acetylamino)pyridin-3-yl]-4-(5-methyl-4-phenyl-1,3-thiazol-2-yl)piperazine-1-carboxamide A mixture of 2,2,2-trichloroethyl [6-(acetylamino)pyridin-3-yl]carbamate (277 mg, 0.848 mmol), 1-(5-methyl-4-phenyl-1,3-thiazol-2-yl)piperazine (200 mg, 0.771 mmol) and diisopropylethylamine (0.148 ml, 0.848 mmol) in dimethylsulfoxide (2.6 ml) was stirred at 70° C. for 18 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 161 mg (47.8%) of the desired product as a solid.

$^1$H-NMR (CDCl$_3$+DMSO-d$_6$) δ; 2.18 (3H, s), 2.44 (3H, s), 3.50-3.53 (4H, m), 3.68-3.75 (4H, m), 7.26-7.32 (1H, m), 7.37-7.42 (2H, m), 7.60-7.62 (2H, m), 7.77-7.80 (1H, m), 8.07-8.10 (1H, m), 8.31 (1H, br s), 8.46-8.47 (1H, m), 9.36 (1H, br s).

Example 216

4-[4-(2-Fluorophenyl)-1,3-thiazol-2-yl]-N-pyridin-3-ylpiperazine-1-carboxamide

(1) 2-Bromo-1-(2-fluorophenyl)ethanone

To a solution of 1-(2-fluorophenyl)ethanone (5.00 g, 36.2 mmol) in diethyl ether (100 ml) was slowly added dropwise bromine (5.78 g, 36.2 mmol), and the mixture was stirred at room temperature for 4 hours. The reaction solution was distilled off under reduced pressure to give the desired product (5.89 g, 74.9%) as an oil.
$^1$H-NMR (CDCl$_3$) δ; 4.53 (2H, s), 7.14-7.21 (1H, m), 7.25-7.31 (1H, m), 7.55-7.60 (1H, m), 7.92-7.97 (1H, m).

(2) 2-(2-Fluorophenyl)-2-oxoethyl thiocyanate

A solution of 2-bromo-1-(2-fluorophenyl)ethanone (5.00 g, 23.0 mmol) and potassium thiocyanate (2.24 g, 23.0 mmol) in ethanol (50 ml) was stirred at 80° C. for 2 hours. After cooling to room temperature, water (60 ml) was poured into the reaction solution, and the mixture was extracted with chloroform. The extract was washed with water and dried over anhydrous magnesium sulfate, and the solvent was distilled off under reduced pressure to give the desired product (4.29 g, 95.5%) as a solid.
$^1$H-NMR (CDCl$_3$) δ; 4.65-4.66 (2H, m), 7.19-7.25 (1H, m), 7.29-7.35 (1H, m), 7.62-7.69 (1H, m), 7.96-8.02 (1H, m).

(3) 2-Bromo-4-(2-fluorophenyl)-1,3-thiazole

To a solution of 2-(2-fluorophenyl)-2-oxoethyl thiocyanate (4.20 g, 21.5 mmol) in acetic acid (40 ml) was added a solution of 25% hydrogen bromide/acetic acid (40 ml), and the mixture was stirred at 130° C. for 2 hours. Water was poured into the reaction solution, and the mixture was extracted with chloroform. The extract was washed with water and dried over anhydrous magnesium sulfate, and the solvent was distilled off under reduced pressure. The residue was purified by silica gel column chromatography (hexane:ethyl acetate=9:1) to give the desired product (3.41 g, 61.4%) as an oil.
$^1$H-NMR (CDCl$_3$) δ; 7.10-7.35 (3H, m), 7.69 (1H, s), 8.14-8.19 (1H, m).

(4) tert-Butyl 4-[4-(2-fluorophenyl)-1,3-thiazol-2-yl]piperazine-1-carboxylate A solution of 2-bromo-4-(4-fluorophenyl)-1,3-thiazole (3.41 g, 13.2 mmol), tert-butyl piperazine-1-carboxylate (4.92 g, 26.4 mmol) and potassium carbonate (1.83 g, 13.2 mmol) in dimethylformamide (45 ml) was stirred at 120° C. for 15 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give the desired product (3.83 g, 79.8%) as an oil.
$^1$H-NMR (CDCl$_3$) δ; 1.49 (9H, s), 3.48-3.61 (8H, m), 7.05-7.27 (4H, m), 8.10-8.16 (1H, m).

(5) 1-[4-(2-Fluorophenyl)-1,3-thiazol-2-yl]piperazine

To a solution tert-butyl 4-[4-(2-fluorophenyl)-1,3-thiazol-2-yl]piperazine-1-carboxylate (3.83 g, 10.5 mmol) in ethyl acetate (100 ml) was added a 4N solution (100 ml) of hydrogen chloride in ethyl acetate, and the mixture was stirred at room temperature for 12 hours. The solvent was distilled off under reduced pressure, and the residue was dissolved in water. The solution was neutralized with 1N aqueous sodium hydroxide solution, and the mixture was extracted with chloroform. The extract was washed with water and dried over anhydrous magnesium sulfate, and the solvent was distilled off under reduced pressure to give the desired product (2.61 g, 94.1%) as an oil.
$^1$H-NMR (CDCl$_3$) δ; 2.99-3.02 (4H, m), 3.50-3.54 (4H, m), 7.05-7.25 (4H, m), 8.12-8.18 (1H, m).

(6) 4-[4-(2-Fluorophenyl)-1,3-thiazol-2-yl]-N-pyridin-3-ylpiperazine-1-carboxamide A mixture of 2,2,2-trichloroethyl pyridin-3-ylcarbamate (225 mg, 0.835 mmol), 1-[4-(2-fluorophenyl)-1,3-thiazol-2-yl]piperazine (200 mg, 0.760 mmol) and diisopropylethylamine (0.265 ml, 1.52 mmol) in dimethylsufoxide (2.5 ml) was stirred at 70° C. for 12 hours. Water was poured into the reaction solution, and the mixture was extracted with ethyl acetate. The extract was washed with water and dried over anhydrous magnesium sulafate, and the solvent was distilled off under reduced pressure. The residue was recrystallized from a mixed solvent of hexane and ethyl acetate to give the desired product (90.9 mg, 31.2%) as a solid.
$^1$H-NMR (CDCl$_3$) δ; 3.64-3.73 (8H, m), 6.75 (1H, br s), 7.06-7.29 (5H, m), 7.99-8.03 (1H, m), 8.10-8.16 (1H, m), 8.29 (1H, d, J=4.8 Hz), 8.48-8.49 (1H, m).

Example 217

4-[4-(3-Fluorophenyl)-1,3-thiazol-2-yl]-N-pyridin-3-ylpiperazine-1-carboxamide

(1) 2-(3-Fluorophenyl)-2-oxoethyl thiocyanate

A solution of 2-bromo-1-(3-fluorophenyl)ethanone (1.00 g, 4.61 mmol) and potassium thiocyanate (448 mg, 4.61 mmol) in ethanol (10 ml) was stirred at 80° C. for 3 hours. After cooling to room temperature, water (12 ml) was poured into the reaction solution, and a crystal was separated by filtration, which was washed with 50% aqueous ethanol solution to give the desired product (668 mg, 74.3%) as a solid.
$^1$H-NMR (CDCl$_3$) δ; 4.70 (2H, s), 7.35-7.42 (1H, m), 7.50-7.57 (1H, m), 7.62-7.67 (1H, m), 7.71-7.74 (1H, m).

(2) 2-Bromo-4-(3-fluorophenyl)-1,3-thiazole

To a solution of 2-(3-fluorophenyl)-2-oxoethyl thiocyanate (1.76 g, 9.02 mmol) in acetic acid (15 ml) was added a 25% hydrogen bromide/acetic acid solution (15 ml), and the mixture was stirred at 130° C. for 2 hours and at room temperature for 2 hours. Water was poured into the reaction solution, and the mixture was extracted with chloroform. The extract was washed with water and dried over anhydrous magnesium sulfate, and the solvent was distilled off under reduced pressure. The residue was purified by silica gel column chromatography (hexane: ethyl acetate=9:1) to give the desired product (2.31 g, 99.0%) as an oil.
$^1$H-NMR (CDCl$_3$) δ; 7.04-7.05 (1H, m), 7.34-7.42 (1H, m), 7.43 (1H, s), 7.56-7.64 (2H, m).

(3) tert-Butyl 4-[4-(3-fluorophenyl)-1,3-thiazol-2-yl]piperazine-1-carboxylate A solution of 2-bromo-4-(3-fluorophenyl)-1,3-thiazole (800 mg, 3.10 mmol), tert-butyl piperazine-1-carboxylate (1.15 g, 6.20 mmol) and potassium carbonate (428 mg, 3.10 mmol) in dimethylformamide (10 ml) was stirred at 120° C. for 12 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give 781 mg (69.4%) of the desired product as an oil.

$^1$H-NMR (CDCl$_3$) δ; 1.49 (9H, s), 3.51-3.61 (8H, m), 6.82 (1H, s), 6.94-7.00 (1H, m), 7.29-7.36 (1H, m), 7.53-7.60 (2H, m).

(4) 1-[4-(3-Fluorophenyl)-1,3-thiazol-2-yl]piperazine

To a solution of tert-butyl 4-[4-(3-fluorophenyl)-1,3-thiazol-2-yl]piperazine-1-carboxylate (780 mg, 2.15 mmol) in ethyl acetate (50 ml) was added a 4N solution (25 ml) of hydrogen chloride in ethyl acetate, and the mixture was stirred at room temperature for 14 hours. The solvent was distilled off under reduced pressure, and the residue was dissolved in water. The solution was neutralized with 1N aqueous sodium hydroxide solution, and the mixture was extracted with chloroform. The extract was washed with water and dried over anhydrous magnesium sulfate, and the solvent was distilled off under reduced pressure to give the desired product (487 mg, 86.3%) as a solid.

$^1$H-NMR (CDCl$_3$) δ; 2.99-3.03 (4H, m), 3.50-3.54 (4H, m), 6.79 (1H, s), 6.93-6.99 (1H, m), 7.28-7.35 (1H, m), 7.53-7.61 (2H, m).

(5) 4-[4-(3-Fluorophenyl)-1,3-thiazol-2-yl]-N-pyridin-3-ylpiperazine-1-carboxamide A mixture of 2,2,2-trichloroethyl pyridin-3-ylcarbamate (225 mg, 0.835 mmol), 1-[4-(3-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 4 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give the desired product (147 mg, 50.5%) as a solid.

$^1$H-NMR (CDCl$_3$) δ; 3.61-3.72 (8H, m), 6.84 (1H, s), 6.94-7.01 (1H, m), 7.02 (1H, br s), 7.23-7.37 (2H, m), 7.53-7.60 (2H, m), 7.95-7.99 (1H, m), 8.28-8.30 (1H, m), 8.45-8.46 (1H, m).

Example 218

4-[4-(4-Fluorophenyl)-1,3-thiazol-2-yl]-N-pyridin-3-ylpiperazine-1-carboxamide (1) 2-(4-Fluorophenyl)-2-oxoethyl thiocyanate A solution of 2-bromo-1-(4-fluorophenyl)ethanone (5.00 g, 23.0 mmol) and potassium thiocyanate (2.24 g, 23.0 mmol) in ethanol (50 ml) was stirred at 80° C. for 3 hours. After cooling to room temperature, water (60 ml) was poured into the reaction solution, and a crystal was separated by filtration, which was washed with 50% aqueous ethanol solution to give the desired product (3.71 g, 82.5%) as a solid.

$^1$H-NMR (CDCl$_3$) δ; 4.71 (2H, s), 7.18-7.22 (2H, m), 7.96-8.01 (2H, m).

(2) 2-Bromo-4-(4-fluorophenyl)-1,3-thiazole

To a solution of 2-(4-fluorophenyl)-2-oxoethyl thiocyanate (3.70 g, 19.0 mmol) in acetic acid (35 ml) was added a 25% hydrogen bromide/acetic acid (35 ml) solution, and the mixture was stirred at 130° C. for 2 hours and at room temperature for 2 hours. Water was poured into the reaction solution, and the mixture was extracted with chloroform. The extract was washed with water and dried over anhydrous magnesium sulfate, and the solvent was distilled off under reduced pressure. The residue was recrystallized from a mixed solvent of ethanol and water to give the desired product (4.50 g, 91.9%) as a solid.

$^1$H-NMR (CDCl$_3$) δ; 7.07-7.14 (2H, m), 7.34 (1H, s), 7.80-7.86 (2H, m).

(3) tert-Butyl 4-[4-(4-fluorophenyl)-1,3-thiazol-2-yl]piperazine-1-carboxylate

A solution of 2-bromo-4-(4-fluorophenyl)-1,3-thiazole (4.49 g, 17.4 mmol), tert-butyl piperazine-1-carboxylate (6.48 g, 34.8 mmol) and potassium carbonate (2.4 g, 17.4 mmol) in dimethylformamide (55 ml) was stirred at 120° C. for 8 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give the desired product (3.29 g, 52%) as an oil.

$^1$H-NMR (CDCl$_3$) δ; 1.49 (9H, s), 3.50-3.60 (8H, m), 6.71 (1H, s), 7.02-7.08 (2H, m), 7.77-7.82 (2H, m).

(4) 1-[4-(4-Fluorophenyl)-1,3-thiazol-2-yl]piperazine dihydrochloride

To a solution of tert-butyl 4-[4-(4-fluorophenyl)-1,3-thiazol-2-yl]piperazine-1-carboxylate (3.29 g, 9.05 mmol) in ethyl acetate (100 ml) was added a 4N solution (100 ml) of hydrogen chloride in ethyl acetate, and the mixture was stirred at room temperature for 3 hours. The solvent was distilled off under reduced pressure to give 2.32 g (76.3%) of the desired product as a solid.

(5) 1-[4-(4-Fluorophenyl)-1,3-thiazol-2-yl]piperazine

1-[4-(4-Fluorophenyl)-1,3-thiazol-2-yl]piperazine hydrochloride (1.00 g, 2.97 mmol) was dissolved in water. The solution was neutralized with 1N aqueous sodium hydroxide solution, and the mixture was extracted with chloroform. The extract was washed with water and dried over anhydrous magnesium sulfate, and the solvent was distilled off under reduced pressure to give the desired product (696 mg, 67.2%) as an oil.

$^1$H-NMR (CDCl$_3$) δ; 2.94-2.99 (4H, m), 3.45-3.50 (4H, m), 6.64 (1H, s), 6.96-7.05 (2H, m), 7.24-7.80 (2H, m).

(6) 4-[4-(4-Fluorophenyl)-1,3-thiazol-2-yl]-N-pyridin-3-ylpiperazine-1-carboxamide A mixture of 2,2,2-trichloroethyl pyridin-3-ylcarbamate (225 mg, 0.835 mmol), 1-[4-(4-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 18 hours. Water was poured into the reaction solution, and the mixture was extracted with ethyl acetate. The extract was washed with water and dried over anhydrous magnesium sulfate, and the solvent was distilled off under reduced pressure. The residue was recrystallized from a mixed solvent of hexane and ethyl acetate to give the desired product (199 mg, 68.5%) as a solid.

$^1$H-NMR (CDCl$_3$) δ; 3.65-3.71 (8H, m), 6.53 (1H, br s), 6.75 (1H, s), 7.04-7.10 (2H, m), 7.24-7.29 (1H, m), 7.78-7.83 (2H, m), 7.97-8.01 (1H, m), 8.30-8.32 (1H, m), 8.46-8.47 (1H, m).

Example 219

N-(3,4-Dimethylisoxazol-5-yl)-4-[4-(2-fluorophenyl)-1,3-thiazol-2-yl]piperazine-1-carboxamide A mixture of 2,2,2-trichloroethyl (3,4-dimethylisoxazol-5-yl)carbamate (240 mg, 0.834 mmol), 1-[4-(2-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 14 hours. Water was poured into the reaction solution, and the mixture was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give the desired product (115 mg, 37.8%) as a solid.

$^1$H-NMR (CDCl$_3$) δ; 1.89 (3H, s), 2.20 (3H, s), 3.63-3.69 (8H, m), 6.71 (1H, s), 7.07-7.26 (4H, m), 8.10-8.16 (1H, m).

Example 220

N-(3,4-Dimethylisoxazol-5-yl)-4-[4-(3-fluorophenyl)-1,3-thiazol-2-yl]piperazine-1-carboxamide A mixture of 2,2,2-trichloroethyl (3,4-dimethylisoxazol-5-yl)carbamate (300 mg, 1.04 mmol), 1-[4-(3-fluorophenyl)-1,3-thiazol-2-yl]piperazine (250 mg, 0.949 mmol) and diisopropylethylamine (0.330 ml, 1.90 mmol) in dimethylsulfoxide (3.2 ml) was stirred at 70° C. for 4 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate:hexane=1:1) and recrystallized from a mixed solvent of hexane and ethyl acetate to give the desired product (163 mg, 42.7%) as a solid.

$^1$H-NMR (CDCl$_3$) δ; 1.87 (3H, s), 2.19 (3H, s), 3.59-3.69 (8H, m), 6.84 (1H, s), 6.94-7.01 (1H, m), 7.07 (1H, br s), 7.29-7.37 (1H, m), 7.52-7.60 (2H, m).

Example 221

N-(3,4-Dimethylisoxazol-5-yl)-4-[4-(4-fluorophenyl)-1,3-thiazol-2-yl]piperazine-1-carboxamide A mixture of 2,2,2-trichloroethyl (3,4-dimethylisoxazol-5-yl)carbamate (240 mg, 0.834 mmol), 1-[4-(4-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 18 hours. Water was poured into the reaction solution, and the mixture was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give the desired product (153 mg, 50.2%) as a solid.

$^1$H-NMR (CDCl$_3$) δ; 1.89 (3H, s), 2.20 (3H, s), 3.62-3.69 (8H, m), 6.72 (1H, s), 6.75 (1H, s), 7.03-7.09 (2H, m), 7.77-7.82 (2H, m).

Example 222

N-[6-(Acetylamino)pyridin-3-yl]-4-[4-(2-fluorophenyl)-1,3-thiazol-2-yl]piperazine-1-carboxamide A mixture of 2,2,2-trichloroethyl [6-(acetylamino)pyridin-3-yl]carbamate (273 mg, 0.835 mmol), 1-[4-(2-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 12 hours. Water was poured into the reaction solution, and the mixture was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give the desired product (153 mg, 45.8%) as a solid.

$^1$H-NMR (DMSO-d$_6$) δ; 2.06 (3H, s), 3.54-3.66 (8H, m), 7.23-7.36 (4H, m), 7.78-7.82 (1H, m), 7.96-7.99 (1H, m), 8.05-8.11 (1H, m), 8.40-8.41 (1H, m), 8.77 (1H, s), 10.33 (1H, s).

Example 223

N-[6-(Acetylamino)pyridin-3-yl]-4-[4-(4-fluorophenyl)-1,3-thiazol-2-yl]piperazine-1-carboxamide A mixture of 2,2,2-trichloroethyl [6-(acetylamino)pyridin-3-yl]carbamate (273 mg, 0.835 mmol), 1-[4-(4-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 12 hours. Water was poured into the reaction solution, and the mixture was extracted with ethyl acetate. The extract was washed with water and dried over anhydrous magnesium sulfate, and the solvent was distilled off under reduced pressure. The residue was crystallized from a mixed solvent of hexane and tetrahydrofuran to give the desired product (110 mg, 32.9%) as a solid.

$^1$H-NMR (DMSO-d$_6$) δ; 2.04 (3H, s), 3.51-3.62 (8H, m), 7.18-7.24 (2H, m), 7.28 (1H, s), 7.76-7.80 (1H, m), 7.87-7.97 (3H, m), 8.38-8.39 (1H, m), 8.75 (1H, s), 10.31 (1H, s).

Example 224

4-(5-Ethyl-4-phenyl-1,3-thiazol-2-yl)-N-pyridin-3-ylpiperazine-1-carboxamide (1) 2-Bromo-1-phenylbutan-1-one To a solution of 1-phenylbutan-1-one (10.0 g, 67.5 mmol) in diethyl ether (200 ml) was slowly added dropwise bromine (10.8 g, 67.5 mmol), and the mixture was stirred at room temperature for 4 hours. The reaction solution was distilled off under reduced pressure to give the desired product (11.1 g, 72.3%) as an oil.

$^1$H-NMR (CDCl$_3$) δ; 1.09 (3H, t, J=7.5 Hz), 2.09-2.30 (2H, m), 5.07 (1H, dd, J=6.6, 7.8 Hz), 7.43-7.63 (3H, m), 8.00-8.04 (2H, m).

(2) 1-Ethyl-2-phenylprop-2-en-1-yl thiocyanate

A solution of 2-bromo-1-phenylbutan-1-one (5.00 g, 22.0 mmol) and potassium thiocyanate (2.14 g, 22.0 mmol) in ethanol (50 ml) was stirred at 80° C. for 2 hours. After cooling to room temperature, water (50 ml) was poured into the reaction solution, and the mixture was extracted with chloroform. The extract was washed with water and dried over anhydrous magnesium sulfate, and the solvent was distilled off under reduced pressure to give the desired product (4.16 g, 92.0%) as a solid.

$^1$H-NMR (CDCl$_3$) δ; 1.05 (3H, t, J=7.5 Hz), 2.13-2.35 (2H, m), 5.01 (1H, t, J=6.0 Hz), 7.50-7.56 (2H, m), 7.63-7.69 (1H, m), 7.91-7.94 (2H, m).

(3) 2-Bromo-5-ethyl-4-phenyl-1,3-thiazole

To a solution of 1-ethyl-2-phenylprop-2-en-1-yl thiocyanate (4.15 g, 20.2 mmol) in acetic acid (40 ml) was added a 25% hydrogen bromide/acetic acid (40 ml) solution, and the mixture was stirred at 130° C. for 2 hours. Water was poured into the reaction solution, and the mixture was extracted with chloroform. The extract was washed with water and dried over anhydrous magnesium sulfate, and the solvent was distilled off under reduced pressure. The residue was purified by silica gel column chromatography (hexane:ethyl acetate=9:1) to give the desired product (4.02 g, 74.2%) as an oil.

$^1$H-NMR (CDCl$_3$) δ; 1.31 (3H, t, J=7.8 Hz), 2.94 (2H, q, J=7.8 Hz), 7.32-7.48 (3H, m), 7.54-7.58 (2H, m).

(4) tert-Butyl 4-(5-ethyl-4-phenyl-1,3-thiazol-2-yl)piperazine-1-carboxylate A solution of 2-bromo-5-ethyl-4-phenyl-1,3-thiazole (4.00 g, 14.9 mmol), tert-butyl piperazine-1-carboxylate (8.33 g, 44.7 mmol) and potassium carbonate (2.06 g, 14.9 mmol) in dimethylformamide (50 ml) was stirred at 120° C. for 13 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give the desired product (2.35 g, 42.2%) as an oil.

$^1$H-NMR (CDCl$_3$) δ; 1.27 (3H, t, J=7.5 Hz), 1.48 (9H, s), 2.83 (2H, q, J=7.5 Hz), 3.44-3.47 (4H, m), 3.54-3.57 (4H, m), 7.28-7.32 (1H, m), 7.36-7.41 (2H, m), 7.55-7.58 (2H, m).

(5) 1-(5-Ethyl-4-phenyl-1,3-thiazol-2-yl)piperazine

To a solution of tert-butyl 4-(5-ethyl-4-phenyl-1,3-thiazol-2-yl)piperazine-1-carboxylate (2.35 g, 6.29 mmol) in ethyl acetate (100 ml) was added a 4N solution (50 ml) of hydrogen chloride in ethyl acetate, and the mixture was stirred at room temperature for 5 hours, and the solvent was distilled off under reduced pressure to yield the hydrochloride. The hydrochloride was dissolved in water. The solution was neutralized with 1N aqueous sodium hydroxide solution, and the mixture was extracted with chloroform. The extract was washed with water and dried over anhydrous magnesium sulfate, and the solvent was distilled under reduced pressure to give the desired product (1.73 g, quant.) as a solid.

$^1$H-NMR (CDCl$_3$) δ; 1.26 (3H, t, J=7.5 Hz), 2.82 (2H, q, J=7.5 Hz), 2.97-3.00 (4H, m), 3.44-3.47 (4H, m), 7.27-7.31 (1H, m), 7.34-7.40 (2H, m), 7.55-7.58 (2H, m).

(6) 4-(5-Ethyl-4-phenyl-1,3-thiazol-2-yl)-N-pyridin-3-ylpiperazine-1-carboxamide A mixture of 2,2,2-trichloroethyl pyridin-3-ylcarbamate (217 mg, 0.805 mmol), 1-(5-ethyl-4-phenyl-1,3-thiazol-2-yl)piperazine (200 mg, 0.732 mmol) and diisopropylethylamine (0.255 ml, 1.46 mmol) in dimethylsulfoxide (2.5 ml) was stirred at 70° C. for 15 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give the desired product (140 mg, 48.5%) as a solid.

$^1$H-NMR (CDCl$_3$) δ; 1.28 (3H, t, J=7.5 Hz), 2.84 (2H, q, J=7.5 Hz), 3.56-3.59 (4H, m), 3.65-3.69 (4H, m), 6.69 (1H, br s), 7.23-7.33 (2H, m), 7.37-7.42 (2H, m), 7.55-7.58 (2H, m), 7.97-8.00 (1H, m), 8.29-8.30 (1H, m), 8.46 (1H, br s).

Example 225

N-(3,4-Dimethylisoxazol-5-yl)-4-(5-ethyl-4-phenyl-1,3-thiazol-2-yl)piperazine-1-carboxamide A mixture of 2,2,2-trichloroethyl (3,4-dimethylisoxazol-5-yl)carbamate (231 mg, 0.805 mmol), 1-(5-ethyl-4-phenyl-1,3-thiazol-2-yl)piperazine (200 mg, 0.732 mmol) and diisopropylethylamine (0.255 ml, 1.46 mmol) in dimethylsulfoxide (2.5 ml) was stirred at 70° C. for 15 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate:hexane=1:1) and recrystallized from a mixed solvent of hexane and tetrahydrofuran to give the desired product (106 mg, 35.3%) as a solid.

$^1$H-NMR (CDCl$_3$) δ; 1.28 (3H, t, J=7.5 Hz), 1.88 (3H, s), 2.20 (3H, s), 2.84 (2H, q, J=7.5 Hz), 3.55-3.57 (4H, m), 3.62-3.65 (4H, m), 6.75 (1H, br s), 7.28-7.33 (1H, m), 7.37-7.42 (2H, m), 7.54-7.57 (2H, m).

Example 226

N-[6-(Acetylamino)pyridin-3-yl]-4-(5-ethyl-4-phenyl-1,3-thiazol-2-yl)piperazine-1-carboxamide A mixture of 2,2,2-trichloroethyl [6-(acetylamino)pyridin-3-yl]carbamate (263 mg, 0.805 mmol), 1-(5-ethyl-4-phenyl-1,3-thiazol-2-yl)piperazine (200 mg, 0.732 mmol) and diisopropylethylamine (0.255 ml, 1.46 mmol) in dimethylsulfoxide (2.5 ml) was stirred at 70° C. for 15 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give the desired product (90.1 mg, 27.3%) as a solid.

$^1$H-NMR (CDCl$_3$+DMSO-d$_6$) δ; 1.27 (3H, t, J=7.5 Hz), 2.10 (3H, s), 2.83 (2H, q, J=7.5 Hz), 3.47-3.50 (4H, m), 3.65-3.67 (4H, m), 7.26-7.32 (1H, m), 7.36-7.41 (2H, m), 7.53-7.56 (2H, m), 7.75-7.79 (1H, m), 7.98-8.01 (1H, m), 8.42-8.43 (1H, m), 8.65 (1H, s), 10.20 (1H, s).

Example 227

4-[4-(2-Fluorophenyl)-1,3-thiazol-2-yl]-N-pyridazin-3-ylpiperazine-1-carboxamide A mixture of 2,2,2-trichloroethyl pyridazin-3-ylcarbamate (226 mg, 0.835 mmol), 4-[4-(2-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 3 days. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give the desired product (104 mg, 35.6%) as a solid.

$^1$H-NMR (DMSO-d$_6$) δ; 3.55-3.57 (4H, m), 3.68-3.70 (4H, m), 7.23-7.34 (4H, m), 7.56-7.61 (1H, m), 8.00-8.11 (2H, m), 8.85-8.86 (1H, m), 10.04 (1H, s).

Example 228

4-[4-(3-Fluorophenyl)-1,3-thiazol-2-yl]-N-pyridazin-3-ylpiperazine-1-carboxamide A mixture of 2,2,2-trichloroethyl pyridazin-3-ylcarbamate (226 mg, 0.835 mmol), 4-[4-(3-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 3 days. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give the desired product (92.7 ml, 28.1%) as a solid. mp 176-177° C.

$^1$H-NMR (DMSO-d$_6$) δ; 3.53-3.56 (4H, m), 3.68-3.71 (4H, m), 7.09-7.15 (1H, m), 7.40-7.47 (1H, m), 7.45 (1H, s), 7.57-7.61 (1H, m), 7.65-7.74 (2H, m), 8.00-8.03 (1H, m), 8.85-8.86 (1H, m), 10.04 (1H, s).

Example 229

4-[4-(3-Fluorophenyl)-1,3-thiazol-2-yl]-N-pyrazin-2-ylpiperazine-1-carboxamide

A mixture of 2,2,2-trichloroethyl pyrazin-2-ylcabamate (226 mg, 0.835 mmol), 4-[4-(3-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 3 days. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give the desired product (152 mg, 51.9%) as a solid. mp 158-159° C.

$^1$H-NMR (CDCl$_3$) δ; 3.65-3.76 (8H, m), 6.86 (1H, s), 6.96-7.01 (1H, m), 7.15 (1H, br s), 7.30-7.37 (1H, m), 7.54-7.61 (2H, m), 8.17-8.19 (1H, m), 8.27-8.28 (1H, m), 9.37 (1H, s).

Example 230

4-[4-(4-Fluorophenyl)-1,3-thiazol-2-yl]-N-pyrazin-2-ylpiperazine-1-carboxamide

A mixture if 2,2,2-trichloroethyl pyrazin-2-ylcarbamate (226 mg, 0.835 mmol), 4-[4-(4-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 3 days. Water was poured into the reaction solution, and the mixture was extracted with ethyl acetate. The extract was wash washed with water and dried over anhydrous magnesium sulfate, and the solvent was distilled off under reduced pressure. The residue was purified silica gel column chromatography (ethyl acetate) and recrystallized from a mixed solvent of hexane and tetrahydrofuran to give the desired product (99.7 mg, 34.0%) as a solid.

$^1$H-NMR (CDCl$_3$) δ; 3.66-3.75 (8H, m), 6.76 (1H, s), 7.04-7.10 (2H, m), 7.15 (1H, br s), 7.78-7.83 (2H, m), 8.17-8.19 (1H, m), 8.27-8.28 (1H, m), 9.37 (1H, s).

Example 231

4-[4-(2-Fluorophenyl)-1,3-thiazol-2-yl]-N-pyrazin-2-ylpiperazine-1-carboxamide

A mixture of 2,2,2-trichloroethyl pyrazin-2-ylcarbamate (226 mg, 0.835 mmol), 4-[4-(2-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 3.5 days. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give the desired product (16.0 mg, 5.5%) as a solid.

$^1$H-NMR (CDCl$_3$) δ; 3.69-3.74 (8H, m), 7.14-7.26 (5H, m), 8.14-8.18 (2H, m), 8.27 (1H, br s), 9.38 (1H, br s).

Example 232

4-[4-(4-Fluorophenyl)-1,3-thiazol-2-yl]-N-pyridazin-3-ylpiperazine-1-carboxamide A mixture of 2,2,2-trichloroethyl pyridazin-3-ylcarbamate (226 mg, 0.835 mmol), 4-[4-(4-fluorophenyl)-1,3-thiazol-2-yl]piperazine (200 mg, 0.760 mmol) and diisopropylethylamine (0.265 ml, 1.52 mmol) in dimethylsulfoxide (2.5 ml) was stirred at 70° C. for 3 days. Water was poured into the reaction solution, and the mixture was extracted with ethyl acetate. The extract was washed with water and dried over anhydrous magnesium sulfate, and the solvent was distilled off under reduced pressure. The residue was purified by high performance liquid chromatography (YMC HPLC column; Solution A: 0.1% trifluoroacetic acid solution in acetonitrile; Solution B: 0.1% aqueous trifluoroacetic acid solution; eluted with 10% Solution A to 100% Solution A), and a saturated aqueous sodium hydrogen carbonate solution was added. The mixture was extracted with ethyl acetate. The extract was washed with water and dried over magnesium sulfate anhydrous, and the solvent was distilled off under reduced pressure. The residue was recrystallized from a mixed solvent of hexane and tetrahydrofuran to give the desired product (32.3 mg, 11.1%) as a solid.

$^1$H-NMR (DMSO-d$_6$) δ; 3.52-3.55 (4H, m), 3.67-3.71 (4H, m), 7.19-7.25 (2H, m), 7.29 (1H, s), 7.56-7.61 (1H, m), 7.88-

7.93 (2H, m), 7.99-8.02 (1H, m), 8.85-8.86 (1H, m), 10.03 (1H, s).

The following Table 10 shows the structural formulae of the compounds obtained in Examples 191 to 232.

TABLE 10

TABLE 10-continued
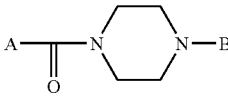
| Example No. | A | B |
|---|---|---|
| 198 | 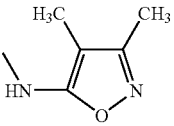 | 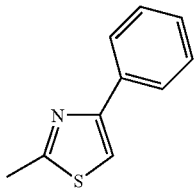 |
| 199 | 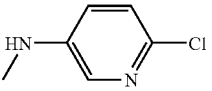 | 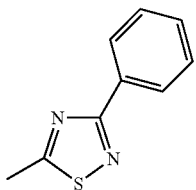 |
| 200 | 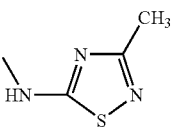 | 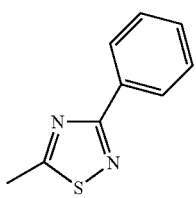 |
| 201 | 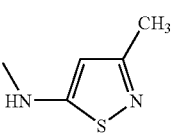 | 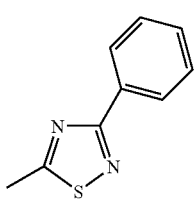 |
| 202 | 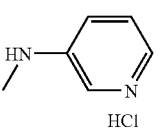 HCl | 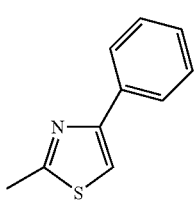 |
| 203 | 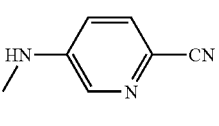 | 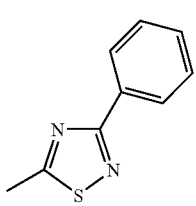 |
| 204 | 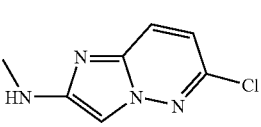 | 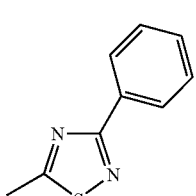 |

TABLE 10-continued
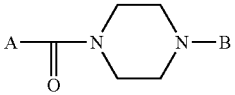
| Example No. | A | B |
|---|---|---|
| 205 | 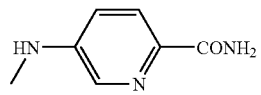 | 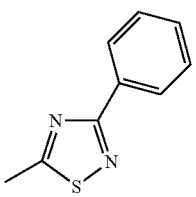 |
| 206 | 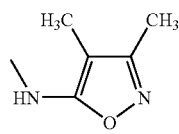 | 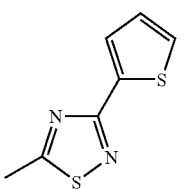 |
| 207 | 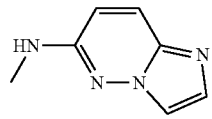 | 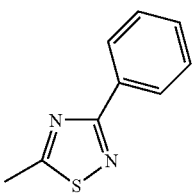 |
| 208 | 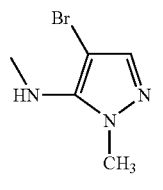 | 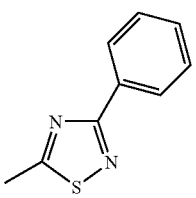 |
| 209 | 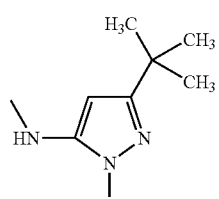 | 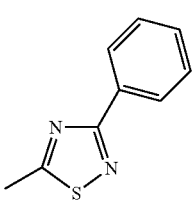 |
| 210 | 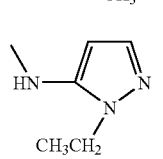 | 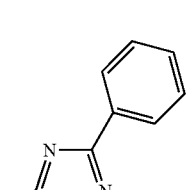 |
| 211 | 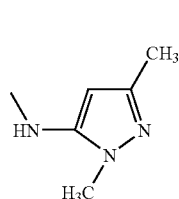 | 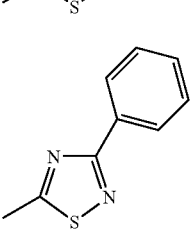 |

TABLE 10-continued
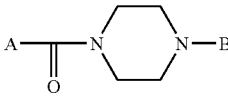
| Example No. | A | B |
|---|---|---|
| 212 | 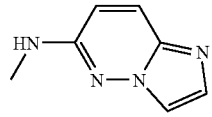 | 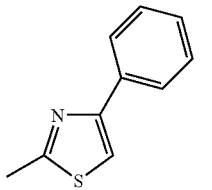 |
| 213 | 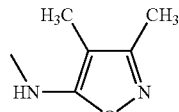 | 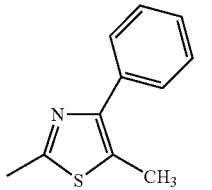 |
| 214 | 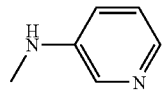 | 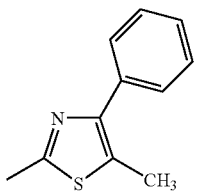 |
| 215 | 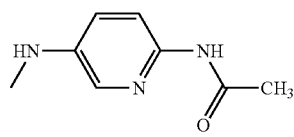 | 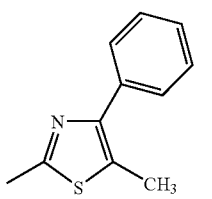 |
| 216 | 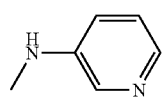 | 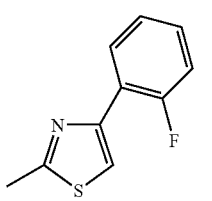 |
| 217 | 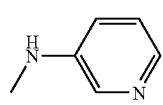 | 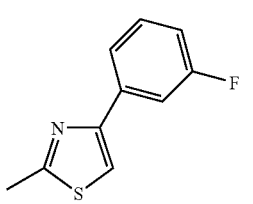 |
| 218 | 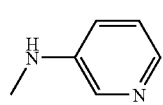 | 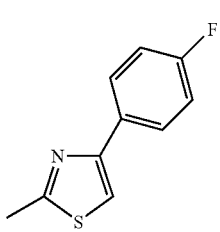 |

TABLE 10-continued

A—C(=O)—N(piperazine)N—B

| Example No. | A | B |
|---|---|---|
| 219 | 5-(methylamino)-3,4-dimethylisoxazole | 4-(2-fluorophenyl)-2-methylthiazole |
| 220 | 5-(methylamino)-3,4-dimethylisoxazole | 4-(3-fluorophenyl)-2-methylthiazole |
| 221 | 5-(methylamino)-3,4-dimethylisoxazole | 4-(4-fluorophenyl)-2-methylthiazole |
| 222 | N-[5-(methylamino)pyridin-2-yl]acetamide | 4-(2-fluorophenyl)-2-methylthiazole |
| 223 | N-[5-(methylamino)pyridin-2-yl]acetamide | 4-(4-fluorophenyl)-2-methylthiazole |
| 224 | 3-(methylamino)pyridine | 5-ethyl-2-methyl-4-phenylthiazole |
| 225 | 5-(methylamino)-3,4-dimethylisoxazole | 5-ethyl-2-methyl-4-phenylthiazole |

TABLE 10-continued

A—C(=O)—N(piperazine)N—B

| Example No. | A | B |
|---|---|---|
| 226 | 5-(methylamino)-2-(acetylamino)pyridine (HN(CH₃)-pyridine-NH-C(O)CH₃) | 5-ethyl-2-methyl-4-phenylthiazole |
| 227 | 3-(methylamino)pyridazine | 4-(2-fluorophenyl)-2-methylthiazole |
| 228 | 3-(methylamino)pyridazine | 4-(3-fluorophenyl)-2-methylthiazole |
| 229 | 3-(methylamino)pyrazine | 4-(3-fluorophenyl)-2-methylthiazole |
| 230 | 3-(methylamino)pyrazine | 4-(4-fluorophenyl)-2-methylthiazole |
| 231 | 5-(methylamino)pyrazine | 4-(2-fluorophenyl)-2-methylthiazole |

TABLE 10-continued

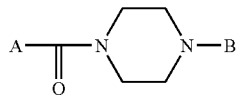

| Example No. | A | B |
|---|---|---|
| 232 | 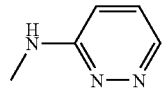 | 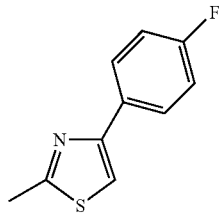 |

Example 233

4-[4-(3-Fluorophenyl)-1,3-thiazol-2-yl]-N-pyridin-3-ylpiperidine-1-carboxamide dihydrochloride (1) tert-Butyl 4-[4-(3-fluorophenyl)-1,3-thiazol-2-yl]piperidine-1-carboxylate A solution of 2-bromo-1-(3-fluorophenyl)ethanone (1.95 g, 8.98 mmol), tert-butyl 4-(aminocarbonothioyl)piperidine-1-carboxylate (2.00 g, 8.18 mmol) and potassium carbonate (2.26 g, 16.4 mmol) in dimethylformamide (60 ml) was stirred at 110° C. for 1.5 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give the desired product (2.89 g, 97.0%) as an oil.

$^1$H-NMR (CDCl$_3$) δ; 1.48 (9H, s), 1.72-1.85 (2H, m), 2.12-2.17 (2H, m), 2.88-2.96 (2H, m), 3.17-3.24 (1H, m), 4.19-4.23 (2H, m), 6.98-7.04 (1H, m), 7.33-7.40 (1H, m), 7.38 (1H, s), 7.58-7.66 (2H, m).

(2) 1-[4-(3-Fluorophenyl)-1,3-thiazol-2-yl]piperidine dihydrochloride

To a solution of tert-butyl 4-[4-(3-fluorophenyl)-1,3-thiazol-2-yl]piperidine-1-carboxylate (2.89 g, 7.95 mmol) in ethyl acetate (200 ml) was added a 4N solution (50 ml) of hydrogen chloride in ethyl acetate, and the mixture was stirred at room temperature for 30 hours. The solvent was distilled off under reduced pressure to give 1.86 g (70.0%) of the desired product as a solid.

(3) 1-[4-(3-Fluorophenyl)-1,3-thiazol-2-yl]piperidine

1-[4-(3-Fluorophenyl)-1,3-thiazol-2-yl]piperidine dihydrochloride (1.00 g, 2.99 mmol) was dissolved in water. The solution was neutralized with 1N aqueous sodium hydroxide solution, and the mixture was extracted with chloroform. The extract was washed with water and dried over magnesium sulfate anhydrous, and the solvent distilled off under reduced pressure to give the desired product (780 mg, 99.4%) as an oil.

$^1$H-NMR (CDCl$_3$) δ; 1.67-1.80 (2H, m), 2.13-2.18 (2H, m), 2.74-2.83 (2H, m), 3.18-3.23 (3H, m), 7.00-7.01 (1H, m), 7.33-7.38 (1H, m), 7.38 (1H, s), 7.59-7.66 (2H, m).

(4) 4-[4-(3-Fluorophenyl)-1,3-thiazol-2-yl]-N-pyridin-3-ylpiperidine-1-carboxamide A mixture of 2,2,2-trichloroethyl pyridin-3-ylcarbamate (226 mg, 0.839 mmol), 1-[4-(3-fluorophenyl)-1,3-thiazol-2-yl]piperazine (200 mg, 0.762 mmol) and diisopropylethylamine (0.266 ml, 1.52 mmol) in dimethylsulfoxide (2.5 ml) was stirred at 70° C. for 3 hours. Water was poured into the reaction solution, and the mixture was extracted with ethyl acetate. The extract was washed with water and dried over magnesium sulfate anhydrous, and the solvent distilled off under reduced pressure. The residue was purified by silica gel column chromatography (ethyl acetate) to give the desired product (280 mg, 96.1%) as an oil.

$^1$H-NMR (CDCl$_3$) δ; 1.82-2.03 (2H, m), 2.24-2.30 (2H, m), 3.09-3.37 (3H, m), 4.18-4.25 (2H, m), 6.66 (1H, br s), 6.99-7.07 (1H, m), 7.22-7.43 (3H, m), 7.59-7.67 (2H, m), 7.99-8.03 (1H, m), 8.27-8.29 (1H, m), 8.45-8.46 (1H, m).

(5) 4-[4-(3-Fluorophenyl)-1,3-thiazol-2-yl]-N-pyridin-3-ylpiperidine-1-carboxamide dihydrochloride To a solution of 4-[4-(3-fluorophenyl)-1,3-thiazol-2-yl]-N-pyridin-3-ylpiperidine-1-carboxamide (280 mg, 0.732 mmol) in tetrahydrofuran (20 ml) was added a 4N solution (5 ml) of hydrogen chloride in ethyl acetate, and the mixture was stirred at room temperature for 1 hour. The reaction solution was distilled off under reduced pressure, and the residue was recrystallized from a mixed solvent of methanol and diethyl ether to give the desired product (179 mg, 49.8%) as a solid.

$^1$H-NMR (DMSO-d$_6$) δ; 1.67-1.78 (2H, m), 2.14-2.18 (2H, m), 3.06-3.14 (2H, m), 3.34-3.42 (1H, m), 4.32-4.36 (2H, m), 5.45 (2H, br s), 7.14-7.20 (1H, m), 7.44-7.52 (1H, m), 7.74-7.82 (2H, m), 7.94-7.99 (1H, m), 8.15 (1H, s), 8.48-8.50 (1H, m), 8.66-8.69 (1H, m), 9.19 (1H, s), 9.99 (1H, s).

Example 234

4-[4-(4-Fluorophenyl)-1,3-thiazol-2-yl]-N-pyridin-3-ylpiperidine-1-carboxamide (1) tert-Butyl 4-[4-(4-fluorophenyl)-1,3-thiazol-2-yl]piperidine-1-carboxylate A solution of 4-bromo-1-(3-fluorophenyl)ethanone (1.95 g, 9.00 mmol), tert-butyl 4-(aminocarbonothioyl)piperidine-1-carboxylate (2.0 g, 8.18 mmol) and potassium carbonate (2.26 g, 16.4 mmol) in dimethylformamide (60 ml) was stirred at 110° C. for 1.5 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=1:1) to give the desired product (2.49 g, 83.7%) as an oil.

$^1$H-NMR (CDCl$_3$) δ; 1.48 (9H, s), 1.71-1.85 (2H, m), 2.12-2.16 (2H, m), 2.87-2.96 (2H, m), 3.15-3.25 (1H, m), 4.19-4.23 (2H, m), 7.06-7.12 (2H, m), 7.29 (1H, s), 7.83-7.88 (2H, m).

(2) 1-[4-(4-Fluorophenyl)-1,3-thiazol-2-yl]piperidine dihydrochloride

To a solution of tert-butyl 4-[4-(4-fluorophenyl)-1,3-thiazol-2-yl]piperidine-1-carboxylate (2.49 g, 6.85 mmol) in ethyl acetate (100 ml) was added a 4N solution (100 ml) of hydrogen chloride in ethyl acetate, and the mixture was stirred at room temperature for 12 hours. The solvent was distilled off under reduced pressure to give 1.88 g (82.0%) of the desired product as a solid.

(3) 1-[4-(4-fluorophenyl)-1,3-thiazol-2-yl]piperidine

1-[4-(4-Fluorophenyl)-1,3-thiazol-2-yl]piperidine hydrochloride (1.00 g, 2.99 mmol) was dissolved in water. The solution was neutralized with 1N aqueous sodium hydroxide solution, and the mixture was extracted with chloroform. The extract was washed with water and dried over magnesium sulfate anhydrous, and the solvent was distilled off under reduced pressure to give the desired product (772 mg, 98.4 mmol) as an oil.

$^1$H-NMR (CDCl$_3$) δ; 1.70-1.84 (2H, m), 2.14-2.18 (2H, m), 2.74-2.83 (2H, m), 3.13-3.23 (3H, m), 7.05-7.13 (2H, m), 7.82-7.89 (2H, m).

(4) 4-[4-(4-Fluorophenyl)-1,3-thiazol-2-yl]-N-pyridin-3-ylpiperidine-1-carboxamide A mixture of 2,2,2-trichloroethyl pyridin-3-ylcarbamate (226 mg, 0.839 mmol), 1-[4-(4-fluorophenyl)-1,3-thiazol-2-yl]piperazine (200 mg, 0.762 mmol) and diisopropylethylamine (0.266 ml, 1.52 mmol) in dimethylsulfoxide (2.5 ml) was stirred at 70° C. for 14 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give the desired product (170 mg, 58.2%) as a solid.

$^1$H-NMR (CDCl$_3$) δ; 1.86-2.00 (2H, m), 2.00-2.24 (2H, m), 2.24-2.28 (2H, m), 3.11-3.21 (2H, m), 3.27-3.35 (1H, m), 4.22-4.26 (2H, m), 6.88 (1H, br s), 7.07-7.13 (2H, m), 7.28-7.30 (1H, m), 7.31 (1H, s), 7.84-7.88 (2H, m), 8.10-8.13 (1H, m), 8.26-8.27 (1H, m), 8.56-8.57 (1H, m).

Example 235

N-(3,4-Dimethylisoxazol-5-yl)-4-[4-(3-fluorophenyl)-1,3-thiazol-2-yl]piperidine-1-carboxamide A mixture of 2,2,2-trichloroethyl (3,4-dimethylisoxazol-5-yl)carbamate (241 mg, 0.839 mmol), 1-[4-(3-fluorophenyl)-1,3-thiazol-2-yl]piperidine (200 mg, 0.762 mmol) and diisopropylethylamine (0.266 ml, 1.52 mmol) in dimethylsulfoxide (2.5 ml) was stirred at 70° C. for 3.5 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate:hexane=1:1) and recrystallized from a mixed solvent of hexane and ethyl acetate to give the desired product (127 mg, 41.5%) as a solid.

$^1$H-NMR (CDCl$_3$) δ; 1.85-1.98 (2H, m), 1.89 (3H, s), 2.20 (3H, s), 2.22-2.28 (2H, m), 3.01-3.19 (2H, m), 3.25-3.35 (1H, m), 4.12-4.17 (2H, m), 6.69 (1H, br s), 6.99-7.06 (1H, m), 7.34-7.39 (1H, m), 7.41 (1H, s), 7.59-7.67 (2H, m).

Example 236

N-(3,4-Dimethylisoxazol-5-yl)-4-[4-(4-fluorophenyl)-1,3-thiazol-2-yl]piperidine-1-carboxamide A mixture of 2,2,2-trichloroethyl (3,4-dimethylisoxazol-5-yl)carbamate (241 mg, 0.839 mmol), 1-[4-(4-fluorophenyl)-1,3-thiazol-2-yl]piperidine (200 mg, 0.762 mmol) and diisopropylethylamine (0.266 ml, 1.52 mmol) in dimethylsulfoxide (2.5 ml) was stirred at 70° C. for 14 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate:hexane=4:1) and recrystallized from a mixed solvent of hexane and ethyl acetate to give the desired product (136 mg, 44.4%) as a solid. mp 170-171° C.

$^1$H-NMR (CDCl$_3$) δ; 1.85-1.98 (2H, m), 1.89 (3H, s), 2.20 (3H, s), 2.22-2.27 (2H, m), 3.09-3.19 (2H, m), 3.24-3.33 (1H, m), 4.12-4.16 (2H, m), 6.66 (1H, br s), 7.07-7.13 (2H, m), 7.31 (1H, s), 7.84-7.88 (2H, m).

Example 237

N-[6-(Acetylamino)pyridin-3-yl]-4-[4-(3-fluorophenyl)-1,3-thiazol-2-yl]piperidine-1-carboxamide A mixture of 2,2,2-trichloroethyl [6-(acetylamino)pyridin-3-yl]carbamate (274 mg, 0.839 mmol), 4-[4-(3-fluorophenyl)-1,3-thiazol-2-yl]piperidine (200 mg, 0.762 mmol) and diisopropylethylamine (0.266 ml, 1.52 mmol) in dimethylsulfoxide (2.5 ml) was stirred at 70° C. for 12 hours. Water was poured into the reaction solution, and the mixture was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give the desired product (193 mg, 57.5%) as a solid.

$^1$H-NMR (DMSO-d$_6$) δ; 1.64-1.76 (2H, m), 2.06 (3H, s), 2.06-2.15 (2H, m), 2.98-3.06 (2H, m), 4.20-4.24 (2H, m), 7.14-7.20 (1H, m), 7.44-7.52 (1H, m), 7.74-7.82 (3H, m), 7.94-7.97 (1H, m), 8.13 (1H, s), 8.41-8.42 (1H, m), 8.65 (1H, s), 10.32 (1H, s).

Example 238

N-[6-(Acetylamino)pyridin-3-yl]-4-[4-(4-fluorophenyl)-1,3-thiazol-2-yl]piperidine-1-carboxamide A mixture of 2,2,2-trifluoroethyl [6-(acetylamino)pyridin-3-yl]carbamate (274 mg, 0.839 mmol), 4-[4-(4-fluorophenyl)-1,3-thiazol-2-yl]piperidine (200 mg, 0.762 mmol) and diisopropylethylamine (0.266 ml, 1.52 mmol) in dimethylsulfoxide (2.5 ml) was stirred at 70° C. for 12 hours. Water was poured into the reaction solution, and the mixture was extracted with ethyl acetate. The extract was washed with water and dried over anhydrous magnesium sulfate, and the solvent was distilled off under reduced pressure. The residue was recrystallized from a mixed solvent of hexane and tetrahydrofuran to give the desired product (193 mg, 57.6%) as a solid.

$^1$H-NMR (CH$_3$Cl+DMSO-d$_6$) δ; 1.82-1.94 (2H, m), 2.17 (3H, s), 2.17-2.24 (2H, m), 3.02-3.10 (2H, m), 3.25-3.33 (1H, m), 4.31-4.35 (2H, m), 7.07-7.14 (2H, m), 7.38 (1H, s), 7.77-7.81 (1H, m), 7.86-7.91 (2H, m), 8.05-8.08 (1H, m), 8.17 (1H, s), 8.47-8.48 (1H, m), 9.41 (1H, br s).

Example 239

4-[4-(3-Fluorophenyl)-1,3-thiazol-2-yl]-N-pyridazin-3-ylpiperidine-1-carboxamide A mixture of 2,2,2-trichloroethyl pyridazin-3-ylcarbamate (250 mg, 0.922 mmol), 4-[4-(3-fluorophenyl)-1,3-thiazol-2-yl]piperidine (220 mg, 0.839 mmol) and diisopropylethylamine (0.292 ml, 1.68 mmol) in dimethylsulfoxide (2.8 ml) was stirred at 70° C. for 6 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give the desired product (141 mg, 43.7%) as a solid.

$^1$H-NMR (CDCl$_3$) δ; 1.89-1.99 (2H, m), 2.26-2.30 (2H, m), 3.16-3.24 (2H, m), 3.28-3.38 (1H, m), 4.26-4.31 (2H, m), 6.99-7.05 (1H, m), 7.34-7.45 (2H, m), 7.41 (1H, s), 7.59-7.67 (2H, m), 8.05 (1H, br s), 8.29-8.32 (1H, m), 8.84-8.85 (1H, m).

Example 240

4-[4-(4-Fluorophenyl)-1,3-thiazol-2-yl]-N-pyridazin-3-ylpiperidine-1-carboxamide A mixture of 2,2,2-trichloroethyl pyridazin-3-ylcarbamate (170 mg, 0.629 mmol), 4-[4-(4-fluorophenyl)-1,3-thiazol-2-yl]piperidine (150 mg, 0.572 mmol) and diisopropylethylamine (0.199 ml, 1.14 mmol) in dimethylsulfoxide (2.0 ml) was stirred at 70° C. for 6 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give the desired product (127 mg, 58.0%) as a solid.

$^1$H-NMR (CDCl$_3$) δ; 1.86-1.99 (2H, m), 2.26-2.29 (2H, m), 3.15-3.23 (2H, m), 3.28-3.36 (1H, m), 4.27-4.31 (2H, m), 7.08-7.14 (2H, m), 7.32 (1H, s), 7.41-7.45 (1H, m), 7.83-7.90 (2H, m), 8.08 (1H, br s), 8.29-8.32 (1H, d, J=9.0 Hz), 8.84-8.85 (1H, m).

Example 241

4-[4-(3-Fluorophenyl)-1,3-thiazol-2-yl]-N-pyrazin-2-ylpiperidine-1-carboxamide

A mixture of 2,2,2-trichloroethyl pyrazin-2-ylcarbamate (227 mg, 0.839 mmol), 4-[4-(3-fluorophenyl)-1,3-thiazol-2-yl]piperidine (200 mg, 0.762 mmol) and diisopropylethylamine (0.266 ml, 1.52 mmol) in dimethylsulfoxide (2.5 ml) was stirred at 70° C. for 6 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give the desired product (207 mg, 70.9%) as a solid.

$^1$H-NMR (CDCl$_3$) δ; 1.87-2.04 (2H, m), 2.25-2.31 (2H, m), 3.15-3.24 (2H, m), 3.29-3.38 (1H, m), 4.21-4.25 (2H, m), 6.99-7.05 (1H, m), 7.19 (1H, br s), 7.34-7.41 (2H, m), 7.59-7.67 (2H, m), 8.16-8.17 (1H, m), 8.25-8.26 (1H, m), 9.38-9.39 (1H, m).

Example 242

4-[4-(4-Fluorophenyl)-1,3-thiazol-2-yl]-N-pyrazin-2-ylpiperidine-1-carboxamide

A mixture of 2,2,2-trichloroethyl pyrazin-2-ylcarbamate (227 mg, 0.839 mmol), 4-[4-(4-fluorophenyl)-1,3-thiazol-2-yl]piperidine (200 mg, 0.762 mmol) and diisopropylethylamine (0.266 ml, 1.52 mmol) in dimethylsulfoxide (2.5 ml) was stirred at 70° C. for 6 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and ethyl acetate to give the desired product (202 mg, 69.2%) as a solid.

$^1$H-NMR (CDCl$_3$) δ; 1.87-2.01 (2H, m), 2.25-2.30 (2H, m), 3.14-3.24 (2H, m), 3.27-3.36 (1H, m), 4.21-4.25 (2H, m), 7.07-7.17 (3H, m), 7.32 (1H, s), 7.83-7.89 (2H, m), 8.16-8.17 (1H, m), 8.25-8.26 (1H, m), 9.38-9.39 (1H, m).

Example 243

4-[4-(2-Fluorophenyl)-1,3-thiazol-2-yl]-N-pyridine-3-ylpiperidine-1-carboxamide (1) tert-Butyl 4-[4-(2-fluorophenyl)-1,3-thiazol-2-yl]piperidine-1-carboxylate A solution of 2-bromo-1-(2-fluorophenyl)ethanone (977 mg, 4.50 mmol), tert-butyl 4-(aminocarbonothioyl)piperidine-1-carboxylate (1.0 g, 4.09 mmol) and potassium carbonate (1.13 g, 8.18 mmol) in dimethylformamide (30 ml) was stirred at 110° C. for 1 hour. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (hexane:ethyl acetate=9:1) to give the desired product (391 mg, 26.3%) as an oil.

$^1$H-NMR (CDCl$_3$) δ; 1.48 (9H, s), 1.73-1.86 (2H, m), 2.13-2.17 (2H, m), 2.89-2.97 (2H, m), 3.17-3.25 (1H, m), 4.16-4.19 (2H, m), 7.10-7.32 (3H, m), 7.64-7.65 (1H, m), 8.17-8.23 (1H, m).

(2) 4-[4-(2-Fluorophenyl)-1,3-thiazol-2-yl]piperidine

To a solution of tert-butyl 4-[4-(2-fluorophenyl)-1,3-thiazol-2-yl]piperidine-1-carboxylate (390 mg, 1.07 mmol) in ethyl acetate (10 ml) was added a 4N solution (10 ml) of hydrogen chloride in ethyl acetate, and the mixture was stirred at room temperature for 5 hours. The solvent was distilled off under reduced pressure, and the residue was dissolved in water. The solution was neutralized with 1N aqueous sodium hydroxide solution, and the mixture was extracted with chloroform. The extract was washed with water and dried over anhydrous magnesium sulfate, and the solvent was distilled off under reduced pressure to give the desired product (181 mg, 64.3%) as a solid.

$^1$H-NMR (CDCl$_3$) δ; 1.71-1.85 (2H, m), 2.15-2.19 (2H, m), 2.75-2.84 (2H, m), 3.14-3.24 (3H, m), 7.10-7.32 (3H, m), 7.63-7.64 (1H, m), 8.18-8.24 (1H, m).

(3) 4-[4-(2-Fluorophenyl)-1,3-thiazol-2-yl]-N-pyridin-3-ylpiperidine-1-carboxamide A mixture of 2,2,2-trichloroethyl pyridin-3-ylcarbamate (102 mg, 0.377 mmol), 4-[4-(2-fluorophenyl)-1,3-thiazol-2-yl]piperidine (90 mg, 0.343 mmol) and diisopropylethylamine (0.120 ml, 0.686 mmol) in dimethylsulfoxide (1.5 ml) was stirred at 70° C. for 6 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized form a mixed solvent of hexane and ethyl acetate to give the desired product (75.7 mg, 57.7%) as a solid.

$^1$H-NMR (CDCl$_3$) δ; 1.88-2.00 (2H, m), 2.26-2.30 (2H, m), 3.12-3.21 (2H, m), 3.29-3.36 (1H, m), 4.18-4.22 (2H, m), 6.52 (1H, s), 7.11-7.31 (4H, m), 7.66-7.67 (1H, m), 7.99-8.02 (1H, m), 8.18-8.23 (1H, m), 8.28-8.29 (1H, m), 8.44-8.45 (1H, m).

Example 244

N-(3,4-Dimethylisoxazol-5-yl)-4-[4-(2-fluorophenyl)-1,3-thiazol-2-yl]piperidine-1-carboxamide A mixture of 2,2,2-trichloroethyl (3,4-dimethylisoxazol-5-yl)carbamate (109 mg, 0.377 mmol), 4-[4-(2-fluorophenyl)-1,3-thiazol-2-yl]piperidine (90 mg, 0.343 mmol) and diisopropylethylamine (0.120 ml, 0.686 mmol) in dimethylsulfoxide (1.5 ml) was stirred at 70° C. for 6 hours. Water was poured into the reaction solution, and the mixture was extracted with ethyl acetate. The extract was washed with water and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give the desired product (42.0 mg, 30.6%) as a solid.

$^1$H-NMR (CDCl$_3$) δ; 1.90 (3H, s), 1.90-2.00 (2H, m), 2.20 (3H, s), 2.20-2.28 (2H, m), 3.11-3.21 (2H, m), 3.27-3.35 (1H, m), 4.11-4.16 (2H, m), 6.57 (1H, s), 7.11-7.31 (3H, m), 7.66-7.67 (1H, m), 8.17-8.23 (1H, m).

The following Table 11 shows the structural formulae of the compounds obtained in Examples 233 to 244.

TABLE 11

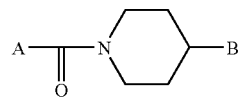

| Example No. | A | B |
|---|---|---|
| 233 | 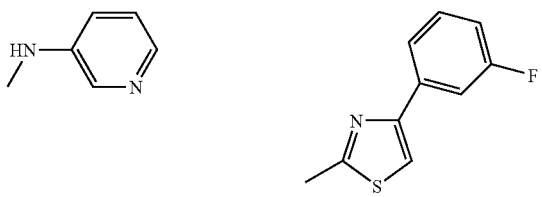 | |
| 234 | 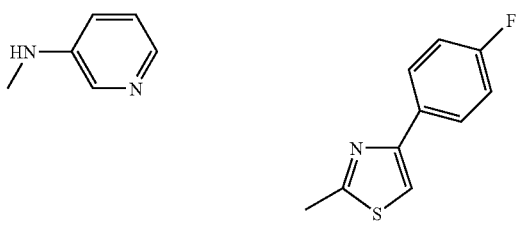 | |
| 235 | 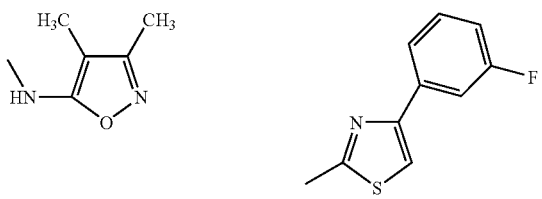 | |

TABLE 11-continued
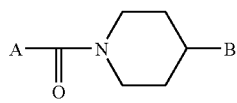
| Example No. | A | B |
| --- | --- | --- |
| 236 | | |
| 237 | | |
| 238 | | |
| 239 | | |
| 240 | | |
| 241 | | |

TABLE 11-continued

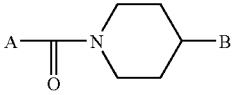

| Example No. | A | B |
|---|---|---|
| 242 | 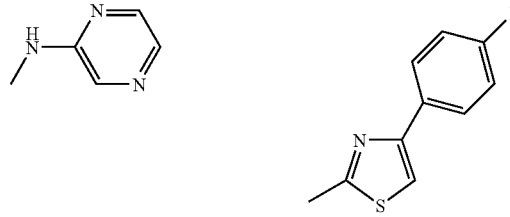 | 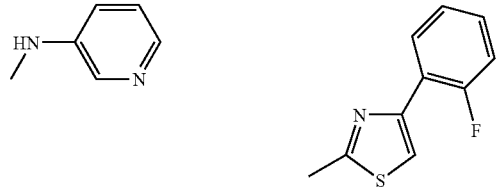 |
| 243 | 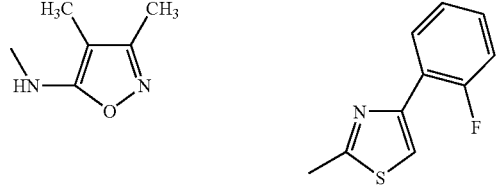 | 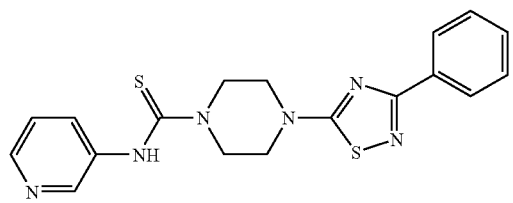 |
| 244 | (H3C, CH3 isoxazol-5-yl-amino) | (2-fluorophenyl-methylthiazole) |

Example 245

4-(3-Phenyl-1,2,4-thiadiazol-5-yl)-N-pyridin-3-ylpiperazine-1-carbothioamide

To a solution of 1-(3-phenyl-1,2,4-thiadiazol-5-yl)piperazine (246 mg, 1.00 mmol) and triethylamine (0.139 ml, 1.00 mmol) in tetrahydrofuran (6 ml) was added 3-pyridylisothiocyanate (0.167 ml, 1.50 mmol), the mixture was stirred at room temperature for 3 hours and the solvent was distilled off under reduced pressure. The residue was recrystallized from a mixed solvent of tetrahydrofuran and ethyl acetate to obtain the desired product (233 mg, 61.0%) as a solid.

$^1$H-NMR (DMSO-$d_6$) δ; 3.74 (4H, br s), 4.15-4.18 (4H, m), 7.33-7.38 (1H, m), 7.47-7.49 (3H, m), 7.73-7.77 (1H, m), 8.11-8.15 (2H, m), 8.30-8.32 (1H, m), 8.49-8.50 (1H, m), 9.63 (1H, br s).

Example 246

N-(2-Methyl-1,3-benzoxazol-6-yl)-4-(3-phenyl-1,2,4-thiadiazol-5-yl)piperazine-1-carboxamide (1) 2,2,2-Trichloroethyl (2-methyl-1,3-benzoxazol-6-yl)carbamate To a solution of 2-methyl-1,3-benzoxazol-6-amine (1.00 g, 6.74 mmol) and pyridine (1.64 ml, 20.2 mmol) in N,N-dimethylacetamide (20 ml) was added 2,2,2-trichloroethyl chloroformate (1.39 ml, 10.1 mmol) under ice-cooling, and the mixture was stirred for 2 hours under ice-cooling. The reaction mixture was poured into ice-water, and the mixture was extracted with ethyl acetate. The extract was washed with water and dried over anhydrous magnesium sulfate, and the solvent was distilled off under reduced pressure. The residue was recrystallized from a mixed solvent of hexane and ethyl acetate, and 1.45 g (66.5%) of the desired product was collected by filtration as a solid.

$^1$H-NMR (CDCl$_3$) δ; 2.64 (3H, s), 4.84 (2H, s), 7.00 (1H, br s), 7.35 (1H, d, J=8.4 Hz), 7.42 (1H, d, J=8.4 Hz), 7.74 (1H, br s).

(2) N-(2-Methyl-1,3-benzoxazol-6-yl)-4-(3-phenyl-1,2,4-thiadiazol-5-yl)piperazine-1-carboxamide A solution of 2,2,2-trichloroethyl (2-methyl-1,3-benzoxazol-6-yl)carbamate (200 mg, 0.618 mmol), 1-(3-phenyl-1,2,4-thiadiazol-5-yl)piperazine (152 mg, 0.618 mmol), diisopropylethylamine (0.215 ml, 1.24 mmol) and dimethyl sulfoxide (4 ml) was stirred at 70° C. for 24 hours, the reaction mixture was poured into water, and the mixture was extracted with ethyl acetate. The extract was washed with water, and dried over anhydrous magnesium sulfate. The solvent was distilled off under reduced pressure. The residue was purified by silica gel column chromatography (ethyl acetate) to give the desired product as a solid. The solid was recrystallized from ethyl acetate to give 75.6 mg (29.1%) of the desired product as a solid.

$^1$H-NMR (DMSO-d$_6$) δ; 2.58 (3H, s), 3.67 (8H, br s), 7.36-7.54 (5H, m), 7.79 (1H, d, J=2.1 Hz), 8.11-8.14 (2H, m), 8.79 (1H, s).

Example 247

N-(2-Methyl-1,3-benzoxazol-6-yl)-4-(4-phenyl-1,3-thiazol-2-yl)piperazine-1-carboxamide A solution of 2,2,2-trichloroethyl (2-methyl-1,3-benzoxazol-6-yl)carbamate (200 mg, 0.618 mmol), 1-(4-phenyl-1,3-thiazol-2-yl)piperazine (152 mg, 0.618 mmol), diisopropylethylamine (0.215 ml, 1.24 mmol) and dimethyl sulfoxide (4 ml) was stirred at 70° C. for 24 hours, and the reaction mixture was poured into water, and the mixture was extracted with ethyl acetate. The extract was washed with water, and dried over anhydrous magnesium sulfate. The solvent was distilled off under reduced pressure. The residue was purified by silica gel column chromatography (ethyl acetate) to give the desired product as a solid. The solid was recrystallized from ethyl acetate to give 100 mg (38.6%) of the desired product as a solid.

$^1$H-NMR (DMSO-d$_6$) δ; 2.58 (3H, s), 3.54 (4H, br s), 3.63 (4H, br s), 7.29-7.42 (5H, m), 7.52 (1H, d, J=9.0 Hz), 7.80 (1H, s), 7.87 (2H, d, J=7.5 Hz), 8.75 (1H, s).

Example 248

N-[4-(2-Oxopyrrolidin-1-yl)phenyl]-4-(3-phenyl-1,2,4-thiadiazol-5-yl)piperazine-1-carboxamide (1) 1-(4-Aminophenyl)pyrrolidin-2-one A mixture of 1-(4-nitrophenyl)pyrrolidin-2-one (1.00 g, 4.85 mmol), 10% palladium on carbon (100 mg), methanol (20 ml) and tetrahydrofuran (20 ml) was stirred under hydrogen atmosphere for 12 hours, insoluble substances were removed by filtration, and the filtrate was concentrated to give 790 mg (92.5%) of the desired product as an oil.

$^1$H-NMR (CDCl$_3$) δ; 2.08-2.18 (2H, m), 2.57 (2H, t, J=8.4 Hz), 3.62 (2H, br s), 3.80 (2H, t, J=6.6 Hz), 6.68 (2H, d, J=9.0 Hz), 7.34 (2H, d, J=9.0 Hz).

(2) Bis(2,2,2-trichloroethyl) [4-(2-oxopyrrolidin-1-yl)phenyl]imidodicarbonate

To a solution of 1-(4-aminophenyl)pyrrolidin-2-one (760 mg, 4.32 mmol) and pyridine (1.05 ml, 13.0 mmol) in N,N-dimethylacetamide (20 ml) was added 2,2,2-trichloroethyl chloroformate (1.19 ml, 8.64 mmol) under ice-cooling, and the mixture was stirred under ice-cooling for 2 hours. The reaction mixture was poured into ice-water, and 1.75 g (76.8%) of the desired product was collected by filtration as a solid.

$^1$H-NMR (CDCl$_3$) δ; 2.12-2.22 (2H, m), 2.61 (2H, t, J=8.1 Hz), 3.86 (2H, t, J=6.9 Hz), 4.82 (2H, s), 4.86 (2H, s), 7.42 (2H, d, J=8.4 Hz), 7.59 (2H, d, J=8.4 Hz).

(3) N-[4-(2-Oxopyrrolidin-1-yl)phenyl]-4-(3-phenyl-1,2,4-thiadiazol-5-yl)piperazine-1-carboxamide A solution of bis(2,2,2-trichloroethyl) [4-(2-oxopyrrolidin-1-yl)phenyl]imidodicarbonate (200 mg, 0.380 mmol), 1-(3-phenyl-1,2,4-thiadiazol-5-yl)piperazine (140 mg, 0.569 mmol), diisopropylethylamine (0.198 ml, 1.14 mmol) and dimethyl sulfoxide (4 ml) was stirred at 70° C. for 24 hours, the reaction mixture was poured into water, and the mixture was extracted with ethyl acetate. The extract was washed with water, and dried over anhydrous magnesium sulfate. The solvent was distilled off under reduced pressure, and the residue was recrystallized from ethyl acetate to give 51.0 mg (30.0%) of the desired product as a solid.

$^1$H-NMR (DMSO-d$_6$) δ; 1.99-2.07 (2H, m), 2.44-2.51 (2H, m), 3.64 (8H, br s), 3.77-3.82 (2H, m), 7.44-7.57 (7H, m), 8.10-8.14 (2H, m), 8.70 (1H, s).

Example 249

N-[4-(2-Oxopyrrolidin-1-yl)phenyl]-4-(4-phenyl-1,3-thiazol-2-yl)piperazine-1-carboxamide A solution of bis(2,2,2-trichloroethyl) [4-(2-oxopyrrolidin-1-yl)phenyl]imidodicarbonate (200 mg, 0.379 mmol), 1-(4-phenyl-1,3-thiazol-2-yl)piperazine (196 mg, 0.758 mmol), diisopropylethylamine (0.132 ml, 0.758 mmol) and dimethyl sulfoxide (4 ml) was stirred at 70° C. for 24 hours, the reaction mixture was poured into water, and the mixture was extracted with ethyl acetate. The extract was washed with water, and dried over anhydrous magnesium sulfate. The solvent was distilled off under reduced pressure, and the residue was recrystallized from ethyl acetate to give 116 mg (68.2%) of the desired product as a solid.

$^1$H-NMR (DMSO-d$_6$) δ; 2.02-2.09 (2H, m), 2.44-2.50 (2H, m), 3.52 (4H, br s), 3.63 (4H, br s), 3.79 (2H, t, J=6.9 Hz), 7.26-7.54 (8H, m), 7.87 (2H, d, J=8.7 Hz), 8.67 (1H, s).

Example 250

4-[3-(2-Fluorophenyl)-1,2,4-thiadiazol-5-yl]-N-[4-(2-oxopyrrolidin-1-yl)phenyl]piperazine-1-carboxamide A solution of bis(2,2,2-trichloroethyl) [4-(2-oxopyrrolidin-1-yl)phenyl]imidodicarbonate (200 mg, 0.379 mmol), 1-[3-(2-fluorophenyl)-1,2,4-thiadiazol-5-yl]piperazine (196 mg, 0.742 mmol), diisopropylethylamine (0.132 ml, 0.758 mmol) and dimethyl sulfoxide (4 ml) was stirred at 70° C. for 24 hours, and the reaction mixture was poured into water, and the mixture was extracted with ethyl acetate. The extract was washed with water, and dried over anhydrous magnesium sulfate. The solvent was distilled off under reduced pressure, and the residue was recrystallized from ethyl acetate to give 25.3 mg (14.3%) of the desired product as a solid.

$^1$H-NMR (DMSO-d$_6$) δ; 2.02-2.09 (2H, m), 2.44-2.50 (2H, m), 3.64 (8H, br s), 3.80 (2H, t, J=7.2 Hz), 7.29-7.58 (7H, m), 8.00-8.06 (1H, m), 8.70 (1H, s).

Example 251

4-(3-Phenyl-1,2,4-thiadiazol-5-yl)-N-[4-(propionylamino)phenyl]piperazine-1-carboxamide (1) N-(4-Nitrophenyl)propanamide Propionyl chloride (25.0 g, 270 mmol) was added dropwise to a solution of 4-nitroaniline (24.9 g, 180 mmol) and pyridine (43.7 ml, 540 mmol) in tetrahydrofuran (500 ml) under ice-cooling, the mixture was stirred under ice-cooling for 2 hour, and the solvent was distilled off under reduced pressure. The residue was poured into ice-water, and 33.5 g (95.7%) of the desired product was collected by filtration as a solid.

$^1$H-NMR (CDCl$_3$) δ; 1.27 (3H, t, J=7.5 Hz), 2.46 (2H, q, J=7.5 Hz), 7.45 (1H, br s), 7.71 (2H, d, J=9.0 Hz), 8.21 (2H, d, J=9.0 Hz).

(2) N-(4-Aminophenyl)propanamide

A mixture of N-(4-nitrophenyl)propanamide (10 g, 51.5 mmol), 10% palladium on carbon (1 g), methanol (500 ml) and tetrahydrofuran (100 ml) was stirred under hydrogen atmosphere for 12 hours, insoluble substances were removed by filtration, and the filtrate was concentrated to give 8.00 g (94.8%) of the desired product as an oil.

$^1$H-NMR (CDCl$_3$) δ; 1.23 (3H, t, J=7.5 Hz), 2.34 (2H, q, J=7.5 Hz), 3.20 (2H, br s), 6.64 (2H, d, J=8.7 Hz), 7.13 (1H, br s), 7.26 (2H, d, J=8.7 Hz).

(3) 2,2,2-Trichloroethyl [4-(propionylamino)phenyl]carbamate

To a solution of N-(4-aminophenyl)propanamide (2.00 g, 10.3 mmol) and pyridine (2.50 ml, 30.9 mmol) in N,N-dimethylacetamide (40 ml) was added 2,2,2-trichloroethyl chloroformate (2.13 ml, 15.5 mmol) under ice-cooling, and the mixture was stirred under ice-cooling for 2 hours. The reaction mixture was poured into ice-water, and 3.41 g (97.4%) of the desired product was collected by filtration as a solid.

$^1$H-NMR (CDCl$_3$) δ; 1.21 (3H, t, J=7.5 Hz), 2.37 (2H, q, J=7.5 Hz), 4.83 (2H, s), 7.45 (2H, d, J=8.4 Hz), 7.53 (2H, d, J=8.4 Hz), 8.70 (1H, br s), 8.87 (1H, br s).

(4) 4-(3-Phenyl-1,2,4-thiadiazol-5-yl)-N-[4-(propionylamino)phenyl]piperazine-1-carboxamide A solution of 2,2,2-trichloroethyl [4-(propionylamino) phenyl]carbamate (200 mg, 0.589 mmol), 1-(3-phenyl-1,2,4-thiadiazol-5-yl)piperazine (145 mg, 0.589 mmol), diisopropylethylamine (0.206 ml, 1.18 mmol) and dimethyl sulfoxide (4 ml) was stirred at 70° C. for 24 hours, the reaction mixture was poured into water, and the mixture was extracted with ethyl acetate. The extract was washed with water, and dried over anhydrous magnesium sulfate. The solvent was distilled off under reduced pressure, and the residue was recrystallized from ethyl acetate to give 76.0 mg (29.6%) of the desired product as a solid.

$^1$H-NMR (DMSO-d$_6$) δ; 1.07 (3H, t, J=7.5 Hz), 2.28 (2H, q, J=7.5 Hz), 3.64 (8H, br s), 7.34-7.49 (7H, m), 8.10-8.14 (2H, m), 8.62 (1H, s), 9.71 (1H, s).

Example 252

4-(4-Phenyl-1,3-thiazol-2-yl)-N-[4-(propionylamino) phenyl]piperazine-1-carboxamide A solution of 2,2,2-trichloroethyl [4-(propionylamino) phenyl]carbamate (200 mg, 0.589 mmol), 1-(4-phenyl-1,3-thiazol-2-yl)piperazine (145 mg, 0.589 mmol), diisopropylethylamine (0.206 ml, 1.18 mmol) and dimethyl sulfoxide (4 ml) was stirred at 70° C. for 24 hours, and the reaction mixture was poured into water, and the mixture was extracted with ethyl acetate. The extract was washed with water, and dried over anhydrous magnesium sulfate. The solvent was distilled off under reduced pressure, and the residue was recrystallized from ethyl acetate to give 113 mg (44.0%) of the desired product as a solid.

$^1$H-NMR (DMSO-d$_6$) δ; 1.07 (3H, t, J=7.5 Hz), 2.28 (2H, q, J=7.5 Hz), 3.51 (4H, br s), 3.60 (4H, br s), 7.29-7.47 (8H, m), 7.87 (2H, d, J=7.5 Hz), 8.59 (1H, s), 9.71 (1H, s).

Example 253

4-[3-(2-Fluorophenyl)-1,2,4-thiadiazol-5-yl]-N-[4-(propionylamino)phenyl]piperazine-1-carboxamide (1) tert-Butyl 4-[3-(2-fluorophenyl)-1,2,4-thiadiazol-5-yl]piperazine-1-carboxylate Triethylamine (14.7 ml, 105 mmol) was added to a solution of 1-(tert-butoxycarbonyl)piperazine (5.64 g, 26.3 mmol) and 5-chloro-3-(2-fluorophenyl)-1,2,4-thiadiazole (4.89 g, 26.3 mmol) in N,N-dimethylformamide (100 ml), the mixture was stirred was stirred at room temperature for 30 minutes, the reaction mixture was poured into water, and the mixture was extracted with ethyl acetate. The extract was washed with water, and dried over anhydrous magnesium sulfate, and the solvent was distilled off under reduced pressure. The residue was recrystallized from a mixed solvent of hexane and ethyl acetate to give 6.28 g (65.6%) of the desired product as a crystal.

$^1$H-NMR (CDCl$_3$) δ; 1.49 (9H, s), 3.60 (8H, s), 7.13-7.23 (2H, m), 7.36-7.43 (1H, m), 8.06-8.12 (1H, m).

(2) 1-[3-(2-Fluorophenyl)-1,2,4-thiadiazol-5-yl]piperazine hydrochloride

A mixture of tert-butyl 4-[3-(2-fluorophenyl)-1,2,4-thiadiazol-5-yl]piperazine-1-carboxylate (5.70 g, 15.6 mmol), 4 N hydrogen chloride/ethyl acetate (200 ml) and methanol (100 ml) was stirred at room temperature for 12 hours. The solvent was distilled off under reduced pressure, and the residue was recrystallized from a mixed solvent of methanol and ether to give 4.31 g (86.5%) of the desired product as a solid.

$^1$H-NMR (DMSO-d$_6$) δ; 3.26-3.28 (4H, m), 3.80-3.83 (4H, m), 7.28-7.36 (2H, m), 7.51-7.57 (1H, m), 7.99-8.05 (1H, m), 9.42 (2H, br s).

(3) 1-[3-(2-Fluorophenyl)-1,2,4-thiadiazol-5-yl]piperazine

A mixture of 1-[3-(2-fluorophenyl)-1,2,4-thiadiazol-5-yl] piperazine hydrochloride (3.00 g, 10.0 mmol) and a 1 N sodium hydroxide aqueous solution (30 ml) was extracted with chloroform (100 ml). The extract was dried over anhydrous magnesium sulfate, and the solvent was distilled off under reduced pressure to give 2.60 g (98.5%) of the desired product as a solid.

$^1$H-NMR (CDCl$_3$) δ; 3.00-3.03 (4H, m), 3.56-3.60 (4H, m), 7.12-7.42 (3H, m), 8.06-8.12 (1H, m).

(1) 4-[3-(2-Fluorophenyl)-1,2,4-thiadiazol-5-yl]-N-[4-(propionylamino)phenyl]piperazine-1-carboxamide A solution of 2,2,2-trichloroethyl [4-(propionylamino) phenyl]carbamate (200 mg, 0.589 mmol), 1-[3-(2-fluorophenyl)-1,2,4-thiadiazol-5-yl]piperazine (145 mg, 0.589 mmol), diisopropylethylamine (0.206 ml, 1.18 mmol) and dimethyl sulfoxide (4 ml) was stirred at 70° C. for 24 hours, the reaction mixture was poured into water, and the mixture was extracted with ethyl acetate. The extract was washed with water, and dried over anhydrous magnesium sulfate. The solvent was distilled off under reduced pressure, and the residue was recrystallized from ethyl acetate to give 60.5 mg (22.6%) of the desired product as a solid.

$^1$H-NMR (DMSO-d$_6$) δ; 1.07 (3H, t, J=6.9 Hz), 2.28 (2H, q, J=6.9 Hz), 3.63 (8H, br s), 7.28-7.53 (7H, m), 8.01-8.05 (1H, m), 8.61 (1H, s), 9.71 (1H, s).

Example 254

4-(3-Phenyl-1,2,4-thiadiazol-5-yl)-N-[4-(1H-pyrazol-1-yl)phenyl]piperazine-1-carboxamide (1) 2,2,2-Trichloroethyl [4-(1H-pyrazol-1-yl)phenyl]carbamate To a solution of 4-(1H-pyrazol-1-yl)aniline (1.00 g, 6.28 mmol) and pyridine (1.52 ml, 18.8 mmol) in N,N-dimethylacetamide (20 ml) was added 2,2,2-trichloroethyl chloroformate (1.30 ml, 9.42 mmol) under ice-cooling, and the mixture was stirred under ice-cooling for 2 hours. The reaction mixture was poured into ice-water, and 2.00 g (95.2%) of the desired product was collected by filtration as a solid.

$^1$H-NMR (CDCl$_3$) δ; 4.84 (2H, s), 6.46-6.47 (1H, m), 7.00 (1H, br s), 7.51 (2H, d, J=8.7 Hz), 7.67 (2H, d, J=8.7 Hz), 7.71-7.72 (1H, m), 7.88-7.89 (1H, m).

(2) 4-(3-Phenyl-1,2,4-thiadiazol-5-yl)-N-[4-(1H-pyrazol-1-yl)phenyl]piperazine-1-carboxamide A solution of 2,2,2-trichloroethyl [4-(1H-pyrazol-1-yl)phenyl]carbamate (200 mg, 0.598 mmol), 1-[3-(2-fluorophenyl)-1,2,4-thiadiazol-5-yl]piperazine (147 mg, 0.598 mmol), diisopropylethylamine (0.208 ml, 1.20 mmol) and dimethyl sulfoxide (4 ml) was stirred at 70° C. for 24 hours, the reaction mixture was poured into water, and the mixture was extracted with ethyl acetate. The extract was washed with water, and dried over anhydrous magnesium sulfate. The solvent was distilled off under reduced pressure, and the residue was purified by silica gel column chromatography (ethyl acetate) to give the desired product as a solid. The solid was recrystallized from ethyl acetate to give 63.7 mg (24.7%) of the desired product as a solid.

$^1$H-NMR (DMSO-d$_6$) δ; 3.67 (8H, br s), 6.50-6.51 (1H, m), 7.47-7.49 (3H, m), 7.59 (2H, d, J=9.0 Hz), 7.69-7.73 (3H, m), 8.11-8.14 (2H, m), 8.38-8.39 (1H, m), 8.84 (1H, s).

Example 255

4-(4-Phenyl-1,3-thiazol-2-yl)-N-[4-(1H-pyrazol-1-yl)phenyl]piperazine-1-carboxamide A solution of 2,2,2-trichloroethyl [4-(1H-pyrazol-1-yl)phenyl]carbamate (200 mg, 0.598 mmol), 1-(4-phenyl-1,3-thiazol-2-yl)piperazine (147 mg, 0.598 mmol), diisopropylethylamine (0.208 ml, 1.20 mmol) and dimethyl sulfoxide (4 ml) was stirred at 70° C. for 24 hours, the reaction mixture was poured into water, and the mixture was extracted with ethyl acetate. The extract was washed with water, and dried over anhydrous magnesium sulfate. The solvent was distilled off under reduced pressure, and the residue was purified by silica gel column chromatography (ethyl acetate) to give the desired product as a solid. The solid was recrystallized from ethyl acetate to give 73.6 mg (28.6%) of the desired product as a solid.

$^1$H-NMR (DMSO-d$_6$) δ; 3.56 (4H, br s), 3.66 (4H, br s), 6.49-6.51 (1H, m), 7.29-7.42 (4H, m), 7.59 (2H, d, J=9.3 Hz), 7.70-7.73 (3H, m), 7.88 (2H, d, J=8.7 Hz), 8.38-8.39 (1H, m), 8.81 (1H, s).

Example 256

4-(3-Phenyl-1,2,4-thiadiazol-5-yl)-N-{4-[(trifluoroacetyl)amino]phenyl}piperazine-1-carboxamide (1) 2,2,2-Trichloroethyl {4-[(trifluoroacetyl)amino]phenyl}carbamate To a solution of 4-trifluoroacetylaminoaniline (1.00 g, 4.90 mmol) and pyridine (1.20 ml, 15.0 mmol) in N,N-dimethylacetamide (20 ml) was added 2,2,2-trichloroethyl chloroformate (1.01 ml, 7.35 mmol) under ice-cooling, and the mixture was stirred under ice-cooling for 2 hours. The reaction mixture was poured into ice-water, and a solid was collected by filtration to give 1.80 g (96.8%) of the desired product as a solid.

$^1$H-NMR (CDCl$_3$) δ; 4.84 (2H, s), 7.52 (2H, d, J=9.3 Hz), 7.64 (2H, d, J=9.3 Hz), 8.64 (1H, br s), 10.17 (1H, br s).

(2) 4-(3-Phenyl-1,2,4-thiadiazol-5-yl)-N-{4-[(trifluoroacetyl)amino]phenyl}piperazine-1-carboxamide A solution of 2,2,2-trichloroethyl {4-[(trifluoroacetyl)amino]phenyl}carbamate (200 mg, 0.527 mmol), 1-(3-phenyl-1,2,4-thiadiazol-5-yl)piperazine (130 mg, 0.527 mmol), diisopropylethylamine (0.184 ml, 1.05 mmol) and dimethyl sulfoxide (4 ml) was stirred at 70° C. for 12-hours, the reaction mixture was poured into water, and the mixture was extracted with ethyl acetate. The extract was washed with water, and dried over anhydrous magnesium sulfate. The solvent was distilled off under reduced pressure, and the residue was purified by silica gel column chromatography (ethyl acetate) to give the desired product as a solid. The solid was recrystallized from a mixed solvent of ethyl acetate and hexane to give 43.0 mg (17.1%) of the desired product as a solid.

$^1$H-NMR (DMSO-d$_6$) δ; 3.65 (8H, br s), 7.47-7.56 (7H, m), 8.10-8.13 (2H, m), 8.79 (1H, s), 11.13 (1H, s).

Example 257

4-(4-Phenyl-1,3-thiazol-2-yl)-N-{4-[(trifluoroacetyl)amino]phenyl}piperazine-1-carboxamide A solution of 2,2,2-trichloroethyl {4-[(trifluoroacetyl)amino]phenyl}carbamate (200 mg, 0.527 mmol), 1-(4-phenyl-1,3-thiazol-2-yl)piperazine (129 mg, 0.527 mmol), diisopropylethylamine (0.184 ml, 1.05 mmol) and dimethyl sulfoxide (4 ml) was stirred at 70° C. for 24 hours, the reaction mixture was poured into water, and the mixture was extracted with ethyl acetate. The extract was washed with water, and dried over anhydrous magnesium sulfate. The solvent was distilled off under reduced pressure, and the residue was recrystallized from ethyl acetate to give 100 mg (39.8%) of the desired product as a solid.

$^1$H-NMR (DMSO-d$_6$) δ; 3.52 (4H, br s), 3.64 (4H, br s), 7.26-7.42 (4H, m), 7.49 (2H, d, J=9.3 Hz), 7.54 (2H, d, J=9.3 Hz), 7.87 (2H, d, J=8.7 Hz), 8.76 (1H, s), 11.12 (1H, s).

Example 258

N-[6-(Acetylamino)pyridin-3-yl]-4-[4-(3-fluorophenyl)-1,3-thiazol-2-yl]piperazine-1-carboxamide A mixture of 2,2,2-trichloroethyl [6-(acetylamino)pyridin-3-yl]carbamate (273 mg, 0.835 mmol), 1-[4-(3-fluorophenyl)-1,3-thiazol-2-yl]piperazine (200 mg, 0.760 mmol) and diisopropylethylamine (0.265 ml, 1.52 mmol) in dimethyl sulfoxide (2.5 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was recrystallized from a mixed solvent of hexane and tetrahydrofuran to give 137 mg (40.8%) of the desired product as a solid.

$^1$H-NMR (DMSO-$d_6$) δ; 2.06 (3H, s), 3.54 (4H, br s), 3.64 (4H, br s), 7.09-7.15 (1H, m), 7.40-7.44 (2H, m), 7.66-7.74 (2H, m), 7.80-7.82 (1H, m), 7.96-7.99 (1H, m), 8.41 (1H, br s), 8.78 (1H, s), 10.34 (1H, s).

Example 259

4-[4-(2,4-Difluorophenyl)-1,3-thiazol-2-yl]-N-pyridin-3-ylpiperazine-1-carboxamide (1) 2-(2,4-Difluorophenyl)-2-oxoethyl thiocyanate A solution of 2-bromo-1-(2,4-difluorophenyl)ethanone (5.0 g, 21.3 mmol) and potassium thiocyanate (2.07 g, 21.3 mmol) in ethanol (50 ml) was stirred at 80° C. for 2 hours. After cooling to room temperature, water (70 ml) was poured to the reaction mixture. A crystal was collected by filtration and washed with 50% aqueous ethanol to give 3.39 g (74.7%) of the desired product as a solid.

$^1$H-NMR (CDCl$_3$) δ; 4.61 (1H, s), 4.62 (1H, s), 6.92-7.09 (2H, m), 8.02-8.10 (1H, m).

(2) 2-Bromo-4-(2,4-difluorophenyl)-1,3-thiazole

A 25% hydrogen bromide/acetic acid (25 ml) solution was added to a solution of 2-(2,4-difluorophenyl)-2-oxoethyl thiocyanate (3.39 g, 15.9 mmol) in acetic acid (25 ml), and the mixture was stirred at 130° C. for 2 hours and stirred at room temperature for 1 hour. Water was poured to the reaction mixture, and crystals were collected by filtration and washed with water to give 3.23 g (73.6%) of the desired product as a solid.

$^1$H-NMR (CDCl$_3$) δ; 6.86-7.00 (2H, m), 7.62 (1H, s), 8.12-8.20 (1H, m).

(3) tert-Butyl 4-[4-(2,4-difluorophenyl)-1,3-thiazol-2-yl]piperazine-1-carboxylate A solution of 2-bromo-4-(2,4-difluorophenyl)-1,3-thiazole (3.23 mg, 11.7 mmol), tert-butyl piperazine-1-carboxylate (4.36 g, 23.4 mmol) and potassium carbonate (1.62 g, 11.7 mmol) in dimethylformamide (40 ml) was stirred at 120° C. for 12 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 3.83 g (85.9%) of the desired product as a solid.

$^1$H-NMR (CDCl$_3$) δ; 1.49 (9H, s), 3.48-3.60 (8H, m), 6.81-6.95 (2H, m), 7.02-7.03 (1H, m), 8.08-8.16 (1H, m).

(4) 1-[4-(2,4-Difluorophenyl)-1,3-thiazol-2-yl]piperazine

A 4 N solution (50 ml) of hydrogen chloride in ethyl acetate was added to a solution of tert-butyl 4-[4-(2,4-difluorophenyl)-1,3-thiazol-2-yl]piperazine-1-carboxylate (3.80 g, 9.96 mmol) in ethyl acetate (100 ml), and the mixture was stirred at room temperature for 14 hours. Hexane was poured to the reaction mixture, and crystals were collected by filtration to give 1-[4-(2,4-difluorophenyl)-1,3-thiazol-2-yl]piperazine hydrochloride. The hydrochloride was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 2.06 g, (73.7%) of the desired product as a solid.

$^1$H-NMR (CDCl$_3$) δ; 2.99-3.02 (4H, m), 3.49-3.53 (4H, m), 6.81-6.94 (2H, m), 6.99-7.00 (1H, m), 8.09-8.17 (1H, m).

(5) 4-[4-(2,4-Difluorophenyl)-1,3-thiazol-2-yl]-N-pyridin-3-ylpiperazine-1-carboxamide A mixture of 2,2,2-trichloroethyl pyridin-3-ylcarbamate (211 mg, 0.782 mmol), 1-[4-(2,4-difluorophenyl)-1,3-thiazol-2-yl]piperazine (200 mg, 0.711 mmol) and diisopropylethylamine (0.248 ml, 1.42 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate) and recrystallized from a mixed solvent of hexane and tetrahydrofuran to give 169 mg (59.4%) of the desired product as a solid.

$^1$H-NMR (CDCl$_3$) δ; 3.63-3.73 (8H, m), 6.58 (1H, br s), 6.83-6.96 (2H, m), 7.06-7.07 (1H, m), 7.24-7.29 (1H, m), 7.97-8.01 (1H, m), 8.08-8.16 (1H, m), 8.30-8.32 (1H, m), 8.46-8.47 (1H, m).

Example 260

4-[4-(2,4-Difluorophenyl)-1,3-thiazol-2-yl]-N-(3,4-dimethylisoxazol-5-yl)piperazine-1-carboxamide A mixture of 2,2,2-trichloroethyl (3,4-dimethylisoxazol-5-yl)carbamate (225 mg, 0.782 mmol), 1-[4-(2,4-difluorophenyl)-1,3-thiazol-2-yl]piperazine (200 mg, 0.711 mmol) and diisopropylethylamine (0.248 ml, 1.42 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=1:1), and recrystallized from a mixed solvent of hexane and tetrahydrofuran to give 103 mg (34.4%) of the desired product as a solid. mp 166-167° C.

$^1$H-NMR (CDCl$_3$) δ; 1.89 (3H, s), 2.20 (3H, s), 3.61-3.70 (8H, m), 6.72 (1H, br s), 6.83-6.96 (2H, m), 7.05-7.06 (1H, m), 8.08-8.16 (1H, m).

Example 261

N-[6-(Acetylamino)pyridin-3-yl]-4-[4-(2,4-difluorophenyl)-1,3-thiazol-2-yl]piperazine-1-carboxamide A mixture of 2,2,2-trichloroethyl [6-(acetylamino)pyridin-3-yl]carbamate (255 mg, 0.782 mmol), 1-[4-(2,4-difluorophenyl)-1,3-thiazol-2-yl]piperazine (200 mg, 0.711 mmol) and diisopropylethylamine (0.248 ml, 1.42 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was recrystallized from a mixed solvent of hexane and tetrahydrofuran to give 190 mg (58.2%) of the desired product as a solid.

$^1$H-NMR (DMSO-d$_6$) δ; 2.07 (3H, s), 3.55-3.65 (8H, m), 7.15-7.21 (2H, m), 7.30-7.37 (1H, m), 7.79-7.83 (1H, m), 7.97-8.00 (1H, m), 8.07-8.16 (1H, m), 8.41 (1H, s), 8.79 (1H, s), 10.35 (1H, s).

Example 262

4-[4-(2,3-Difluorophenyl)-1,3-thiazol-2-yl]-N-pyridin-3-ylpiperazine-1-carboxamide (1) 2-Bromo-1-(2,3-difluorophenyl)ethanone Bromine (4.96 g, 31.1 mmol) was slowly added dropwise to a solution of 1-(2,3-difluorophenyl)ethanone (4.85 g, 31.1 mmol) in diethyl ether (100 ml), and the mixture was stirred at room temperature for 5 hours. The reaction mixture was distilled off under reduced pressure to give 7.29 g (99.9%) of the desired product as an oil.

$^1$H-NMR (CDCl$_3$) δ; 4.51 (2H, s), 7.19-7.26 (1H, m), 7.38-7.47 (1H, m), 7.66-7.72 (1H, m).

(2) 2-(2,3-Difluorophenyl)-2-oxoethyl thiocyanate

A solution of 2-bromo-1-(2,3-difluorophenyl)ethanone (7.20 g, 30.6 mmol) and potassium thiocyanate (3.01 g, 30.6 mmol) in ethanol (70 ml) was stirred at 80° C. for 2 hours. After cooling to room temperature, water (85 ml) was poured to the reaction mixture, and the mixture was extracted with chloroform. The extract was washed with water, and dried over anhydrous magnesium sulfate, and the solvent was distilled off under reduced pressure to give 5.67 g (86.8%) of the desired product as an oil.

$^1$H-NMR (CDCl$_3$) δ; 4.62 (1H, s), 4.63 (1H, s), 7.23-7.31 (1H, m), 7.44-7.53 (1H, m), 7.72-7.77 (1H, m).

(3) 2-Bromo-4-(2,3-difluorophenyl)-1,3-thiazole

A 25% hydrogen bromide/acetic acid (40 ml) solution was added to a solution of 2-(2,3-difluorophenyl)-2-oxoethyl thiocyanate (5.67 g, 26.6 mmol) in acetic acid (40 ml), and the mixture was stirred at 130° C. for 2 hours and at room temperature for 1 hour. Water was poured to the reaction mixture, and crystals were collected by filtration and washed with water to give 6.74 g (91.8%) of the desired product as a solid.

$^1$H-NMR (CDCl$_3$) δ; 7.10-7.18 (2H, m), 7.72 (1H, s), 7.89-7.95 (1H, m).

(4) tert-Butyl 4-[4-(2,3-difluorophenyl)-1,3-thiazol-2-yl]piperazine-1-carboxylate A solution of 2-bromo-4-(2,3-difluorophenyl)-1,3-thiazole (6.74 g, 24.4 mmol), tert-butyl piperazine-1-carboxylate (9.09 g, 48.4 mmol) and potassium carbonate (3.37 g, 24.4 mmol) in dimethylformamide (80 ml) was stirred at 120° C. for 13 hours. Water was poured to the reaction mixture, and the mixture was extracted with ethyl acetate. The extract was washed with water, and dried over anhydrous magnesium sulfate, and the solvent was distilled off under reduced pressure. Hexane was added to the residue, and crystals were collected by filtration to give 4.20 g (45.1%) of the desired product as a solid.

$^1$H-NMR (CDCl$_3$) δ; 1.49 (9H, s), 3.51-3.61 (8H, m), 7.02-7.11 (2H, m), 7.12-7.13 (1H, m), 7.85-7.91 (1H, m).

(5) 1-[4-(2,3-Difluorophenyl)-1,3-thiazol-2-yl]piperazine

A 4 N solution (50 ml) of hydrogen chloride in ethyl acetate was added to a solution of tert-butyl 4-[4-(2,3-difluorophenyl)-1,3-thiazol-2-yl]piperazine-1-carboxylate (4.20 g, 11.0 mmol) in ethyl acetate (100 ml), and the mixture was stirred at room temperature for 14 hours. Hexane was added to the reaction mixture, and crystals were collected by filtration to give 1-[4-(2,3-difluorophenyl)-1,3-thiazol-2-yl]piperazine hydrochloride. The hydrochloride was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 1.76 g (56.8%) of the desired product as a solid.

$^1$H-NMR (CDCl$_3$) δ; 2.98-3.02 (4H, m), 3.49-3.53 (4H, m), 7.00-7.13 (3H, m), 7.85-7.91 (1H, m).

(6) 4-[4-(2,3-Difluorophenyl)-1,3-thiazol-2-yl]-N-pyridin-3-ylpiperazine-1-carboxamide A mixture of 2,2,2-trichloroethyl pyridin-3-ylcarbamate (211 mg, 0.782 mmol), 1-[4-(2,3-difluorophenyl)-1,3-thiazol-2-yl]piperazine (200 mg, 0.711 mmol) and diisopropylethylamine (0.248 ml, 1.42 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 157 mg (55.0%) of the desired product as a solid. mp 172-173° C.

$^1$H-NMR (CDCl$_3$) δ; 3.64-3.73 (8H, m), 6.67 (1H, br s), 7.03-7.13 (2H, m), 7.16-7.17 (1H, m), 7.24-7.29 (1H, m), 7.85-7.91 (1H, m), 7.97-8.00 (1H, m), 8.30-8.31 (1H, m), 8.46-8.47 (1H, m).

Example 263

4-[4-(2,3-Difluorophenyl)-1,3-thiazol-2-yl]-N-(3,4-dimethylisoxazol-5-yl)piperazine-1-carboxamide A mixture of 2,2,2-trichloroethyl (3,4-dimethylisoxazol-5-yl)carbamate (225 mg, 0.782 mmol), 1-[4-(2,3-difluorophenyl)-1,3-thiazol-2-yl]piperazine (200 mg, 0.711 mmol) and diisopropylethylamine (0.248 ml, 1.42 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane: ethyl acetate=1:1), and recrystallized from a mixed solvent of hexane and tetrahydrofuran to give 117 mg (39.1%) of the desired product as a solid.

$^1$H-NMR (CDCl$_3$) δ; 1.89 (3H, s), 2.20 (3H, s), 3.62-3.70 (8H, m), 6.71 (1H, br s), 7.06-7.14 (2H, m), 7.16-7.17 (1H, m), 7.84-7.90 (1H, m).

Example 264

N-[6-(Acetylamino)pyridin-3-yl]-4-[4-(2,3-difluorophenyl)-1,3-thiazol-2-yl]piperazine-1-carboxamide A mixture of 2,2,2-trichloroethyl [6-(acetylamino)pyridin-3-yl]carbamate (255 mg, 0.782 mmol), 1-[4-(2,3-difluorophenyl)-1,3-thiazol-2-yl]piperazine (200 mg, 0.711 mmol)

and diisopropylethylamine (0.248 ml, 1.42 mmol) in dimethyl sulfoxide (2.5 ml) was stirred at 70° C. for 15 hours. Water was poured to the reaction mixture, and the mixture was extracted with ethyl acetate. The extract was washed with water, and dried over magnesium sulfate anhydrous, and the solvent was distilled off under reduced pressure. The residue was recrystallized from a mixed solvent of hexane and tetrahydrofuran to give 119 mg (36.6%) of the desired product as a solid.

$^1$H-NMR (DMSO-$d_6$) δ; 2.06 (3H, s), 3.54-3.64 (8H, m), 7.23-7.43 (3H, m), 7.79-7.90 (2H, m), 7.96-7.99 (1H, m), 8.40-8.41 (1H, m), 8.78 (1H, s), 10.35 (1H, s).

Example 265

4-[4-(3-Fluorophenyl)-1,3-thiazol-2-yl]-N-(1-methyl-1H-pyrazol-5-yl)piperazine-1-carboxamide A mixture of trichloromethyl 2,2,2-trichloroethyl (1-methyl-1H-pyrazol-5-yl)imidodicarbonate (255 mg, 0.570 mmol), 4-[4-(3-fluorophenyl)-1,3-thiazol-2-yl]piperazine (300 mg, 1.14 mmol) and diisopropylethylamine (0.198 ml, 1.14 mmol) in dimethyl sulfoxide (3.8 ml) was stirred at 70° C. for 16 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 129 mg (58.8%) of the desired product as a solid.

$^1$H-NMR (CDCl$_3$) δ; 3.65 (8H, s), 3.74 (3H, s), 6.08-6.09 (1H, m), 6.27 (1H, br s), 6.85 (1H, s), 6.95-7.02 (1H, m), 7.30-7.37 (1H, m), 7.42-7.43 (1H, m), 7.53-7.60 (2H, m).

Example 266

4-[4-(2-Fluorophenyl)-1,3-thiazol-2-yl]-N-(1-methyl-1H-pyrazol-5-yl)piperazine-1-carboxamide A mixture of trichloromethyl 2,2,2-trichloroethyl (1-methyl-1H-pyrazol-5-yl)imidodicarbonate (255 mg, 0.570 mmol), 4-[4-(2-fluorophenyl)-1,3-thiazol-2-yl]piperazine (300 mg, 1.14 mmol) and diisopropylethylamine (0.198 ml, 1.14 mmol) in dimethyl sulfoxide (3.8 ml) was stirred at 70° C. for 16 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 41.4 mg (18.8%) of the desired product as a solid.

$^1$H-NMR (CDCl$_3$) δ; 3.66 (8H, s), 3.75 (3H, s), 6.09-6.10 (1H, m), 6.18 (1H, br s), 7.08-7.26 (4H, m), 7.42-7.43 (1H, m), 8.10-8.15 (1H, m). mp 156-157° C.

Example 267

4-[4-(4-Fluorophenyl)-1,3-thiazol-2-yl]-N-(1-methyl-1H-pyrazol-5-yl)piperazine-1-carboxamide A mixture of trichloromethyl 2,2,2-trichloroethyl (1-methyl-1H-pyrazol-5-yl)imidodicarbonate (255 mg, 0.570 mmol), 4-[4-(4-fluorophenyl)-1,3-thiazol-2-yl]piperazine (300 mg, 1.14 mmol) and diisopropylethylamine (0.198 ml, 1.14 mmol) in dimethyl sulfoxide (3.8 ml) was stirred at 70° C. for 18 hours. Water was poured to the reaction mixture, and the mixture was extracted with ethyl acetate. The extract was washed with water, and dried over magnesium sulfate anhydrous, and the solvent was distilled off under reduced pressure. The residue was purified by silica gel column chromatography (ethyl acetate), and recrystallized from a mixed solvent of hexane and tetrahydrofuran to give 87.1 mg (39.6%) of the desired product as a solid.

$^1$H-NMR (CDCl$_3$) δ; 3.61-3.67 (8H, m), 3.73 (3H, s), 6.08-6.09 (1H, m), 6.31 (1H, br s), 6.75 (1H, s), 7.04-7.09 (2H, m), 7.42-7.43 (1H, m), 7.78-7.83 (2H, m).

Example 268

4-[4-(3-Chlorophenyl)-1,3-thiazol-2-yl]-N-pyridin-3-ylpiperazine-1-carboxamide (1) 2-Bromo-1-(3-chlorophenyl)ethanone Bromine (5.17 g, 32.3 mmol) was slowly added dropwise to a solution of 1-(3-chlorophenyl)ethanone (5.00 g, 32.3 mmol) in diethyl ether (100 ml), and the mixture was stirred at room temperature for 4 hours. The reaction mixture was distilled off under reduced pressure, and the desired product was obtained quantitatively as an oil.

$^1$H-NMR (CDCl$_3$) δ; 4.42 (2H, s), 7.41-7.47 (1H, m), 7.56-7.60 (1H, m), 7.84-7.88 (1H, m), 7.95-7.96 (1H, m).

(2) 2-(3-Chlorophenyl)-2-oxoethyl thiocyanate

A solution of 2-bromo-1-(3-chlorophenyl)ethanone (7.55 g, 32.3 mmol) and potassium thiocyanate (3.14 g, 32.3 mmol) in ethanol (70 ml) was stirred at 80° C. for 2 hours. After cooling to room temperature, water (70 ml) was poured to the reaction mixture. Crystals were collected by filtration and washed with water to give 4.92 g (69.8%) of the desired product as a solid.

$^1$H-NMR (CDCl$_3$) δ; 4.69 (2H, s), 7.46-7.51 (1H, m), 7.62-7.66 (1H, m), 7.80-7.84 (1H, m), 7.92-7.93 (1H, m).

(3) 2-Bromo-4-(3-chlorophenyl)-1,3-thiazole

A 25% hydrogen bromide/acetic acid (45 ml) solution was added to a solution of 2-(3-chlorophenyl)-2-oxoethyl thiocyanate (4.90 g, 23.2 mmol) in acetic acid (45 ml), and the mixture was stirred at 130° C. for 2 hours and at room temperature for 1 hour. Water (50 ml) was poured to the reaction mixture, and crystals were collected by filtration and washed with water to give 6.36 g (100%) of the desired product as a solid.

$^1$H-NMR (CDCl$_3$) δ; 7.30-7.38 (2H, m), 7.43 (1H, s), 7.71-7.74 (1H, m), 7.86-7.87 (1H, m).

(4) tert-Butyl 4-[4-(3-chlorophenyl)-1,3-thiazol-2-yl]piperazine-1-carboxylate

A solution of 2-bromo-4-(3-chlorophenyl)-1,3-thiazole (6.36 g, 23.2 mmol), tert-butyl piperazine-1-carboxylate (6.47 g, 34.7 mmol) and potassium carbonate (3.20 g, 23.2 mmol) in dimethylformamide (80 ml) was stirred at 120° C. for 14 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 5.19 g (59.0%) of the desired product as an oil.

¹H-NMR (CDCl₃) δ; 1.49 (9H, s), 3.51-3.60 (8H, m), 6.81 (1H, s), 7.22-7.32 (2H, m), 7.66-7.70 (1H, m), 7.83-7.84 (1H, m).

(5) 1-[4-(3-Chlorophenyl)-1,3-thiazol-2-yl]piperazine

A 4 N solution (50 ml) of hydrogen chloride in ethyl acetate was added to a solution of tert-butyl 4-[4-(3-chlorophenyl)-1,3-thiazol-2-yl]piperazine-1-carboxylate (5.15 g, 13.6 mmol) in ethyl acetate (100 ml), the mixture was stirred at room temperature for 6 hours, and the solvent was distilled off under reduced pressure. The residue was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 3.29 g (86.8%) of the desired product as an oil.

¹H-NMR (CDCl₃) δ; 2.98-3.03 (4H, m), 3.49-3.54 (4H, m), 6.78 (1H, s), 7.21-7.33 (2H, m), 7.66-7.71 (1H, m), 7.83-7.85 (1H, m).

(6) 4-[4-(3-Chlorophenyl)-1,3-thiazol-2-yl]-N-pyridin-3-ylpiperazine-1-carboxamide A mixture of 2,2,2-trichloroethyl pyridin-3-ylcarbamate (212 mg, 0.786 mmol), 1-[4-(3-chlorophenyl)-1,3-thiazol-2-yl]piperazine (200 mg, 0.715 mmol) and diisopropylethylamine (0.249 ml, 1.43 mmol) in dimethyl sulfoxide (2.5 ml) was stirred at 70° C. for 15 hours. Water was poured to the reaction mixture, and extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 113 mg (39.7%) of the desired product as a solid.

¹H-NMR (CDCl₃) δ; 3.68-3.70 (8H, m), 6.54 (1H, br s), 6.85 (1H, s), 7.26-7.33 (3H, m), 7.68-7.70 (1H, m), 7.84-7.85 (1H, m), 7.96-8.00 (1H, m), 8.30-8.32 (1H, m), 8.46-8.47 (1H, m).

Example 269

4-[4-(3-Cyanophenyl)-1,3-thiazol-2-yl]-N-pyridin-3-ylpiperazine-1-carboxamide (1) 3-(Bromoacetyl)benzonitrile Bromine (5.50 g, 34.4 mmol) was slowly added dropwise to a solution of 3-acetylbenzonitrile (5.00 g, 34.4 mmol) in diethyl ether (100 ml), and the mixture was stirred at room temperature for 4 hours. The reaction mixture was distilled off under reduced pressure to give the desired product as an oil.

¹H-NMR (CDCl₃) δ; 4.43 (2H, s), 7.62-7.69 (1H, m), 7.88-7.91 (1H, m), 8.20-8.28 (2H, m).

(2) 2-(3-Cyanophenyl)-2-oxoethyl thiocyanate

A solution of 3-(bromoacetyl)benzonitrile (7.72 g, 34.5 mmol) and potassium thiocyanate (3.35 g, 34.5 mmol) in ethanol (70 ml) was stirred at 80° C. for 2 hours. After cooling to room temperature, water (70 ml) was poured to the reaction mixture, and crystals were collected by filtration and washed with water to give 4.39 g (63.0% (2 steps)) of the desired product as a solid.

¹H-NMR (CDCl₃) δ; 4.69 (2H, s), 7.68-7.73 (1H, m), 7.94-7.97 (1H, m), 8.16-8.19 (1H, m), 8.23-8.25 (1H, m).

(3) 3-(2-Bromo-1,3-thiazol-4-yl)benzonitrile

A 25% hydrogen bromide/acetic acid (10 ml) solution was added to a solution of 2-(3-cyanophenyl)-2-oxoethyl thiocyanate (1.0 g, 4.94 mmol) in acetic acid (10 ml), and the mixture was stirred at 130° C. for 2 hours and at room temperature for 1 hour. Water was poured to the reaction mixture, and crystals were collected by filtration and washed with water to give 990 mg (75.6%) of the desired product as a solid.

¹H-NMR (CDCl₃) δ; 7.52 (1H, s), 7.53-7.57 (1H, m), 7.62-7.65 (1H, m), 8.07-8.10 (1H, m), 8.16-8.18 (1H, m).

(4) tert-Butyl 4-[4-(3-cyanophenyl)-1,3-thiazol-2-yl]piperazine-1-carboxylate

A solution of 3-(2-bromo-1,3-thiazol-4-yl)benzonitrile (990 mg, 4.90 mmol), tert-butyl piperazine-1-carboxylate (1.37 g, 7.34 mmol) and potassium carbonate (677 mg, 4.90 mmol) in dimethylformamide (16 ml) was stirred at 120° C. for 6 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 920 mg (50.7%) of the desired product as a solid.

¹H-NMR (CDCl₃) δ; 1.50 (9H, s), 3.52-3.61 (8H, m), 6.87 (1H, s), 7.44-7.49 (1H, m), 7.53-7.56 (1H, m), 8.00-8.04 (1H, m), 8.15-8.16 (1H, m).

(5) 3-(2-piperazin-1-yl-1,3-thiazol-4-yl)benzonitrile

A 4 N solution (25 ml) of hydrogen chloride in ethyl acetate was added to a solution of tert-butyl 4-[4-(3-cyanophenyl)-1,3-thiazol-2-yl]piperazine-1-carboxylate (920 mg, 2.48 mmol) in ethyl acetate (50 ml), the mixture was stirred at room temperature for 6 hours, and the solvent was distilled off under reduced pressure. The residue was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 438 mg (65.2%) of the desired product as a solid.

¹H-NMR (CDCl₃) δ; 2.99-3.04 (4H, m), 3.51-3.56 (4H, m), 6.84 (1H, s), 7.41-7.57 (2H, m), 8.00-8.05 (1H, m), 8.15-8.16 (1H, m).

(6) 4-[4-(3-Cyanophenyl)-1,3-thiazol-2-yl]-N-pyridin-3-ylpiperazine-1-carboxamide A mixture of 2,2,2-trichloroethyl pyridin-3-ylcarbamate (219 mg, 0.814 mmol), 1-[4-(3-chlorophenyl)-1,3-thiazol-2-yl]piperazine (200 mg, 0.740 mmol) and diisopropylethylamine (0.258 ml, 1.48 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 76.6 mg (26.5%) of the desired product as a solid.

¹H-NMR (CDCl₃) δ; 3.66-3.73 (8H, m), 6.65 (1H, br s), 6.91 (1H, s), 7.24-7.29 (1H, m), 7.45-7.50 (1H, m), 7.55-7.58 (1H, m), 7.96-8.04 (2H, m), 8.16-8.17 (1H, m), 8.30-8.32 (1H, m), 8.48-8.49 (1H, m).

Example 270

4-(4-Phenyl-1,3-thiazol-2-yl)-N-1,2,3-thiadiazol-5-ylpiperazine-1-carboxamide

(1) (1,3-Dioxo-1,3-dihydro-2H-isoindol-2-yl)acetaldehyde

A 6 N aqueous hydrochloric acid solution (20 ml) was added to a solution of 2-(2,2-diethoxyethyl)-1H-isoindol-1,3 (2H)-dione (1.0 g, 3.80 mmol) in acetone (20 ml), the mixture was stirred at room temperature for 6 hours, and the solvent was distilled off under reduced pressure. A saturated sodium hydrogen carbonate aqueous solution was added to the residue, and the mixture was extracted with chloroform. The extract was washed with water and dried over anhydrous magnesium sulfate, and the solvent was distilled off under reduced pressure to give the desired product as an oil.

$^1$H-NMR (CDCl$_3$) δ; 4.57 (2H, s), 7.72-7.79 (2H, m), 7.85-7.91 (2H, m), 9.66 (1H, s).

(2) Ethyl (2E)-2-[2-(1,3-dioxo-1,3-dihydro-2H-isoindol-2-yl)ethylidene]hydrazinecarboxylate A solution of ethyl carbazate (435 mg, 4.18 mmol) in toluene (6 ml) was slowly added dropwise to a solution of (1,3-dioxo-1,3-dihydro-2H-isoindol-2-yl)acetaldehyde (719 mg, 3.80 mmol) in toluene (12 ml), and the mixture was stirred at 75° C. for 3 hours. Crystals were collected by filtration and washed with diethyl ether to give 612 mg (58.5% (2 steps)) of the desired product as a solid.

$^1$H-NMR (CDCl$_3$) δ; 1.27 (3H, t, J=7.2 Hz), 4.22 (2H, q, J=7.2 Hz), 4.54 (2H, d, J=4.5 Hz), 7.72-7.79 (2H, m), 7.84-7.92 (3H, m).

(3) 2-(1,2,3-Thiadiazol-5-yl)-1H-isoindol-1,3(2H)-dione

Ethyl (2E)-2-[2-(1,3-dioxo-1,3-dihydro-2H-isoindol-2-yl)ethylidene]hydrazinecarboxylate (612 mg, 2.22 mmol) was slowly added to thionyl chloride (1.5 ml), and the mixture was stirred for 1 day. Crystals were collected by filtration and washed with ethyl acetate to give 308 mg (59.9%) of the desired product as a solid.

$^1$H-NMR (DMSO-d$_6$) δ; 7.95-8.11 (4H, m), 9.58 (1H, s).

(4) 2,2,2-Trichloroethyl 1,2,3-thiadiazol-5-ylcarbamate

A solution of hydrazine hydrate (140 mg, 2.78 mmol) in ethanol (1.8 ml) was slowly added to a solution of 2-(1,2,3-thiadiazol-5-yl)-1H-isoindol-1,3(2H)-dione (308 mg, 1.33 mmol) in ethanol (4.5 ml), and the mixture was stirred at 80° C. for 2 hours. A solid was filtered and washed with diethyl ether, and the residue was distilled off under reduced pressure to give 1,2,3-thiadiazol-5-amine as a solid.

To a solution of 1,2,3-thiadiazol-5-amine and pyridine (0.129 ml, 4.00 mmol) in tetrahydrofuran (4.5 ml) was added 2,2,2-trichloroethyl chloroformate (0.220 ml, 2.00 mmol) under ice-cooling, and the mixture was stirred at room temperature for 2 hours. Water was poured to the reaction mixture, and the mixture was extracted with ethyl acetate. The extract was washed with water, and dried over anhydrous magnesium sulfate, and the solvent was distilled off under reduced pressure. Hexane was added to the residue, and 190 mg (51.6%) of the desired product was collected by filtration as a solid.

$^1$H-NMR (CDCl$_3$) δ; 4.96 (2H, s), 8.50 (1H, s), 12.13 (1H, br s).

(5) 4-(4-Phenyl-1,3-thiazol-2-yl)-N-1,2,3-thiadiazol-5-ylpiperazine-1-carboxamide A mixture of 2,2,2-trichloroethyl 1,2,3-thiadiazol-5-ylcarbamate (190 mg, 0.686 mmol), 1-(4-phenyl-1,3-thiazol-2-yl) piperazine (153 mg, 0.624 mmol) and diisopropylethylamine (0.217 ml, 1.25 mmol) in dimethyl sulfoxide (2.5 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was recrystallized from a mixed solvent of hexane and tetrahydrofuran to give 159 mg (68.4%) of the desired product as a solid.

$^1$H-NMR (CDCl$_3$+DMSO-d$_6$) δ; 3.60-3.64 (4H, m), 3.77-3.78 (4H, m), 6.99 (1H, s), 7.24-7.29 (1H, m), 7.34-7.39 (2H, m), 7.83-7.86 (2H, m), 8.53 (1H, s), 10.89 (1H, br s).

Example 271

4-[4-(3-Methoxyphenyl)-1,3-thiazol-2-yl]-N-pyridin-3-ylpiperazine-1-carboxamide

(1) 2-Bromo-1-(3-methoxyphenyl)ethanone

Bromine (5.32 g, 33.3 mmol) was slowly added dropwise to a solution of 1-(3-methoxyphenyl)ethanone (5.00 g, 33.3 mmol) in diethyl ether (100 ml), and the mixture was stirred at room temperature for 4 hours. The reaction mixture was distilled off under reduced pressure to give the desired product as an oil quantitatively.

$^1$H-NMR (CDCl$_3$) δ; 3.86 (2H, s), 7.13-7.17 (1H, m), 7.37-7.42 (1H, m), 7.50-7.57 (2H, m).

(2) 2-(3-Methoxyphenyl)-2-oxoethyl thiocyanate

A solution of 2-bromo-1-(3-methoxyphenyl)ethanone (7.63 g, 33.3 mmol) and potassium thiocyanate (3.24 g, 33.3 mmol) in ethanol (70 ml) was stirred at 80° C. for 2 hours. After cooling to room temperature, water (70 ml) was added to the reaction mixture, and the mixture was extracted with chloroform. The extract was washed with water, and dried over anhydrous magnesium sulfate, and the solvent was distilled off under reduced pressure to give 6.71 g (97.2%) of the desired product as a solid.

$^1$H-NMR (CDCl$_3$) δ; 3.87 (3H, s), 4.72 (2H, s), 7.19-7.23 (1H, m), 7.40-7.52 (3H, m).

(3) 2-Bromo-4-(3-methoxyphenyl)-1,3-thiazole

A 25% hydrogen bromide/acetic acid (65 ml) solution was added to a solution of 2-(3-methoxyphenyl)-2-oxoethyl thiocyanate (6.50 g, 31.4 mmol) in acetic acid (65 ml), and the mixture was stirred at 130° C. for 2 hours and at room temperature for 1 hour. Water was poured to the reaction mixture, and the mixture was extracted with chloroform. The extract was washed with water, and dried over anhydrous magnesium sulfate, and the solvent was distilled off under reduced pressure. The residue was purified by silica gel column chromatography (hexane:ethyl acetate=9:1) to give 3.80 g (44.8%) of the desired product as a solid.

$^1$H-NMR (CDCl$_3$) δ; 3.87 (3H, s), 6.88-6.92 (1H, m), 7.29-7.35 (1H, m), 7.40 (1H, s), 7.40-7.43 (2H, m).

(4) tert-Butyl 4-[4-(3-methoxyphenyl)-1,3-thiazol-2-yl]piperazine-1-carboxylate A solution of 2-bromo-4-(3-methoxyphenyl)-1,3-thiazole (3.70 g, 13.7 mmol), tert-butyl piperazine-1-carboxylate (3.83 g, 20.5 mmol) and potassium carbonate (1.89 g, 13.7 mmol) in dimethylformamide (50 ml) was stirred at 120° C. for 7 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 2.63 g (51.2%) of the desired product as a solid.

$^1$H-NMR (CDCl$_3$) δ; 1.49 (9H, s), 3.50-3.60 (8H, m), 3.85 (3H, s), 6.79 (1H, s), 6.82-6.86 (1H, m), 7.25-7.31 (1H, m), 7.38-7.41 (2H, m).

(5) 1-[4-(3-Methoxyphenyl)-1,3-thiazol-2-yl]piperazine

A 4 N solution (50 ml) of hydrogen chloride in ethyl acetate was added to a solution of tert-butyl 4-[4-(3-methoxyphenyl)-1,3-thiazol-2-yl]piperazine-1-carboxylate (2.63 g, 7.00 mmol) in ethyl acetate (50 ml), the mixture was stirred at room temperature for 20 hours, and the solvent was distilled off under reduced pressure. The residue was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 1.43 g (74.3%) of the desired product as a solid.

$^1$H-NMR (CDCl$_3$) δ; 2.98-3.03 (4H, m), 3.49-3.55 (4H, m), 3.85 (3H, s), 6.76 (1H, s), 6.80-6.86 (1H, m), 7.23-7.32 (1H, m), 7.38-7.43 (2H, m).

(6) 4-[4-(3-Methoxyphenyl)-1,3-thiazol-2-yl]-N-pyridin-3-ylpiperazine-1-carboxamide A mixture of 2,2,2-trichloroethyl pyridin-3-ylcarbamate (215 mg, 0.799 mmol), 1-[4-(3-methoxyphenyl)-1,3-thiazol-2-yl]piperazine (200 mg, 0.726 mmol) and diisopropylethylamine (0.253 ml, 1.45 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and ethyl acetate to give 168 mg (58.5%) of the desired product as a solid.

$^1$H-NMR (CDCl$_3$) δ; 3.64-3.73 (8H, m), 3.86 (3H, s), 6.57 (1H, br s), 6.83 (1H, s), 6.83-6.87 (1H, m), 7.24-7.32 (2H, m), 7.39-7.42 (2H, m), 7.97-8.01 (1H, m), 8.30-8.32 (1H, m), 8.46-8.47 (1H, m).

Example 272

4-[4-(2,3-Difluorophenyl)-1,3-thiazol-2-yl]-N-pyridazin-3-ylpiperazine-1-carboxamide A mixture of 2,2,2-trichloroethyl pyridazin-3-ylcarbamate (212 mg, 0.782 mmol), 1-[4-(2,3-difluorophenyl)-1,3-thiazol-2-yl]piperazine (200 mg, 0.711 mmol) and diisopropylethylamine (0.248 ml, 1.42 mmol) in dimethyl sulfoxide (2.5 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 101 mg (35.2%) of the desired product as a solid. mp 215-216° C.

$^1$H-NMR (CDCl$_3$) δ; 3.65-3.67 (4H, m), 3.75-3.80 (4H, m), 7.03-7.16 (3H, m), 7.45 (1H, br s), 7.86-7.92 (1H, m), 8.29 (1H, br s), 8.58 (1H, br s), 8.86 (1H, br s).

Example 273

4-[4-(2,4-Difluorophenyl)-1,3-thiazol-2-yl]-N-pyridazin-3-ylpiperazine-1-carboxamide A mixture of 2,2,2-trichloroethyl pyridazin-3-ylcarbamate (212 mg, 0.782 mmol), 1-[4-(2,4-difluorophenyl)-1,3-thiazol-2-yl]piperazine (200 mg, 0.711 mmol) and diisopropylethylamine (0.248 ml, 1.42 mmol) in dimethyl sulfoxide (2.5 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 136 mg (47.4%) of the desired product as a solid.

$^1$H-NMR (CDCl$_3$) δ; 3.65 (4H, br s), 3.79 (4H, br s), 6.82-6.96 (2H, m), 7.05-7.06 (1H, m), 7.43 (1H, br s), 8.09-8.17 (1H, m), 8.28 (1H, br s), 8.44 (1H, br s), 8.85 (1H, br s).

Example 274

N-Pyridin-3-yl-4-{4-[3-(trifluoromethyl)phenyl]-1,3-thiazol-2-yl}piperazine-1-carboxamide

(1) 2-Bromo-1-[3-(trifluoromethyl)phenyl]ethanone

Bromine (4.25 g, 26.6 mmol) was slowly added dropwise to a solution of 1-[3-(trifluoromethyl)phenyl]ethanone (5.00 g, 26.6 mmol) in diethyl ether (100 ml), and the mixture was stirred at room temperature for 4 hours. The reaction mixture was distilled off under reduced pressure to give the desired product as an oil quantitatively.

$^1$H-NMR (CDCl$_3$) δ; 4.46 (2H, s), 7.64-7.69 (1H, m), 7.86-7.89 (1H, m), 8.17-8.19 (1H, m), 8.25 (1H, br s).

(2) 2-Oxo-2-[3-(trifluoromethyl)phenyl]ethyl thiocyanate

A solution of 2-bromo-1-[3-(trifluoromethyl)phenyl]ethanone (7.10 g, 26.6 mmol) and potassium thiocyanate (2.58 g, 26.6 mmol) in ethanol (70 ml) was stirred at 80° C. for 2 hours. After cooling to room temperature, water (70 ml) was poured to the reaction mixture, and crystals were collected by filtration, and washed with water to give 3.88 g (59.5%) of the desired product as a solid.

$^1$H-NMR (DMSO-d$_6$) δ; 5.06 (2H, s), 7.73-7.78 (1H, m), 7.94-7.97 (1H, m), 8.27-8.31 (2H, m).

(3) 2-Bromo-4-[3-(trifluoromethyl)phenyl]-1,3-thiazole

A 25% hydrogen bromide/acetic acid (35 ml) solution was added to a solution of 2-oxo-2-[3-(trifluoromethyl)phenyl]ethyl thiocyanate (3.88 g, 15.8 mmol) in acetic acid (35 ml), and the mixture was stirred at 130° C. for 2 hours and at room temperature for 1 hour. Water was poured to the reaction mixture, and the mixture was extracted with chloroform. The extract was washed with water, and dried over anhydrous magnesium sulfate, and the solvent was distilled off under reduced pressure. The residue was purified by silica gel column chromatography (hexane:ethyl acetate=9:1) to give 2.88 g (59.1%) of the desired product as an oil.

$^1$H-NMR (CDCl$_3$) δ; 7.51-7.63 (3H, m), 8.02-8.05 (1H, m), 8.12-8.13 (1H, m).

(4) tert-Butyl 4-{4-[3-(trifluoromethyl)phenyl]-1,3-thiazol-2-yl}piperazine-1-carboxylate A solution of 2-bromo-4-[3-(trifluoromethyl)phenyl]-1,3-thiazole (2.88 g, 9.35 mmol), tert-butyl piperazine-1-carboxylate (3.48 g, 18.7 mmol) and potassium carbonate (1.29 g, 9.35 mmol) in dimethylformamide (30 ml) was stirred at 120° C. for 12 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 1.85 g (47.9%) of the desired product as an oil.

$^1$H-NMR (CDCl$_3$) δ; 1.49 (9H, s), 3.48-3.61 (8H, m), 6.87 (1H, s), 7.45-7.54 (2H, m), 7.97-8.00 (1H, m), 8.09 (1H, br s).

(5) 1-{4-[3-(Trifluoromethyl)phenyl]-1,3-thiazol-2-yl}piperazine

A 4 N solution (50 ml) of hydrogen chloride in ethyl acetate was added to a solution of tert-butyl 4-[4-(3-trifluoromethylphenyl)-1,3-thiazol-2-yl]piperazine-1-carboxylate (1.85 g, 4.74 mmol) in ethyl acetate (50 ml), an the mixture was stirred at room temperature for 12 hours, and the solvent was distilled off under reduced pressure. The residue was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 678 mg (47.9%) of the desired product as an oil.

$^1$H-NMR (CDCl$_3$) δ; 3.00-3.04 (4H, m), 3.52-3.55 (4H, m), 6.84 (1H, s), 7.44-7.53 (2H, m), 7.98-8.00 (1H, m), 8.10 (1H, br s).

(6) N-Pyridin-3-yl-4-{4-[3-(trifluoromethyl)phenyl]-1,3-thiazol-2-yl}piperazine-1-carboxamide A mixture of 2,2,2-trichloroethyl pyridin-3-ylcarbamate (189 mg, 0.702 mmol), 1-[4-(3-trifluoromethylphenyl)-1,3-thiazol-2-yl]piperazine (200 mg, 0.638 mmol) and diisopropylethylamine (0.222 ml, 1.28 mmol) in dimethyl sulfoxide (2.5 ml) was stirred at 70° C. for 20 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 75.4 mg (27.2%) of the desired product as a solid.

$^1$H-NMR (CDCl$_3$) δ; 3.66-3.73 (8H, m), 6.71 (1H, br s), 6.91 (1H, s), 7.24-7.29 (1H, m), 7.46-7.56 (2H, m), 7.98-8.00 (2H, m), 8.10 (1H, br s), 8.30-8.31 (1H, m), 8.47-8.48 (1H, m).

Example 275

4-[4-(3-Methylphenyl)-1,3-thiazol-2-yl]-N-pyridin-3-ylpiperazine-1-carboxamide (1) 2-Bromo-1-(3-methylphenyl)ethanone Bromine (2.38 g, 14.9 mmol) was slowly added dropwise to a solution of 1-[3-methylphenyl]ethanone (2.00 g, 14.9 mmol) in diethyl ether (50 ml), and the mixture was stirred at room temperature for 4 hours. The reaction mixture was distilled off under reduced pressure to give 3.03 g (95.3%) of the desired product as an oil.

$^1$H-NMR (CDCl$_3$) δ; 2.43 (3H, s), 4.45 (2H, s), 7.35-7.44 (2H, m), 7.76-7.80 (2H, m).

(2) 2-(3-Methylphenyl)-2-oxoethyl thiocyanate

A solution of 2-bromo-1-(3-methylphenyl)ethanone (3.03 g, 14.2 mmol) and potassium thiocyanate (1.45 g, 14.2 mmol) in ethanol (30 ml) was stirred at 80° C. for 2 hours. After cooling to room temperature, water (30 ml) was poured to the reaction mixture, and crystals were collected by filtration and washed with water to give 2.29 mg (84.2%) of the desired product as a solid.

$^1$H-NMR (CDCl$_3$) δ; 2.44 (3H, s), 4.74 (2H, s), 7.38-7.50 (2H, m), 7.71-7.75 (2H, m).

(3) 2-Bromo-4-(3-methylphenyl)-1,3-thiazole

A 25% hydrogen bromide/acetic acid (20 ml) solution was added to a solution of 2-(3-methylphenyl)-2-oxoethyl thiocyanate (2.29 g, 12.0 mmol) in acetic acid (20 ml), and the mixture was stirred at 130° C. for 2 hours. Water was poured to the reaction mixture, and the mixture was extracted with chloroform. The extract was washed with water, and dried over anhydrous magnesium sulfate, and the solvent was distilled off under reduced pressure. The residue was purified by silica gel column chromatography (hexane:ethyl acetate=9:1) to give 2.03 g (66.8%) of the desired product as an oil.

$^1$H-NMR (CDCl$_3$) δ; 2.40 (3H, s), 7.15-7.19 (1H, m), 7.28-7.33 (1H, m), 7.39 (1H, s), 7.61-7.64 (1H, m), 7.70-7.71 (1H, m).

(4) tert-Butyl 4-[4-(3-methylphenyl)-1,3-thiazol-2-yl]piperazine-1-carboxylate

A solution of 2-bromo-4-(3-methylphenyl)-1,3-thiazole (2.03 g, 7.99 mmol), tert-butyl piperazine-1-carboxylate (2.98 g, 16.0 mmol) and potassium carbonate (1.10 g, 7.99 mmol) in dimethylformamide (25 ml) was stirred at 120° C. for 12 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 2.00 g (69.7%) of the desired product as an oil.

$^1$H-NMR (CDCl$_3$) δ; 1.49 (9H, s), 3.50-3.60 (8H, m), 6.77 (1H, s), 7.08-7.11 (1H, m), 7.23-7.28 (1H, m), 7.59-7.62 (1H, m), 7.65-7.66 (1H, m).

(5) 1-[4-(3-Methylphenyl)-1,3-thiazol-2-yl]piperazine

A 4 N solution (50 ml) of hydrogen chloride in ethyl acetate was added to a solution of tert-butyl 4-[4-(3-methylphenyl)-1,3-thiazol-2-yl]piperazine-1-carboxylate (2.00 g, 5.56 mmol) in ethyl acetate (50 ml), the mixture was stirred at room temperature for 12 hours, and the solvent was distilled off under reduced pressure. The residue was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 910 mg (62.9%) of the desired product as an oil.

$^1$H-NMR (CDCl$_3$) δ; 2.38 (3H, s), 2.99-3.02 (4H, m), 3.50-3.54 (4H, m), 6.75 (1H, s), 7.07-7.10 (1H, m), 7.23-7.28 (1H, m), 7.60-7.66 (2H, m).

(6) 4-[4-(3-Methylphenyl)-1,3-thiazol-2-yl]-N-pyridin-3-ylpiperazine-1-carboxamide A mixture of 2,2,2-trichloroethyl pyridin-3-ylcarbamate (229 mg, 0.848 mmol), 1-[4-(3-methylphenyl)-1,3-thiazol-2-yl]piperazine (200 mg, 0.771 mmol) and diisopropylethylamine (0.269 ml, 1.54 mmol) in dimethyl sulfoxide (2.5 ml) was stirred at 70° C. for 20 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 103 mg (35.1%) of the desired product as a solid. mp 157-158° C.

$^1$H-NMR (CDCl$_3$) δ; 2.39 (3H, s), 3.64-3.71 (8H, m), 6.72 (1H, br s), 6.81 (1H, s), 7.10-7.12 (1H, m), 7.24-7.30 (2H, m), 7.60-7.66 (2H, m), 7.97-8.00 (1H, m), 8.29-8.30 (1H, m), 8.45-8.46 (1H, m).

Example 276

4-[4-(3-Chlorophenyl)-1,3-thiazol-2-yl]-N-(3,4-dimethylisoxazol-5-yl)piperazine-1-carboxamide A mixture of 2,2,2-trichloroethyl (3,4-dimethylisoxazol-5-yl)carbamate (226 mg, 0.786 mmol), 1-[4-(3-chlorophenyl)-1,3-thiazol-2-yl]piperazine (200 mg, 0.715 mmol) and diisopropylethylamine (0.249 ml, 1.43 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=1:1), and recrystallized from a mixed solvent of hexane and ethyl acetate to give 124 mg (41.4%) of the desired product as a solid. mp 201-202° C.

$^1$H-NMR (CDCl$_3$) δ; 1.88 (3H, s), 2.19 (3H, s), 3.60-3.67 (8H, m), 6.84 (1H, s), 7.02 (1H, br s), 7.24-7.33 (2H, m), 7.67-7.70 (1H, m), 7.83-7.85 (1H, m).

Example 277

N-(3,4-Dimethylisoxazol-5-yl)-4-[4-(3-methoxyphenyl)-1,3-thiazol-2-yl]piperazine-1-carboxamide A mixture of 2,2,2-trichloroethyl (3,4-dimethylisoxazol-5-yl)carbamate (230 mg, 0.799 mmol), 1-[4-(3-methoxyphenyl)-1,3-thiazol-2-yl]piperazine (200 mg, 0.726 mmol) and diisopropylethylamine (0.253 ml, 1.45 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=1:1), and recrystallized from a mixed solvent of hexane and ethyl acetate to give 129 mg (42.8%) of the desired product as a solid. mp 158-159° C.

$^1$H-NMR (CDCl$_3$) δ; 1.88 (3H, s), 2.20 (3H, s), 3.62-3.67 (8H, m), 3.86 (3H, s), 6.82-6.89 (3H, m), 7.26-7.32 (1H, m), 7.39-7.41 (2H, m).

Example 278

N-(3,4-Dimethylisoxazol-5-yl)-4-{4-[3-(trifluoromethyl)phenyl]-1,3-thiazol-2-yl}piperazine-1-carboxamide A mixture of 2,2,2-trichloroethyl (3,4-dimethylisoxazol-5-yl)carbamate (154 mg, 0.536 mmol), 1-[4-(3-trifluoromethylphenyl)-1,3-thiazol-2-yl]piperazine (150 mg, 0.487 mmol) and diisopropylethylamine (0.170 ml, 0.974 mmol) in dimethyl sulfoxide (2.0 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=1:1), and recrystallized from a mixed solvent of hexane and tetrahydrofuran to give 94.8 mg (43.1%) of the desired product as a solid. mp 230-231° C.

$^1$H-NMR (CDCl$_3$) δ; 1.89 (3H, s), 2.21 (3H, s), 3.64-3.70 (8H, m), 6.71 (1H, br s), 6.91 (1H, s), 7.46-7.55 (2H, m), 7.97-8.00 (1H, m), 8.10 (1H, br s).

Example 279

4-[4-(3-Cyanophenyl)-1,3-thiazol-2-yl]-N-(3,4-dimethylisoxazol-5-yl)piperazine-1-carboxamide A mixture of 2,2,2-trichloroethyl (3,4-dimethylisoxazol-5-yl)carbamate (277 mg, 0.964 mmol), 3-(2-piperazin-1-yl-1,3-thiazol-4-yl)benzonitrile (237 mg, 0.877 mmol) and diisopropylethylamine (0.305 ml, 1.75 mmol) in dimethyl sulfoxide (2.9 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=1:1), and recrystallized from a mixed solvent of hexane and ethyl acetate to give 142 mg (39.6%) of the desired product as a solid.

$^1$H-NMR (DMSO-d$_6$) δ; 1.77 (3H, s), 2.13 (3H, s), 3.54-3.62 (8H, m), 7.56 (1H, s), 7.61 (1H, dd, J=7.6, 7.6Hz), 7.75 (1H, d, J=7.6 Hz), 8.20 (1H, d, J=7.6 Hz), 8.31 (1H, br s), 9.31 (1H, br s).

Example 280

N-(3,4-Dimethylisoxazol-5-yl)-4-[4-(3-methylphenyl)-1,3-thiazol-2-yl]piperazine-1-carboxamide A mixture of 2,2,2-trichloroethyl (3,4-dimethylisoxazol-5-yl)carbamate (244 mg, 0.848 mmol), 1-[4-(3-methylphenyl)-1,3-thiazol-2-yl]piperazine (200 mg, 0.771 mmol) and diisopropylethylamine (0.269 ml, 1.54 mmol) in dimethyl sulfoxide (2.5 ml) was stirred at 70° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=1:1), and recrystallized from a mixed solvent of hexane and ethyl acetate to give 132 mg (43.0%) of the desired product as a solid. mp 175-176° C.

$^1$H-NMR (CDCl$_3$) δ; 1.88 (3H, s), 2.20 (3H, s), 2.39 (3H, s), 3.60-31.75 (8H, m), 6.80 (1H, s), 6.88 (1H, br s), 7.09-7.11 (1H, m), 7.24-7.29 (1H, m), 7.60-7.65 (2H, m).

Example 281

4-[4-(2-Chlorophenyl)-1,3-thiazol-2-yl]-N-pyridin-3-ylpiperazine-1-carboxamide (1) 2-(2-Chlorophenyl)-2-oxoethyl thiocyanate Bromine (5.18 g, 32.3 mmol) was slowly added dropwise to a solution of 1-[2-chlorophenyl]ethanone (5.00 g, 32.3 mmol) in diethyl ether (100 ml), and the mixture was stirred at room temperature for 4 hours. The reaction mixture was distilled off under reduced pressure to give 2-bromo-1-(2-chlorophenyl)ethanone as an oil quantitatively.

A solution of 2-bromo-1-(2-chlorophenyl)ethanone (7.55 g, 32.3 mmol) and potassium thiocyanate (3.14 g, 32.3 mmol) in ethanol (70 ml) was stirred at 80° C. for 2 hours. After cooling to room temperature, water (70 ml) was poured to the reaction mixture, and crystals were collected by filtration and washed with water to give 5.15 g (75.3%) of the desired product as a solid.

$^1$H-NMR (CDCl$_3$) δ; 4.69 (2H, s), 7.37-7.54 (3H, m), 7.69-7.74 (1H, m).

(2) 2-Bromo-4-(2-chlorophenyl)-1,3-thiazole

A 25% hydrogen bromide/acetic acid (50 ml) solution was added to a solution of 2-(2-chlorophenyl)-2-oxoethyl thiocyanate (5.15 g, 24.3 mmol) in acetic acid (50 ml), and the mixture was stirred at 130° C. for 2 hours. Water (100 ml) was poured to the reaction mixture, and crystals were collected by filtration and washed with water to give 4.48 g (67.1%) of the desired product as a solid.

$^1$H-NMR (CDCl$_3$) δ; 7.25-7.36 (2H, m), 7.44-7.47 (1H, m), 7.78 (1H, s), 7.91-7.94 (1H, m).

(3) tert-Butyl 4-[4-(2-chlorophenyl)-1,3-thiazol-2-yl]piperazine-1-carboxylate

A solution of 2-bromo-4-(2-chlorophenyl)-1,3-thiazole (4.48 g, 16.3 mmol), tert-butyl piperazine-1-carboxylate (6.08 g, 32.6 mmol) and potassium carbonate (2.26 g, 16.3 mmol) in dimethylformamide (50 ml) was stirred at 120° C. for 15 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 4.15 g (66.9%) of the desired product as a solid.

$^1$H-NMR (CDCl$_3$) δ; 1.49 (9H, s), 3.48-3.62 (8H, m), 7.16 (1H, s), 7.16-7.34 (2H, m), 7.40-7.44 (1H, m), 7.90-7.95 (1H, m).

(4) 1-[4-(2-Chlorophenyl)-1,3-thiazol-2-yl]piperazine

A 4 N solution (100 ml) of hydrogen chloride in ethyl acetate was added to a solution of tert-butyl 4-[4-(2-chlorophenyl)-1,3-thiazol-2-yl]piperazine-1-carboxylate (4.15 g, 10.9 mmol) in ethyl acetate (100 ml), the mixture was stirred at room temperature for 5 hours, and the solvent was distilled off under reduced pressure. The residue was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 2.07 g (67.6%) of the desired product as a solid.

$^1$H-NMR (CDCl$_3$) δ; 2.98-3.02 (4H, m), 3.49-3.52 (4H, m), 7.13 (1H, s), 7.17-7.22 (1H, m), 7.26-7.31 (1H, m), 7.39-7.43 (1H, m), 7.92-7.95 (1H, m).

(5) 4-[4-(2-Chlorophenyl)-1,3-thiazol-2-yl]-N-pyridin-3-ylpiperazine-1-carboxamide A mixture of 2,2,2-trichloroethyl pyridin-3-ylcarbamate (212 mg, 0.786 mmol), 1-[4-(3-chlorophenyl)-1,3-thiazol-2-yl]piperazine (200 mg, 0.715 mmol) and diisopropylethylamine (0.249 ml, 1.43 mmol) in dimethyl sulfoxide (2.5 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and ethyl acetate to give 101 mg (35.3%) of the desired product as a solid.

$^1$H-NMR (CDCl$_3$) δ; 3.62-3.72 (8H, m), 6.64 (1H, br s), 7.18-7.33 (4H, m), 7.42-7.45 (1H, m), 7.89-7.93 (1H, m), 7.96-8.00 (1H, m), 8.29-8.31 (1H, m), 8.45-8.46 (1H, m).

Example 282

4-[4-(2-Chlorophenyl)-1,3-thiazol-2-yl]-N-(3,4-dimethylisoxazol-5-yl)piperazine-1-carboxamide A mixture of 2,2,2-trichloroethyl (3,4-dimethylisoxazol-5-yl)carbamate (226 mg, 0.786 mmol), 1-[4-(3-methylphenyl)-1,3-thiazol-2-yl]piperazine (200 mg, 0.715 mmol) and diisopropylethylamine (0.249 ml, 1.43 mmol) in dimethyl sulfoxide (2.5 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=1:1), and recrystallized from a mixed solvent of hexane and ethyl acetate to give 89.9 mg (30.1%) of the desired product as a solid.

$^1$H-NMR (CDCl$_3$) δ; 1.87 (3H, s), 2.19 (3H, s), 3.59-3.66 (8H, m), 6.94 (1H, br s), 7.17 (1H, s), 7.19-7.33 (2H, m), 7.41-7.44 (1H, m), 7.89-7.92 (1H, m).

Example 283

4-[4-(2,3-Dichlorophenyl)-1,3-thiazol-2-yl]-N-pyridin-3-ylpiperazine-1-carboxamide (1) 2-(2,3-Dichlorophenyl)-2-oxoethyl thiocyanate Bromine (2.54 g, 15.9 mmol) was slowly added dropwise to a solution of 1-(2,3-dichlorophenyl)ethanone (3.00 g, 15.9 mmol) in diethyl ether (60 ml), and the mixture was stirred at room temperature for 4 hours. The reaction mixture was distilled off under reduced pressure to give 2-bromo-1-(2,3-dichlorophenyl)ethanone as an oil quantitatively.

A solution of 2-bromo-1-(2,3-dichlorophenyl)ethanone (4.25 g, 15.9 mmol) and potassium thiocyanate (1.54 g, 15.9 mmol) in ethanol (40 ml) was stirred at 80° C. for 2 hours. After cooling to room temperature, water (70 ml) was poured to the reaction mixture, and crystals were collected by filtration and washed with water to give 3.10 g (79.5%) of the desired product as a solid.

$^1$H-NMR (CDCl$_3$) δ; 4.58 (2H, s), 7.33-7.40 (1H, m), 7.48-7.53 (1H, m), 7.65-7.70 (1H, m).

(2) 2-Bromo-4-(2,3-dichlorophenyl)-1,3-thiazole

A 25% hydrogen bromide/acetic acid (30 ml) solution was added to a solution of 2-(2,3-dichlorophenyl)-2-oxoethyl thiocyanate (3.10 g, 12.6 mmol) in acetic acid (30 ml), and the mixture was stirred at 130° C. for 2 hours. Water (60 ml) was poured to the reaction mixture, and crystals were collected by filtration and washed with water to give 3.68 g (94.6%) of the desired product as a solid.

$^1$H-NMR (CDCl$_3$) δ; 7.25-7.31 (1H, m), 7.47-7.50 (1H, m), 7.77-7.80 (2H, m).

(3) tert-Butyl 4-[4-(2,3-dichlorophenyl)-1,3-thiazol-2-yl]piperazine-1-carboxylate A solution of 2-bromo-4-(2,3-dichlorophenyl)-1,3-thiazole (3.68 mg, 12.3 mmol), tert-butyl piperazine-1-carboxylate (4.44 g, 24.6 mmol) and potassium carbonate (1.65 g, 12.3 mmol) in dimethylformamide (40 ml) was stirred at 120° C. for 13 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 376 mg (7.6%) of the desired product as a solid.

$^1$H-NMR (CDCl$_3$) δ; 1.49 (9H, s), 3.48-3.59 (8H, m), 7.11 (1H, s), 7.18-7.26 (1H, m), 7.39-7.44 (1H, m), 7.75-7.78 (1H, m).

(4) 1-[4-(2,3-Dichlorophenyl)-1,3-thiazol-2-yl]piperazine

A 4 N solution (15 ml) of hydrogen chloride in ethyl acetate was added to a solution of tert-butyl 4-[4-(2,3-dichlorophenyl)-1,3-thiazol-2-yl]piperazine-1-carboxylate (370 mg, 0.893 mmol) in ethyl acetate (15 ml), the mixture was stirred at room temperature for 14 hours, and the solvent was distilled off under reduced pressure. The residue was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 231 mg (82.1%) of the desired product as a solid.

$^1$H-NMR (CDCl$_3$) δ; 2.99-3.02 (4H, m), 3.48-3.52 (4H, m), 7.08 (1H, s), 7.19-7.24 (1H, m), 7.38-7.42 (1H, m), 7.77-7.80 (1H, m).

(5) 4-[4-(2,3-Dichlorophenyl)-1,3-thiazol-2-yl]-N-pyridin-3-ylpiperazine-1-carboxamide A mixture of 2,2,2-trichloroethyl pyridin-3-ylcarbamate (94.3 mg, 0.350 mmol), 1-[4-(2,3-dichlorophenyl)-1,3-thiazol-2-yl]piperazine (100 mg, 0.318 mmol) and diisopropylethylamine (0.111 ml, 0.636 mmol) in dimethyl sulfoxide (1.0 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and ethyl acetate to give 34.3 mg (24.8%) of the desired product as a solid. mp 132-133° C.

$^1$H-NMR (CDCl$_3$) δ; 3.63-3.72 (8H, m), 6.54 (1H, br s), 7.13 (1H s), 7.21-7.28 (2H, m), 7.41-7.44 (1H, m), 7.74-7.78 (1H, m), 7.96-8.01 (1H, m), 8.30-8.32 (1H, m), 8.46-8.47 (1H, m).

Example 284

4-[4-(2,3-Dichlorophenyl)-1,3-thiazol-2-yl]-N-(3,4-dimethylisoxazol-5-yl)piperazine-1-carboxamide A mixture of 2,2,2-trichloroethyl (3,4-dimethylisoxazol-5-yl)carbamate (121 mg, 0.420 mmol), 1-[4-(2,3-dichlorophenyl)-1,3-thiazol-2-yl]piperazine (120 mg, 0.382 mmol) and diisopropylethylamine (0.133 ml, 0.764 mmol) in dimethyl sulfoxide (1.2 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate:hexane=1:1), and recrystallized from a mixed solvent of hexane and ethyl acetate to give 27.0 mg (15.6%) of the desired product as a solid. mp 175-176° C.

$^1$H-NMR (CDCl$_3$) δ; 1.88 (3H, s), 2.20 (3H, s), 3.61-3.67 (8H, m), 6.75 (1H, br s), 7.12 (1H, s), 7.21-7.26 (1H, m), 7.41-7.44 (1H, m), 7.74-7.77 (1H, m).

Example 285

4-[4-(2,4-Dichlorophenyl)-1,3-thiazol-2-yl]-N-pyridin-3-ylpiperazine-1-carboxamide (1) 2-(2,4-Dichlorophenyl)-2-oxoethyl thiocyanate Bromine (4.23 g, 26.4 mmol) was slowly added dropwise to a solution of 1-(2,4-dichlorophenyl)ethanone (5.00 g, 26.4 mmol) in diethyl ether (100 ml), and the mixture was stirred at room temperature for 4 hours. The reaction mixture was distilled off under reduced pressure to give 2-bromo-1-(2,4-dichlorophenyl)ethanone as an oil quantitatively.

A solution of 2-bromo-1-(2,4-dichlorophenyl)ethanone (7.09 g, 26.5 mmol) and potassium thiocyanate (2.57 g, 26.5 mmol) in ethanol (70 ml) was stirred at 80° C. for 2 hours. After cooling to room temperature, water (70 ml) was poured to the reaction mixture, and crystals were collected by filtration and washed with water to give 5.97 g (91.7%) of the desired product as a solid.

$^1$H-NMR (CDCl$_3$) δ; 4.67 (2H, s), 7.38-7.43 (1H, m), 7.52-7.53 (1H, m), 7.70-7.74 (1H, m).

(2) 2-Bromo-4-(2,4-dichlorophenyl)-1,3-thiazole

A 25% hydrogen bromide/acetic acid (60 ml) solution was added to a solution of 2-(2,4-dichlorophenyl)-2-oxoethyl thiocyanate (5.97 g, 24.3 mmol) in acetic acid (60 ml), and the mixture was stirred at 130° C. for 2 hours. Water (120 ml) was poured to the reaction mixture, and crystals were collected by filtration and washed with water to give 6.89 g (92.0%) of the desired product as a solid.

¹H-NMR (CDCl₃) δ; 7.31-7.35 (1H, m), 7.47-7.48 (1H, m), 7.81 (1H, s), 7.90-7.93 (1H, m).

(3) tert-Butyl 4-[4-(2,4-dichlorophenyl)-1,3-thiazol-2-yl]piperazine-1-carboxylate A solution of 2-bromo-4-(2,4-dichlorophenyl)-1,3-thiazole (6.89 g, 22.3 mmol), tert-butyl piperazine-1-carboxylate (8.31 g, 44.6 mmol) and potassium carbonate (3.08 g, 22.3 mmol) in dimethylformamide (70 ml) was stirred at 120° C. for 13 hours. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (hexane:ethyl acetate=9:1) to give 2.31 g (25.0%) of the desired product as a solid.

¹H-NMR (CDCl₃) δ; 1.49 (9H, s), 3.53-3.56 (8H, m), 7.17-7.18 (1H, m), 7.24-7.30 (1H, m), 7.43-7.44 (1H, m), 7.90-7.94 (1H, m).

(4) 1-[4-(2,4-Dichlorophenyl)-1,3-thiazol-2-yl]piperazine

A 4 N solution (70 ml) of hydrogen chloride in ethyl acetate was added to a solution of tert-butyl 4-[4-(2,4-dichlorophenyl)-1,3-thiazol-2-yl]piperazine-1-carboxylate (2.31 g, 5.58 mmol) in ethyl acetate (70 ml), the mixture was stirred at room temperature for 12 hours, and the solvent was distilled off under reduced pressure. The residue was dissolved in water, neutralized with a 1 N sodium hydroxide aqueous solution, and extracted with chloroform. The extract was washed with water, and dried over anhydrous magnesium sulfate, and the solvent was distilled off under reduced pressure to give 1.46 g (83.3%) of the desired product as a solid.

¹H-NMR (CDCl₃) δ; 2.98-3.02 (4H, m), 3.48-3.51 (4H, m), 7.15 (1H, s), 7.24-7.28 (1H, m), 7.42-7.43 (1H, m), 7.91-7.94 (1H, m).

(5) 4-[4-(2,4-Dichlorophenyl)-1,3-thiazol-2-yl]-N-pyridin-3-ylpiperazine-1-carboxamide A mixture of 2,2,2-trichloroethyl pyridin-3-ylcarbamate (189 mg, 0.700 mmol), 1-[4-(2,4-dichlorophenyl)-1,3-thiazol-2-yl]piperazine (200 mg, 0.636 mmol) and diisopropylethylamine (0.222 ml, 1.27 mmol) in dimethyl sulfoxide (2.5 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was purified by silica gel column chromatography (ethyl acetate), and recrystallized from a mixed solvent of hexane and tetrahydrofuran to give 126 mg (45.5%) of the desired product as a solid.

¹H-NMR (CDCl₃) δ; 3.62-3.75 (8H, m), 6.72 (1H, br s), 7.20 (1H, s), 7.24-7.30 (2H, m), 7.44-7.45 (1H, m), 7.89-7.91 (1H, m), 7.96-8.00 (1H, m), 8.29-8.31 (1H, m), 8.46-8.47 (1H, m).

Example 286

4-[4-(2,4-Dichlorophenyl)-1,3-thiazol-2-yl]-N-(3,4-dimethylisoxazol-5-yl)piperazine-1-carboxamide A mixture of 2,2,2-trichloroethyl (3,4-dimethylisoxazol-5-yl)carbamate (201 mg, 0.700 mmol), 1-[4-(2,4-dichlorophenyl)-1,3-thiazol-2-yl]piperazine (200 mg, 0.636 mmol) and diisopropylethylamine (0.222 ml, 1.27 mmol) in dimethyl sulfoxide (2.5 ml) was stirred at 70° C. for 3 days. Water was poured to the reaction mixture, and the mixture was extracted with ethyl acetate. The extract was washed with water, and dried over anhydrous magnesium sulfate, and the solvent was distilled off under reduced pressure. The residue was recrystallized from a mixed solvent of hexane and tetrahydrofuran to give 116 mg (40.3%) of the desired product as a solid.

¹H-NMR (CDCl₃) δ; 1.88 (3H, s), 2.20 (3H, s), 3.61-3.67 (8H, m), 6.76 (1H, br s), 7.20 (1H, s), 7.27-7.30 (1H, m), 7.44-7.45 (1H, m), 7.88-7.91 (1H, m).

The structural formulas of the compounds obtained in Examples 246 to 286 are shown in Table 12.

TABLE 12

| Example No. | A | B |
|---|---|---|
| 246 | 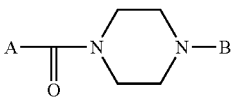 | |
| 247 | 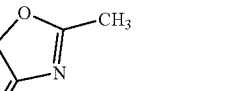 | |

TABLE 12-continued
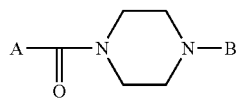
| Example No. | A | B |
|---|---|---|
| 248 | 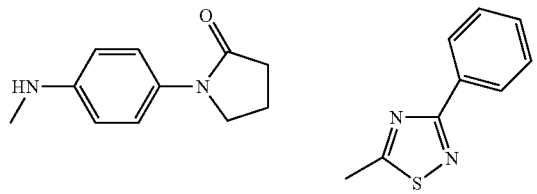 | |
| 249 | 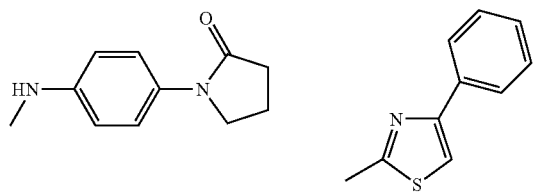 | |
| 250 | 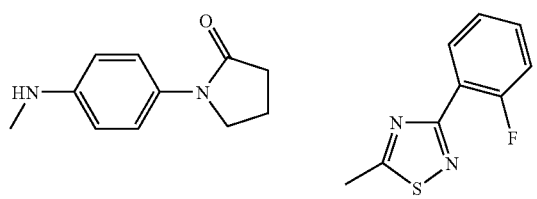 | |
| 251 | 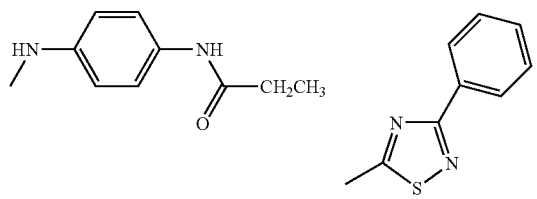 | |
| 252 | 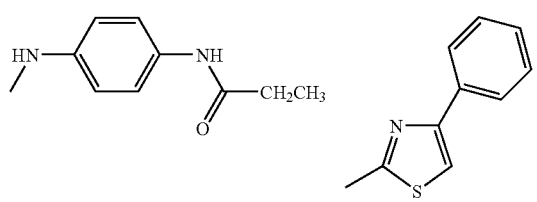 | |
| 253 | 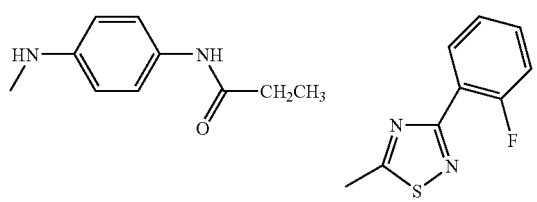 | |
| 254 | 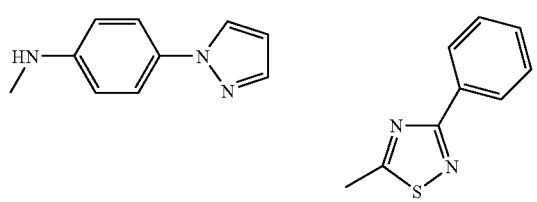 | |

TABLE 12-continued
| Example No. | A | B |
|---|---|---|
| 255 | | |
| 256 | | |
| 257 | | |
| 258 | | |
| 259 | | |
| 260 | | |
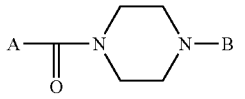

TABLE 12-continued
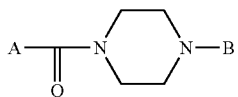
| Example No. | A | B |
|---|---|---|
| 261 | 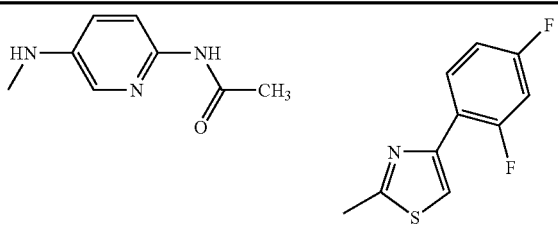 | |
| 262 | 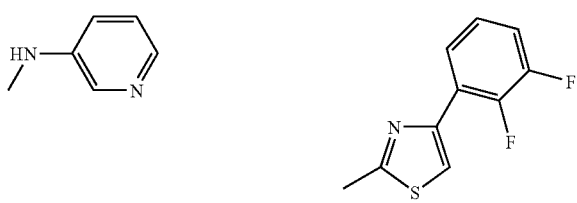 | |
| 263 | 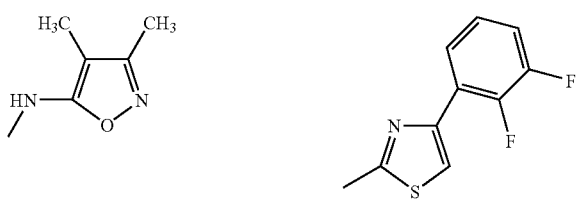 | |
| 264 | 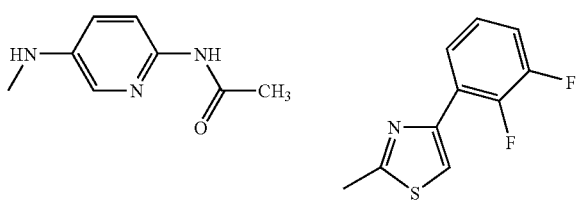 | |
| 265 | 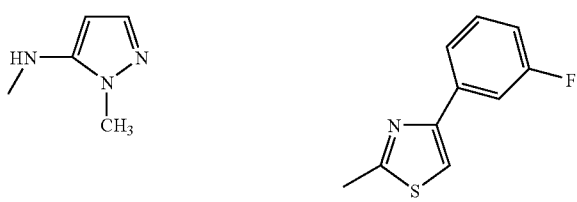 | |
| 266 | 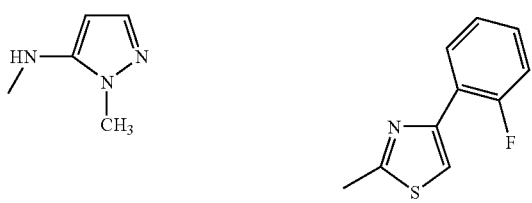 | |
| 267 | 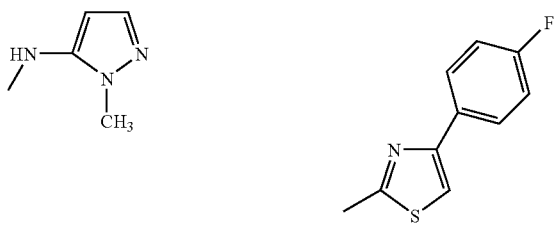 | |

TABLE 12-continued
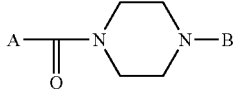
| Example No. | A | B |
|---|---|---|
| 268 | 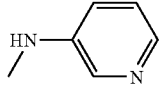 | 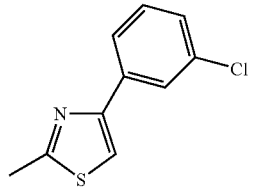 |
| 269 | 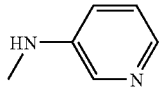 | 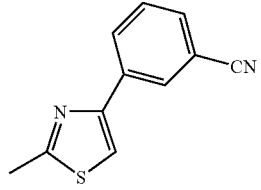 |
| 270 | 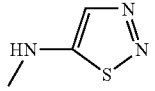 | 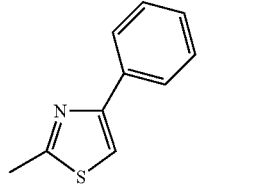 |
| 271 | 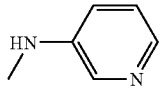 | 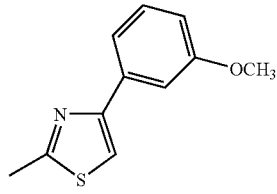 |
| 272 | 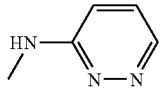 | 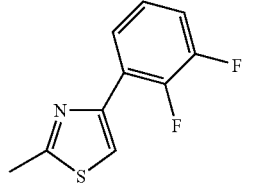 |
| 273 | 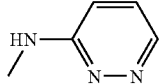 | 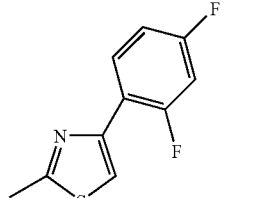 |
| 274 | 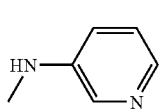 | 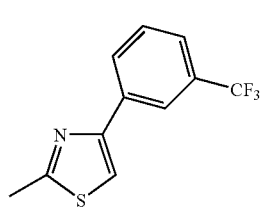 |

TABLE 12-continued
| Example No. | A | B |
|---|---|---|
| 275 | 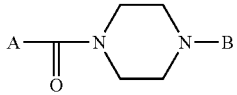 | 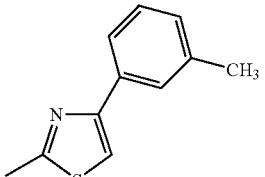 |
| 276 | 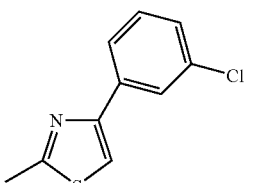 | 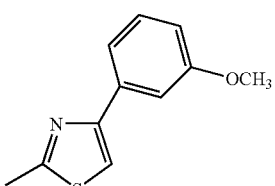 |
| 277 | 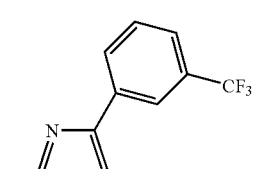 | 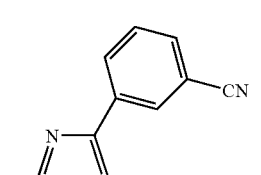 |
| 278 | 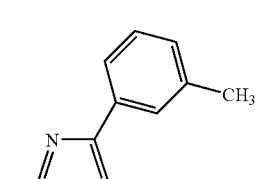 | 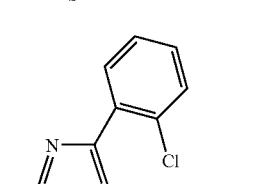 |
| 279 | | |
| 280 | | |
| 281 | | |

TABLE 12-continued

| Example No. | A | B |
|---|---|---|
| 282 | 3,4-dimethylisoxazol-5-ylamino (H₃C, CH₃ on isoxazole, HN-) | 2-methyl-4-(2-chlorophenyl)thiazol-? |
| 283 | pyridin-3-ylamino (HN-) | 2-methyl-4-(2,3-dichlorophenyl)thiazol-? |
| 284 | 3,4-dimethylisoxazol-5-ylamino | 2-methyl-4-(2,3-dichlorophenyl)thiazol-? |
| 285 | pyridin-3-ylamino | 2-methyl-4-(2,4-dichlorophenyl)thiazol-? |
| 286 | 3,4-dimethylisoxazol-5-ylamino | 2-methyl-4-(2,4-dichlorophenyl)thiazol-? |

Example 287

N-(3,4-Dimethylisoxazol-5-yl)-4-(5-phenyl-1,3,4-oxadiazol-2-yl)piperidine-1-carboxamide

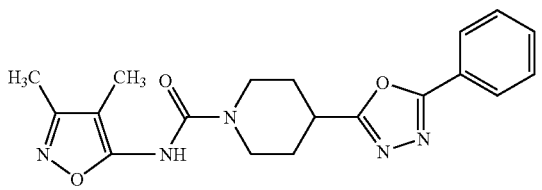

A solution of 2,2,2-trichloroethyl (3,4-dimethylisoxazol-5-yl)carbamate (293 mg, 1.02 mmol), 4-(5-phenyl-1,3,4-oxadiazol-2-yl)piperidine (234 mg, 1.02 mmol), diisopropylethylamine (0.387 ml, 2.05 mmol) and dimethyl sulfoxide (4 ml) was stirred at 70° C. for 12 hours, the reaction mixture was poured into water, and the mixture was extracted with ethyl acetate. The extract was washed with water, and dried over anhydrous magnesium sulfate. The solvent was distilled off under reduced pressure, and the residue was recrystallized from ethyl acetate to give 142 mg (37.9%) of the desired product as a solid.

$^1$H-NMR (DMSO-$d_6$) δ; 1.70-1.81 (5H, m), 2.09-2.13 (5H, m), 3.08-3.16 (2H, m), 3.32-3.35 (1H, m), 4.03-4.07 (2H, m), 7.56-7.64 (3H, m), 7.79-8.02 (2H, m), 9.18 (1H, s).

Reference Example 1

5-Chloro-3-phenyl-1,2,4-thiadiazole

To a solution of benzamidine hydrochloride (5.00 g, 31.9 mmol) and perchloromethyl mercaptan (3.43 ml, 39.2 mmol) in dichloromethane (32 ml) was added dropwise a solution of sodium hydroxide (6.38 g, 160 mmol) in water (13 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=9:1) to give 2.90 g (46.2%) of the desired product as a solid.

$^1$H-NMR (CDCl$_3$) δ; 7.46-7.51 (3H, m), 8.22-8.27 (2H, m).

Reference Example 2

5-Chloro-3-(4-fluorophenyl)-1,2,4-thiadiazole (1) 4-Fluorobenzenecarboximidamide To a solution of hexamethyldisilazane (19.4 g, 120 mmol) in diethyl ether (200 ml) was added dropwise a 1.6 N solution (75.0 ml, 120 mmol) of n-butyllithium in hexane under ice-cooling. Thereto 4-fluorobenzonitrile (7.01 g, 57.9 mmol) was added, followed by stirring at room temperature for 2 hours. Thereto 3 N hydrochloric acid (80 ml) was added dropwise under ice-cooling, and the reaction mixture was stirred under ice-cooling for 0.5 hour. Water (200 ml) was added thereto, and the diethyl ether layer was removed. The aqueous layer was basified with an aqueous 3 N sodium hydroxide solution, and then extracted with chloroform. The extracts were dried over anhydrous magnesium sulfate and the solvent was distilled off under reduced pressure to give 4.90 g (61.3%) of the desired product as a solid.

$^1$H-NMR (CDCl$_3$) δ; 5.43 (3H, br s), 7.05-7.13 (2H, m), 7.59-7.63 (2H, m).

(2) 5-Chloro-3-(4-fluorophenyl)-1,2,4-thiadiazole

To a solution of 4-fluorobenzenecarboximidamide (1.38 g, 10.0 mmol) and perchloromethyl mercaptan (1.07 ml, 10.0 mmol) in dichloromethane (10 ml) was added dropwise a solution of sodium hydroxide (1.60 g, 40.0 mmol) in water (4 ml) under ice-cooling. Then, the reaction mixture was stirred under ice-cooling for 1 hour and at room temperature for 1.5 hours. The organic layer was separated, washed with water, and then dried over anhydrous magnesium sulfate. The solvent was distilled off under reduced pressure, and the residue was purified by silica gel column chromatography (hexane:ethyl acetate=9:1) to give 1.82 g (84.7%) of the desired product as a solid.

$^1$H-NMR (CDCl$_3$) δ; 7.12-7.19 (2H, m), 8.22-8.27 (2H, m).

Reference Example 3

5-Chloro-3-(3-fluorophenyl)-1,2,4-thiadiazole (1) 3-Fluorobenzenecarboximidamide hydrochloride To a solution of hexamethyldisilazane (13.8 g, 85.6 mmol) in diethyl ether (143 ml) was added dropwise a 1.6 N solution (53.5 ml, 85.6 mmol) of n-butyllithium in hexane under ice-cooling. Thereto 3-fluorobenzonitrile (5.00 g, 41.3 mmol) was added, followed by stirring at room temperature for 2 hours. Thereto 3 N hydrochloric acid (57 ml) was added dropwise under ice-cooling, and the reaction mixture was stirred at room temperature for 0.5 hour. Water (200 ml) was added thereto, and the ether layer was removed. The aqueous layer was basified with an aqueous 3 N sodium hydroxide solution, and then extracted with chloroform. The extract was dried over anhydrous magnesium sulfate and the solvent was distilled off under reduced pressure. A 4 N solution (50 ml) of hydrogen chloride in ethyl acetate was added to the residue, and 4.65 g (64.5%) of the desired product as a solid was collected by filtration.

$^1$H-NMR (DMSO-d$_6$) δ; 7.58-7.79 (4H, m), 9.50 (4H, br s).

(2) 5-Chloro-3-(3-fluorophenyl)-1,2,4-thiadiazole

To a solution of 3-fluorobenzenecarboximidamide hydrochloride (1.75 g, 10.0 mmol) and perchloromethyl mercaptan (1.07 ml, 10.0 mmol) in dichloromethane (20 ml) was added dropwise a solution of sodium hydroxide (2.00 g, 50.0 mmol) in water (4 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=9:1) to give 1.52 g (71.0%) of the desired product as a solid.

$^1$H-NMR (CDCl$_3$) δ; 7.15-7.22 (1H, m), 7.42-7.49 (1H, m), 7.93-7.97 (1H, m), 8.03-8.06 (1H, m).

Reference Example 4

5-Chloro-3-(2-fluorophenyl)-1,2,4-thiadiazole (1) 2-Fluorobenzenecarboximidamide To a solution of hexamethyldisilazane (19.4 g, 120 mmol) in diethyl ether (200 ml) was added dropwise a 1.6 N solution (75.0 ml, 120 mmol) of n-butyllithium in hexane under ice-cooling. Thereto 2-fluorobenzonitrile (7.01 g, 57.9 mmol) was added, followed by stirring at room temperature for 2 hours. Thereto 3 N hydrochloric acid (80 ml) was added dropwise under ice-cooling, and the reaction mixture was stirred at room temperature for 0.5 hour. Water (200 ml) was added thereto, and the ether layer was removed. The aqueous layer was basified with an aqueous 3 N sodium hydroxide solution, and then extracted with chloroform. The extracts were dried over anhydrous magnesium sulfate and the solvent was distilled off under reduced pressure to give 5.17 g (64.7%) of the desired product as a solid.

$^1$H-NMR (CDCl$_3$) δ; 5.61 (3H, br s), 7.09-7.23 (2H, m), 7.37-7.45 (1H, m), 7.60-7.65 (1H, m).

(2) 5-Chloro-3-(2-fluorophenyl)-1,2,4-thiadiazole

To a solution of 2-fluorobenzenecarboximidamide (1.38 g, 10.0 mmol) and perchloromethyl mercaptan (1.07 ml, 10.0 mmol) in dichloromethane (10 ml) was added dropwise a solution of sodium hydroxide (1.60 g, 40.0 mmol) in water (4 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane: ethyl acetate=9:1) to give 1.88 g (87.4%) of the desired product as an oil.

$^1$H-NMR (CDCl$_3$) δ; 7.22-7.30 (2H, m), 7.44-7.52 (1H, m), 8.14-8.19 (1H, m).

Reference Example 5

3-(4-Chlorophenyl)-5-chloro-1,2,4-thiadiazole

To a solution of 4-fluorobenzenecarboximidamide hydroiodide (5.00 g, 17.7 mmol) and perchloromethyl mercaptan (1.90 ml, 17.7 mmol) in dichloromethane (100 ml) was added dropwise a solution of sodium hydroxide (3.55 g, 88.8 mmol) in water (7 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=9:1) to give 1.78 g (31.2%) of the desired product as a solid.

$^1$H-NMR (CDCl$_3$) δ; 7.46 (2H, d, J=8.7 Hz), 8.62 (2H, d, J=8.7 Hz).

Reference Example 6

5-Chloro-3-(4-methylphenyl)-1,2,4-thiadiazole

To a solution of 4-methylbenzenecarboximidamide hydrochloride (1.70 g, 10.0 mmol) and perchloromethyl mercaptan (1.07 ml, 10.0 mmol) in dichloromethane (10 ml) was added dropwise a solution of sodium hydroxide (1.60 g, 40.0 mmol) in water (4 ml) under ice-cooling. Then, the reaction mixture was stirred under ice-cooling for 1 hour and at room temperature for 1.5 hours. The organic layer was separated, washed with water, and then dried over anhydrous magnesium sulfate. The solvent was distilled off under reduced pressure, and the residue was purified by silica gel column chromatography (hexane:ethyl acetate=9:1) to give 1.05 g (50.0%) of the desired product as a solid.

$^1$H-NMR (CDCl$_3$) δ; 2.41 (3H, s), 7.27 (2H, d, J=8.4 Hz), 8.12 (2H, d, J=8.4 Hz).

Reference Example 7

5-Chloro-3-[4-(trifluoromethyl)phenyl]-1,2,4-thiadiazole

To a solution of 4-(trifluoromethyl)benzenecarboximidamide hydrochloride (2.60 g, 10.0 mmol) and perchloromethyl mercaptan (1.07 ml, 10.0 mmol) in dichloromethane (10 ml) was added dropwise a solution of sodium hydroxide (1.60 g, 40.0 mmol) in water (4 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=9:1) to give 770 mg (29.2%) of the desired product as an oil.

$^1$H-NMR (CDCl$_3$) δ; 7.75 (2H, d, J=8.7 Hz), 8.37 (2H, d, J=8.7 Hz).

Reference Example 8

5-Chloro-3-(phenoxymethyl)-1,2,4-thiadiazole

To a solution of 2-phenoxyethanimidamide hydrochloride (2.00 g, 10.7 mmol) and perchloromethyl mercaptan (1.15 ml, 10.7 mmol) in dichloromethane (40 ml) was added dropwise a solution of sodium hydroxide (2.15 g, 53.7 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by a silica gel column chromatography (hexane:ethyl acetate=9:1) to give 1.66 g (68.3%) of the desired product as an oil.

$^1$H-NMR (CDCl$_3$) δ; 5.29 (2H, s), 6.98-7.03 (3H, m), 7.26-7.33 (2H, m).

Reference Example 9

5-Chloro-3-isopropyl-1,2,4-thiadiazole

To a solution of 2-methylpropanimidamide hydrochloride (2.00 g, 16.3 mmol) and perchloromethyl mercaptan (1.75 ml, 16.3 mmol) in dichloromethane (40 ml) was added dropwise a solution of sodium hydroxide (3.26 g, 81.5 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=9:1) to give 1.22 g (46.2%) of the desired product as an oil.

$^1$H-NMR (CDCl$_3$) δ; 1.37 (6H, d, J=7.2 Hz), 3.22-3.31 (1H, m).

Reference Example 10

5-Chloro-3-(2-thienyl)-1,2,4-thiadiazole

To a solution of thiophene-2-carboximidamide hydrochloride (1.62 g, 10.0 mmol) and perchloromethyl mercaptan (1.07 ml, 10.0 mmol) in dichloromethane (10 ml) was added dropwise a solution of sodium hydroxide (1.60 g, 40.0 mmol) in water (4 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=9:1) to give 1.40 g (69.3%) of the desired product as an oil.

$^1$H-NMR (CDCl$_3$) δ; 7.12-7.15 (1H, m), 7.46-7.49 (1H, m), 7.82-7.87 (1H, m).

Reference Example 11

5-Chloro-3-(3-thienyl)-1,2,4-thiadiazole

To a solution of thiophene-3-carboximidamide hydrochloride (2.00 g, 12.3 mmol) and perchloromethyl mercaptan (1.32 ml, 12.3 mmol) in dichloromethane (40 ml) was added dropwise a solution of sodium hydroxide (2.46 g, 61.5 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=9:1) to give 1.57 g (59.5%) of the desired product as an oil.

$^1$H-NMR (CDCl$_3$) δ; 7.26-7.40 (1H, m), 7.74-7.76 (1H, m), 8.14-8.15 (1H, m).

Reference Example 12

5-Chloro-3-(3-furyl)-1,2,4-thiadiazole

To a solution of furan-3-carboximidamide hydrochloride (2.00 g, 13.6 mmol) and perchloromethyl mercaptan (1.47 ml, 13.6 mmol) in dichloromethane (40 ml) was added dropwise a solution of sodium hydroxide (2.72 g, 68.0 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=9:1) to give 0.82 g (32.2%) of the desired product as an oil.

$^1$H-NMR (CDCl$_3$) δ; 6.96-6.97 (1H, m), 7.49-7.50 (1H, m), 8.15-8.16 (1H, m).

Reference Example 13

4-(5-Chloro-1,2,4-thiadiazol-3-yl)pyridine

To a solution of pyridine-4-carboximidamide hydrochloride (2.00 g, 12.7 mmol) and perchloromethyl mercaptan (1.75 ml, 16.3 mmol) in dichloromethane (40 ml) was added dropwise a solution of sodium hydroxide (3.26 g, 81.5 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=1:1 to give 150 mg (5.98%) of the desired product as a solid.

$^1$H-NMR (CDCl$_3$) δ; 8.07-8.09 (2H, m), 8.76-8.78 (2H, m).

Reference Example 14

3-(5-Chloro-1,2,4-thiadiazol-3-yl)pyridine

To a solution of pyridine-3-carboximidamide hydrochloride (2.00 g, 12.7 mmol) and perchloromethyl mercaptan (1.75 ml, 16.3 mmol) in dichloromethane (40 ml) was added dropwise a solution of sodium hydroxide (3.26 g, 81.5 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=1:1) to give 110 mg (4.38%) of the desired product as a solid.

$^1$H-NMR (CDCl$_3$) δ; 7.40-7.44 (1H, m), 8.48-8.52 (1H, m), 8.70-8.73 (1H, m), 9.45-9.46 (1H, m).

Reference Example 15

2-(5-Chloro-1,2,4-thiadiazol-3-yl)pyridine

To a solution of pyridine-2-carboximidamide hydrochloride (2.00 g, 12.7 mmol) and perchloromethyl mercaptan (1.75 ml, 16.3 mmol) in dichloromethane (40 ml) was added dropwise a solution of sodium hydroxide (3.26 g, 81.5 mmol) in water (6 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=2:1) to give 1.05 g (42.0%) of the desired product as an oil.

$^1$H-NMR (CDCl$_3$) δ; 7.40-7.45 (1H, m), 7.84-7.90 (1H, m), 8.31 (1H, d, J=8.1 Hz), 8.79-8.82 (1H, m).

Reference Example 16

4-(5-Chloro-1,2,4-thiadiazol-3-yl)morpholine

To a solution of morpholinoformamidine hydrobromide (2.00 g, 9.52 mmol) and perchloromethyl mercaptan (1.02 ml, 9.52 mmol) in dichloromethane (10 ml) was added dropwise a solution of sodium hydroxide (1.52 g, 38.1 mmol) in water (4 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=3:1) to give 1.07 g (54.6%) of the desired product as a solid.

$^1$H-NMR (CDCl$_3$) δ; 3.63-3.67 (4H, m), 3.76-3.80 (4H, m).

Reference Example 17

1-(5-Chloro-1,2,4-thiadiazol-3-yl)piperidine

To a solution of piperidine-1-carboximidamide hydrobromide (2.00 g, 9.61 mmol) and perchloromethyl mercaptan (1.04 ml, 9.61 mmol) in methylene chloride (10 ml) was added dropwise a solution of sodium hydroxide (1.54 g, 38.4 mmol) in water (4 ml) under ice-cooling. The mixture was stirred under ice-cooling for 1 hour and at room temperature for 1 hour. The reaction mixture was poured to water, and the organic layer was separated and dried over anhydrous magnesium sulfate. The solvent was distilled off under reduced pressure, and the residue was purified by silica gel column chromatography (hexane: ethyl acetate=4:1) to give 500 mg (25.6%) of the desired product as a solid.

$^1$H-NMR (CDCl$_3$) δ; 1.58-1.63 (6H, m), 3.63-3.64 (4H, m).

Reference Example 18

1-Benzyl-4-(5-chloro-1,2,4-thiadiazol-3-yl)piperazine

To a solution of 4-benzylpiperazine-1-carboximidamide (2.50 g, 11.5 mmol) and perchloromethyl mercaptan (1.24 ml, mmol) in methylene chloride (12 ml) was added dropwise a solution of sodium hydroxide (1.84 g, 46.0 mmol) in water (5 ml) under ice-cooling. The mixture was stirred under ice-cooling for 1 hour and at room temperature for 1 hour. The reaction mixture was poured to water, and the organic layer was separated and dried over anhydrous magnesium sulfate. The solvent was distilled off under reduced pressure, and the residue was purified by silica gel column chromatography (hexane:ethyl acetate=4:1) to give 1.00 g (29.6%) of the desired product as an oil.

$^1$H-NMR (CDCl$_3$) δ; 2.50-2.54 (4H, m), 3.55 (2H, s), 3.66-3.69 (4H, m), 7.26-7.34 (5H, m).

Reference Example 19 tert-Butyl 4-(5-chloro-1,2,4-thiadiazol-3-yl)piperazine-1-carboxylate (1) tert-Butyl 4-[amino(imino)methyl]piperazine-1-carboxylate hydrochloride To a solution of tert-butyl piperazine-1-carboxylate (1.86 g, 10.0 mmol) and 1H-pyrazole-1-carboximidamide (1.46 g, 10.0 mmol) in acetonitrile (12.5 ml) was added triethylamine (1.39 ml, 10.0 mmol), and the mixture was stirred at 60° C. for 12 hours. After the reaction mixture was cooled to room temperature, a crystal was collected by filtration and washed with acetonitrile and diethyl ether to give 1.84 g (69.7%) of the desired product.

$^1$H-NMR (DMSO-d$_6$) δ; 1.42 (9H, s), 3.40-3.42 (8H, m), 7.62 (4H, br s).

(2) tert-Butyl 4-(5-chloro-1,2,4-thiadiazol-3-yl)piperazine-1-carboxylate

To a solution of tert-butyl 4-[amino(imino)methyl]piperazine-1-carboxylate (1.50 g, 5.67 mmol) and perchloromethyl mercaptan (0.609 ml, 5.67 mmol) in dichloromethane (20 ml) was added dropwise a solution of sodium hydroxide (0.907 g, 22.7 mmol) in water (2.5 ml) under ice-cooling. Then, the reaction mixture was stirred under ice-cooling for 1 hour and at room temperature for 1 hour. The organic layer was separated, washed with water, and then dried over anhydrous magnesium sulfate. The solvent was distilled off under reduced pressure, and the residue was purified by silica gel column chromatography (hexane:ethyl acetate=4:1) to give 1.03 g (59.5%) of the desired product as a solid.

$^1$H-NMR (CDCl$_3$) δ; 1.48 (9H, s), 3.49-3.52 (4H, m), 3.62-3.66 (4H, m).

Reference Example 20

2-Chloro-4-phenyl-1,3-thiazole (1) 2-Oxo-2-phenylethyl thiocyanate

A solution of α-bromoacetophenone (10.0 g, 50.0 mmol) and potassium thiocyanate (4.90 g, 50.0 mmol) in ethanol (80 ml) was stirred at 80° C. for 3 hours. After cooling to room temperature, a precipitated solid was collected by filtration, washed with 50% ethanol in water and dried to give 5.99 g (67.6%) of the desired product.

$^1$H-NMR (CDCl$_3$) δ; 4.75 (2H, s), 7.51-7.56 (2H, m), 7.65-7.71 (1H, m), 7.93-7.97 (2H, m).

(2) 4-Phenyl-1,3-thiazol-2-ol

A mixed solution of 2-oxo-2-phenylethyl thiocyanate (5.67 g, 32.0 mmol), water (3.2 ml), concentrated sulfuric acid (0.832 ml) and acetic acid (26 ml) was stirred at 130° C. for 2 hours and at room temperature for 2 hours. A formed precipitate was collected by filtration and washed with water to give 4.78 g (84.3%) of the desired product.

$^1$H-NMR (CDCl$_3$) δ; 6.26 (1H, s), 7.30-7.43 (3H, m), 7.54-7.58 (2H, m), 11.27 (1H, br s).

(3) 2-Chloro-4-phenyl-1,3-thiazole

A mixed solution of 4-phenyl-1,3-thiazol-2-ol (2.00 g, 11.3 mmol) in phosphorus oxychloride (20 ml) was stirred at 100° C. for 2 hours. The solvent was distilled off under reduced pressure. The residue was poured to ice water and extracted with ethyl acetate. The extract was washed with water and dried over anhydrous magnesium sulfate. The solvent was distilled off under reduced pressure, and the residue was purified by silica gel column chromatography (hexane:ethyl acetate=9:1) to give 1.44 g (65.2%) of the desired product as a solid.

$^1$H-NMR (CDCl$_3$) δ; 7.35-7.45 (4H, m), 7.83-7.87 (2H, m).

Reference Example 21

5-Chloro-3-phenyl-1,2,4-oxadiazole (1) N'-[(Ethoxycarbonyl)oxy]benzenecarboximidamide To a solution of benzamide oxime (25.0 g, 184 mmol) in chloroform (250 ml) was added dropwise a solution of ethyl chlorocarbonate (8.79 ml, 92.0 mmol) in chloroform (60 ml), and the mixture was stirred at room temperature for 3 hours. Insolubles were filtered off, and then the filtrate was concentrated. The residue was recrystallized from a mixed solvent of ethanol and water to yield 18.2 g (94.8%) of the desired product.

$^1$H-NMR (CDCl$_3$) δ; 1.37 (3H, t, J=7.2 Hz), 4.33 (2H, q, J=7.2 Hz), 5.10 (2H, br s), 7.38-7.51 (3H, m), 7.68-7.71 (2H, m).

(2) 3-Phenyl-1,2,4-oxadiazol-5(4H)-one

A solution of N'-[(ethoxycarbonyl)oxy]benzenecarboximidamide (17.0 g, 81.6 mmol) and sodium hydroxide (6.28 g, 157 mmol) in water (380 ml) and ethanol (95 ml) was stirred at room temperature for 3 hours. Thereto 1 N hydrochloric acid (157 ml) was added, and a precipitated solid was collected by filtration and washed with water to give 7.05 g (53.4%) of the desired product.

$^1$H-NMR (CDCl$_3$) δ; 7.46-7.54 (3H, m), 7.82-7.86 (2H, m).

(3) 5-Chloro-3-phenyl-1,2,4-oxadiazole

To a mixed solution of 3-phenyl-1,2,4-oxadiazol-5(4H)-one (2.00 g, 12.3 mmol) in phosphorus oxychloride (36 g) was added pyridine (1.93 ml, 23.9 mmol), and the mixture was stirred at 100° C. for 6 hours. The solvent was distilled off under reduced pressure. The residue was poured to ice water and extracted with ethyl acetate. The extract was washed with water and dried over anhydrous magnesium sulfate, and the solvent was distilled off under reduced pressure. The residue was purified by silica gel column chromatography (hexane: ethyl acetate=2:1) to give 1.17 g (52.4%) of the desired product as a solid.

$^1$H-NMR (CDCl$_3$) δ; 7.47-7.55 (3H, m), 8.03-8.06 (2H, m).

Reference Example 22

2-Chloro-4-phenyl-1,3-oxazole

(1) 4-Phenyl-1,3-oxazol-2(3H)-one

To a solution of 2-hydroxyacetophenone (10.0 g, 73.4 mmol) and potassium cyanate (11.9 g, 147 mmol) in isopropanol (50 ml) was added dropwise acetic acid (10.1 ml, 176 mmol) at 50° C., and the mixture was stirred at 50° C. for 5 hours. The reaction mixture was poured to water and extracted with ethyl acetate. The extract was washed with water and dried over anhydrous magnesium sulfate, and the solvent was distilled off under reduced pressure. The residue was purified by silica gel column chromatography (hexane: ethyl acetate=3:2) to give 4.83 g (40.9%) of the desired product as a solid.

$^1$H-NMR (CDCl$_3$) δ; 7.13 (1H, s), 7.34-7.45 (5H, m), 10.73 (1H, br s).

(2) 2-Chloro-4-phenyl-1,3-oxazole

To a solution of 4-phenyl-1,3-oxazol-2(3H)-one (1.00 g, 62.0 mmol) in phosphorus oxychloride (18 ml) was added pyridine (0.974 ml, 12.0 mmol), and the mixture was stirred at 100° C. for 1 hour and 20 minutes. The solvent was distilled off under reduced pressure. The residue was purified by silica gel column chromatography (hexane: ethyl acetate=9:1) to give 176 mg (15.7%) of the desired product as a solid.

$^1$H-NMR (CDCl$_3$) δ; 7.32-7.48 (3H, m), 7.51-7.71 (2H, m), 7.90 (1H, s).

Reference Example 23

1-(3-Phenyl-1,2,4-thiadiazol-5-yl)piperidine-4-carboxylic acid

(1) Ethyl 1-(3-phenyl-1,2,4-thiadiazol-5-yl)piperidine-4-carboxylate

A mixed solution of ethyl isonipecotate (0.782 ml, 5.08 mmol), 5-chloro-3-phenyl-1,2,4-thiadiazole (1.00 g, 5.08 mmol) and triethylamine (0.708 ml, 5.08 mmol) in N,N-dimethylformamide (10 ml) was stirred at room temperature for 30 minutes. The reaction mixture was poured to water and extracted with ethyl acetate. The extract was washed with water and dried over anhydrous magnesium sulfate, and the solvent was distilled off under reduced pressure. The residue was recrystallized from a mixed solvent of hexane and ethyl acetate to yield 1.22 g (75.8%) of the desired product.

$^1$H-NMR (CDCl$_3$) δ; 1.28 (3H, t, J=7.2 Hz), 1.82-1.95 (2H, m), 2.04-2.11 (2H, m), 2.55-2.63 (1H, m), 3.26-3.35 (2H, m), 3.95-4.00 (2H, m), 4.18 (2H, q, J=7.2 Hz), 7.39-7.44 (3H, m), 8.17-8.20 (2H, m).

(2) 1-(3-Phenyl-1,2,4-thiadiazol-5-yl)piperidine-4-carboxylic acid

A solution of ethyl 1-(3-phenyl-1,2,4-thiadiazol-5-yl)piperidine-4-carboxylate (1.12 g, 3.53 mmol), an aqueous 2 N sodium hydroxide solution (4 ml), tetrahydrofuran (20 ml) and ethanol (12 ml) was stirred at 80° C. for 1 hour. Thereto 2 N hydrochloric acid (4 ml) was added and the solvent was distilled off under reduced pressure. The residue was poured to water and extracted with ethyl acetate. The extract was washed with water and dried over anhydrous magnesium sulfate, and the solvent was distilled off under reduced pressure. The residue was recrystallized from a mixed solvent of hexane and ethyl acetate to yield 910 mg (89.2%) of the desired product.

$^1$H-NMR (CDCl$_3$) δ; 1.82-1.95 (2H, m), 2.06-2.13 (2H, m), 2.54-2.62 (1H, m), 3.28-3.37 (2H, m), 3.94-3.98 (2H, m), 7.38-7.44 (3H, m), 8.15-8.19 (2H, m).

Reference Example 24

1-(3-Phenyl-1,2,4-thiadiazol-5-yl)piperazine

(1) tert-Butyl 4-(3-phenyl-1,2,4-thiadiazol-5-yl)piperazine-1-carboxylate

To a solution of 5-chloro-3-phenyl-1,2,4-thiadiazole (196 mg, 1.00 mmol) and 1-(tert-butoxycarbonyl)-piperazine (186 mg, 1.00 mmol) in dimethylformamide (2 ml) was added triethylamine (0.558 ml, 4.00 mmol) at room temperature, and the mixture was stirred at room temperature for 3 hours. The reaction mixture was poured to water and extracted with ethyl acetate. The extract was washed with water, and the solvent was distilled off under reduced pressure. The residue was recrystallized from a mixed solvent of ethyl acetate and hexane to yield 181 mg (52.3%) of the desired product.

$^1$H-NMR (CDCl$_3$) δ; 1.51 (9H, s), 3.61 (8H, s), 7.40-7.45 (3H, m), 8.17-8.20 (2H, m).

(2) 1-(3-Phenyl-1,2,4-thiadiazol-5-yl)piperazine

To a solution of tert-butyl 4-(3-phenyl-1,2,4-thiadiazol-5-yl)piperazine-1-carboxylate (5.06 g, 14.6 mmol) in ethyl acetate (80 ml) was added a 4 N solution of hydrogen chloride in ethyl acetate (40 ml), and the mixture was stirred at room temperature for 5 hours. Hexane (200 ml) was added to the reaction mixture and a precipitated solid was collected by filtration. The obtained solid was added to an aqueous saturated sodium bicarbonate solution (300 ml), followed by stirring at room temperature for 2 hours. The obtained powder was collected by filtration to yield 2.77 g (77.0%) the desired product.

$^1$H-NMR (CDCl$_3$) δ; 3.00-3.03 (4H, m), 3.56-3.60 (4H, m), 7.39-7.44 (3H, m), 8.17-8.21 (2H, m).

Experimental Example 1

Measurement of FAAH Inhibitory Activity

(1) Preparation of Enzyme Fraction

The FAAH gene was cloned by PCR. That is, a human brain library was used as a cDNA library, 5'-AAAAGAAT-TCGCCACCATGGTGCAGTACGAGCTGTG-3' [SEQ ID NO:1] and 5'-TTTTGTCGACTCAGGATGACTGCTTTT-3' [SEQ ID NO:2] were used as a primer set, and KOD DNA polymerase (Toyobo Co., Ltd.) was used as a DNA polymerase. One cycle of the reaction comprises 95° C. for 30 sec, 55° C. for 30 sec and 72° C. for 2 min, and 45 cycles of the reaction was carried out to obtain an amplified fragment. The amplified fragment was cleaved with restriction enzymes EcoRI and SalI, and then was inserted into a pMSRα vector which had been cleaved with the same restriction enzymes EcoRI and SalI to obtain a pMSRα-human FAAH. A cell line CHO-K1 and the above-obtained plasmid were subjected to a method known per se to prepare the cell line CHO-K1/human FAAH in which human FAAH was stably expressed. The CHO-K1/human FAAH was cultured in a $CO_2$ incubator at 37° C., using a medium (Ham's F-12 medium supplemented with final concentration 10% of fetal bovine serum (FBS) and final concentration 800 μg/ml of G418), and then the cells were harvested. After washing with PBS, the cells were suspended in a buffer (10 mM Tris, 1 mM EDTA and 10 mM $MgCl_2$, all at final concentrations) and disrupted with a Polytron homogenizer. After centrifugation at 900 g, the supernatant was recovered and further centrifuged at 10000 g. A pellet obtained therefrom was suspended in M-PER (Catalog No. 78501; PIERCE) to give an enzyme fraction.

(2) Enzymatic Reaction

Using a white walled 96-well plate (Coster Corp.), the test compound at various concentrations, 60 ng of the enzyme fraction and the substrate anandamide [ethanolamine 1-$^3$H] (final concentration 25 nM) were reacted in 50 μl of a reaction buffer (125 mM Tris-HCl (pH 9.0), 1 mM EDTA, 0.4 mM HEPES, 0.2% glycerol and 0.02% Triton X-100, all at final concentrations) at 37° C. for 30 minutes. The reaction mixture was transferred to a 96-well MultiScreen-HA filter plate (Millipore Corp.) and then was left to stand overnight at room temperature in order to allow the unreacted substrate to be adsorbed on the filter. The plate was washed with PBS using a MultiScreen Vacuum Manifold (Millipore Corp.) and dried. To each well, 50 μl of liquid scintillation cocktail was added and stirred, and then counting was performed with a Top-Count (Perkin-Elmer Corp.). The count of a sample containing a solvent instead of the test compound was taken as 0%, and the count at zero time was taken as 100%, to calculate the inhibitory activity of the compound. The results are presented in Table 13.

TABLE 13

| Compound | Human FAAH Inhibition Rate at 1 μM (%) |
|---|---|
| Example 1 | 100 |
| Example 9 | 98 |
| Example 15 | 102 |
| Example 17 | 95 |
| Example 22 | 94 |
| Example 23 | 100 |
| Example 71 | 108 |
| Example 85 | 100 |
| Example 94 | 100 |
| Example 95 | 100 |
| Example 147 | 101 |
| Example 166 | 106 |
| Example 236 | 106 |
| Example 190 | 103 |
| Example 228 | 106 |
| Example 229 | 105 |
| Example 260 | 102 |
| Example 262 | 106 |
| Example 226 | 104 |
| Example 272 | 102 |
| Example 275 | 94 |
| Example 276 | 104 |
| Example 277 | 100 |
| Example 278 | 104 |
| Example 280 | 86 |
| Example 283 | 102 |
| Example 284 | 128 |

It can be seen from the results of Table 12 that the compound of the invention has excellent FAAH inhibitory activity.

Experimental Example 2

Cerebroprotective Effect in a Rat Cerebral Ischemic Model

The compound obtained in Example 1 as an FAAH inhibitory agent (hereinafter, referred to as Compound A) was administered intravenously to a rat local cerebral ischemic model, and the inhibitory effect of the compound on cerebral infarct volume was examined. For the cerebral ischemic model, 8 weeks-old male SD rats (CLEA Japan, Inc.) were used to generate a middle cerebral artery occlusion model (Kiyota, et al., Experimental Brain Research, 95, 388-396 (1993)). That is, under halothane anesthesia, a silicone-coated plug was inserted into the rat from the right common carotid artery to the origin of middle cerebral artery to induce occlusion for 120 minutes. Compound A of Example was intravenously administered immediately after reperfusion and after 2, 4 and 6 hours, respectively. Two days after the ischemia treatment, the rat brain was extracted, 2 mm-thick slices of anterior maxillary section were prepared therefrom, and the cerebral infarct volume was measured from their TTC-stained images by image analysis. The results are presented in FIG. 1.

It can be seen from FIG. 1 that the infarct volume of the Compound A-administered group is significantly smaller ($p<0.05$) compared with that of the solvent-administered group. The above result shows that inhibition of the function of FAAH results in the cerebral infarction inhibitory action.

Experimental Example 3

Test of Sleep Action (Measurement of Electroencephalogram (EEG))

Grids were attached to an acrylic cylindrical cage with 30 cm in diameter and 50 cm in height, at 7 cm from the bottom at 2 cm intervals, and the bottom of the cage was filled with water. A rat was placed on the grids. A test compound was administered orally to the rat. From immediately after administration, EEG and electromyogram (EMG) were measured. The EEG and EMG data obtained were recorded by a bioamplifier built-in recording apparatus, polymate AP1124 (TEAC Instruments Corporation). The EEG and EMG data obtained were analyzed every 4 seconds at a sampling frequency of 1 kHz by using an EEG analyzing program, SleepSing Ver. 2 (Kissei Comtech). Sleep action of a FAAH inhibitor was evaluated by analyzing change in sleep-wake time during the measuring period.

When the wake time of a solvent control group was taken as 100%, the total wake time of a rat to which 10 mg/kg of the compound of Example 85, 94, 147, 148, 166, 198 or 217 was orally administered during 6 hours after the administration was 90% or less.

INDUSTRIAL APPLICABILITY

According to the present invention, it is possible to provide a potent FAAH inhibitor, and an excellent cerebro-neuroprotective agent and prophylactic or therapeutic agent for sleep disorders which comprise the FAAH inhibitor.

The invention claimed is:

1. A compound represented by the formula (I):

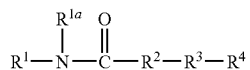

(I)

wherein $R^1$ is a $C_{6-10}$ aryl which may be substituted, or a 5- or 6-membered heterocyclic group containing 1 to 4 heteroatoms selected from oxygen, sulfur, and nitrogen atoms in addition to carbon atoms which may be substituted;

$R^{1a}$ is a hydrogen atom;

$R^2$ is piperazin-1,4-diyl which may be substituted;

$R^3$ is a group formed by eliminating two hydrogen atoms from a 1,2,4-thiadiazole, a 1,3-thiazole, a 1,3-oxazole, or a 1,2,4-oxadiazole; and $R^4$ is a $C_{6-14}$ aryl which may be substituted, or a 5- or 6-membered heterocyclic group containing 1 to 4 heteroatoms selected from oxygen, sulfur, and nitrogen atoms in addition to carbon atoms which may be substituted, or a salt thereof, and from which N-Phenyl-4-(3-phenyl-1,2,4-thiadiazol-5-yl)piperazine-1-carboxamide is excluded.

2. A medicine comprising the compound according to claim 1 or a salt thereof, and a pharmacologically acceptable carrier.

3. A fatty acid amide hydrolase inhibitor comprising the compound according to claim 1 or a salt thereof.

4. A method of inhibition of fatty acid amide hydrolase in a mammal, which comprises administering an effective amount of the compound according to claim 1 or a salt thereof to the mammal in need thereof.

5. A cerebro-neuroprotective agent comprising the compound according to claim 1 or a salt thereof.

6. A method of protection of brain cells and/or neuronal cells in a mammal, which comprises administering an effective amount of the compound according to claim 1 or a salt thereof to the mammal in need thereof.

7. A therapeutic agent for cerebrovascular disorders, head injury or spinal cord damage comprising the compound according to claim 1 or a salt thereof.

8. A therapeutic agent for pain; neuropathic pain; chronic pain; sleep disorder; depression; anxiety; or mental diseases, which comprises the compound according to claim 1 or a salt thereof.

9. A method of treatment for pain; sleep disorder; depression; anxiety; or mental diseases in a mammal, which comprises administering an effective amount of the compound according to claim 1 or a salt thereof to the mammal in need thereof.

10. The compound according to claim 1,
wherein $R^1$ is (1) a phenyl which may be substituted, (2) a 1- or 2-naphthyl which may be substituted, (3) a 2-, 4- or 5-thiazolyl which may be substituted, (4) a 2-, 4- or 5-pyrimidinyl which may be substituted, or (5) a 2-, 3- or 4-pyridyl which may be substituted;

$R^3$ is a group formed by eliminating two hydrogen atoms from a 1,2,4-thiadiazole; and $R^4$ is (1) a phenyl which may be substituted, (2) 2- or 3-thienyl which may be substituted, (3) 2- or 3-furyl which may be substituted, (4) a piperidino which may be substituted, or (5) a 2-, 3- or 4-piperidyl which may be substituted, or a salt thereof.

11. The compound according to claim 1,
wherein $R^1$ is a phenyl which may be substituted, a 1- or 2-naphthyl which may be substituted, or a 2-, 3- or 4-pyridyl which may be substituted;

$R^3$ is a group formed by eliminating two hydrogen atoms from a 1,2,4-thiadiazole; and $R^4$ is a phenyl which may be substituted, or a salt thereof.

12. The compound according to claim 1 wherein $R^1$ is (1) a phenyl which may be substituted, (2) a 1- or 2-naphthyl, or (3) a 2-, 3- or 4-pyridyl;

$R^2$ is a piperazin-1,4-diyl;

$R^3$ is a group formed by eliminating two hydrogen atoms from a 1,2,4-thiadiazol; and $R^4$ is a phenyl, or a salt thereof.

13. The compound according to claim 12, wherein R¹ is (1) a phenyl which may be substituted by a halogen atom, $C_{1-6}$ alkyl group which may be halogenated, or a $C_{1-6}$ alkoxy group, (2) a 1- or 2-naphthyl, or (3) a 2-, 3- or 4-pyridyl, or a salt thereof.

14. The compound according to claim 12, wherein the moiety represented by the formula: —R²—R³—R⁴ is represented by the formula:

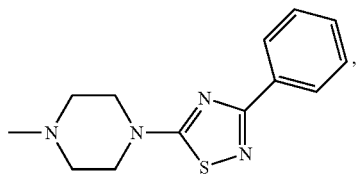

or a salt thereof.

15. The compound according to claim 1, which is:
N-(2-Chlorophenyl)-4-(3-phenyl-1,2,4-thiadiazol-5-yl)piperazine-1-carboxamide,
N-(3-Fluorophenyl)-4-(3-phenyl-1,2,4-thiadiazol-5-yl)piperazine-1-carboxamide,
N-(4-Fluorophenyl)-4-(3-phenyl-1,2,4-thiadiazol-5-yl)piperazine-1-carboxamide,
N-(4-Methoxyphenyl)-4-(3-phenyl-1,2,4-thiadiazol-5-yl)piperazine-1-carboxamide,
N-(3-Methylphenyl)-4-(3-phenyl-1,2,4-thiadiazol-5-yl)piperazine-1-carboxamide,
N-(2-Methoxyphenyl)-4-(3-phenyl-1,2,4-thiadiazol-5-yl)piperazine-1-carboxamide,
N-(3-Chlorophenyl)-4-(3-phenyl-1,2,4-thiadiazol-5-yl)piperazine-1-carboxamide,
N-(4-Methylphenyl)-4-(3-phenyl-1,2,4-thiadiazol-5-yl)piperazine-1-carboxamide,
N-(2-Methylphenyl)-4-(3-phenyl-1,2,4-thiadiazol-5-yl)piperazine-1-carboxamide,
N-(3-Methoxyphenyl)-4-(3-phenyl-1,2,4-thiadiazol-5-yl)piperazine-1-carboxamide,
N-2-Naphthyl-4-(3-phenyl-1,2,4-thiadiazol-5-yl)piperazine-1-carboxamide,
N-(2-Fluorophenyl)-4-(3-phenyl-1,2,4-thiadiazol-5-yl)piperazine-1-carboxamide,
N-(4-Chlorophenyl)-4-(3-phenyl-1,2,4-thiadiazol-5-yl)piperazine-1-carboxamide,
4-(3-Phenyl-1,2,4-thiadiazol-5-yl)-N-[2-(trifluoromethyl)phenyl]piperazine-1-carboxamide,
4-(3-Phenyl-1,2,4-thiadiazol-5-yl)-N-pyridin-4-ylpiperazine-1-carboxamide,
4-(3-Phenyl-1,2,4-thiadiazol-5-yl)-N-pyridin-2-ylpiperazine-1-carboxamide, or
4-(3-Phenyl-1,2,4-thiadiazol-5-yl)-N-pyridin-3-ylpiperazine-1-carboxamide, or a salt thereof.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: Artificial
<220> FEATURE:
<223> OTHER INFORMATION: primer

<400> SEQUENCE: 1
aaaagaattc gccaccatgg tgcagtacga gctgtg        36

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
ttttgtcgac tcaggatgac tgctttt        27